US012685017B2

(12) United States Patent
Kim et al.

(10) Patent No.: US 12,685,017 B2
(45) Date of Patent: Jul. 14, 2026

(54) COMPOUND AND ORGANIC LIGHT EMITTING DIODE COMPRISING SAME

(71) Applicant: LG CHEM, LTD., Seoul (KR)

(72) Inventors: Minjun Kim, Daejeon (KR); Min Woo Jung, Daejeon (KR); Dong Hoon Lee, Daejeon (KR); Sang Duk Suh, Daejeon (KR); Seoyeon Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 756 days.

(21) Appl. No.: 17/294,661

(22) PCT Filed: Mar. 13, 2020

(86) PCT No.: PCT/KR2020/003492

§ 371 (c)(1),
(2) Date: May 17, 2021

(87) PCT Pub. No.: WO2020/185026

PCT Pub. Date: Sep. 17, 2020

(65) Prior Publication Data

US 2022/0029110 A1 Jan. 27, 2022

(30) Foreign Application Priority Data

Mar. 14, 2019 (KR) ........................ 10-2019-0029228

(51) Int. Cl.
*H10K 85/60* (2023.01)
*C07D 405/14* (2006.01)
(Continued)

(52) U.S. Cl.
CPC ....... *H10K 85/6574* (2023.02); *C07D 405/14* (2013.01); *C07D 409/14* (2013.01);
(Continued)

(58) Field of Classification Search
CPC ............... H10K 85/342; H10K 85/615; H10K 85/633; H10K 85/636; H10K 85/654;
(Continued)

(56) References Cited

U.S. PATENT DOCUMENTS

2018/0287068 A1 10/2018 Ha et al.
2019/0047991 A1 2/2019 Jung et al.
(Continued)

FOREIGN PATENT DOCUMENTS

CN 107868067 A * 4/2018 ........... C07D 405/12
CN 108137527 6/2018
(Continued)

OTHER PUBLICATIONS

KR-20170101577-A machine translation (Year: 2017).*
Yang et al. J. Mater. Chem. , 2004, 14 , 947-950 (Year: 2004).*
CN-107868067-A machine translation (Year: 2018).*

*Primary Examiner* — Elizabeth M. Dahlburg
(74) *Attorney, Agent, or Firm* — Bryan Cave Leighton Paisner LLP

(57) ABSTRACT

A compound represented by Chemical Formula 1, and an organic light emitting device including the same, and the compound used as a material of an organic material layer of the organic light emitting device and providing enhanced efficiency, low driving voltage, and improved lifetime prop-
(Continued)

erties of the organic light emitting device.

[Chemical Formula 1]

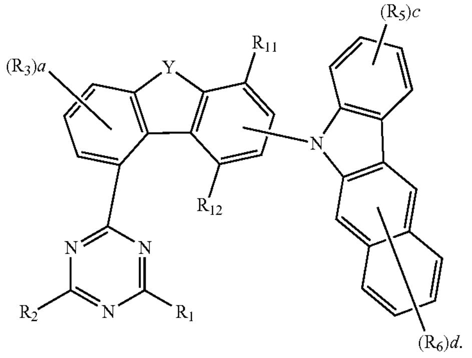

9 Claims, 1 Drawing Sheet

(51) Int. Cl.

| | |
|---|---|
| ***C07D 409/14*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |

(52) U.S. Cl.
CPC ............ *C09K 11/06* (2013.01); *H10K 85/615* (2023.02); *H10K 85/654* (2023.02); *H10K 85/6572* (2023.02); *H10K 85/6576* (2023.02); *C09K 2211/1018* (2013.01); *H10K 50/11* (2023.02); *H10K 2101/10* (2023.02); *H10K 2101/90* (2023.02)

(58) Field of Classification Search
CPC ........... H10K 85/6572; H10K 85/6574; H10K 85/6576; H10K 50/11; H10K 50/12; H10K 50/14; H10K 2101/10; H01L 51/0067; H01L 51/0072; H01L 51/0073; C09K 11/06
See application file for complete search history.

(56) References Cited

U.S. PATENT DOCUMENTS

| | | | | |
|---|---|---|---|---|
| 2019/0312215 | A1* | 10/2019 | Kang .................. | H10K 85/633 |
| 2020/0119285 | A1 | 4/2020 | No et al. | |
| 2020/0123133 | A1 | 4/2020 | No et al. | |

FOREIGN PATENT DOCUMENTS

| | | | |
|---|---|---|---|
| KR | 20160029721 | | 3/2016 |
| KR | 10-2016-0087331 | A | 7/2016 |
| KR | 10-2017-0101577 | A | 9/2017 |
| KR | 10-2018-0041607 | A | 4/2018 |
| KR | 10-2018-0045798 | A | 5/2018 |
| KR | 10-2018-0051355 | A | 5/2018 |
| KR | 10-2018-0061077 | A | 6/2018 |
| KR | 10-2018-0108426 | A | 10/2018 |
| KR | 10-2018-0108427 | A | 10/2018 |

* cited by examiner

【FIG. 1】
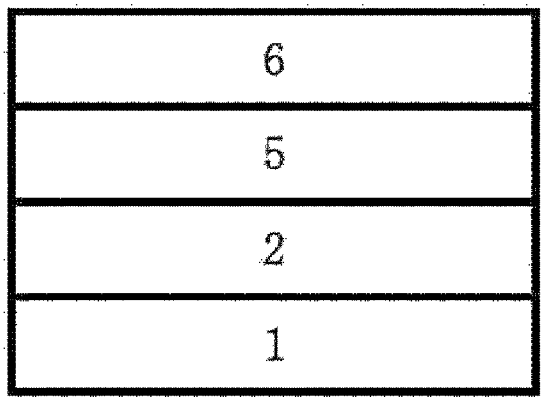
【FIG. 2】
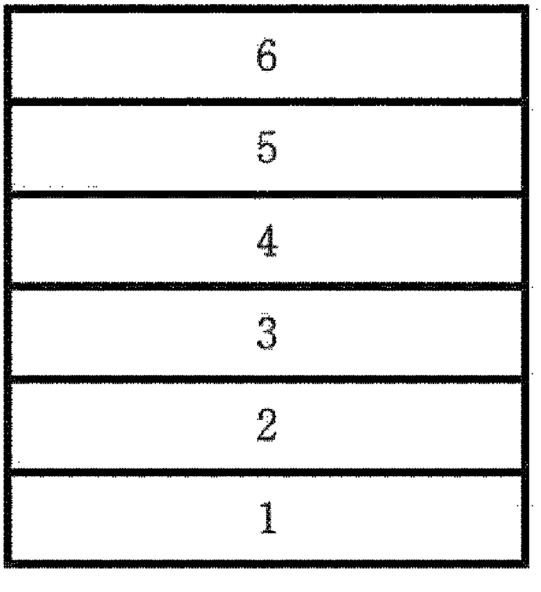

COMPOUND AND ORGANIC LIGHT EMITTING DIODE COMPRISING SAME

CROSS-REFERENCE TO RELATED APPLICATION(S)

This application is a National Stage Application of International Application No. PCT/KR2020/003492 filed on Mar. 13, 2020, which claims priority to Korean Patent Application No. 10-2019-0029228 filed on Mar. 14, 2019, the disclosures of which are incorporated herein by reference in their entireties.

FIELD OF DISCLOSURE

The present specification relates to a compound, and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state. Development of new materials for such an organic light emitting device has been continuously required.

SUMMARY

The present specification is directed to providing a compound, and an organic light emitting device including the same.

One embodiment of the present disclosure provides a compound represented by the following Chemical Formula 1.

[Chemical Formula 1]

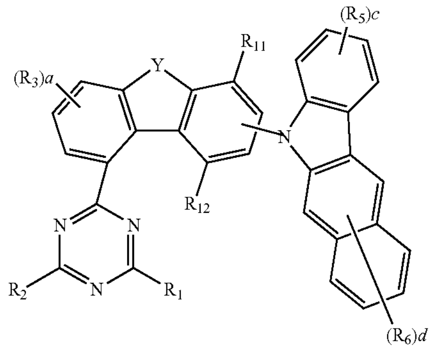

In Chemical Formula 1,

Y is O or S, $R_1$ and $R_2$ are the same as or different from each other, and each independently a substituted or unsubstituted aryl group; or a substituted or unsubstituted heteroaryl group, $R_3$, $R_5$ and $R_6$ are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, or adjacent groups bond to each other to form a ring, $R_{11}$ and $R_{12}$ are hydrogen, a is an integer of 1 to 3, c is an integer of 1 to 4, d is an integer of 1 to 6, and when a, c and d are each 2 or greater, substituents in the parentheses are the same as or different from each other.

Another embodiment of the present disclosure provides an organic light emitting device including a first electrode; a second electrode provided to face the first electrode; and one or more organic material layers provided between the first electrode and the second electrode, wherein one or more layers of the organic material layers include the compound represented by Chemical Formula 1.

ADVANTAGEOUS EFFECTS

A compound according to one embodiment of the present specification can be used as a material of an organic material layer of an organic light emitting device, and by using the same, enhancement in efficiency, low driving voltage, and/or enhancement in lifetime properties can be obtained.

DESCRIPTION OF DRAWINGS

FIG. 1 illustrates an organic light emitting device according to one embodiment of the present specification.

FIG. 2 illustrates an organic light emitting device according to one embodiment of the present specification.

DETAILED DESCRIPTION

Hereinafter, the present specification will be described in more detail.

One embodiment of the present specification provides a compound represented by Chemical Formula 1.

In the present specification, a description of a certain part "including" certain constituents means capable of further including other constituents, and does not exclude other constituents unless particularly stated on the contrary.

In the present specification, a description of a certain member being placed "on" another member includes not only a case of the one member in contact with the another member but a case of still another member being present between the two members.

Examples of substituents in the present specification are described below, however, the substituents are not limited thereto.

The term "substitution" means a hydrogen atom bonding to a carbon atom of a compound being changed to another substituent. The position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of deuterium; a halogen group; a cyano group; a substituted or unsubstituted alkyl group; a substituted or unsubstituted cycloalkyl group; a substituted or unsubstituted silyl group; a substituted or unsubstituted alkoxy group; a substituted or unsubstituted amine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include an aryl group substituted with an aryl group, an aryl group substituted with a heterocyclic group, a heterocyclic group substituted with an aryl group, an aryl group substituted with an alkyl group, and the like.

In the present specification, the alkyl group may be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof may include a methyl group; an ethyl group; a propyl group; an n-propyl group; an isopropyl group; a butyl group; an n-butyl group; an isobutyl group; a tert-butyl group; a sec-butyl group; a 1-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 4-methyl-2-pentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a 1,1-dimethylpropyl group; an isohexyl group; a 4-methylhexyl group; a 5-methylhexyl group and the like, but are not limited thereto.

In the present specification, the cycloalkyl group is not particularly limited, but preferably has 3 to 30 carbon atoms, and more preferably has 3 to 20 carbon atoms. Specific examples thereof may include a cyclopropyl group; a cyclobutyl group; a cyclopentyl group; a 3-methylcyclopentyl group; a 2,3-dimethylcyclopentyl group; a cyclohexyl group; a 3-methylcyclohexyl group; a 4-methylcyclohexyl group; a 2,3-dimethylcyclohexyl group; a 3,4,5-trimethylcyclohexyl group; a 4-tert-butylcyclohexyl group; a cycloheptyl group; a cyclooctyl group and the like, but are not limited thereto.

In the present specification, the alkoxy group may be linear, branched or cyclic. The number of carbon atoms of the alkoxy group is not particularly limited, but is preferably from 1 to 30. Specifically, the number of carbon atoms is preferably from 1 to 20. More specifically, the number of carbon atoms is preferably from 1 to 10. Specific examples thereof may include a methoxy group; an ethoxy group; an n-propoxy group; an isopropoxy group; an n-butoxy group; an isobutoxy group; a tert-butoxy group; a sec-butoxy group; an n-pentyloxy group; a neopentyloxy group; an isopentyloxy group; an n-hexyloxy group; a 3,3-dimethylbutyloxy group; a 2-ethylbutyloxy group; an n-octyloxy group; an n-nonyloxy group; an n-decyloxy group; a benzyloxy group; a p-methylbenzyloxy group and the like, but are not limited thereto.

In the present specification, the amine group may be selected from the group consisting of —$NH_2$; an alkylamine group; an N-alkylarylamine group; an arylamine group; an N-arylheteroarylamine group; an N-alkylheteroarylamine group and a heteroarylamine group, and although not particularly limited thereto, the number of carbon atoms is preferably from 1 to 30. Specific examples of the amine group may include a methylamine group; a dimethylamine group; an ethylamine group; a diethylamine group; a phenylamine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the silyl group may be represented by a chemical formula of —SiRaRbRc, and Ra, Rb and Rc are the same as or different from each other, and may be each independently hydrogen; a substituted or unsubstituted alkyl group; or a substituted or unsubstituted aryl group. Specific examples of the silyl group may include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the aryl group is not particularly limited, but may have 6 to 60 carbon atoms, preferably has 6 to 30 carbon atoms, and more preferably has 6 to 20 carbon atoms. The aryl group may be monocyclic or polycyclic. When the aryl group is a monocyclic aryl group, the number of carbon atoms is not particularly limited, but is preferably from 6 to 30. More specifically, the number of carbon atoms is preferably from 6 to 20. Specific examples of the monocyclic aryl group may include a phenyl group; a biphenyl group; a terphenyl group and the like, but are not limited thereto. When the aryl group is a polycyclic aryl group, the number of carbon atoms is not particularly limited, but is preferably from 10 to 30, and more specifically, the number of carbon atoms is preferably from 10 to 20. Specific examples of the polycyclic aryl group may include a naphthyl group; an anthracenyl group; a phenanthryl group; a triphenylene group; a pyrenyl group; a phenalenyl group; a perylenyl group; a chrysenyl group; a fluorenyl group and the like, but are not limited thereto.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but may be from 2 to 60, is preferably from 2 to 30 and is more preferably from 2 to 20, and the heteroaryl group may be monocyclic or polycyclic. Examples of the heteroaryl group may include a thiophene group; a furanyl group; a pyrrole group; an imidazolyl group; a triazolyl group; an oxazolyl group; an oxadiazolyl group; a pyridyl group; a bipyridyl group; a pyrimidyl group; a triazinyl group; a triazolyl group; an acridyl group; a pyridazinyl group; a pyrazinyl group; a quinolinyl group;

a quinazolinyl group; a quinoxalinyl group; a phthalazinyl group; a pyridopyrimidyl group; a pyridopyrazinyl group; a pyrazinopyrazinyl group; an isoquinolinyl group; an indolyl group; a carbazolyl group; a benzoxazolyl group; a benzimidazolyl group; a benzothiazolyl group; a benzocarbazolyl group; a benzothiophene group; a dibenzothiophene group; a benzofuranyl group; a phenanthrolinyl group; an isoxazolyl group; a thiadiazolyl group; a phenothiazinyl group; a dibenzofuranyl group and the like, but are not limited thereto.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the meaning of adjacent groups bonding to each other to form a ring means, as described above, adjacent groups bonding to each other to form a substituted or unsubstituted hydrocarbon ring or a substituted or unsubstituted heteroring. The ring may be monocyclic or polycyclic, may be aliphatic, aromatic or a fused form thereof, however, the ring is not limited thereto.

In the present specification, the meaning of adjacent groups bonding to each other to form a ring means bonding to adjacent groups to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a combined form thereof.

In the present specification, the aliphatic hydrocarbon ring means, as a ring that is not aromatic, a ring formed only with carbon and hydrogen atoms.

In the present specification, examples of the aromatic hydrocarbon ring may include benzene, naphthalene, anthracene and the like, but are not limited thereto.

In the present specification, the aliphatic heteroring means an aliphatic ring including one or more of heteroatoms.

In the present specification, the aromatic heteroring means an aromatic ring including one or more of heteroatoms.

In the present specification, the arylene group means the aryl group having two bonding sites.

In one embodiment of the present specification, Y is O or S.

In one embodiment of the present specification, Y is O.

In another embodiment, Y is S.

In one embodiment of the present specification, $R_1$ and $R_2$ are the same as or different from each other, and each independently a substituted or unsubstituted aryl group; or a substituted or unsubstituted heteroaryl group.

In one embodiment of the present specification, $R_1$ and $R_2$ are the same as or different from each other, and each independently a substituted or unsubstituted aryl group having 6 to 60 carbon atoms; or a substituted or unsubstituted heteroaryl group having 2 to 60 carbon atoms.

In one embodiment of the present specification, $R_1$ and $R_2$ are the same as or different from each other, and each independently a substituted or unsubstituted aryl group having 6 to 30 carbon atoms; or a substituted or unsubstituted heteroaryl group having 2 to 30 carbon atoms.

In one embodiment of the present specification, $R_1$ and $R_2$ are the same as or different from each other, and each independently a substituted or unsubstituted aryl group having to 15 carbon atoms; or a substituted or unsubstituted heteroaryl group having 2 to 20 carbon atoms.

In one embodiment of the present specification, $R_1$ and $R_2$ are the same as or different from each other, and each independently a substituted or unsubstituted aryl group having 6 to 15 carbon atoms.

In one embodiment of the present specification, $R_1$ and $R_2$ are the same as or different from each other, and each independently a substituted or unsubstituted phenyl group; or a substituted or unsubstituted naphthyl group.

In another embodiment, $R_1$ and $R_2$ are each independently a phenyl group; or a naphthyl group.

In one embodiment of the present specification, $R_3$, $R_5$ and $R_6$ are the same as or different from each other, and each independently hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, or adjacent groups may bond to each other to form a ring.

In one embodiment of the present specification, $R_3$, $R_5$ and $R_6$ are the same as or different from each other, and each independently hydrogen; deuterium; a halogen group; a cyano group; a substituted or unsubstituted alkyl group having 1 to carbon atoms; a substituted or unsubstituted cycloalkyl group having 3 to 30 carbon atoms; a substituted or unsubstituted aryl group having 6 to 30 carbon atoms; or a substituted or unsubstituted heteroaryl group having 2 to 30 carbon atoms, or adjacent groups may bond to each other to form a ring.

In one embodiment of the present specification, $R_3$, $R_5$ and $R_6$ are the same as or different from each other, and each independently hydrogen; deuterium; a substituted or unsubstituted aryl group having 6 to 30 carbon atoms; or a substituted or unsubstituted heteroaryl group having 2 to 30 carbon atoms, or adjacent groups may bond to each other to form a ring.

In one embodiment of the present specification, $R_3$, $R_5$ and $R_6$ are each independently hydrogen; deuterium; a substituted or unsubstituted aryl group having 6 to 30 carbon atoms; or a substituted or unsubstituted heteroaryl group having 2 to 30 carbon atoms, or adjacent groups may bond to each other to form a ring.

In one embodiment of the present specification, $R_3$, $R_5$ and $R_6$ are each independently hydrogen; deuterium; a substituted or unsubstituted aryl group having 6 to 30 carbon atoms; or a substituted or unsubstituted heteroaryl group having 2 to 30 carbon atoms, or adjacent groups may bond to each other to form a benzene ring.

In one embodiment of the present specification, $R_3$ is hydrogen; or adjacent Ras bond to each other to form a substituted or unsubstituted benzene ring.

In one embodiment of the present specification, $R_3$ is hydrogen; or adjacent Ras bond to each other to form a benzene ring.

In one embodiment of the present specification, $R_3$ is hydrogen.

In one embodiment of the present specification, adjacent Ras bond to each other to form a benzene ring.

In one embodiment of the present specification, $R_5$ and $R_6$ are the same as or different from each other, and each independently hydrogen; or adjacent groups bond to each other to form a benzene ring.

In one embodiment of the present specification, $R_6$ is hydrogen; or adjacent $R_5$s bond to each other to form a benzene ring.

In one embodiment of the present specification, $R_6$ is hydrogen.

In one embodiment of the present specification, $R_{11}$ and $R_{12}$ are hydrogen.

In one embodiment of the present specification, the compound of Chemical Formula 1 is represented by the following Chemical Formula 1-1 or 1-2.

[Chemical Formula 1-1]

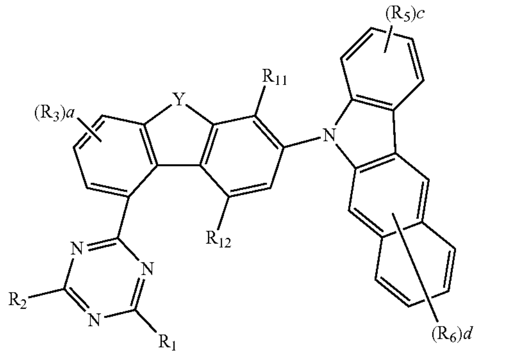

[Chemical Formula 1-2]

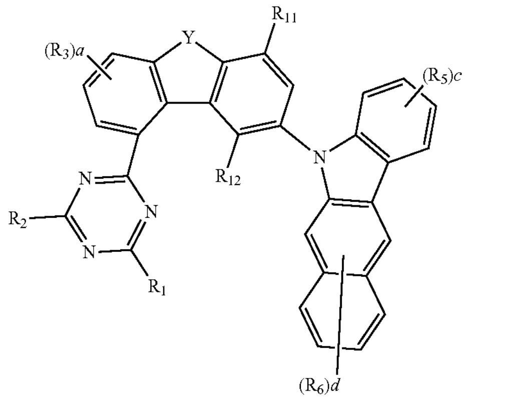

In Chemical Formulae 1-1 and 1-2,

Y, $R_1$, $R_2$, $R_3$, $R_5$, $R_6$, $R_{11}$, $R_{12}$, a, c and d are the same as defined in Chemical Formula 1.

In one embodiment of the present specification, the compound of Chemical Formula 1 is represented by any one of the following Chemical Formulae 1-1-1 to 1-1-3.

[Chemical Formula 1-1-1]

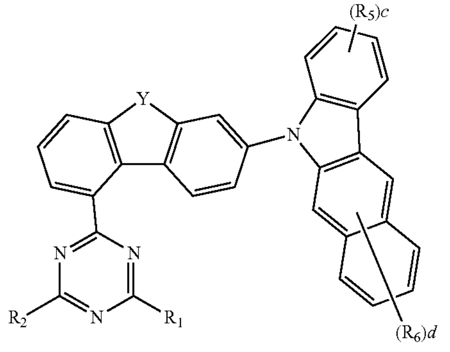

-continued

[Chemical Formula 1-1-2]

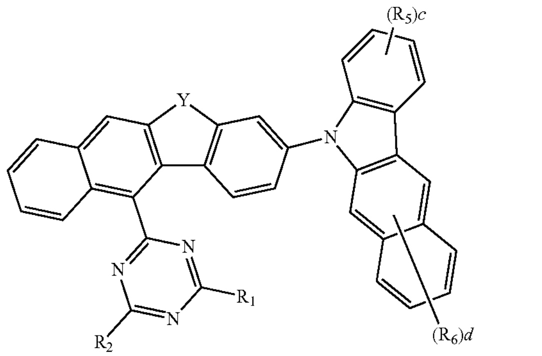

[Chemical Formula 1-1-3]

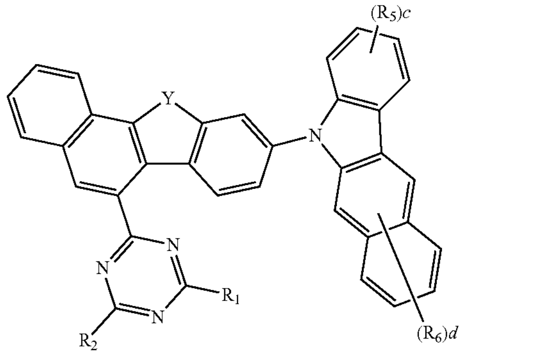

In Chemical Formulae 1-1-1 to 1-1-3,

Y, $R_1$, $R_2$, $R_5$, $R_6$, c and d are the same as defined in Chemical Formula 1.

In one embodiment of the present specification, the compound of Chemical Formula 1 is represented by any one of the following Chemical Formulae 1-2-1 to 1-2-3.

[Chemical Formula 1-2-1]

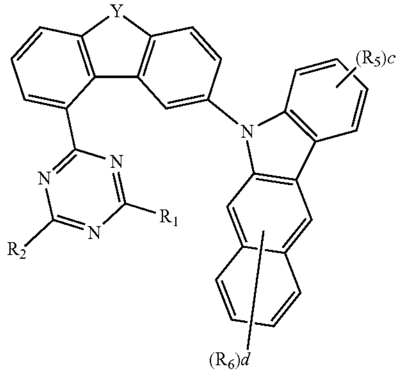

-continued

[Chemical Formula 1-2-2]

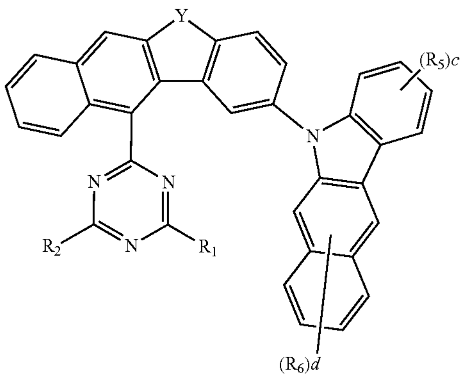

[Chemical Formula 1-2-3]

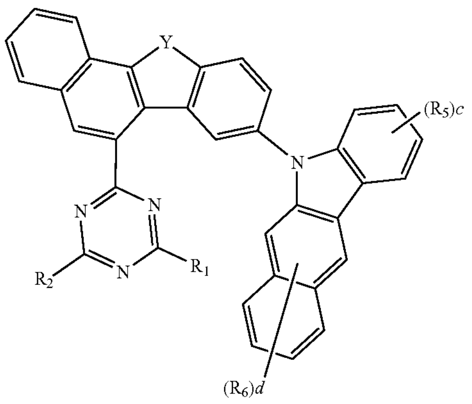

In Chemical Formulae 1-2-1 to 1-2-3,

Y, $R_1$, $R_2$, $R_5$, $R_6$, c and d are the same as defined in Chemical Formula 1.

In one embodiment of the present specification, the compound of Chemical Formula 1 is represented by any one of the following Chemical Formulae 2 to 4.

[Chemical Formula 2]

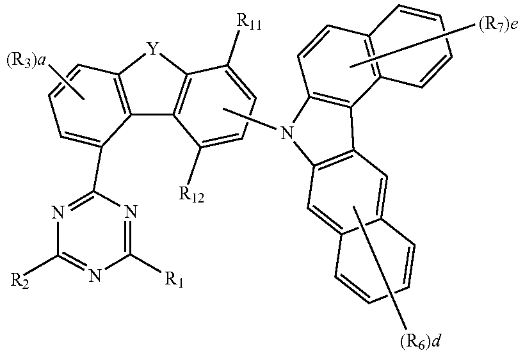

-continued

[Chemical Formula 3]

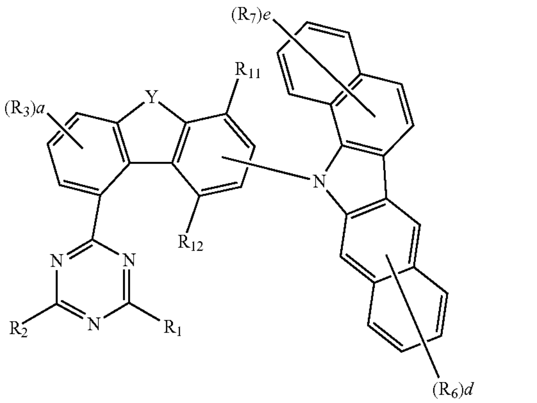

[Chemical Formula 4]

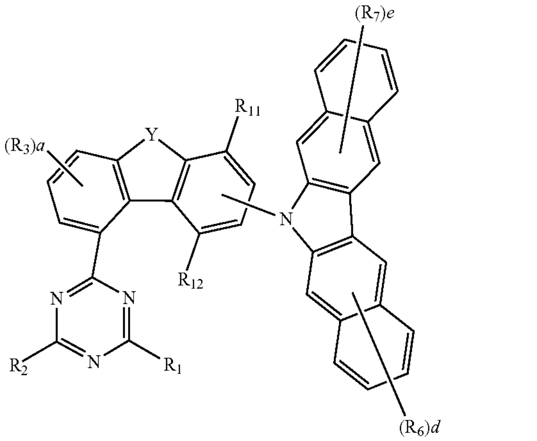

In Chemical Formulae 2 to 4,

Y, $R_1$ to $R_3$, $R_6$, $R_{11}$, $R_{12}$, a and d are the same as defined in Chemical Formula 1, $R_7$ is hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, and e is an integer of 1 to 6, and when e is 2 or greater, each $R_7$ is the same as or different from each other.

In one embodiment of the present specification, the compound represented by Chemical Formula 1 is any one selected from the following compounds.

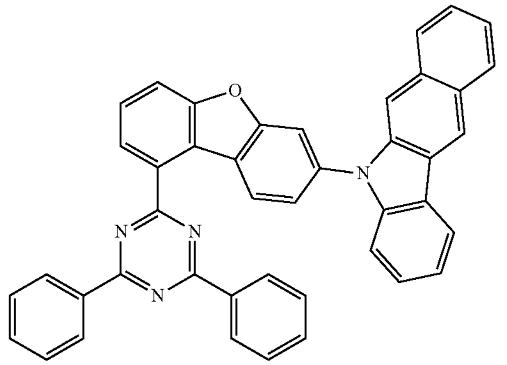

-continued
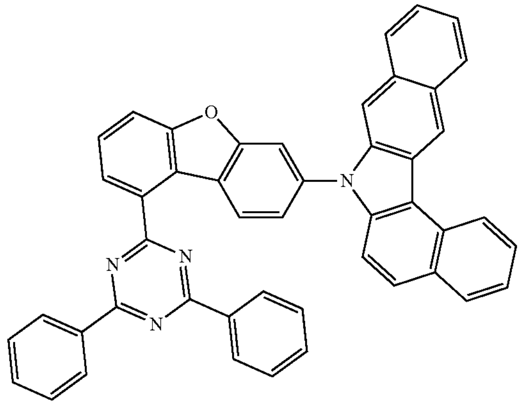
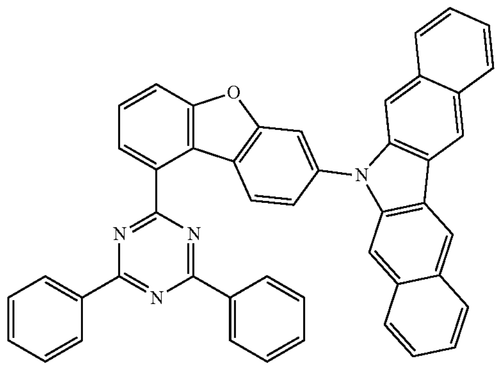
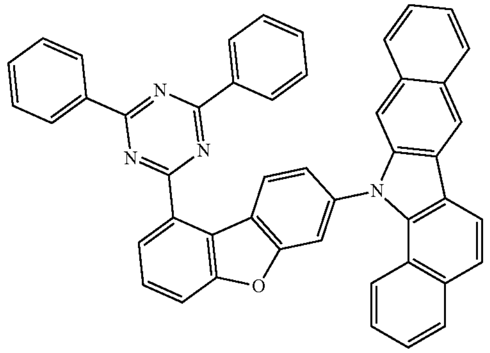
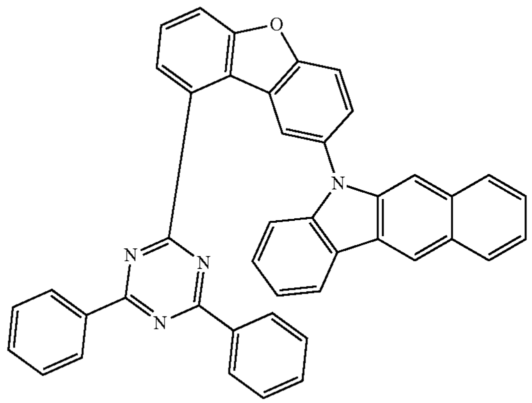
-continued
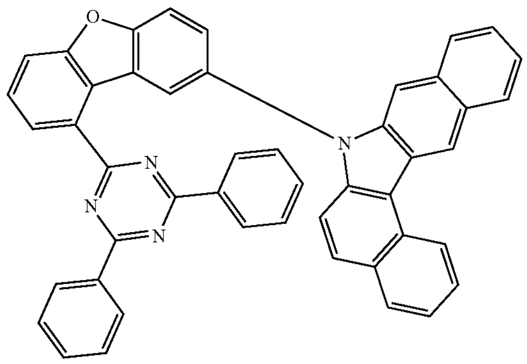
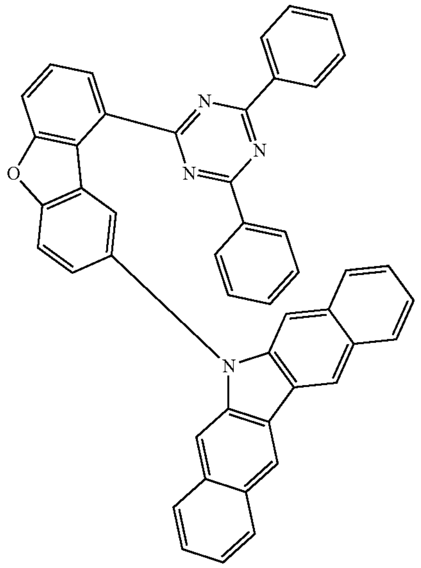
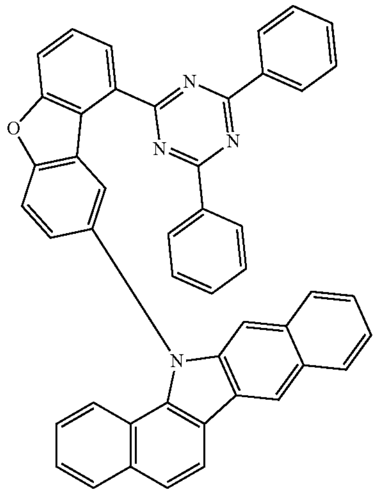

-continued
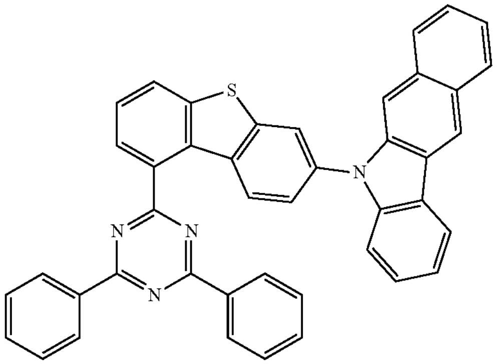
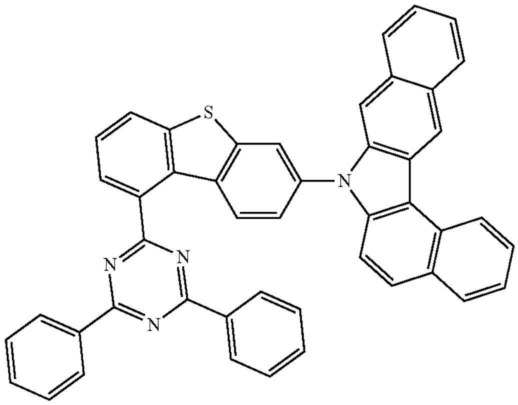
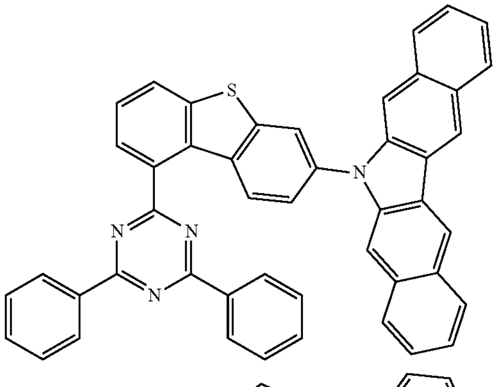
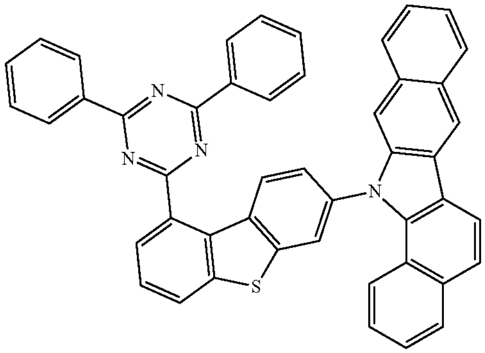
-continued
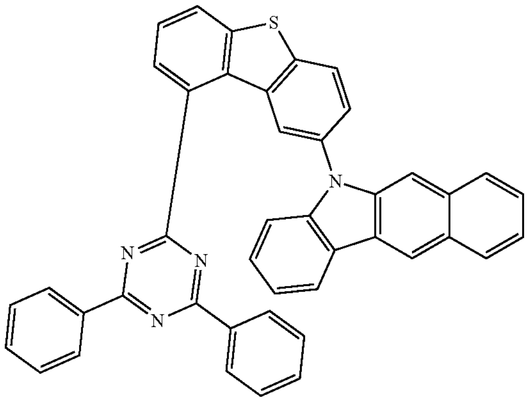
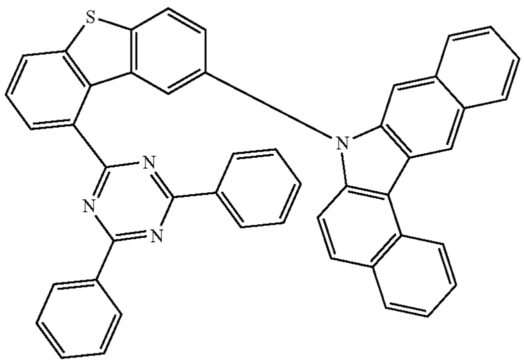
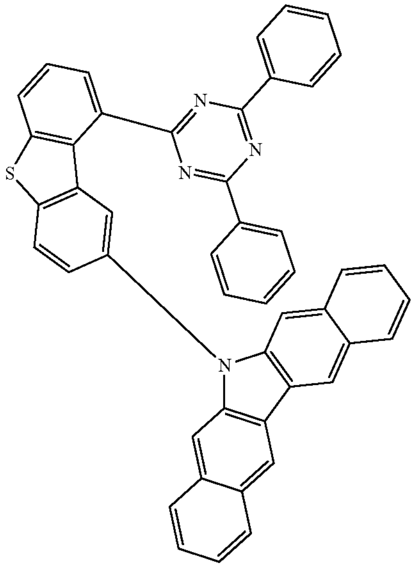

-continued
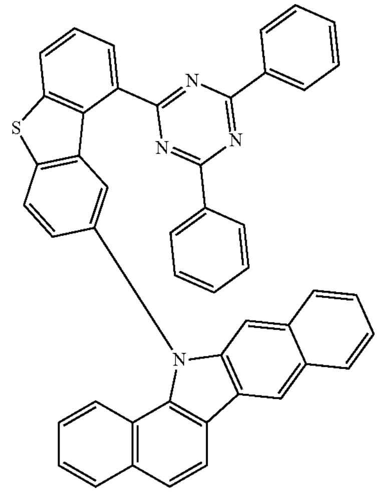
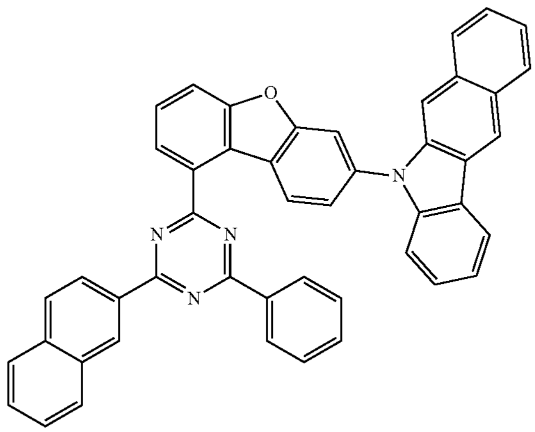
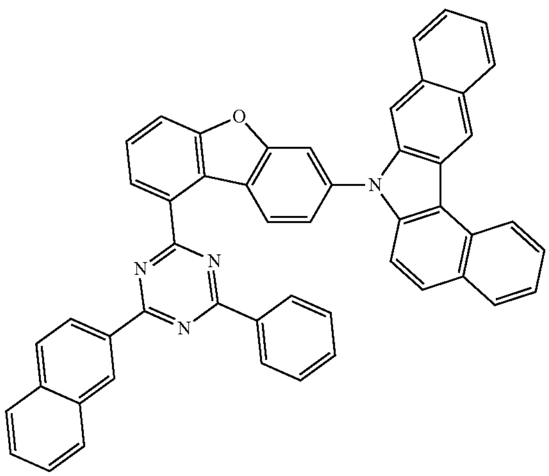
-continued
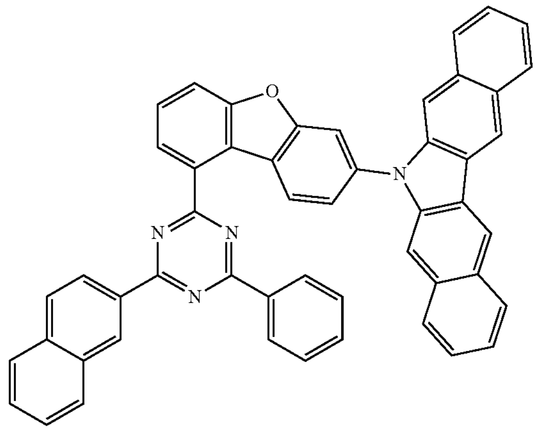
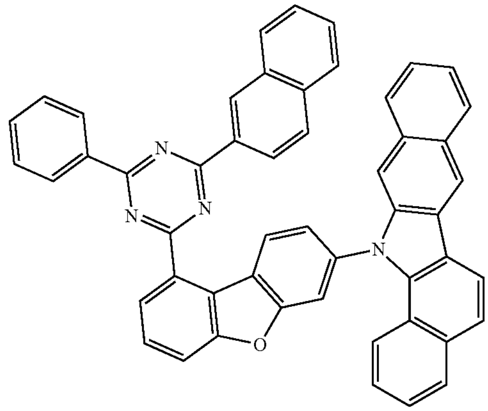
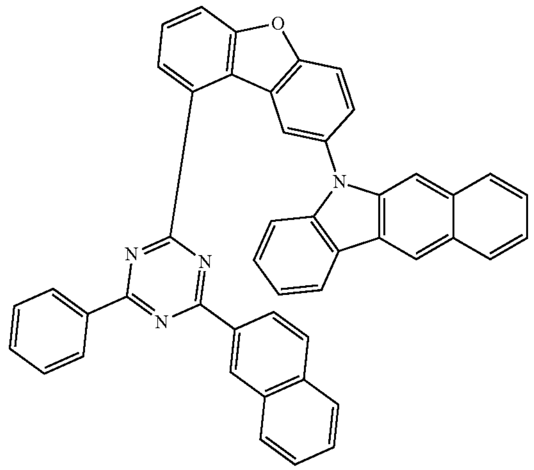
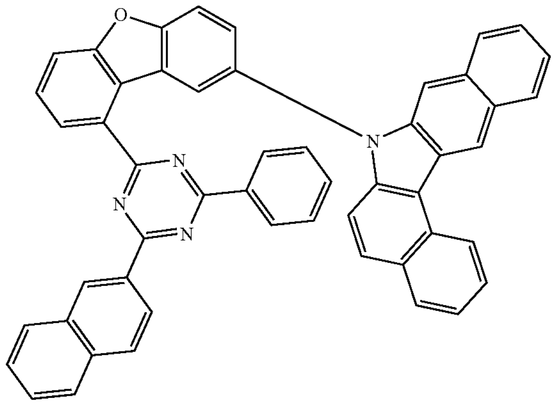

-continued
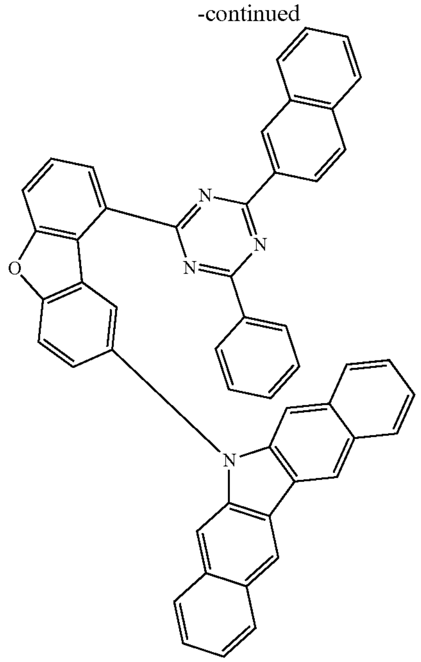
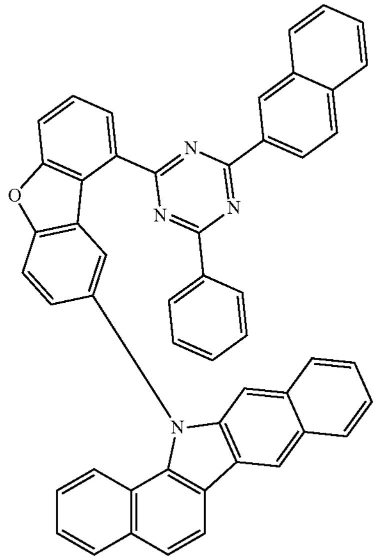
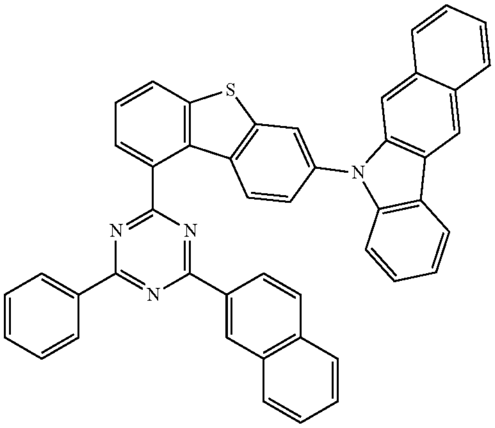
-continued
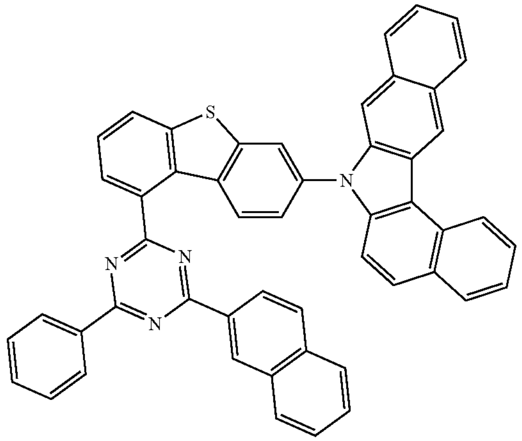
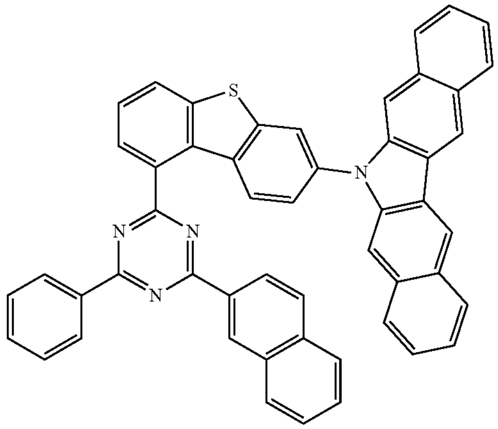
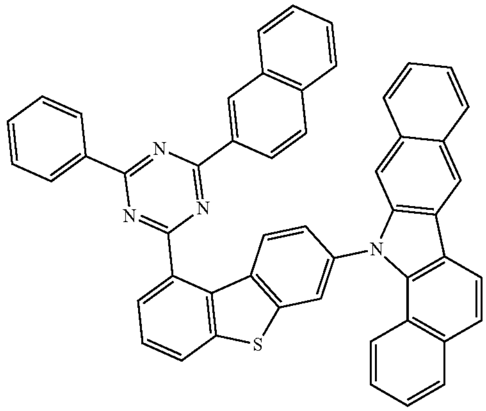

-continued
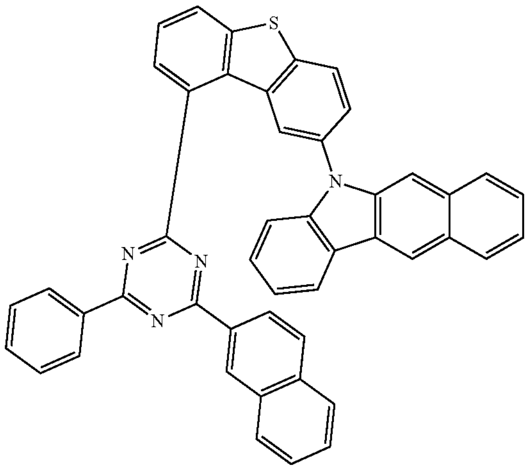
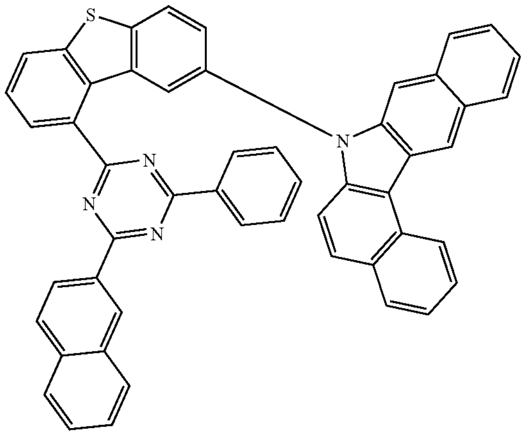
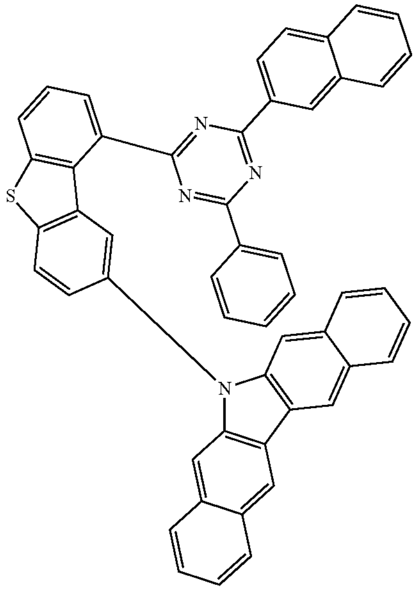
-continued
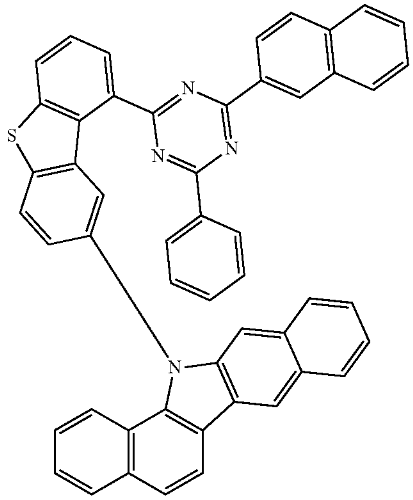
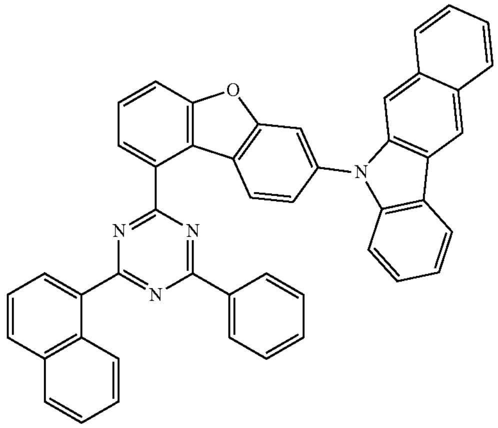
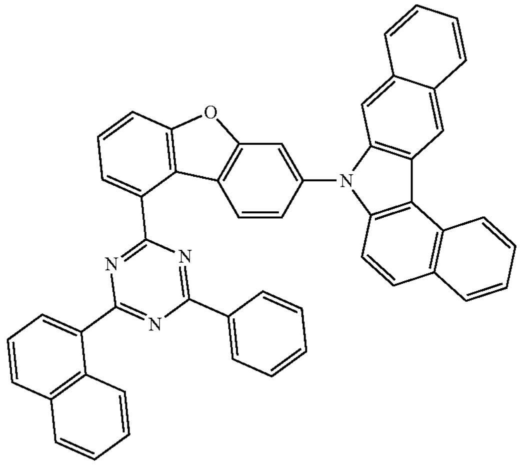

-continued
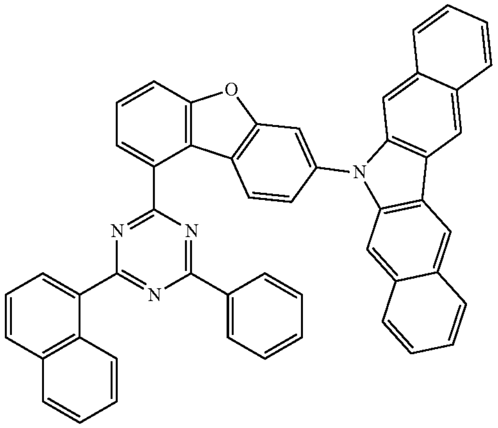
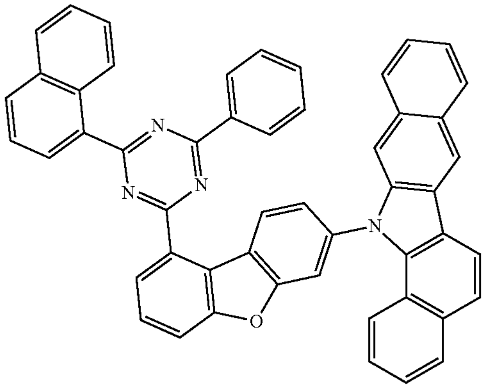
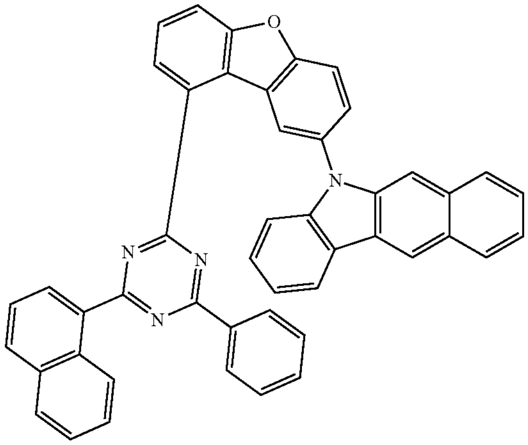
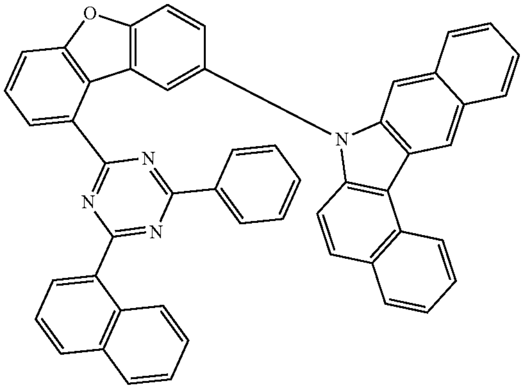
-continued
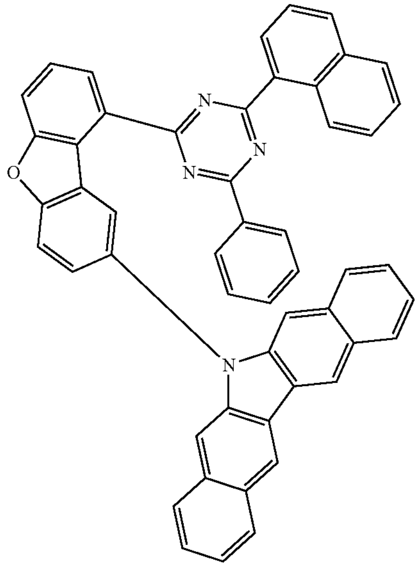
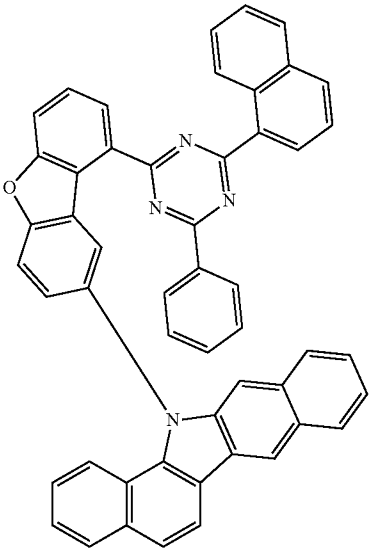
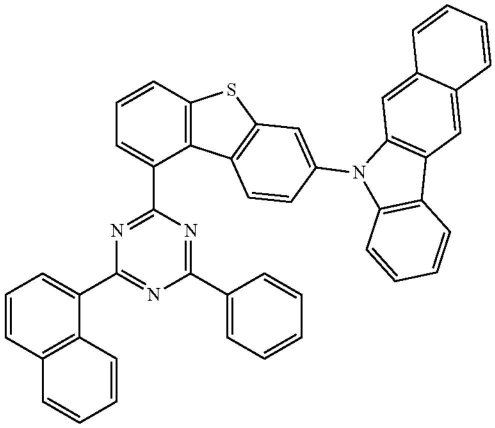

-continued
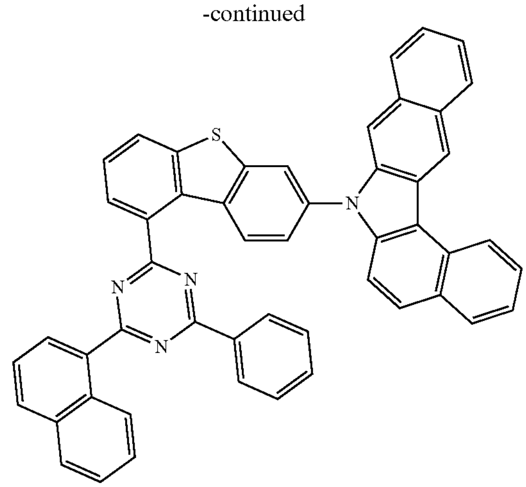
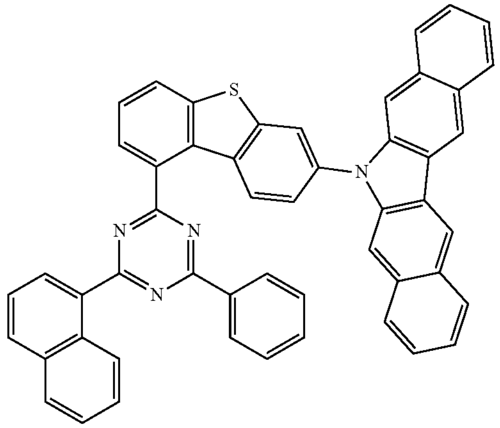
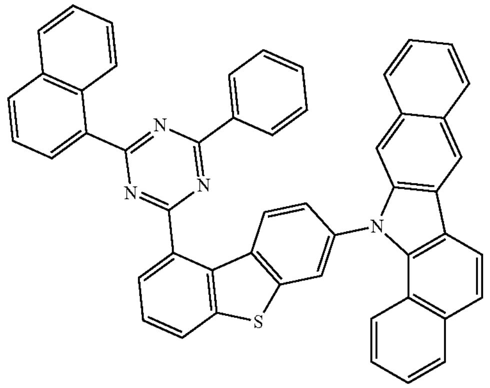
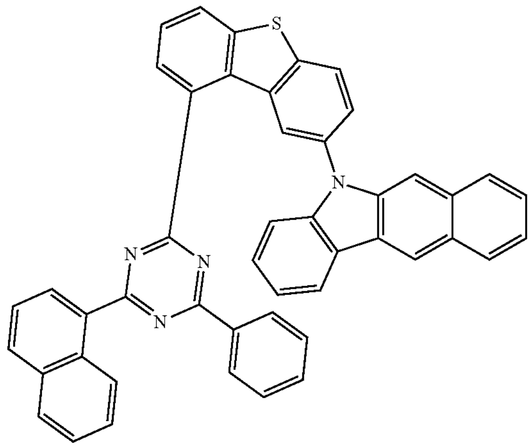
-continued
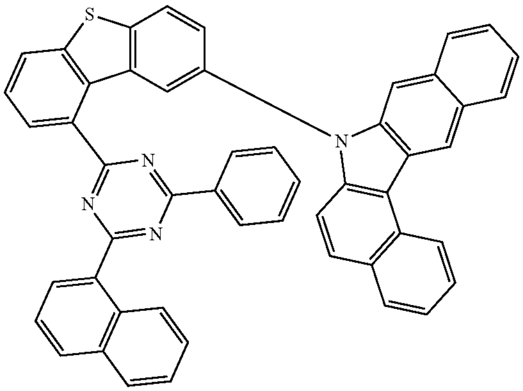
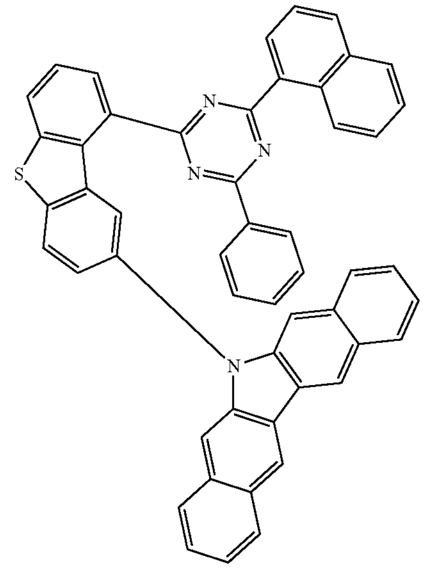
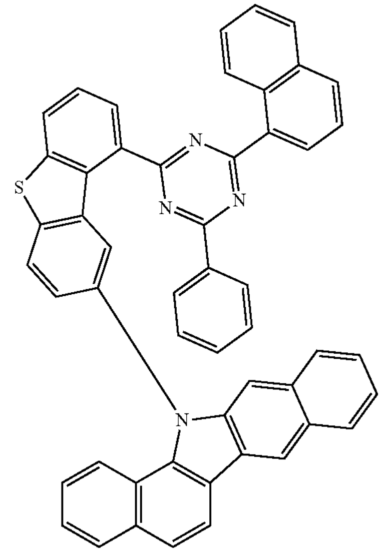

-continued
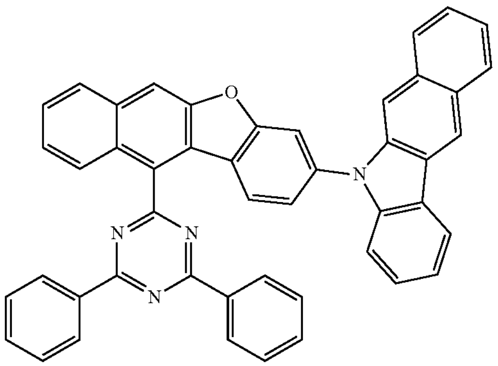
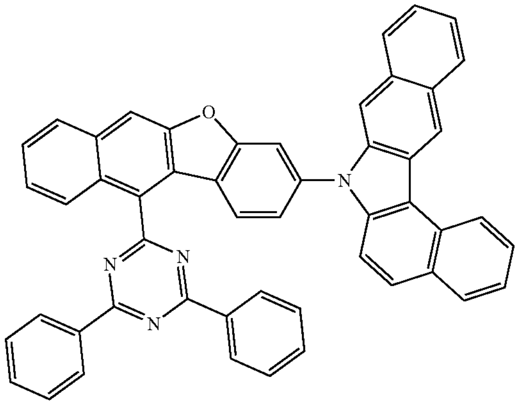
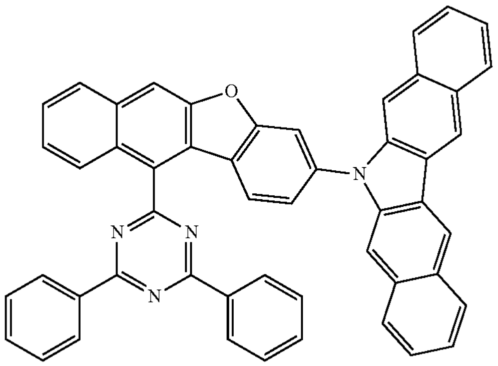
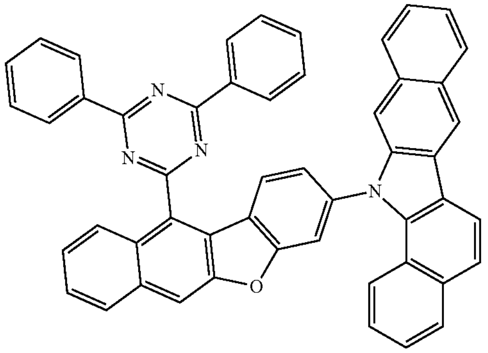
-continued
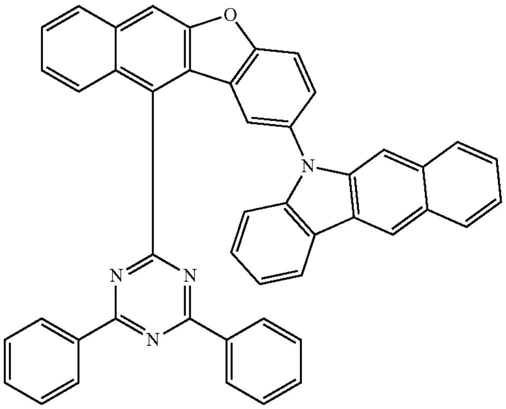
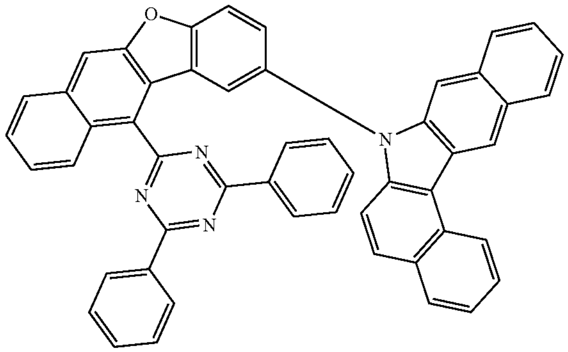
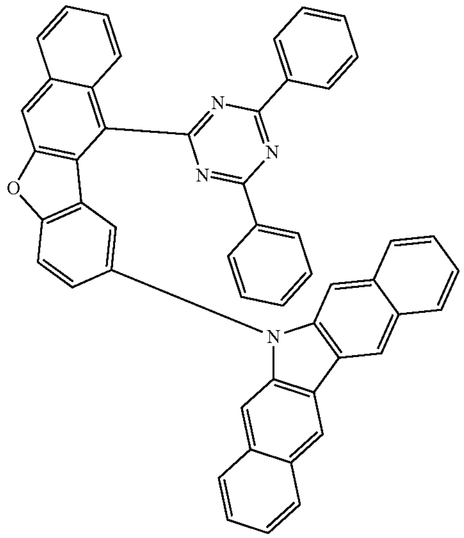

-continued
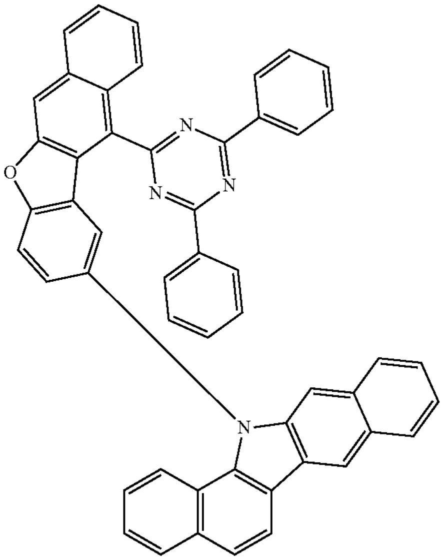
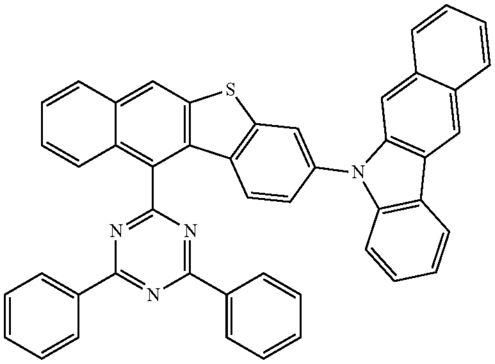
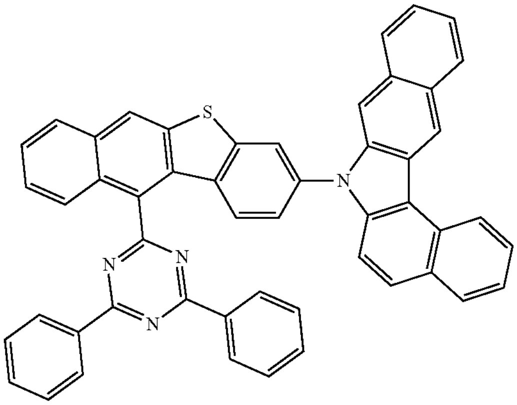
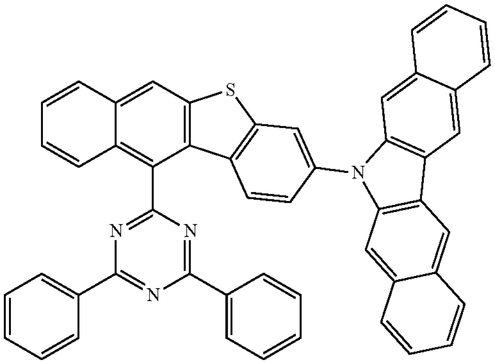
-continued
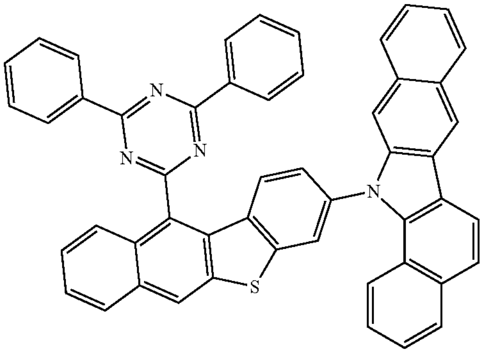
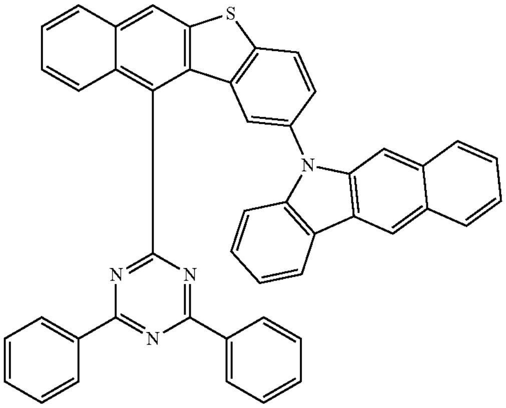
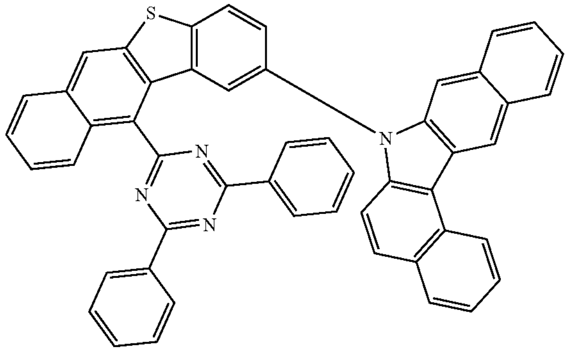
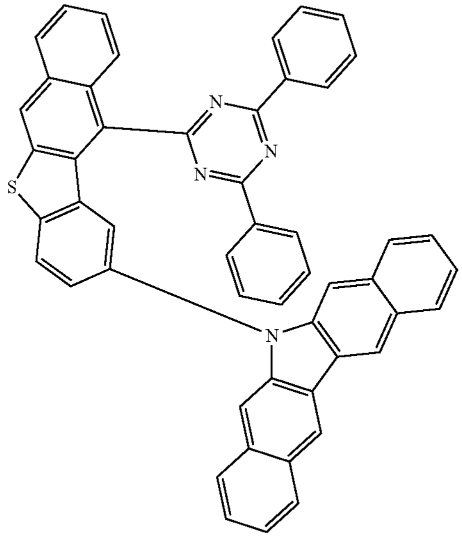

-continued
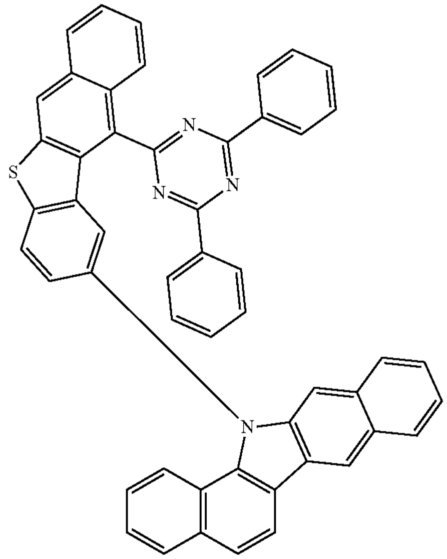
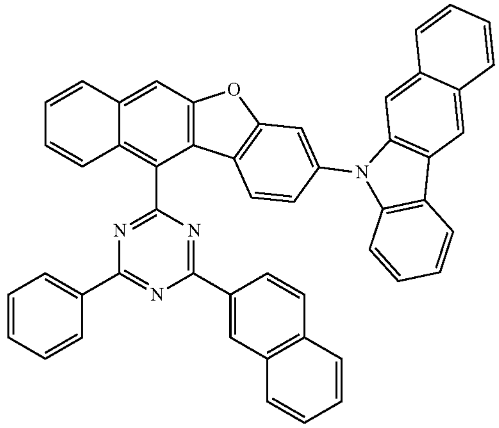
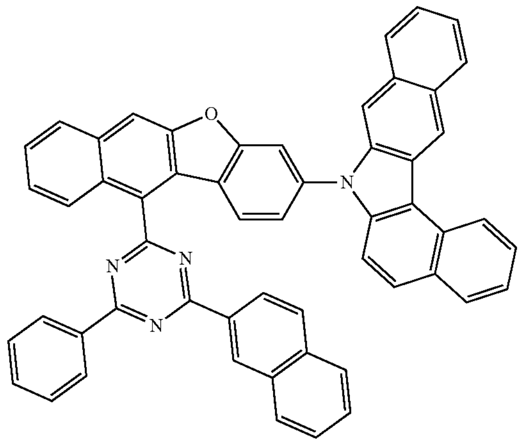
-continued
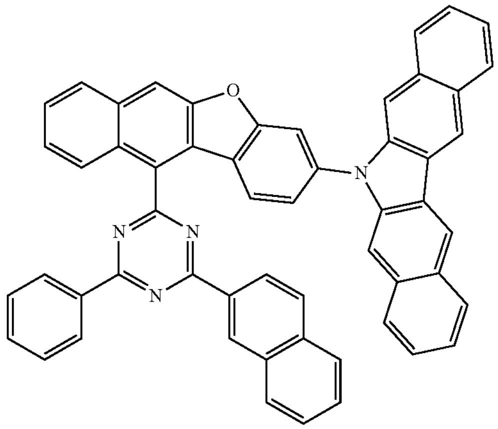
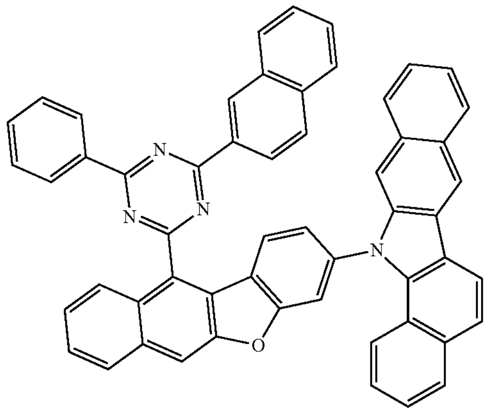
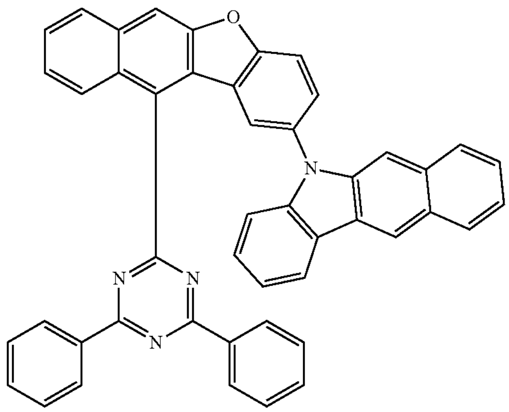
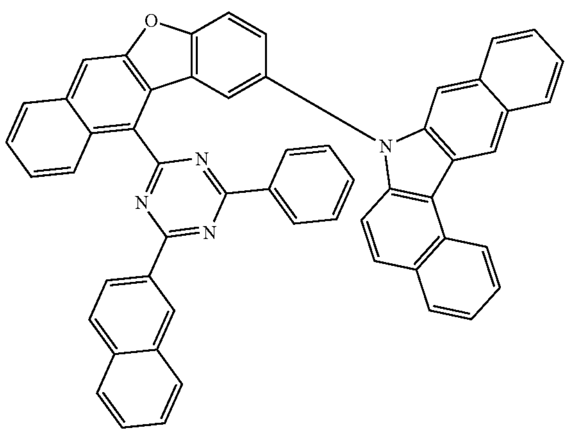

-continued
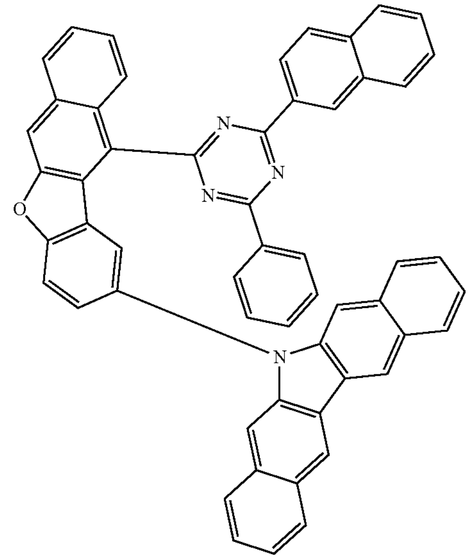
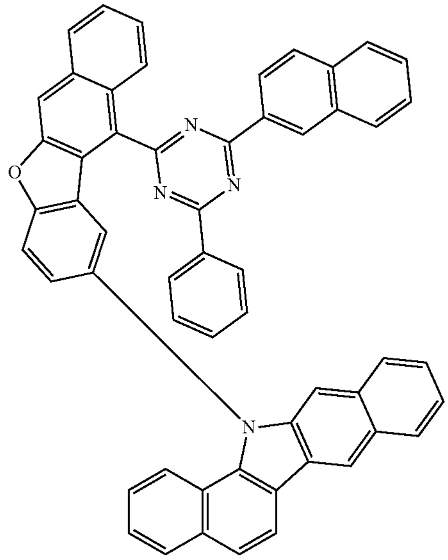
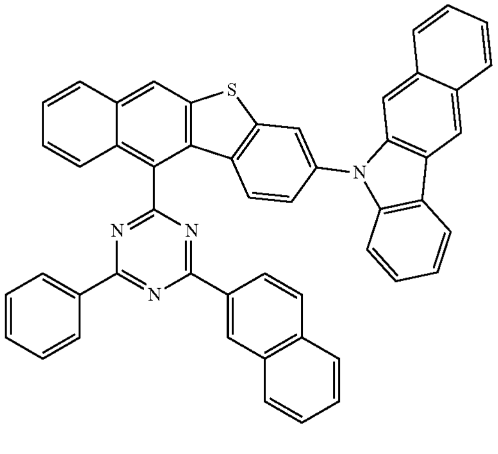
-continued
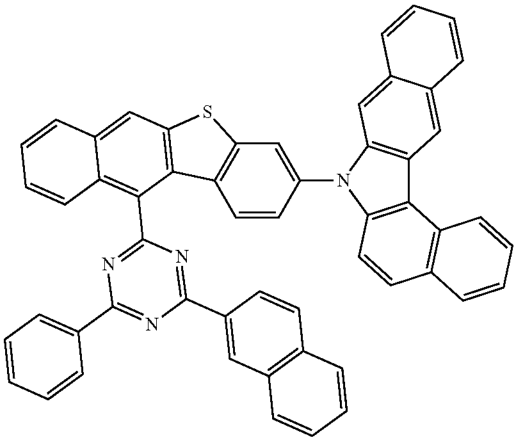
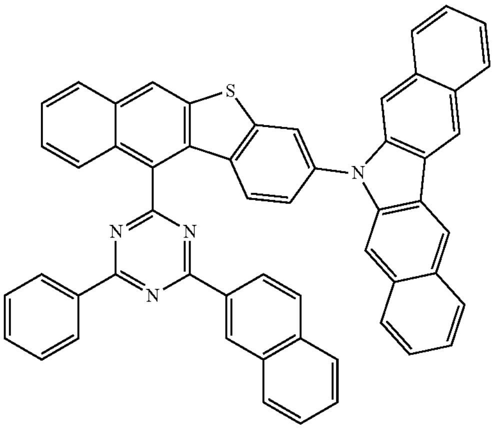
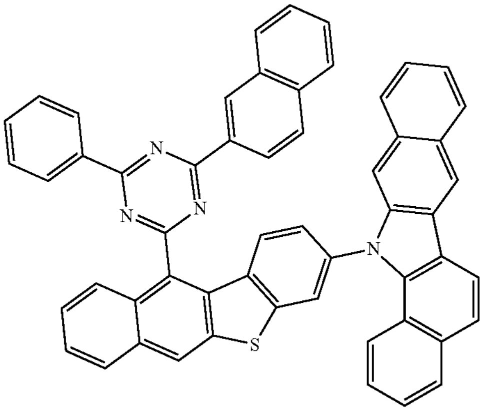

-continued
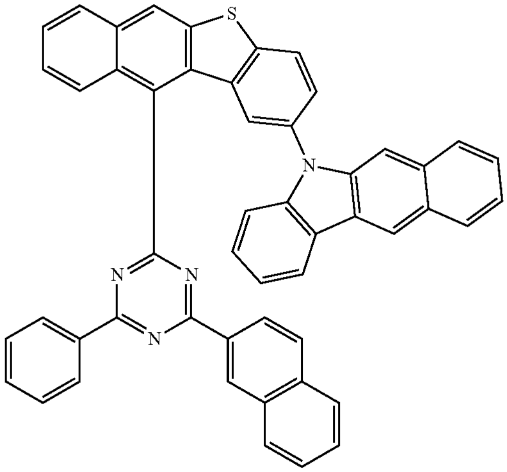
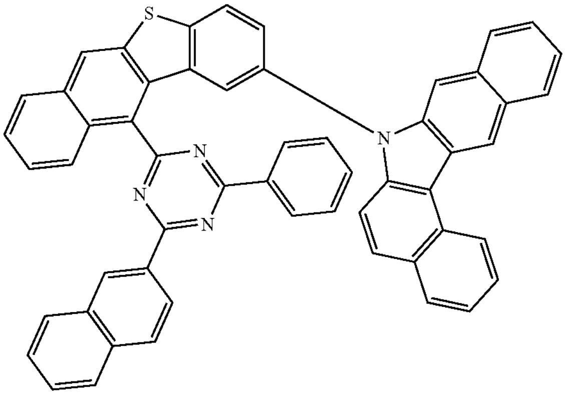
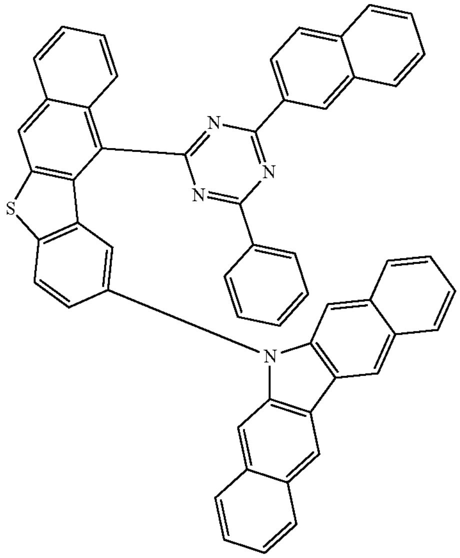
-continued
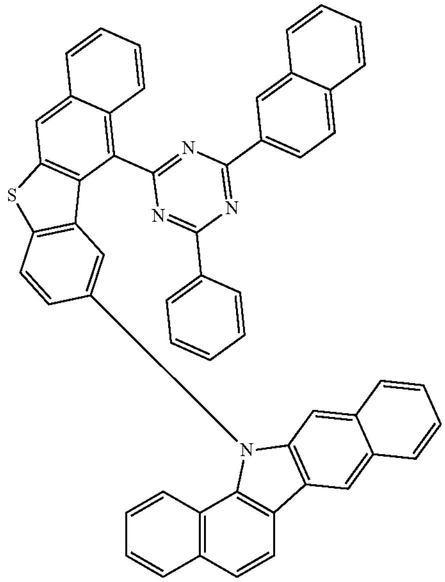
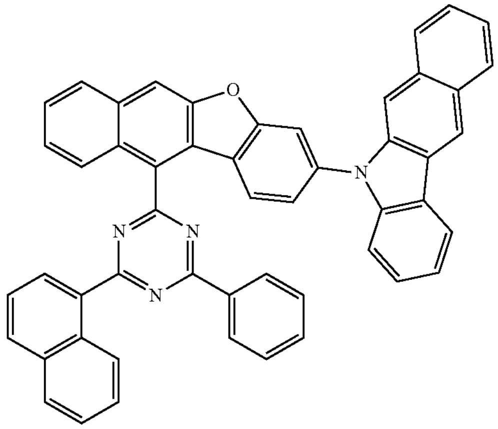
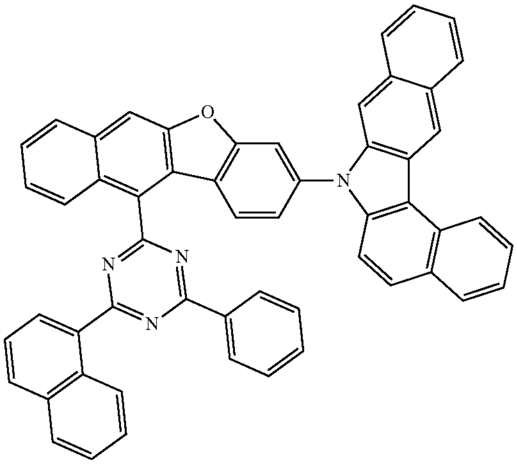

-continued
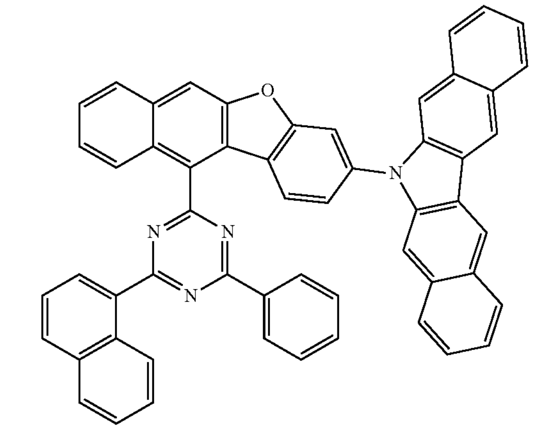
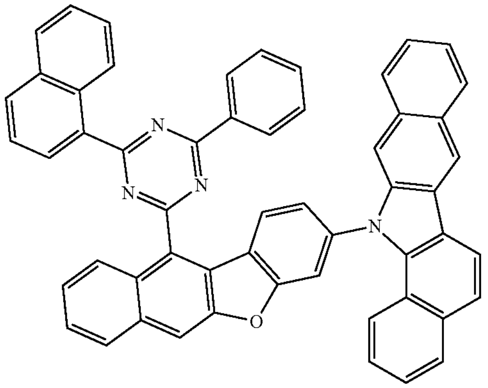
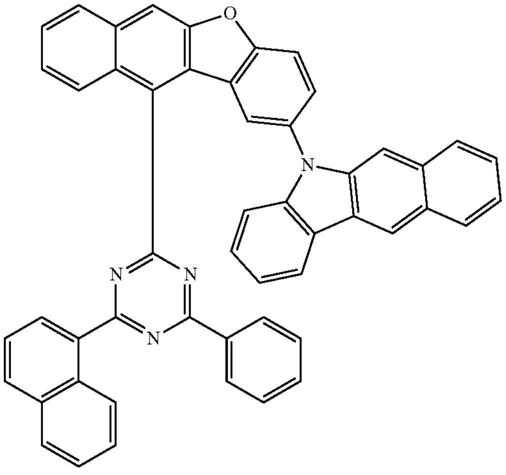
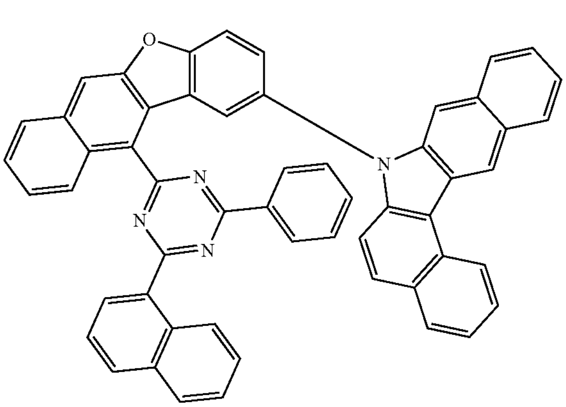
-continued
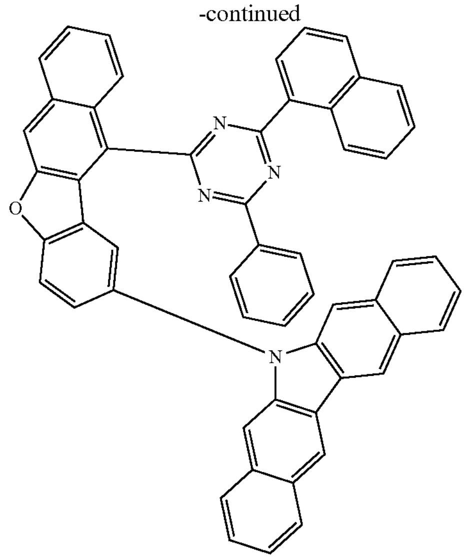
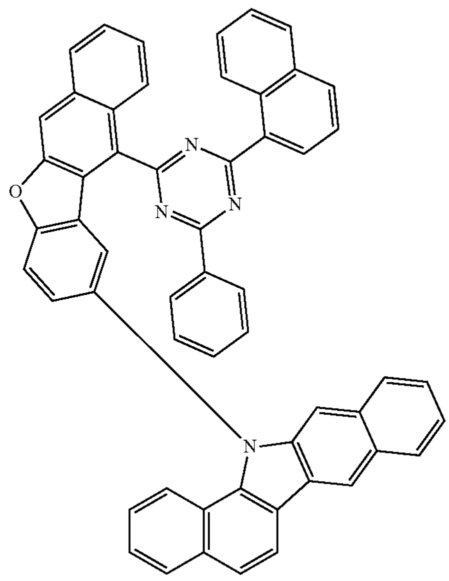
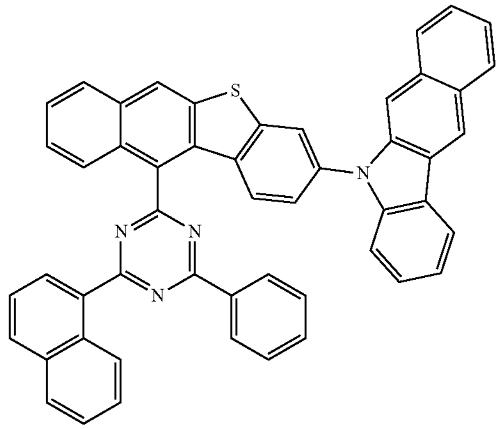

-continued
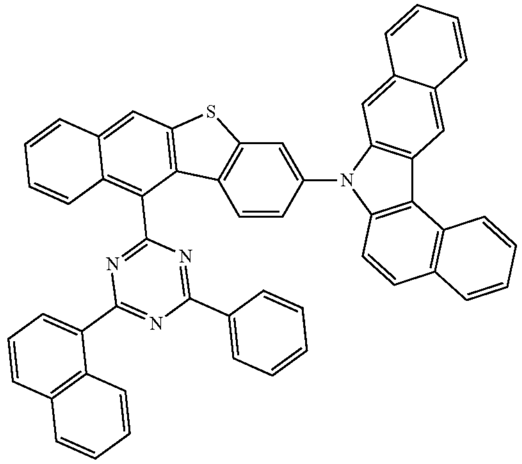
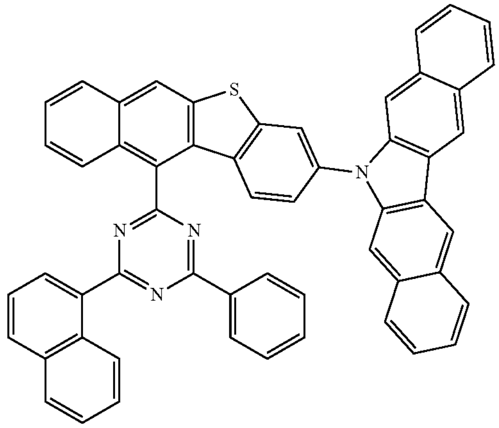
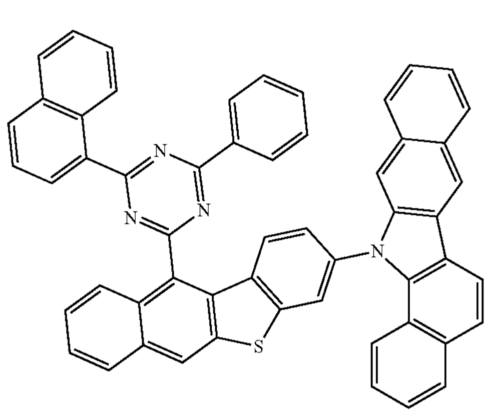
-continued
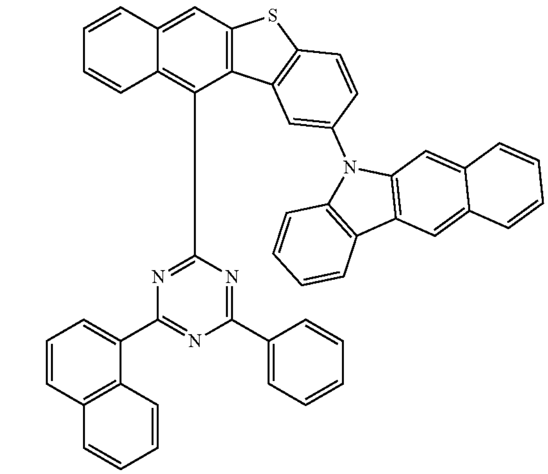
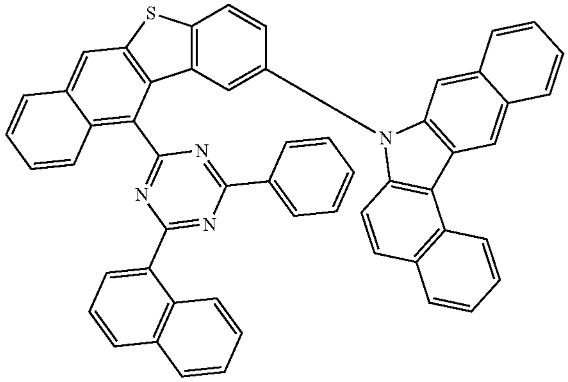
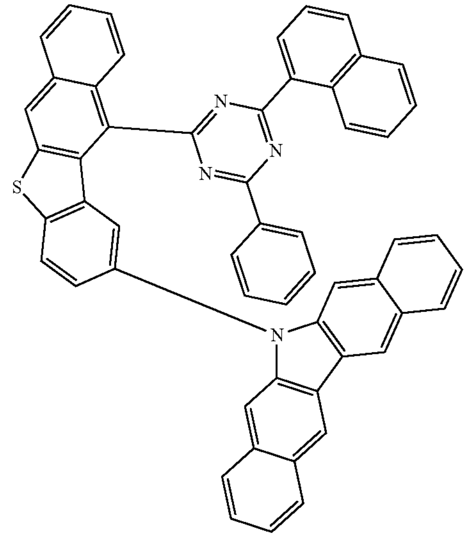

-continued
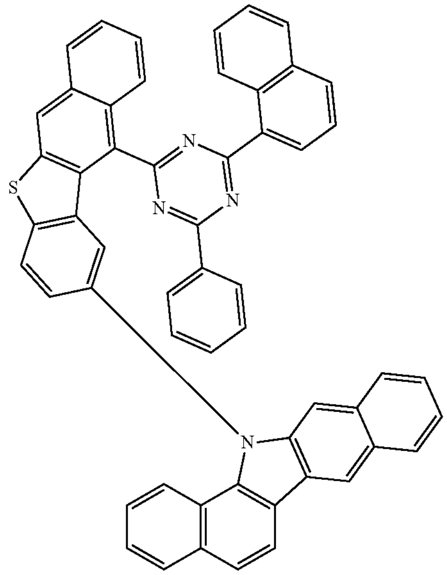
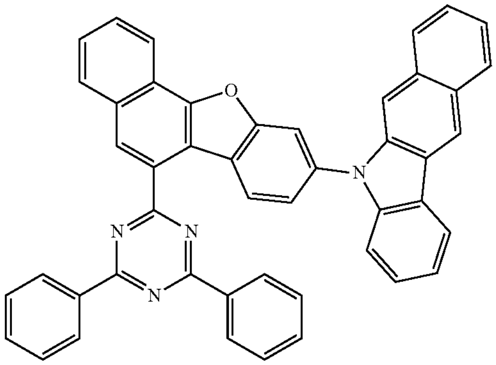
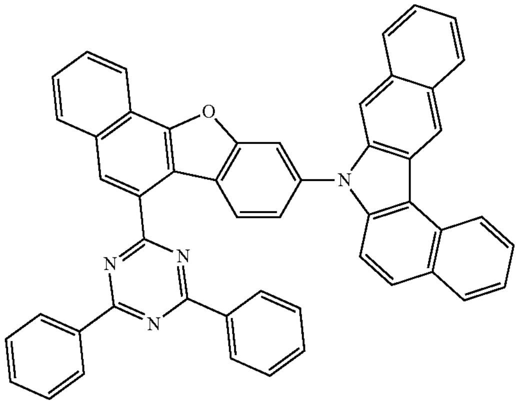
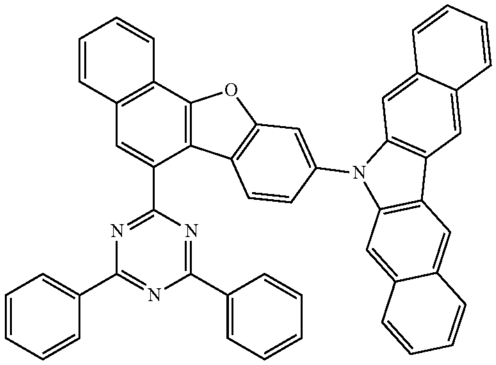
-continued
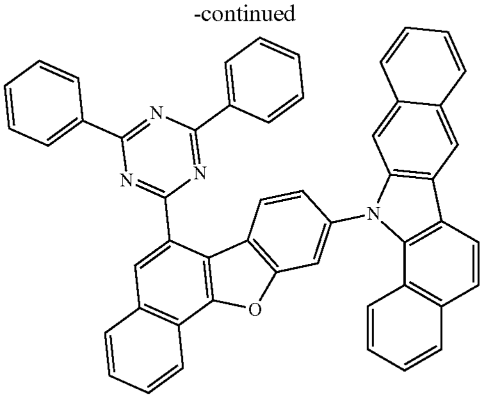
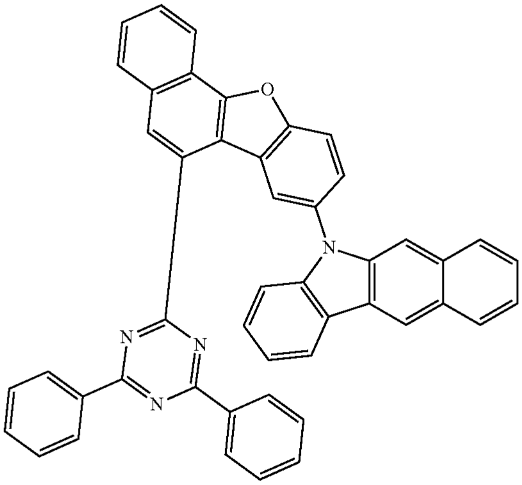
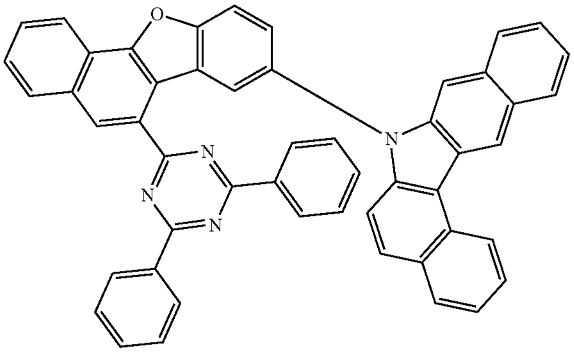

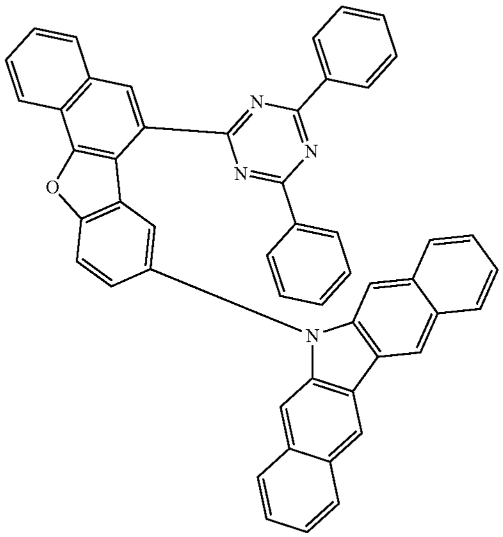
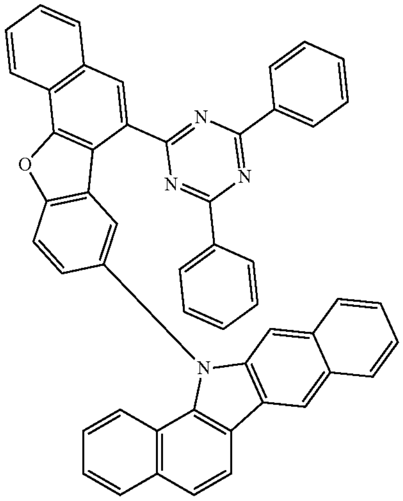
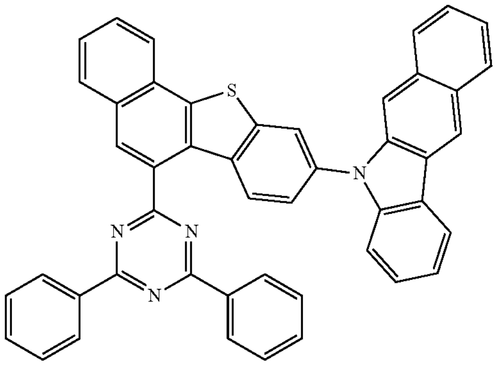
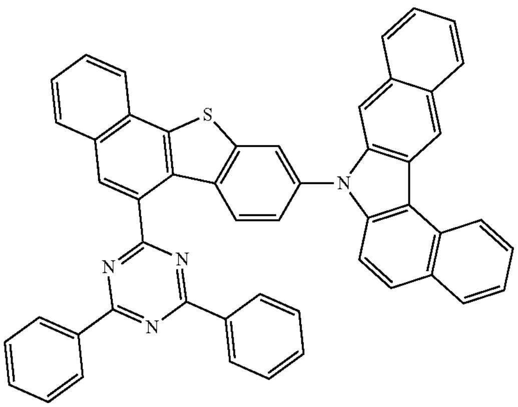
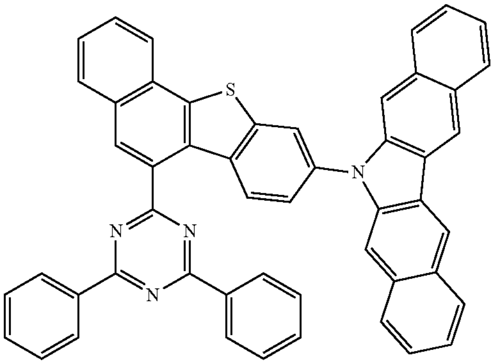
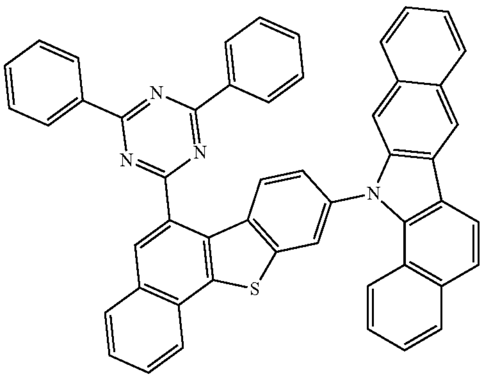
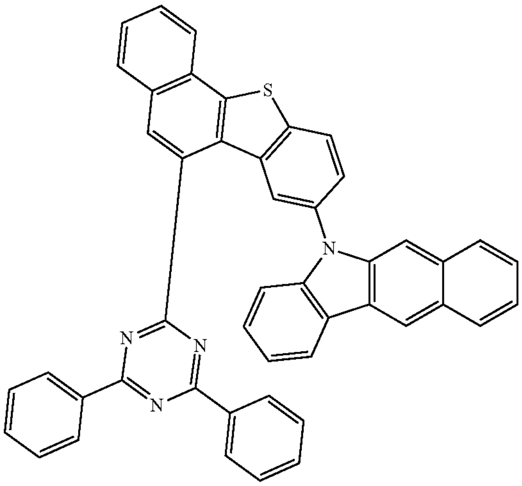

-continued
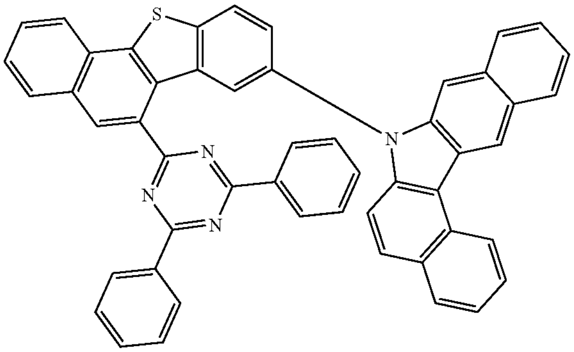
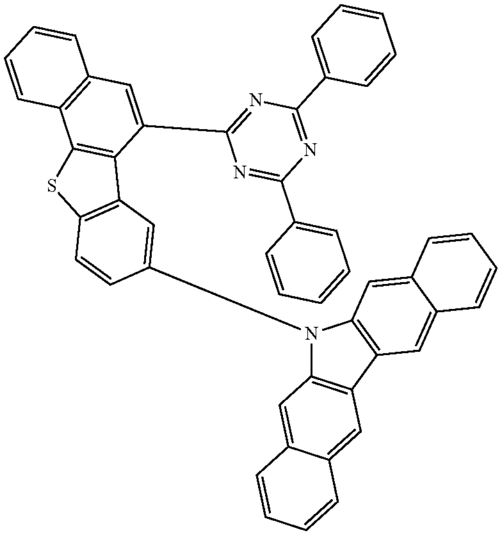
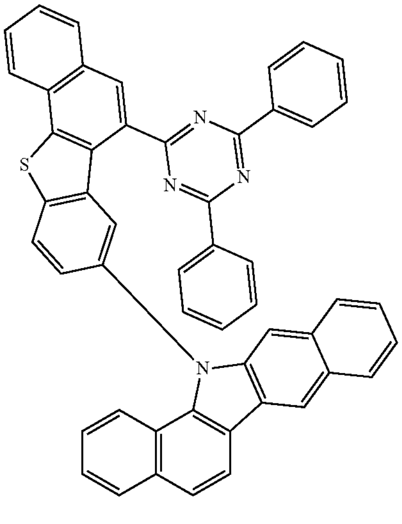
-continued
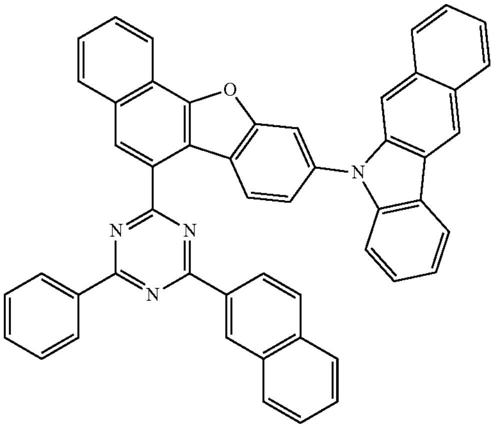
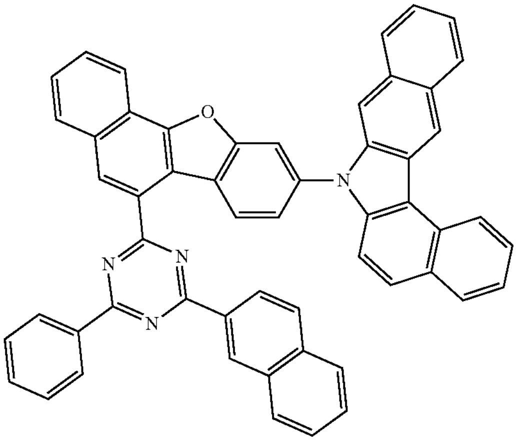
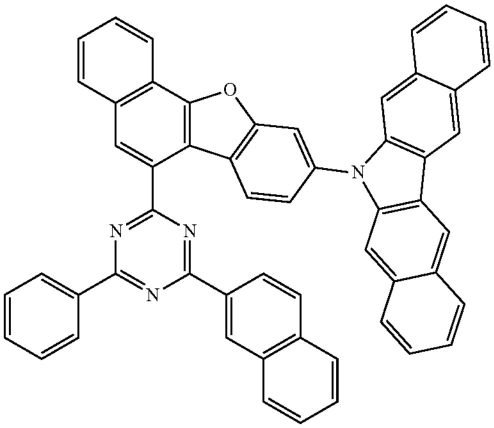
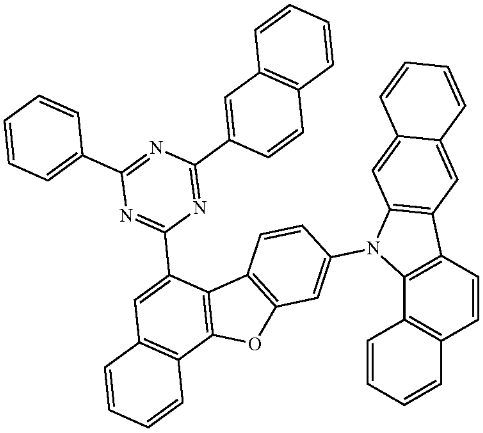

-continued
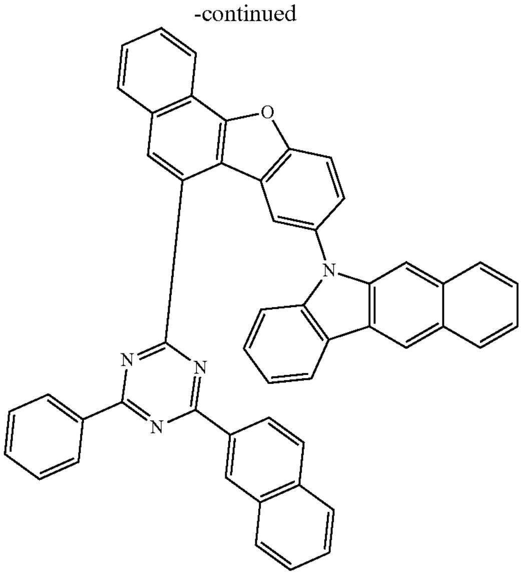
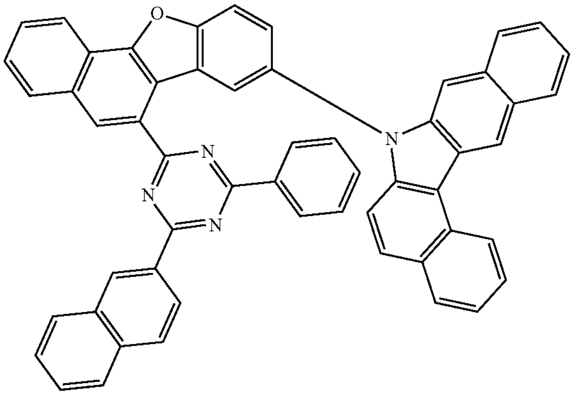
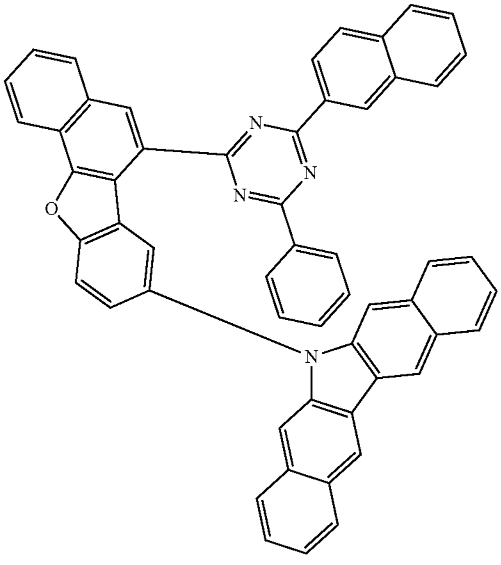
-continued
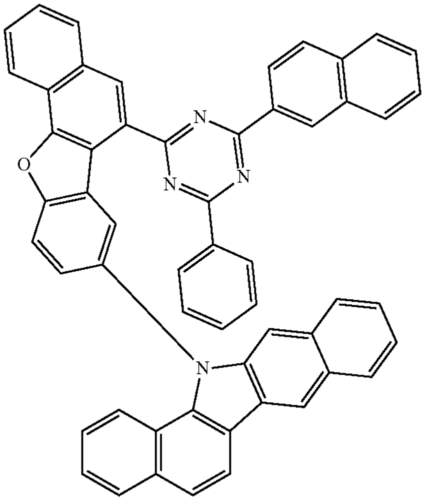
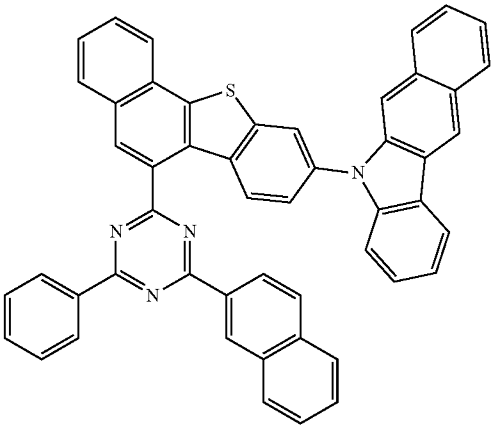
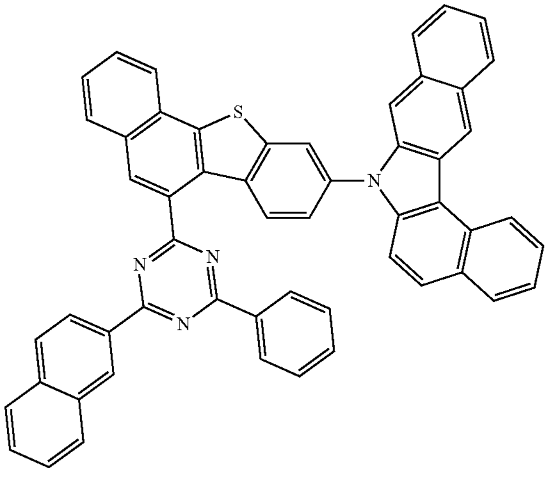

-continued
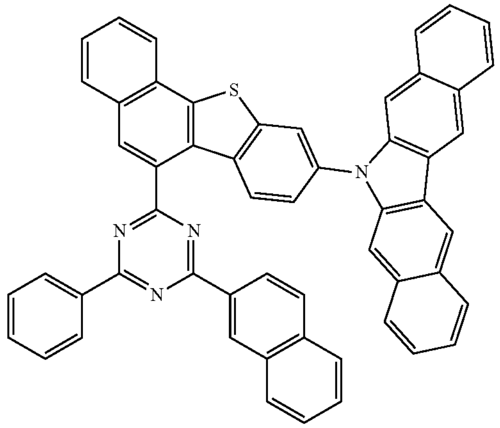
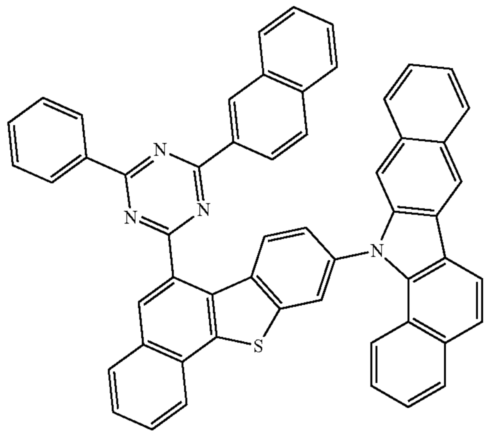
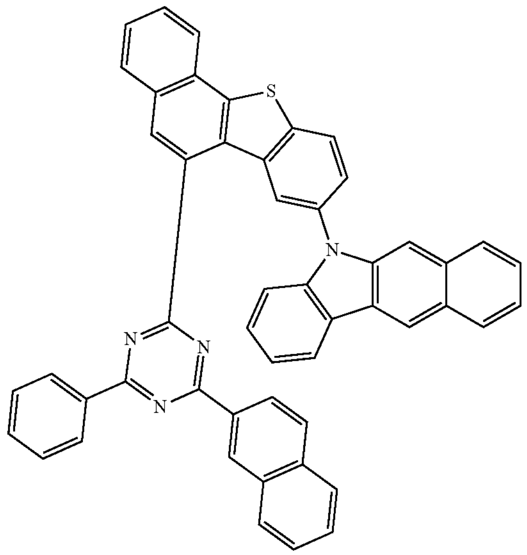
-continued
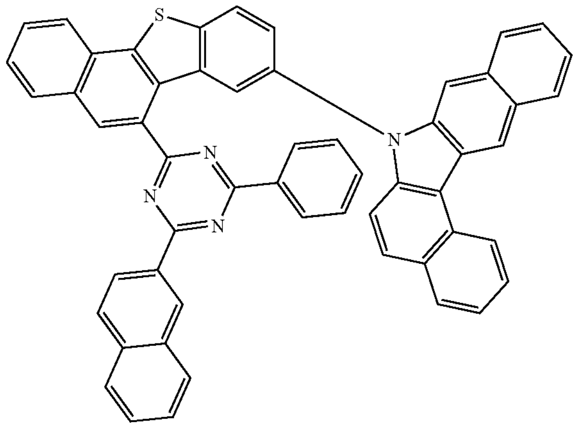
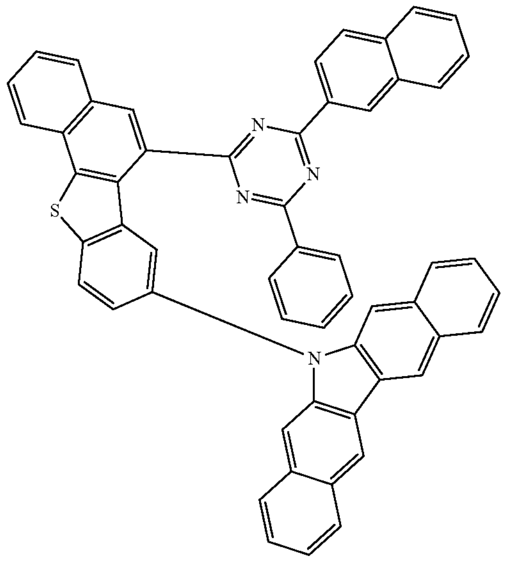
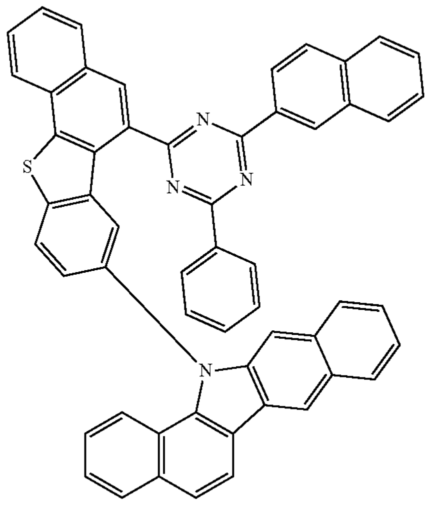

-continued
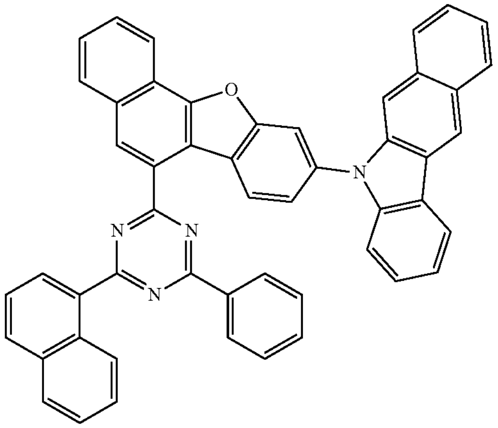
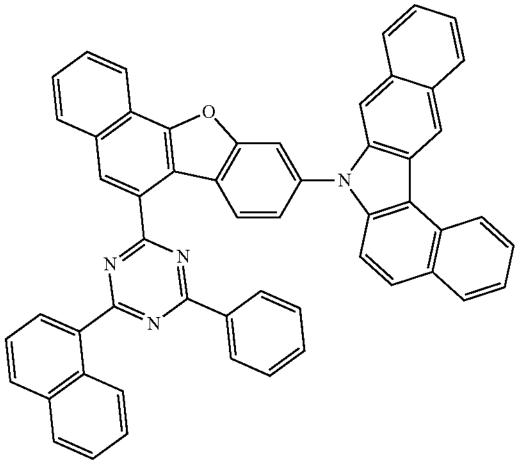
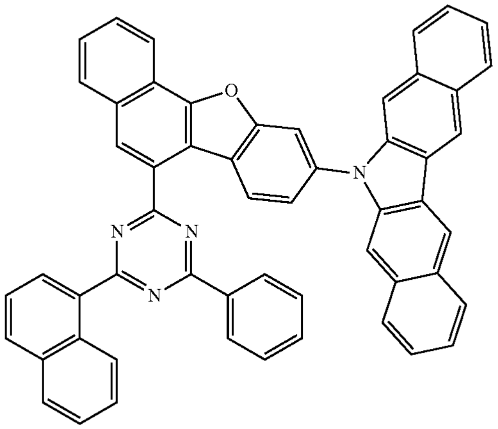
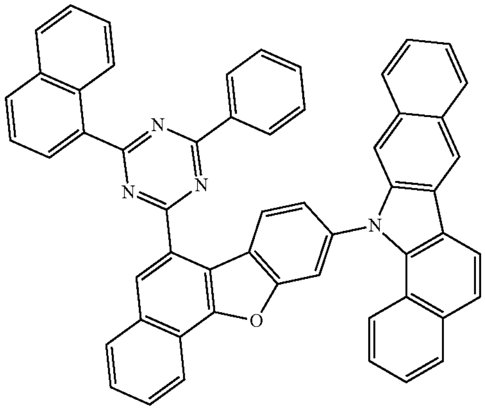
-continued
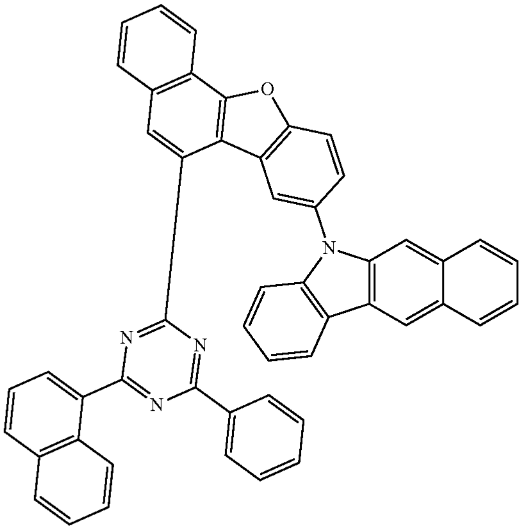
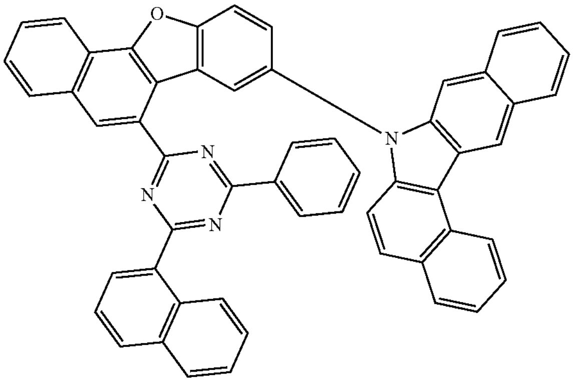
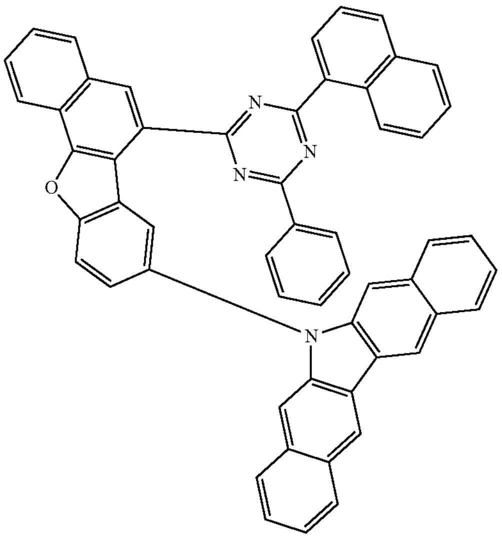

-continued
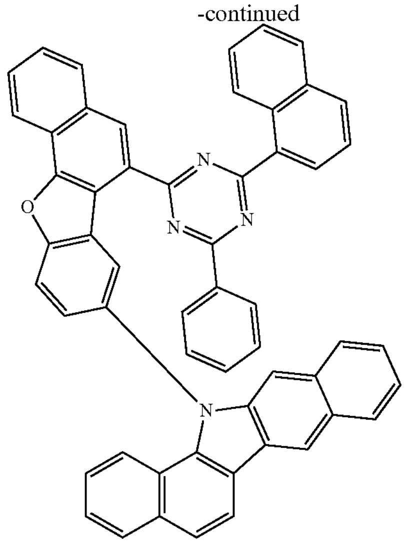
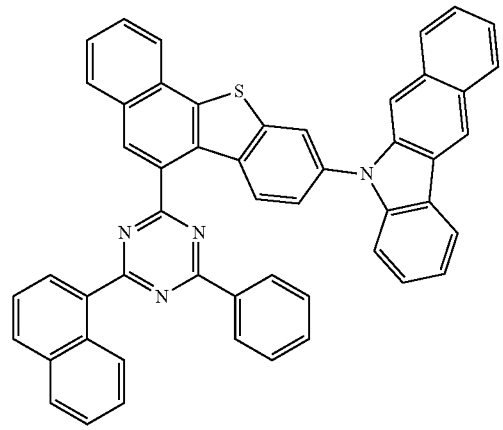
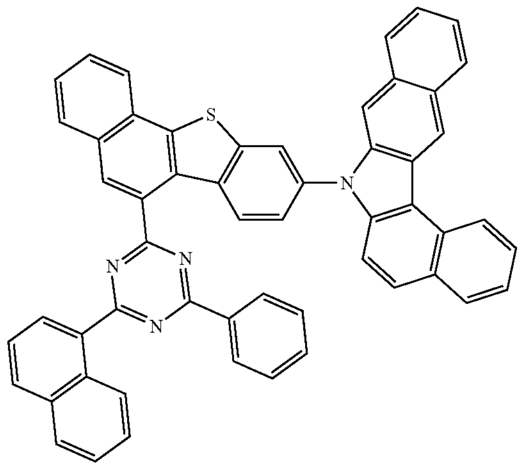
-continued
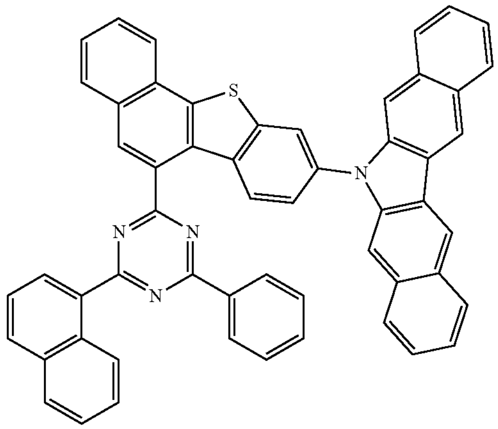
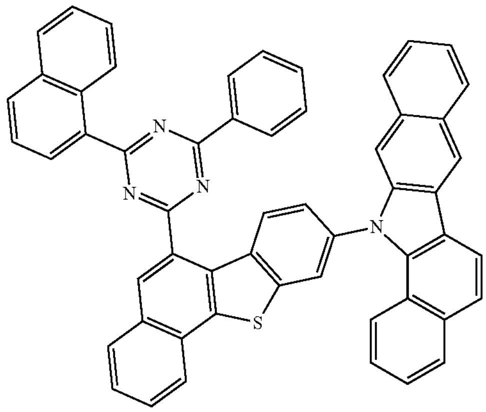
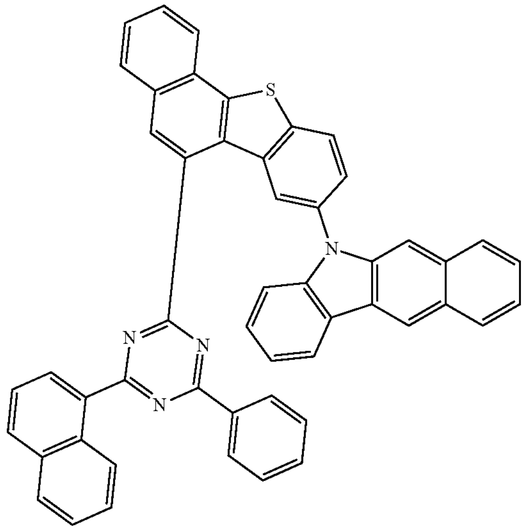

-continued

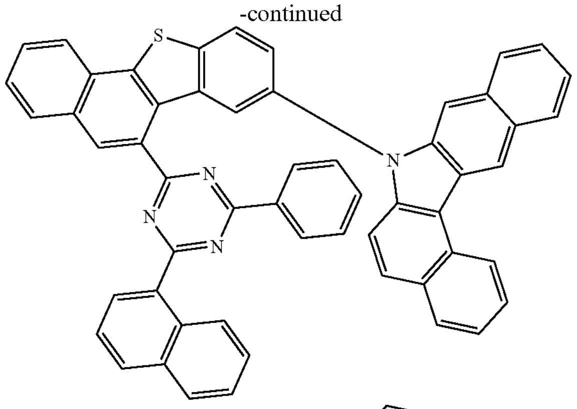

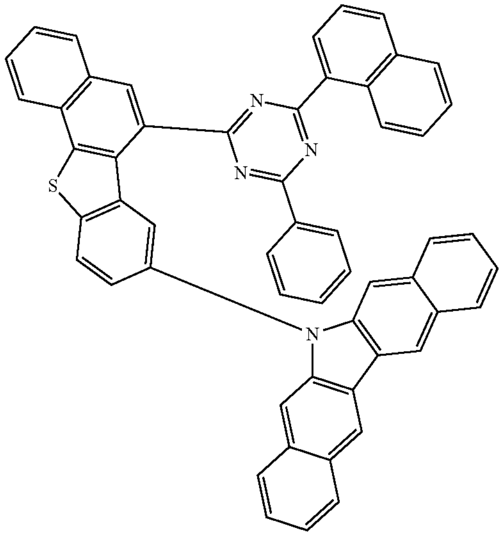

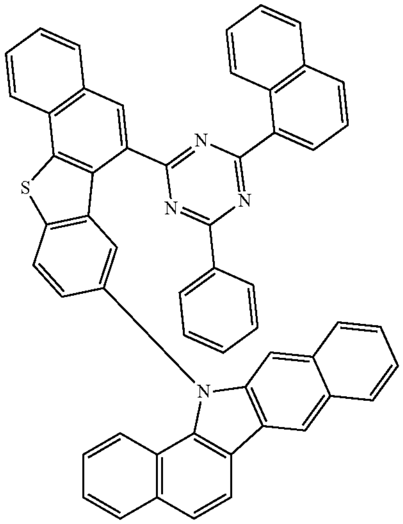

One embodiment of the present specification provides an organic light emitting device including a first electrode; a second electrode provided to face the first electrode; and one, two or more organic material layers provided between the first electrode and the second electrode, wherein one or more layers of the organic material layers include the compound.

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer, an electron blocking layer, a hole blocking layer and the like. However, the structure of the organic light emitting device is not limited thereto, and may include a smaller number of organic layers.

In one embodiment of the present specification, the organic material layers include a light emitting layer, and the light emitting layer includes the compound represented by Chemical Formula 1.

In one embodiment of the present specification, the organic material layers include a light emitting layer, the light emitting layer includes a host, and the host includes the compound represented by Chemical Formula 1.

In one embodiment of the present specification, the organic material layers include a light emitting layer, the light emitting layer includes a phosphorescent host, and the phosphorescent host includes the compound represented by Chemical Formula 1.

In one embodiment of the present specification, the organic material layers include a light emitting layer, the light emitting layer includes the compound represented by Chemical Formula 1, and the compound represented by Chemical Formula 1 is a red light emitting compound.

In one embodiment of the present specification, the organic material layers include two or more light emitting layers, and at least one of the two or more light emitting layers includes the compound represented by Chemical Formula 1. The light emitting layer that does not include the compound represented by Chemical Formula 1 may include a blue, red or green light emitting compound known in the art.

In one embodiment of the present specification, the light emitting layer includes the compound of Chemical Formula 1 as a first host, and further includes a compound represented by the following Chemical Formula 100 as a second host.

[Chemical Formula 100]

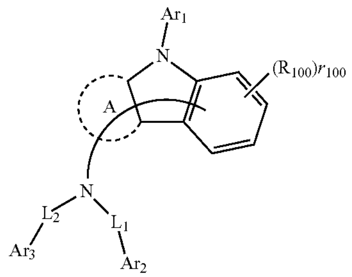

In Chemical Formula 100,

A is substituted or unsubstituted naphthalene, $Ar_1$ is a substituted or unsubstituted aryl group having 6 to 60 carbon atoms, $L_1$ and L2 are the same as or different from each other, and each independently a direct bond; or a substituted or unsubstituted arylene group having 6 to 60 carbon atoms, $Ar_2$ and Ara are the same as or different from each other, and each independently a substituted or unsubstituted aryl group having 6 to 60 carbon atoms; or a substituted or unsubstituted heteroaryl group having 2 to 60 carbon atoms and including one or more heteroatoms selected from the group consisting of N, O and S, $R_{100}$ is hydrogen; deuterium; a halogen group; a cyano group; a substituted or unsubstituted alkyl group; a substituted or unsubstituted cycloalkyl group; a substituted or unsubstituted aryl group; or a substituted or unsubstituted heteroaryl group, and $r_{100}$ is an integer of 0 to 4, and when $r_{100}$ is 2 or greater, each $R_{100}$ is the same as or different from each other.

In one embodiment of the present specification, the light emitting layer further includes the compound represented by Chemical Formula 100 as a second host. Herein, the compound represented by Chemical Formula 1 may be included in 10 parts by weight to 70 parts by weight, and is preferably included in 20 parts by weight to 50 parts by weight based on 100 parts by weight of the entire host included in the light emitting layer.

In one embodiment of the present specification, the light emitting layer may include the compound represented by Chemical Formula 1 in 40 parts by weight to 60 parts by weight and the compound represented by Chemical Formula 100 in 40 parts by weight to 60 parts by weight based on 100 parts by weight of the entire host included in the light emitting layer.

In one embodiment of the present specification, the light emitting layer includes a host, and the host may include the compound represented by Chemical Formula 1:the compound represented by Chemical Formula 100 in a weight ratio of 1:1.

In one embodiment of the present specification, A is naphthalene.

In one embodiment of the present specification, $Ar_1$ is a substituted or unsubstituted aryl group having 6 to 30 carbon atoms.

In one embodiment of the present specification, $Ar_1$ is a substituted or unsubstituted aryl group having 6 to 20 carbon atoms.

In one embodiment of the present specification, $Ar_1$ is a substituted or unsubstituted aryl group having 6 to 12 carbon atoms.

In one embodiment of the present specification, $Ar_1$ is a substituted or unsubstituted phenyl group; a substituted or unsubstituted biphenyl group; a substituted or unsubstituted naphthyl group; or a substituted or unsubstituted terphenyl group.

In one embodiment of the present specification, $Ar_1$ is a phenyl group; a biphenyl group; a naphthyl group; or a terphenyl group.

In one embodiment of the present specification, $L_1$ and $L_2$ are the same as or different from each other, and each independently a direct bond; or a substituted or unsubstituted arylene group having 6 to 30 carbon atoms.

In one embodiment of the present specification, $L_1$ and $L_2$ are the same as or different from each other, and each independently a direct bond; or a substituted or unsubstituted arylene group having 6 to 20 carbon atoms.

In one embodiment of the present specification, $L_1$ and $L_2$ are the same as or different from each other, and each independently a direct bond; or a substituted or unsubstituted arylene group having 6 to 12 carbon atoms.

In one embodiment of the present specification, $L_1$ and $L_2$ are the same as or different from each other, and each independently a direct bond; a substituted or unsubstituted phenylene group; or a substituted or unsubstituted naphthylene group.

In one embodiment of the present specification, $L_1$ and $L_2$ are the same as or different from each other, and each independently a direct bond; a phenylene group unsubstituted or substituted with a phenyl group; or a naphthylene group.

In one embodiment of the present specification, $Ar_2$ and $Ar_3$ are the same as or different from each other, and each independently a substituted or unsubstituted aryl group having to 30 carbon atoms; or a substituted or unsubstituted heteroaryl group having 2 to 30 carbon atoms and including one or more heteroatoms selected from the group consisting of N, O and S.

In one embodiment of the present specification, $Ar_2$ and $Ar_3$ are the same as or different from each other, and each independently a substituted or unsubstituted aryl group having to 20 carbon atoms; or a substituted or unsubstituted heteroaryl group having 2 to 20 carbon atoms and including one or more heteroatoms selected from the group consisting of N, O and S.

In one embodiment of the present specification, $Ar_2$ and $Ar_3$ are the same as or different from each other, and each independently a substituted or unsubstituted aryl group having 6 to 12 carbon atoms; or a substituted or unsubstituted heteroaryl group having 2 to 12 carbon atoms and including one or more heteroatoms selected from the group consisting of N, O and S.

In one embodiment of the present specification, $Ar_2$ and $Ar_3$ are the same as or different from each other, and each independently a substituted or unsubstituted phenyl group; a substituted or unsubstituted biphenyl group; a substituted or unsubstituted naphthyl group; a substituted or unsubstituted terphenyl group; a substituted or unsubstituted dibenzothiophene group; a substituted or unsubstituted dibenzofuranyl group; or a substituted or unsubstituted fluorenyl group.

In one embodiment of the present specification, $Ar_2$ and $Ar_3$ are the same as or different from each other, and each independently a phenyl group; a biphenyl group; a naphthyl group; a terphenyl group; a dibenzothiophene group; a dibenzofuranyl group; or a dimethylfluorenyl group.

In one embodiment of the present specification, $R_{100}$ is hydrogen; deuterium; a halogen group; a cyano group; a substituted or unsubstituted alkyl group having 1 to 30 carbon atoms; a substituted or unsubstituted cycloalkyl group having 3 to 30 carbon atoms; a substituted or unsubstituted aryl group having 6 to 30 carbon atoms; or a substituted or unsubstituted heteroaryl group having 2 to 30 carbon atoms.

In one embodiment of the present specification, $R_{100}$ is hydrogen; deuterium; a halogen group; a cyano group; a substituted or unsubstituted alkyl group having 1 to 20 carbon atoms; a substituted or unsubstituted cycloalkyl group having 3 to 20 carbon atoms; a substituted or unsubstituted aryl group having 6 to 20 carbon atoms; or a substituted or unsubstituted heteroaryl group having 2 to 20 carbon atoms.

In one embodiment of the present specification, $R_{100}$ is hydrogen; deuterium; a halogen group; a cyano group; a substituted or unsubstituted alkyl group having 1 to 10 carbon atoms; a substituted or unsubstituted cycloalkyl group having 3 to 10 carbon atoms; a substituted or unsubstituted aryl group having 6 to 12 carbon atoms; or a substituted or unsubstituted heteroaryl group having 2 to 10 carbon atoms.

In one embodiment of the present specification, $R_{100}$ is hydrogen.

In one embodiment of the present specification, $r_{100}$ is 0.

In one embodiment of the present specification, $r_{100}$ is 1.

In one embodiment of the present specification, $r_{100}$ is 2.

In one embodiment of the present specification, $r_{100}$ is 3.

In one embodiment of the present specification, $r_{100}$ is 4.

In one embodiment of the present specification, Chemical Formula 100 may be represented by any one of the following Chemical Formulae 100-1 to 100-3.

[Chemical Formula 100-1]

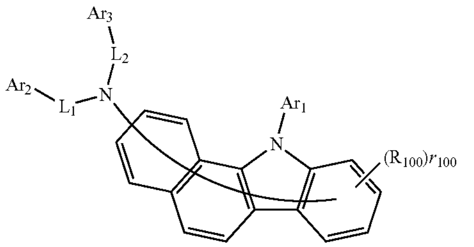

[Chemical Formula 100-2]

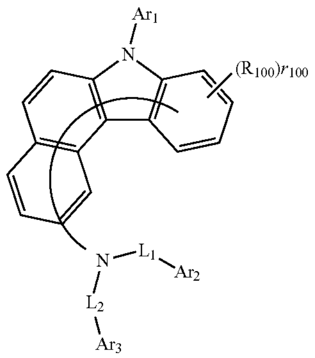

[Chemical Formula 100-3]

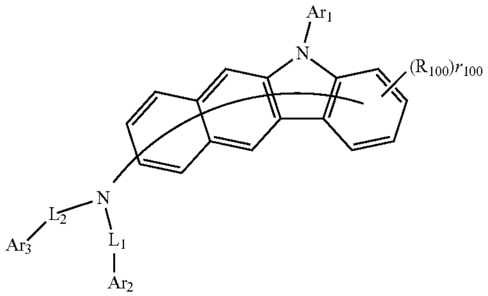

In Chemical Formulae 100-1 to 100-3, the definitions used in Chemical Formula 100 described above are applied to the descriptions on the substituents.

In one embodiment of the present specification, Chemical Formula 100 may be represented by any one of the following compounds.

Z-1

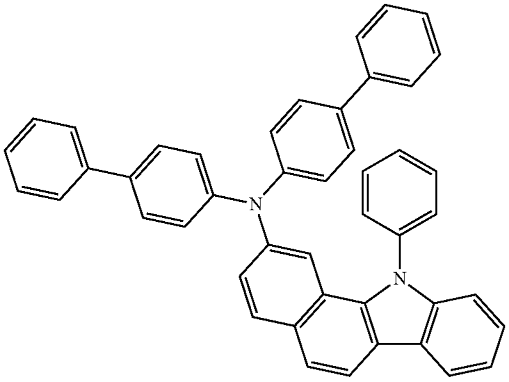

Z-2

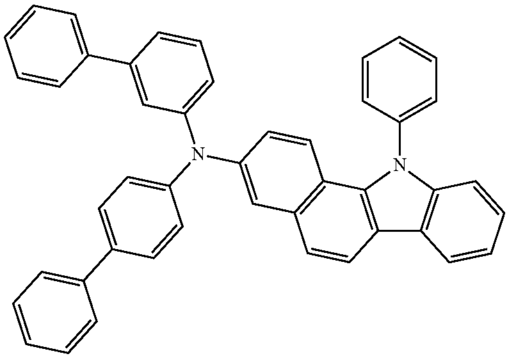

Z-3

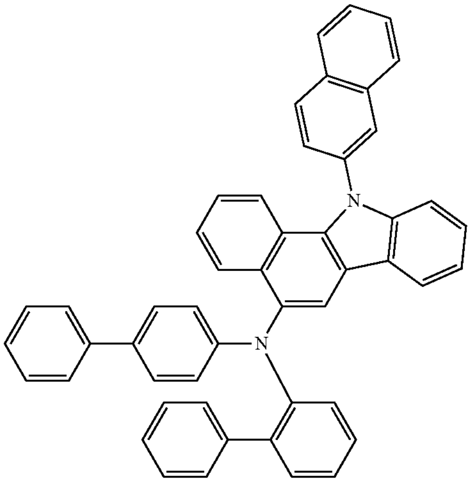

Z-4

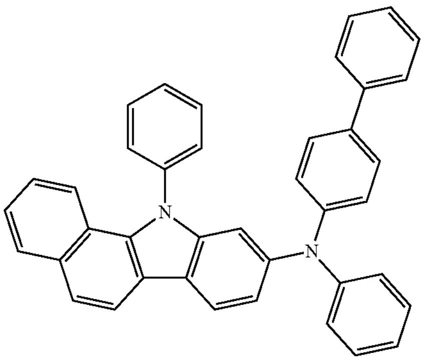

-continued
Z-5
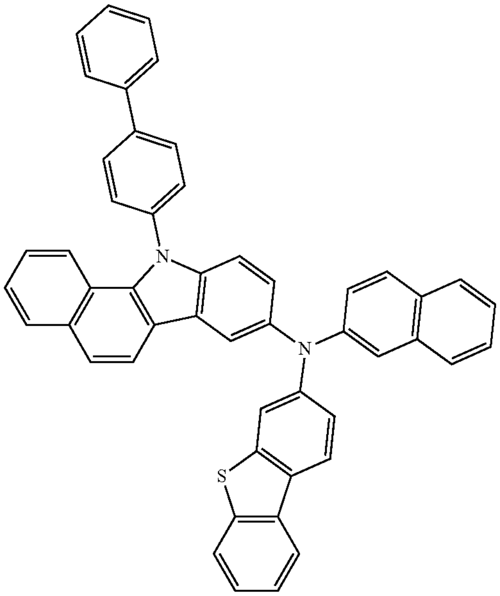
Z-6
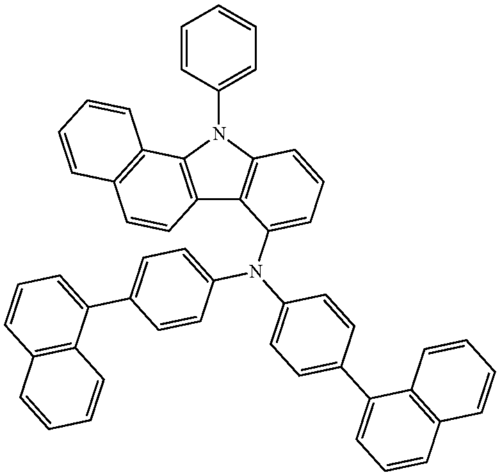
Z-7
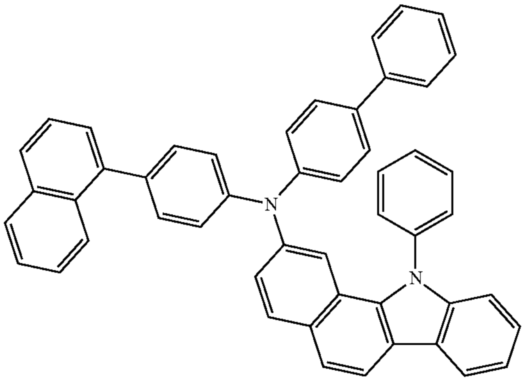
-continued
Z-8
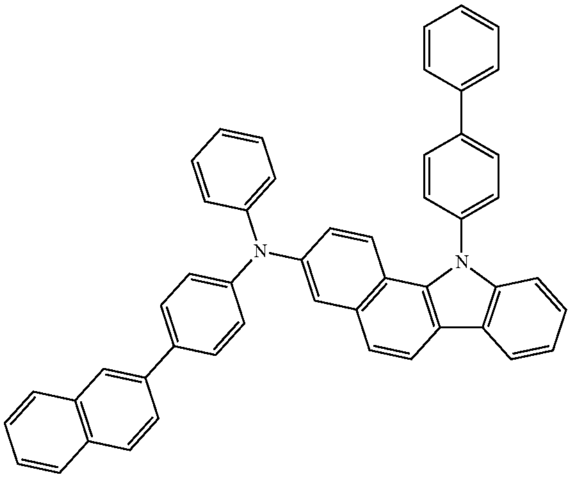
Z-9
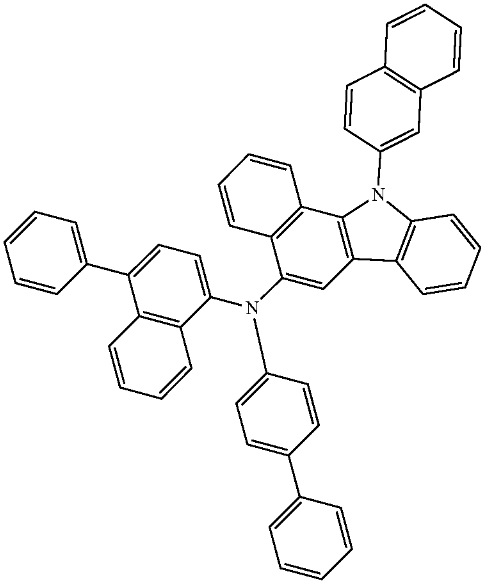
Z-10
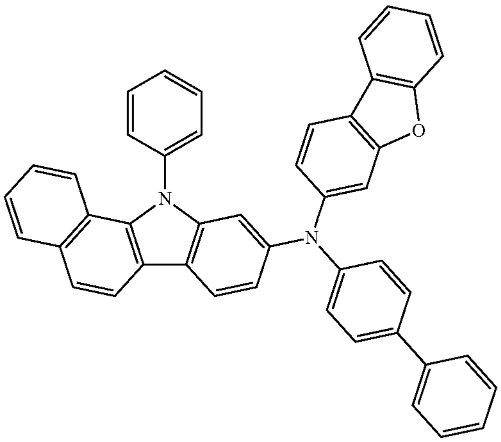

Z-11
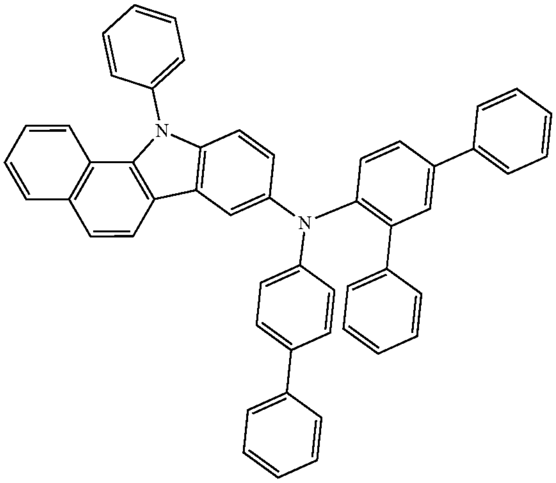
Z-12
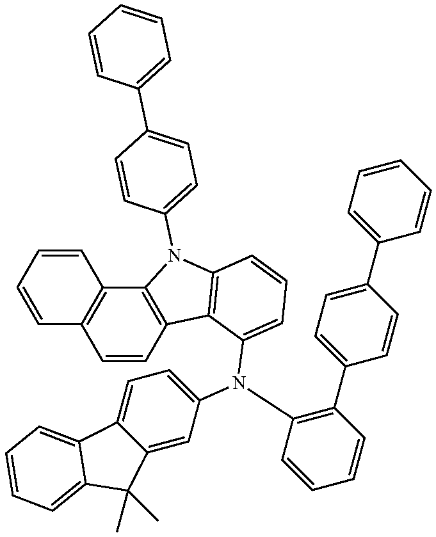
Z-13
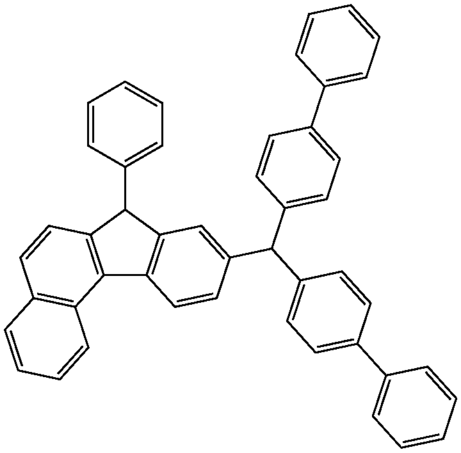
Z-14
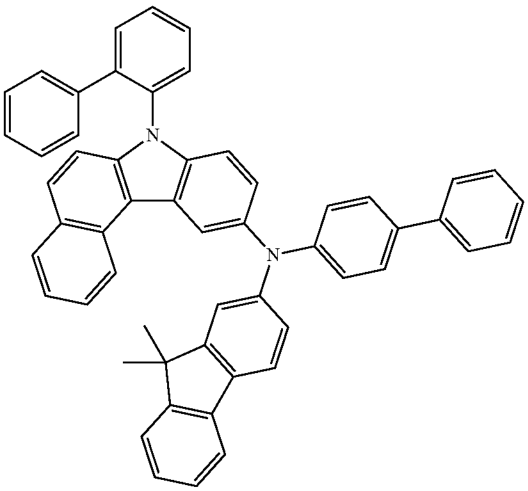
Z-15
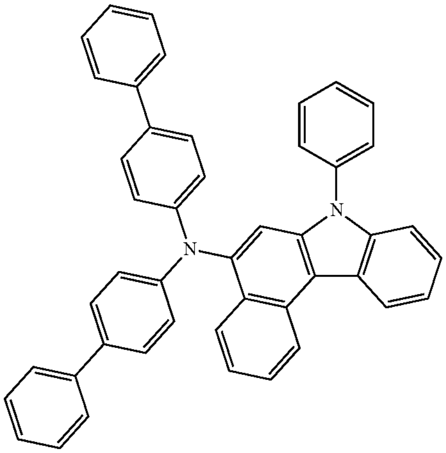
Z-16
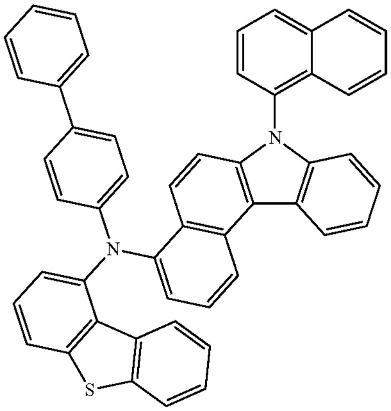

-continued
Z-17
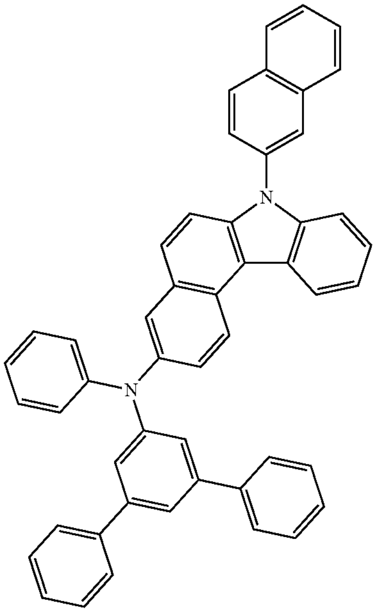
Z-18
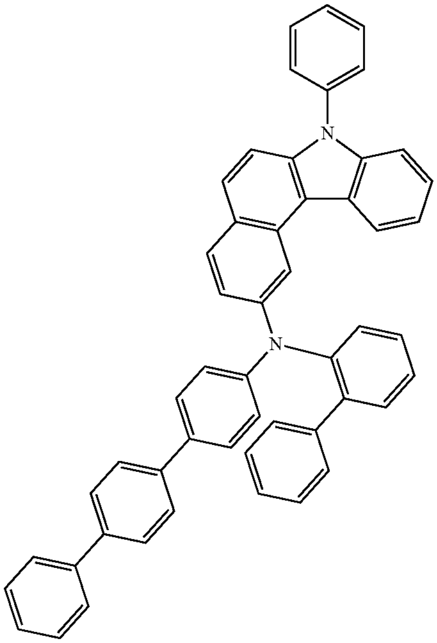
-continued
Z-19
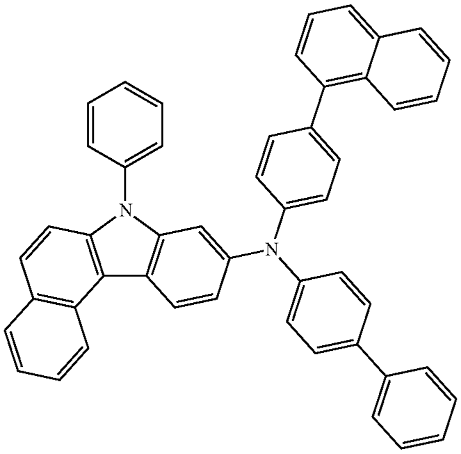
Z-20
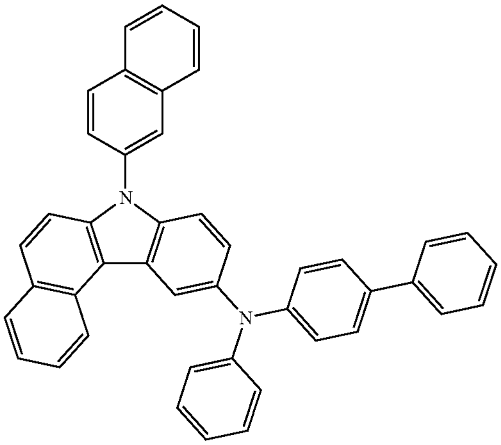
Z-21
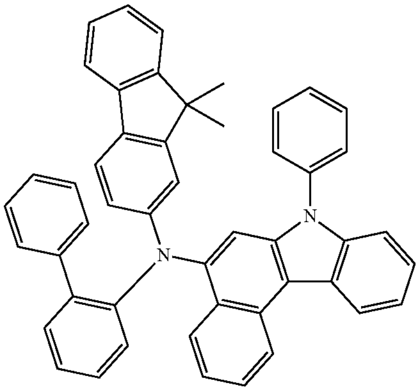

-continued
Z-22
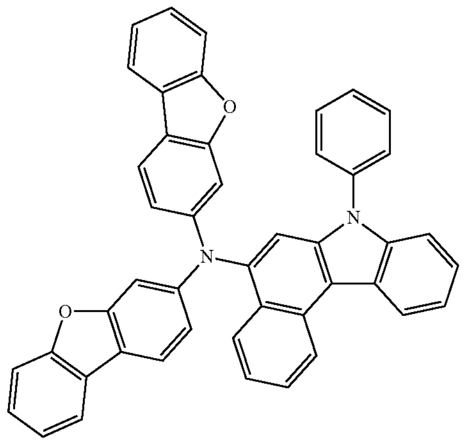
Z-23
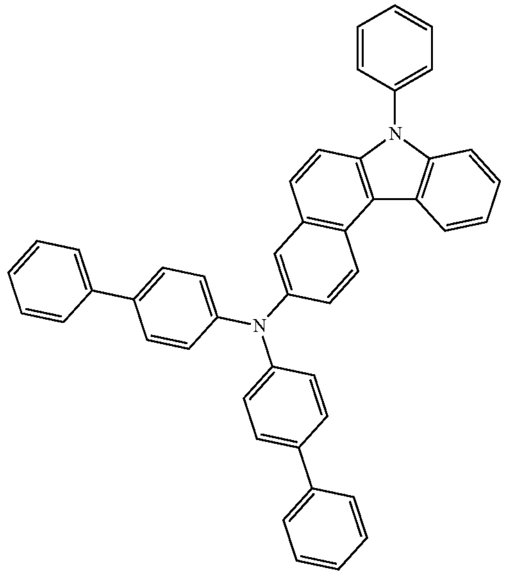
Z-24
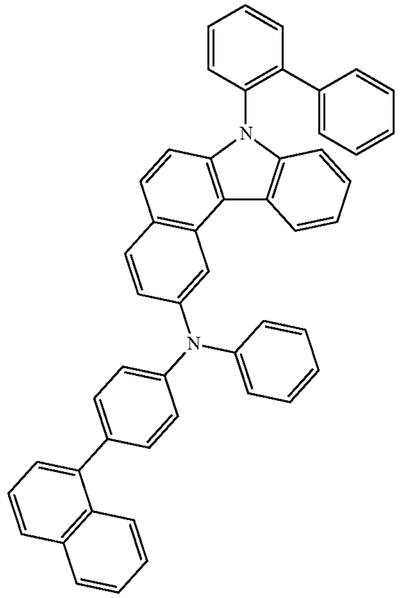
-continued
Z-25
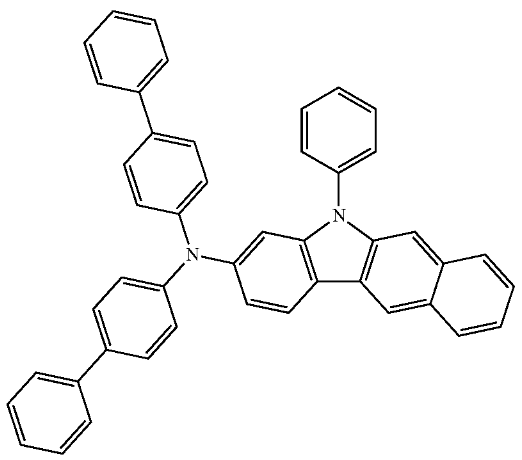
Z-26
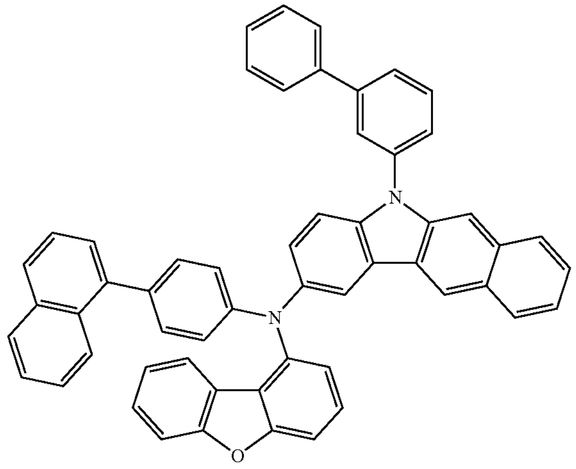
Z-27
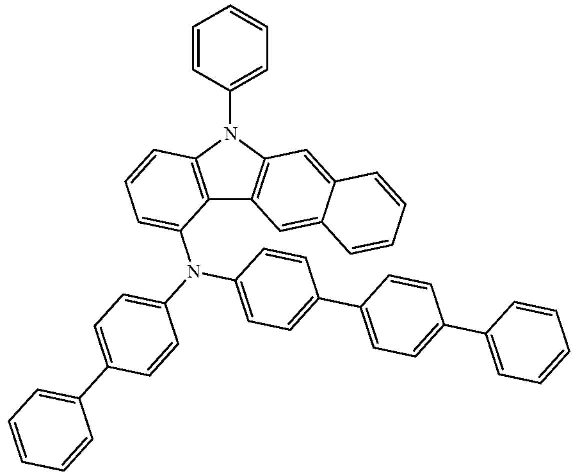

-continued
Z-28
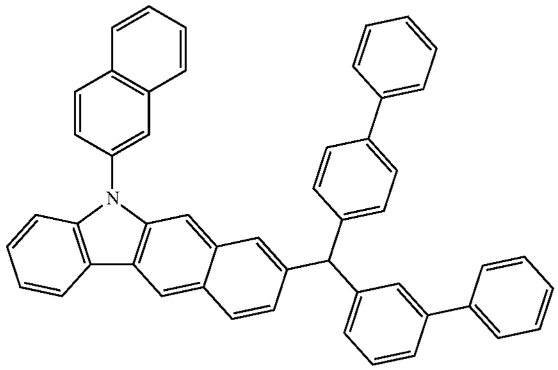
Z-29
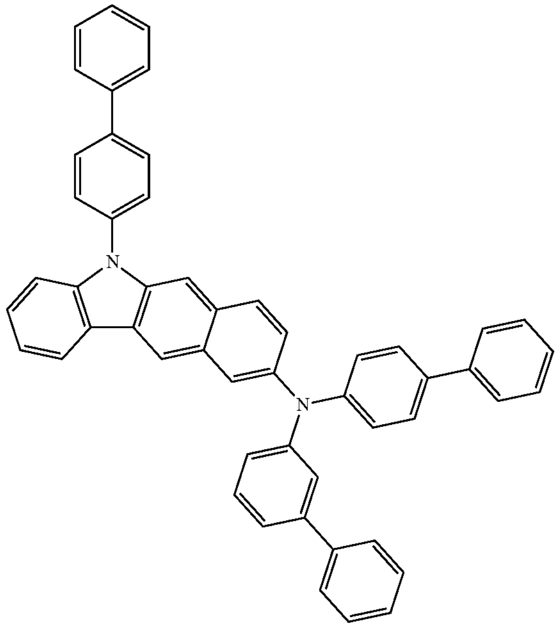
Z-30
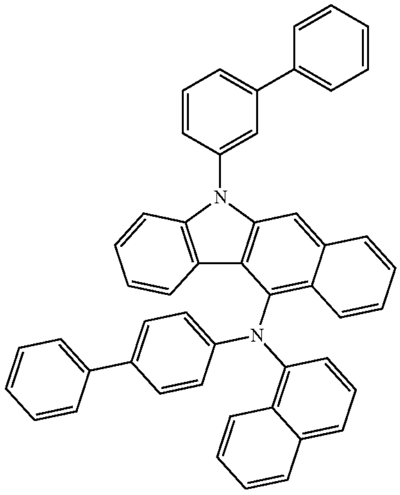
-continued
Z-31
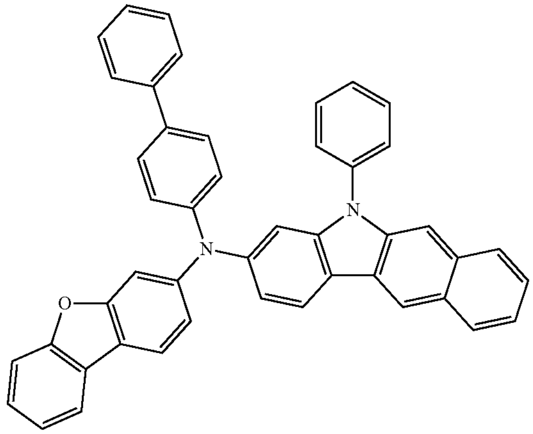
Z-32
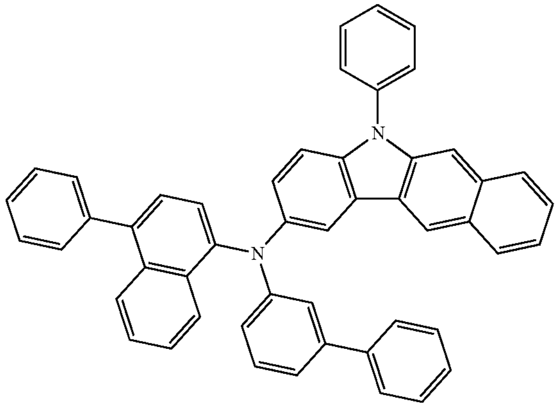
Z-33
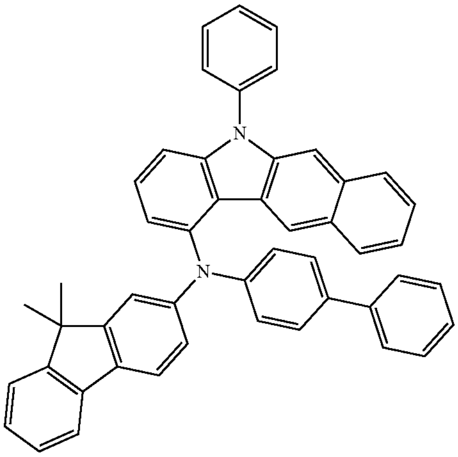

-continued

Z-34

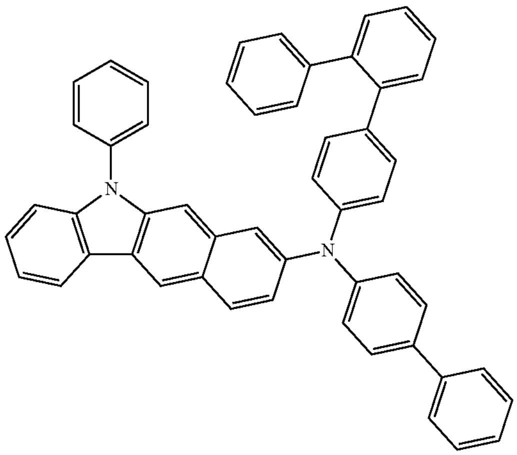

Z-35

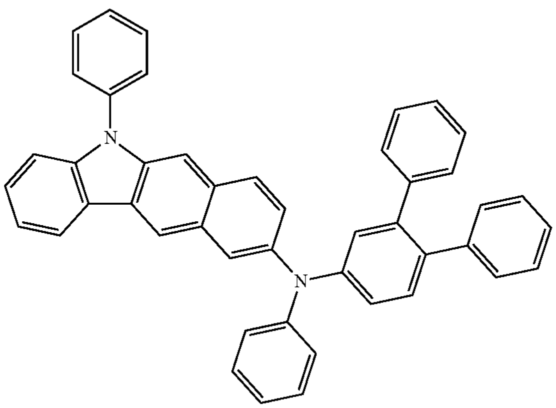

Z-36

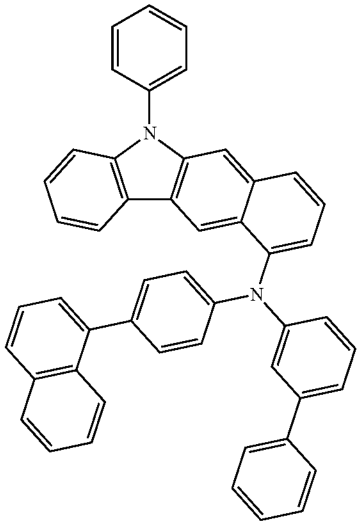

In one embodiment of the present specification, the first electrode is an anode or a cathode.

In one embodiment of the present specification, the second electrode is a cathode or an anode.

In one embodiment of the present specification, the organic light emitting device may be an organic light emitting device having a structure in which an anode, one or more organic material layers and a cathode are consecutively laminated on a substrate (normal type).

In one embodiment of the present specification, the organic light emitting device may be an organic light emitting device having a structure in a reverse direction in which a cathode, one or more organic material layers and an anode are consecutively laminated on a substrate (inverted type).

For example, a structure of the organic light emitting device according to one embodiment of the present specification is illustrated in FIG. 1 or FIG. 2. FIG. 1 and FIG. 2 illustrate the organic light emitting device, and the structure is not limited thereto.

FIG. 1 illustrates a structure of the organic light emitting device in which a first electrode (2), a light emitting layer (5) and a second electrode (6) are consecutively laminated on a substrate (1). The compound represented by Chemical Formula 1 is included in the light emitting layer.

FIG. 2 illustrates a structure of the organic light emitting device in which a first electrode (2), a hole injection layer (3), a hole transfer layer (4), a light emitting layer (5) and a second electrode (6) are consecutively laminated on a substrate (1).

According to one embodiment of the present disclosure, the compound represented by Chemical Formula 1 is included in one or more of the organic material layers. According to another embodiment, the compound represented by Chemical Formula 1 is included in one or more of the hole injection layer, the hole transfer layer and the light emitting layer.

The organic light emitting device of the present specification may be manufactured using materials and methods known in the art, except that one or more layers of the organic material layers include the compound, that is, the compound represented by Chemical Formula 1.

When the organic light emitting device includes a plurality of organic material layers, the organic material layers may be formed with the same materials or different materials.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device may also be manufactured by consecutively laminating a cathode material, an organic material layer and an anode material on a substrate. However, the manufacturing method is not limited thereto.

As the anode material, materials having large work function are normally preferred so that hole injection to an organic material layer is smooth. Examples thereof include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Examples thereof include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like. In addition, the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

In one embodiment of the present specification, the dopant may be any one of the following compounds, but is not limited thereto.

Dp-1

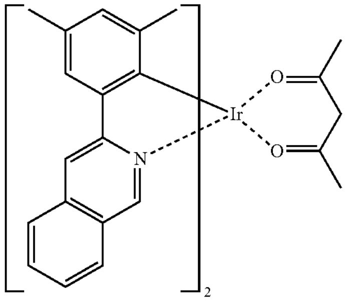

-continued

Dp-2

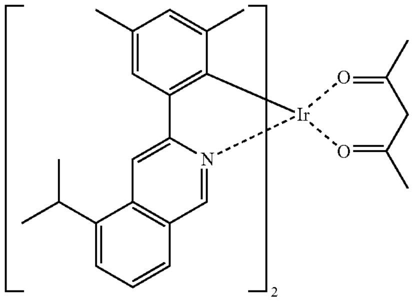

Dp-3

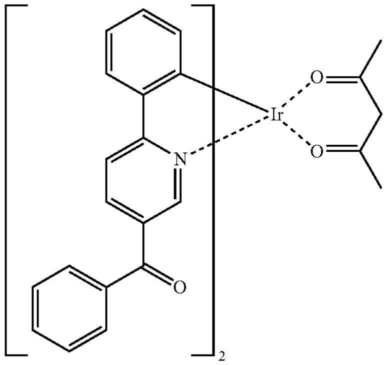

Dp-4

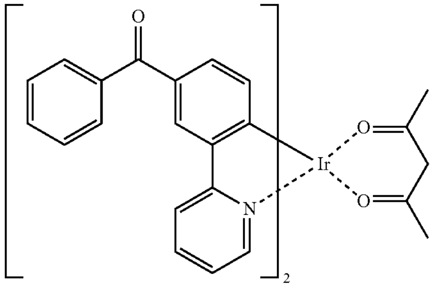

Dp-5

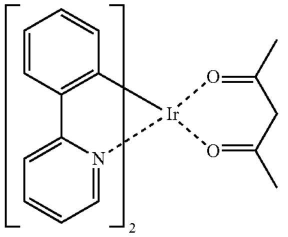

Dp-6

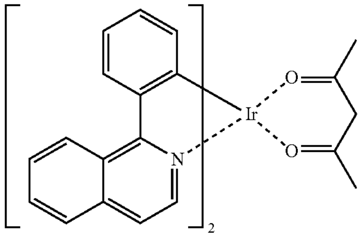

Dp-7
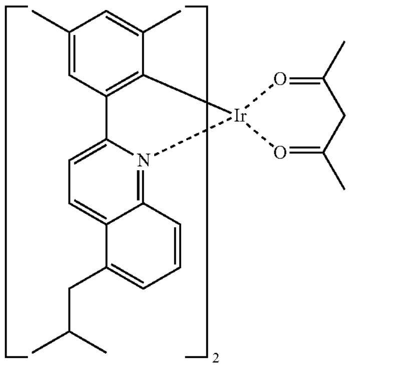
Dp-8
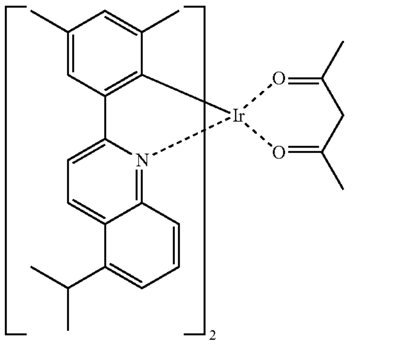
Dp-9
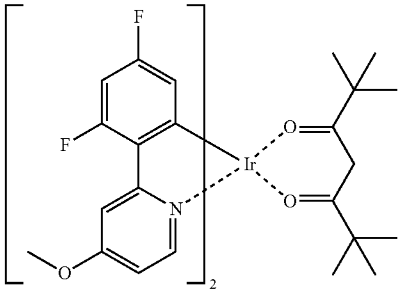
Dp-10
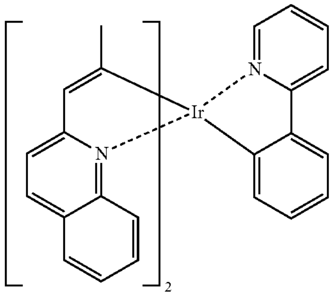
Dp-11
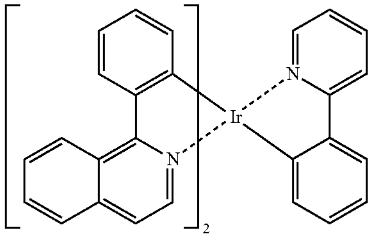
Dp-12
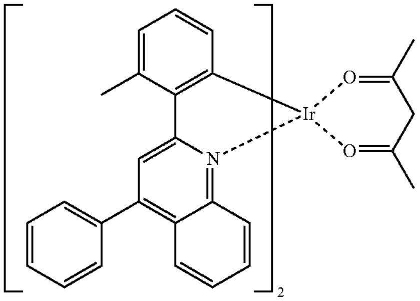
DP-13
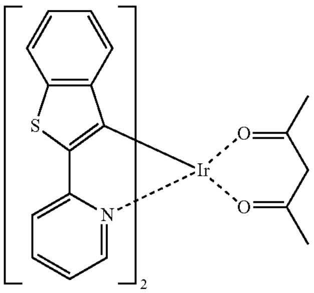
Dp-14
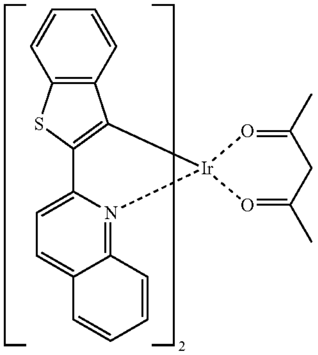
Dp-15
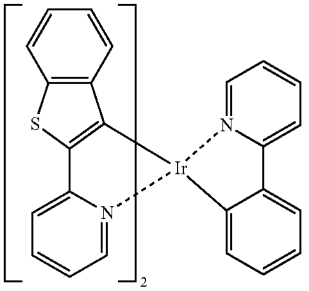
DP-16
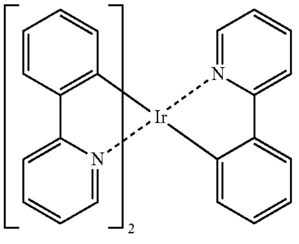

-continued
Dp-17
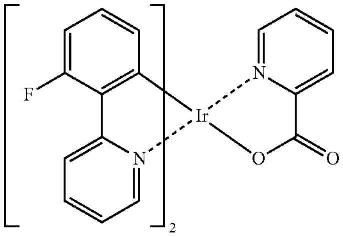
Dp-18
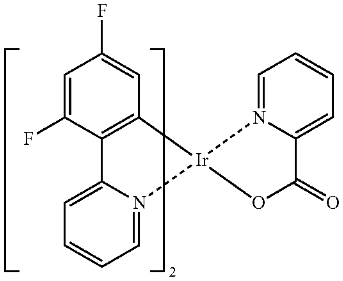
Dp-19
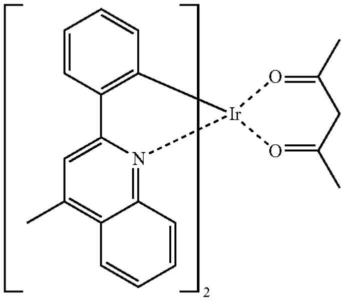
Dp-20
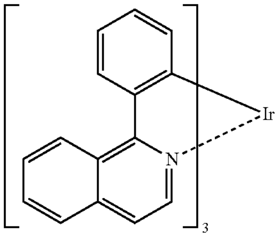
Dp-21
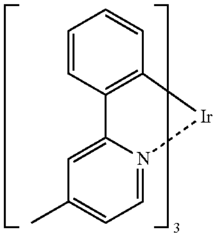
Dp-22
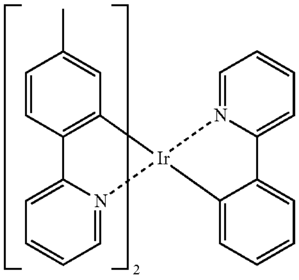
-continued
Dp-23
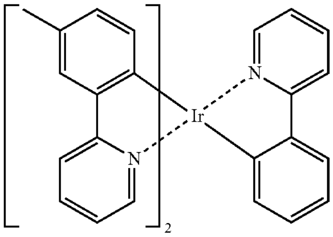
Dp-24
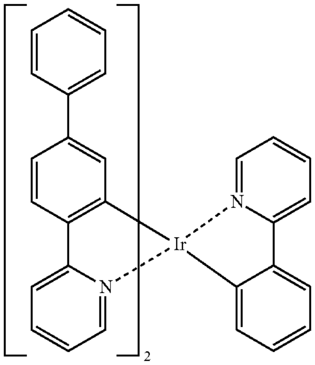
Dp-25
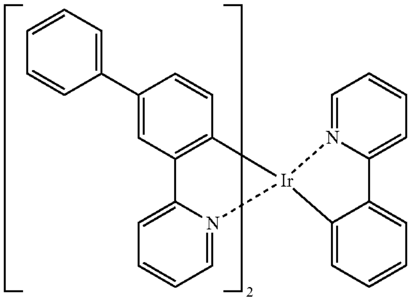
Dp-26
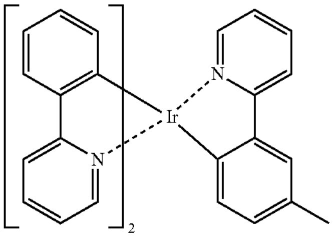
Dp-27
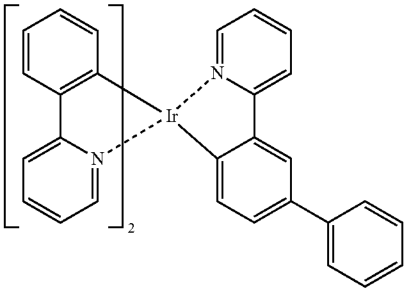

-continued
Dp-28
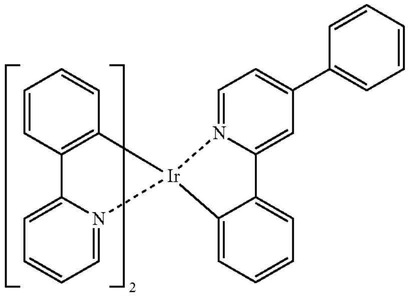
Dp-29
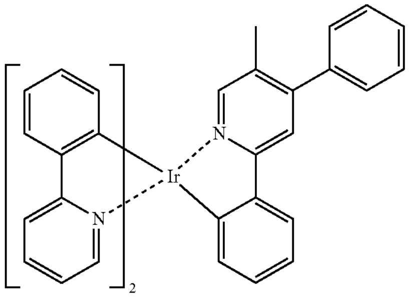
Dp-30
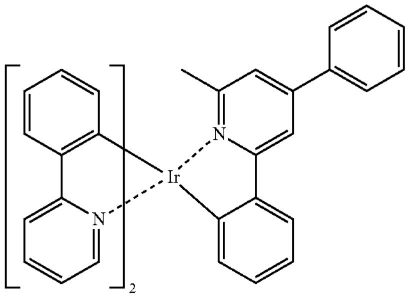
Dp-31
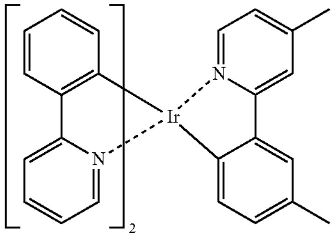
Dp-32
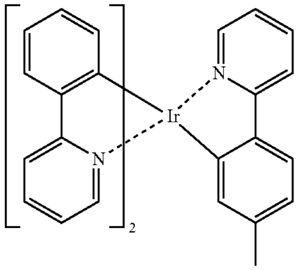
-continued
Dp-33
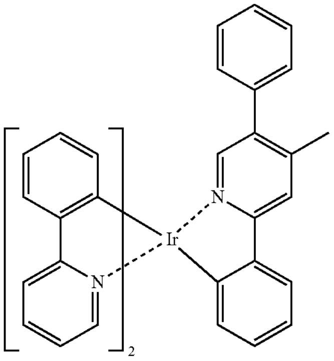
Dp-34
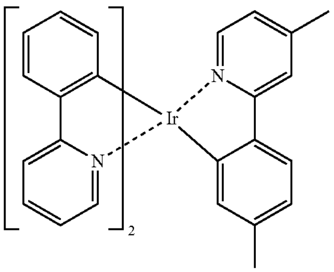
Dp-35
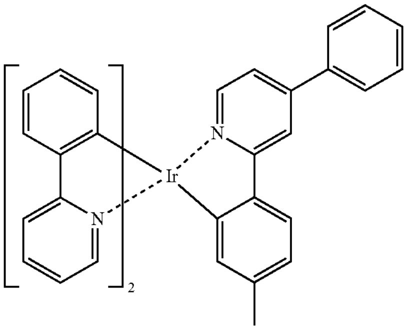
Dp-36
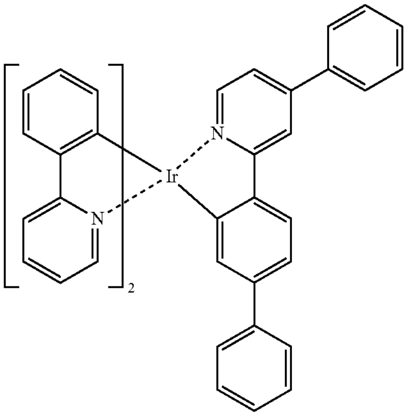

-continued

Dp-37

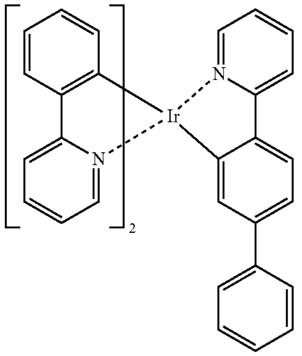

Dp-38

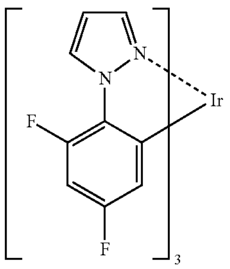

In the present specification, when the compound represented by Chemical Formula 1 is included in an organic material layer other than the light emitting layer or an additional light emitting layer is provided, the light emitting material of the light emitting layer is, as a material capable of emitting light in a visible light region by receiving holes and electrons respectively from a hole transfer layer and an electron transfer layer and binding the holes and the electrons, preferably a material having favorable quantum efficiency for fluorescence or phosphorescence. Examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene; rubrene, and the like, but are not limited thereto.

The hole injection layer is a layer receiving holes from an electrode. The hole injection material preferably has, by having an ability to transfer holes, a hole receiving effect from an anode and an excellent hole injection effect for a light emitting layer or a light emitting material. In addition, the hole injection material is preferably a material having an excellent ability to prevent excitons generated in the light emitting layer from moving to an electron injection layer or an electron injection material. In addition, a material having an excellent thin film forming ability is preferred. In addition, the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials; hexanitrile hexaazatriphenylene-based organic materials; quinacridone-based organic materials; perylene-based organic materials; polythiophene-based conductive polymers such as anthraquinone or polyaniline, and the like, but are not limited thereto.

The hole transfer layer is a layer receiving holes from a hole injection layer and transferring the holes to a light emitting layer. As the hole transfer material, materials having, as a material capable of receiving holes from an anode or a hole injection layer and moving the holes to a light emitting layer, high mobility for the holes are preferred. Specific examples thereof include arylamine-based organic materials, conductive polymers, block copolymers having conjugated parts and non-conjugated parts together, and the like, but are not limited thereto.

The electron transfer layer is a layer receiving electrons from an electron injection layer and transferring the electrons to a light emitting layer. As the electron transfer material, materials capable of favorably receiving electrons from a cathode, moving the electrons to a light emitting layer, and having high mobility for the electrons are preferred. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, the suitable cathode material is a common material having low work function and having an aluminum layer or a silver layer following. Specifically, cesium, barium, calcium, ytterbium, samarium and the like are included, and in each case, an aluminum layer or a silver layer follows.

The electron injection layer is a layer receiving electrons from an electrode. As the electron injection material, materials having an excellent electron transferring ability, having an electron receiving effect from a cathode, and having an excellent electron injection effect for a light emitting layer or light emitting material are preferred. In addition, materials preventing excitons generated in the light emitting layer from moving to a hole injection layer, and having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis (10-hydroxybenzo[h]quinolinato)zinc, bis(2-methyl-8-quinolinato)chlorogallium, bis(2-methyl-8-quinolinato) (0-cresolato)gallium, bis(2-methyl-8-quinolinato) (1-naphtholato)aluminum, bis(2-methyl-8-quinolinato) (2-naphtholato)gallium and the like, but is not limited thereto.

The electron blocking layer is a layer capable of enhancing lifetime and efficiency of a device by preventing electrons injected from an electron injection layer from passing through a light emitting layer and entering a hole injection layer. Known material may be used without limit, and the electron blocking layer may be formed between the light emitting layer and the hole injection layer, or between the light emitting layer and a layer carrying out hole injection and hole transfer at the same time. The hole blocking layer is a layer blocking holes from reaching a cathode, and may be generally formed under the same condition as the electron injection layer. Specific examples thereof may include oxadiazole derivatives, triazole derivatives, phenanthroline derivatives, aluminum complexes and the like, but are not limited thereto.

The organic light emitting device according to the present specification may be a top-emission type, a bottom-emission type or a dual-emission type depending on the materials used.

The organic light emitting device of the present disclosure may be manufactured using common organic light emitting device manufacturing methods and materials except that one or more organic material layers are formed using the compound described above.

PREPARATION EXAMPLES AND SYNTHESIS EXAMPLES

Compounds of the present disclosure were prepared using a Buchwald-Hartwig coupling reaction, a Heck coupling reaction, a Suzuki coupling reaction or the like as a representative reaction.

Preparation Example 1

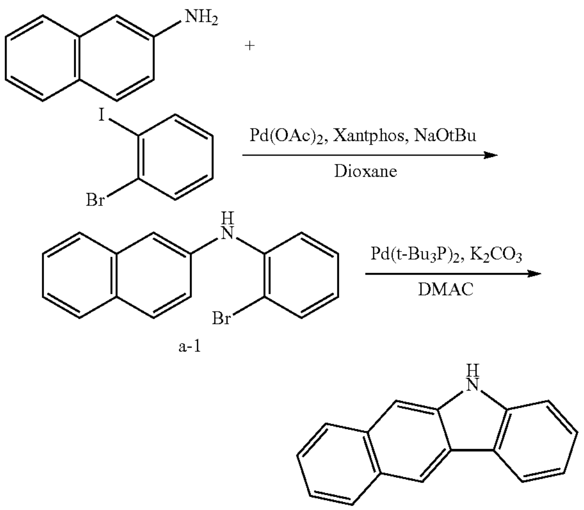

a-1 a
5H-benzo[b]carbozole

1) Preparation of Chemical Formula a-1

Naphthalen-2-amine (300.0 g, 1.0 eq.), 1-bromo-2-iodobenzene (592.7 g, 1.0 eq.), NaOtBu (302.0 g, 1.5 eq.), $Pd(OAc)_2$ (4.70 g, 0.01 eq.) and Xantphos (12.12 g, 0.01 eq.) were dissolved in 1,4-dioxane (5 L), and the result was stirred under reflux. When the reaction was finished after 3 hours, the reaction solution was vacuumed to remove the solvent. After that, the result was completed dissolved in ethyl acetate, washed with water, and vacuumed again to remove approximately 70% of the solvent. Crystals were dropped while introducing hexane thereto under reflux again, and the result was cooled and then filtered. This was column chromatographed to obtain Compound a-1 (443.5 g, yield 71%). $[M+H]^+$=299

2) Preparation of Chemical Formula a (5H-benzo[b]carbazole)

Chemical Formula a-1 (443.5 g, 1.0 eq.), $Pd(t\text{-}Bu_3P)_2$ (8.56 g, 0.01 eq.) and $K_2CO_3$ (463.2 g, 2.00 eq.) were introduced to dimethylacetamide (4 L), and the result was stirred under reflux. After 3 hours, the reaction material was poured into water to drop crystals, and filtered. The filtered solids were completely dissolved in 1,2-dichlorobenzene, then washed with water, and the solution in which the product was dissolved was vacuum concentrated to drop crystals, and cooled and then filtered. This was purified using column chromatography to obtain Chemical Formula a (5H-benzo[b]carbazole) (174.8 g, yield 48%). $[M+H]^+$= 218

Preparation Example 2. Preparation of Chemical Formula b (7H-dibenzo[b,g]carbazole)

7H-dibenzo[b,g]carbazole was synthesized in the same manner as in the method for preparing Chemical Formula a using 1-bromo-2-iodonaphthalene instead of 1-bromo-2-iodobenzene.

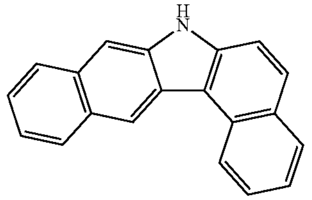

7H-dibenzo[b,g]carbazole

Preparation Example 3. Preparation of Chemical Formula c (6H-dibenzo[b,h]carbazole)

6H-dibenzo[b,h]carbazole was synthesized in the same manner as in the method for preparing Chemical Formula a using 2,3-dibromonaphthalene instead of 1-bromo-2-iodobenzene.

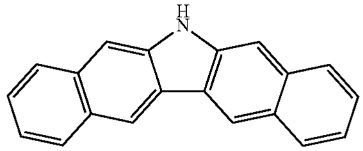

6H-dibenzo[b,h]carbazole

Preparation Example 4. Preparation of Chemical Formula d (13H-dibenzo[a,h]carbazole)

13H-dibenzo[a,h]carbazole was synthesized in the same manner as in the method for preparing Chemical Formula a using 2-bromo-1-iodonaphthalene instead of 1-bromo-2-iodobenzene.

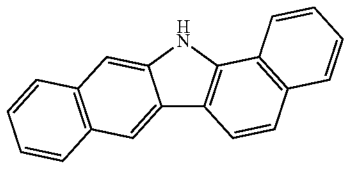

13H-dibenzo[a,h]carbazole

Preparation Example 5. Preparation of Chemical Formula e

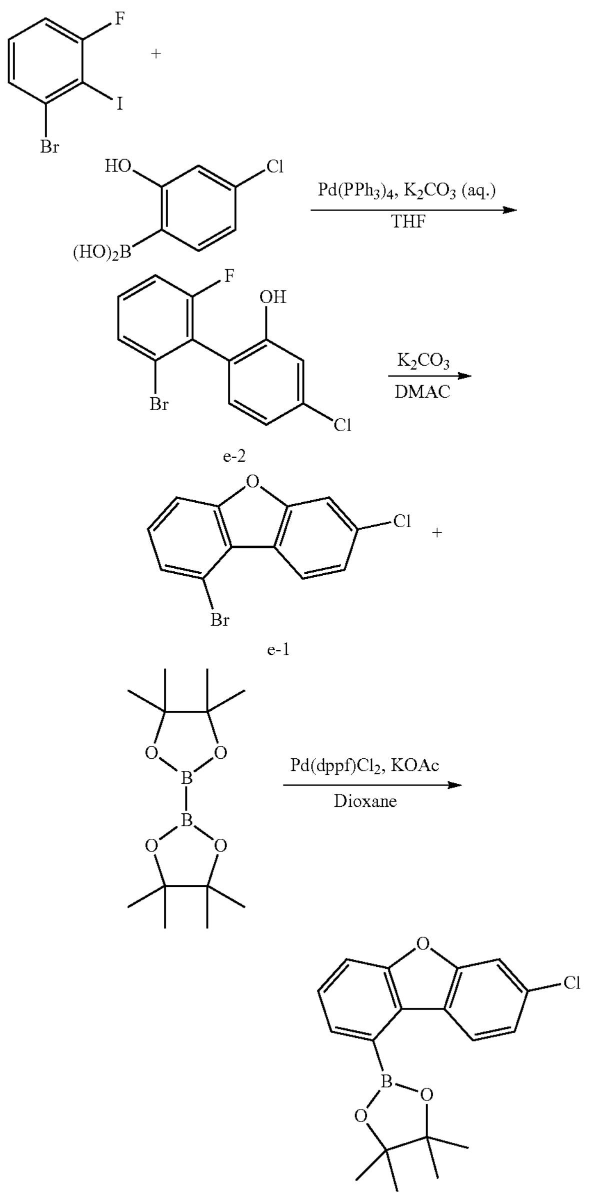

e-2 e-1 e

1) Preparation of Chemical Formula e-2

1-Bromo-3-fluoro-2-iodobenzene (200.0 g, 1.0 eq.), (4-chloro-2-hydroxyphenyl)boronic acid (82.3 g, 1.0 eq.), $K_2CO_3$ (164.6 g, 2.0 eq.) and $Pd(PPh_3)_4$ (13.77 g, 0.02 eq.) were dissolved in THF (3 L), and the result was stirred under reflux. When the reaction was finished after 2 hours, the reaction solution was vacuumed to remove the solvent. After that, the result was completed dissolved in ethyl acetate, washed with water, and vacuumed again to remove approximately 80% of the solvent. Crystals were dropped while introducing hexane thereto under reflux again, and the result was cooled and then filtered. This was column chromatographed to obtain Compound e-2 (129.5 g, yield 72%). $[M+H]^+=300$ 2) Preparation of Chemical Formula e-1

Chemical Formula e-2 (129.5 g, 1.0 eq.) and $K_2CO_3$ (118.5 g, 2.00 eq.) were introduced to dimethylacetamide (2 L), and the result was stirred under reflux. After 1 hour, the reaction material was poured into water to drop crystals, and filtered. The filtered solids were completely dissolved in ethyl acetate, washed with water, and vacuumed again to remove approximately 70% of the solvent. Crystals were dropped while introducing hexane thereto under reflux again, and the result was cooled and then filtered. This was column chromatographed to obtain Compound e-1 (101.6 g, yield 84%). $[M+H]^+=280$ 3) Preparation of Chemical Formula e Chemical Formula e-1 (101.6 g, 1.0 eq.), bis(pinacolato) diboron (119.1 g, 1.3 eq.), $Pd(dppf)Cl_2$ (5.28 g, 0.02 eq.) and KOAc (40.4 g, 2.00 eq.) were introduced to dioxane (2 L), and the result was stirred under reflux. When the reaction was finished after 3 hours, the reaction solution was vacuumed to remove the solvent. The filtered solids were completely dissolved in $CHCl_3$, then washed with water, and the solution in which the product was dissolved was vacuum concentrated to remove approximately 90% of the solvent. Crystals were dropped while introducing ethanol thereto under reflux again, and the result was cooled and then filtered to obtain Chemical Formula e (103.1 g, yield 87%). $[M+H]^+=329$ Preparation Example 6. Preparation of Chemical Formula f Chemical Formula f was synthesized in the same manner as in the method for preparing Chemical Formula e using (5-chloro-2-hydroxyphenyl)boronic acid instead of (4-chloro-2-hydroxyphenyl)boronic acid.

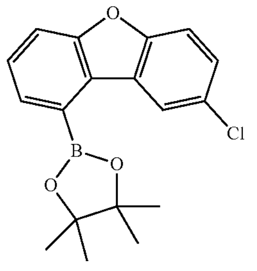 [SMILES: CC1(C)OB(c2cccc3oc4ccc(Cl)cc4c23)OC1(C)C]

Preparation Example 7. Preparation of Chemical Formula g

Chemical Formula g was synthesized in the same manner as in the method for preparing Chemical Formula e using 3-bromo-1-fluoro-2-iodonaphthalene instead of 1-bromo-3-fluoro-2-iodobenzene.

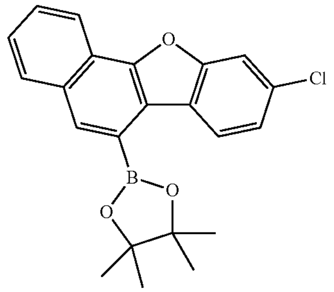 [SMILES: CC1(C)OB(c2cc3ccccc3c3oc4cc(Cl)ccc4c23)OC1(C)C]

Preparation Example 8. Preparation of Chemical Formula h

Chemical Formula h was synthesized in the same manner as in the method for preparing Chemical Formula g using (5-chloro-2-hydroxyphenyl)boronic acid instead of (4-chloro-2-hydroxyphenyl)boronic acid.

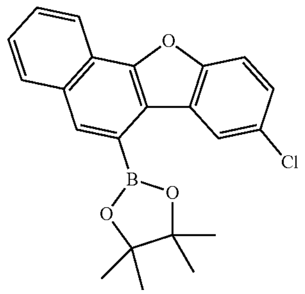 [SMILES: CC1(C)OB(c2cc3ccccc3c3oc4ccc(Cl)cc4c23)OC1(C)C]

Preparation Example 9. Preparation of Chemical Formula i

Chemical Formula i was synthesized in the same manner as in the method for preparing Chemical Formula e using 1-bromo-3-fluoro-2-iodonaphthalene instead of 1-bromo-3-fluoro-2-iodobenzene.

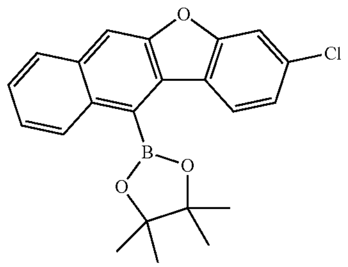 [SMILES: CC1(C)OB(c2c3ccccc3cc3oc4cc(Cl)ccc4c23)OC1(C)C]

Preparation Example 10. Preparation of Chemical Formula j

Chemical Formula j was synthesized in the same manner as in the method for preparing Chemical Formula i using 3-bromo-1-fluoro-2-iodonaphthalene instead of (4-chloro-2-hydroxyphenyl)boronic acid.

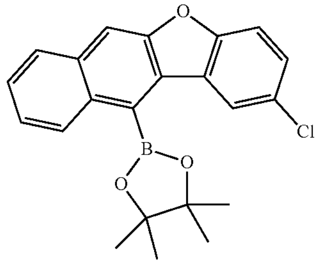 [SMILES: CC1(C)OB(c2c3ccccc3cc3oc4ccc(Cl)cc4c23)OC1(C)C]

Preparation Example 11. Preparation of Chemical Formula k

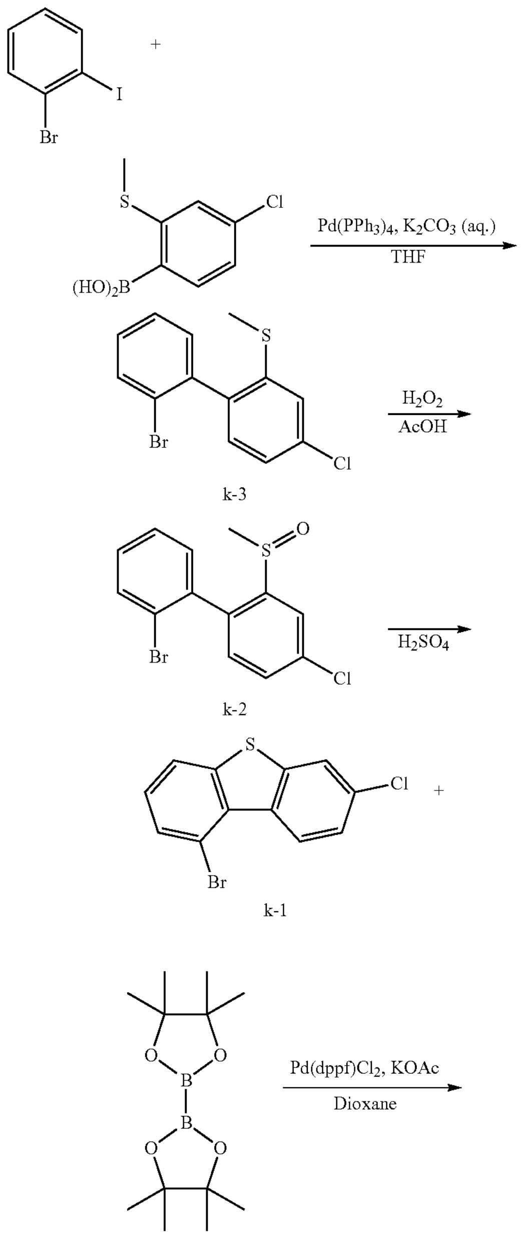

-continued

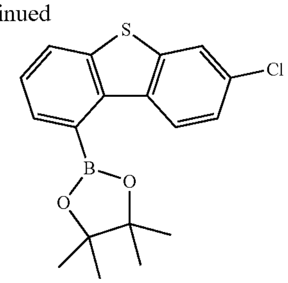

k

1) Preparation of Chemical Formula k-3

1-Bromo-2-iodobenzene (200.0 g, 1.0 eq.), (4-chloro-2-(methylthio)phenyl)boronic acid (105.9 g, 1.0 eq.), $K_2CO_3$ (173.9 g, 2.0 eq.) and $Pd(PPh_3)_4$ (14.55 g, 0.02 eq.) were dissolved in THF (3 L), and the result was stirred under reflux. When the reaction was finished after 2 hours, the reaction solution was vacuumed to remove the solvent. After that, the result was completed dissolved in ethyl acetate, washed with water, and vacuumed again to remove approximately 80% of the solvent. Crystals were dropped while introducing hexane thereto under reflux again, and the result was cooled and then filtered. This was column chromatographed to obtain Compound k-3 (138.36 g, yield 70%). $[M+H]^+=312$ 2) Preparation of Chemical Formula k-2

Chemical Formula k-3 (138.36 g, 1.0 eq.) and $H_2O_2$ (22.5 g, 2.00 eq.) were introduced to acetic acid (1 L), and the result was stirred under reflux. After 1 hour, the reaction material was poured into water to drop crystals, and filtered. The filtered solids were completely dissolved in ethyl acetate, washed with water, and vacuumed again to remove approximately 80% of the solvent. Crystals were dropped while introducing hexane thereto under reflux again, and the result was cooled and then filtered. This was column chromatographed to obtain Compound k-2 (91.61 g, yield 63%). $[M+H]^+=328$ 3) Preparation of Chemical Formula k-1

Chemical Formula k-2 (91.61 g, 1.0 eq.) and $H_2SO_4$ (500 ml) were introduced, and stirred while dissolving under reflux. When the reaction was completed after 2 hours, the reaction material was poured into water to drop crystals, and filtered. The filtered solids were completely dissolved in $CHCl_3$, then washed with water, and the solution in which the product was dissolved was vacuum concentrated to remove approximately 80% of the solvent. Crystals were dropped while introducing hexane thereto under reflux again, and the result was cooled and then filtered to obtain Chemical Formula k-1 (50.45 g, yield 61%). $[M+H]^+=296$ 4) Preparation of Chemical Formula k Chemical Formula k-1 (50.45 g, 1.0 eq.), bis(pinacolato) diboron (55.96 g, 1.3 eq.), $Pd(dppf)Cl_2$ (2.48 g, 0.02 eq.) and KOAc (18.98 g, 2.00 eq.) were introduced to dioxane (800 mL), and the result was stirred under reflux. When the reaction was finished after 3 hours, the reaction solution was vacuumed to remove the solvent. The filtered solids were completely dissolved in $CHCl_3$, then washed with water, and the solution in which the product was dissolved was vacuum concentrated to remove approximately 90% of the solvent. Crystals were dropped while introducing ethanol thereto under reflux again, and the result was cooled and then filtered to obtain Chemical Formula k (49.66 g, yield 84%). $[M+H]^+=345$ Preparation Example 12. Preparation of Chemical Formula 1

Chemical Formula 1 was synthesized in the same manner as in the method for preparing Chemical Formula k using (5-chloro-2-(methylthio)phenyl)boronic acid instead of (4-chloro-2-(methylthio)phenyl)boronic acid.

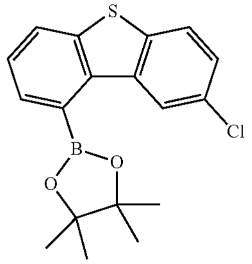 [SMILES: CC1(C)OB(c2cccc3sc4ccc(Cl)cc4c23)OC1(C)C]

Preparation Example 13. Preparation of Chemical Formula m

Chemical Formula m was synthesized in the same manner as in the method for preparing Chemical Formula k using 1-bromo-2-iodonaphthalene instead of 1-bromo-2-iodobenzene.

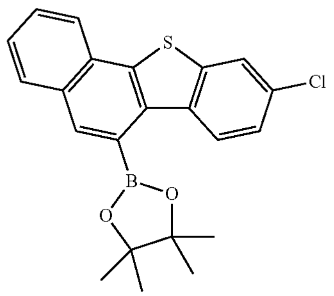 [SMILES: CC1(C)OB(c2cc3ccccc3c3sc4cc(Cl)ccc4c23)OC1(C)C]

Preparation Example 14. Preparation of Chemical Formula n

Chemical Formula n was synthesized in the same manner as in the method for preparing Chemical Formula m using (5-chloro-2-(methylthio)phenyl)boronic acid instead of (4-chloro-2-(methylthio)phenyl)boronic acid.

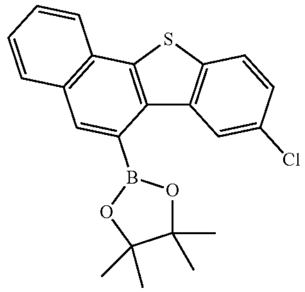 [SMILES: CC1(C)OB(c2cc3ccccc3c3sc4ccc(Cl)cc4c23)OC1(C)C]

Preparation Example 15. Preparation of Chemical Formula o

Chemical Formula o was synthesized in the same manner as in the method for preparing Chemical Formula a using 2-bromo-3-iodonaphthalene instead of 1-bromo-2-iodobenzene.

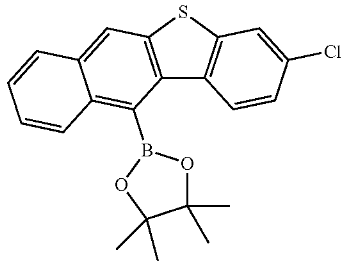 [SMILES: CC1(C)OB(c2c3ccccc3cc3sc4cc(Cl)ccc4c23)OC1(C)C]

Preparation Example 16. Preparation of Chemical Formula p

Chemical Formula p was synthesized in the same manner as in the method for preparing Chemical Formula o using (5-chloro-2-(methylthio)phenyl)boronic acid instead of (4-chloro-2-(methylthio)phenyl)boronic acid.

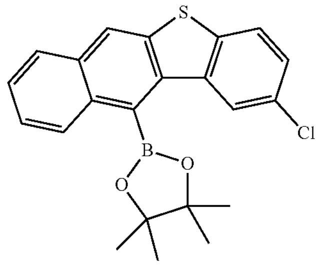 [SMILES: CC1(C)OB(c2c3ccccc3cc3sc4ccc(Cl)cc4c23)OC1(C)C]

Intermediates including triazine were synthesized through a Suzuki coupling reaction using the intermediates synthesized above, and compounds of the following synthesis examples were synthesized.

Synthesis Example 1

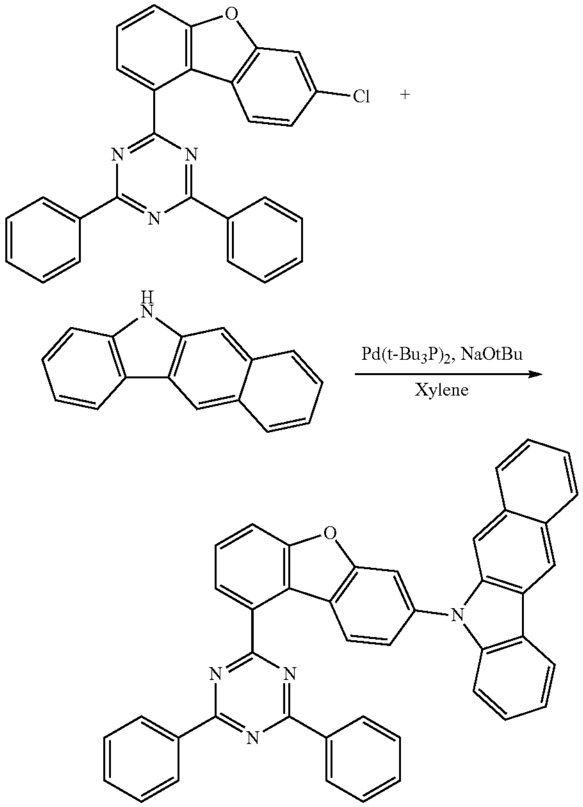

Intermediate 1 (20 g, 46.2 mmol), Chemical Formula a (10 g, 46.2 mmol) and sodium tert-butoxide (8.9 g, 92.4 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 1 (14.7 g). (Yield 52%, MS: $[M+H]^+$=615)

Synthesis Example 2

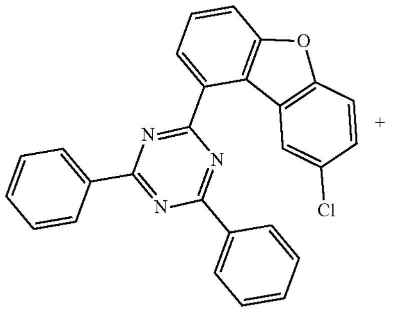

-continued

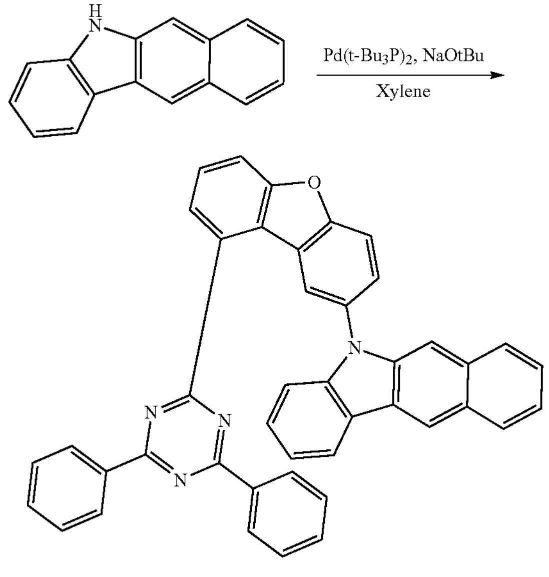

Intermediate 2 (20 g, 46.2 mmol), Chemical Formula a (10 g, 46.2 mmol) and sodium tert-butoxide (8.9 g, 92.4 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 2 (19.3 g). (Yield 68%, MS: $[M+H]^+=615$)

Synthesis Example 3

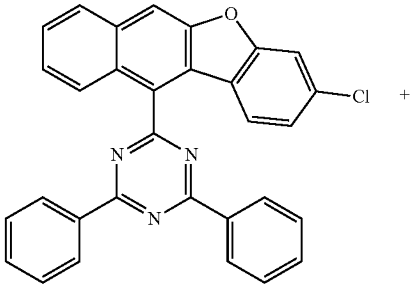

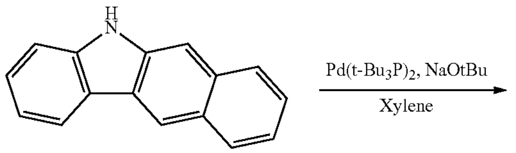

-continued

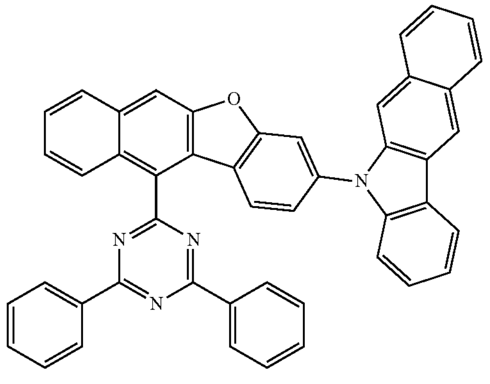

Intermediate 3 (20 g, 41.4 mmol), Chemical Formula a (9 g, 41.4 mmol) and sodium tert-butoxide (8 g, 82.8 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 3 (16.8 g). (Yield 61%, MS: $[M+H]^+=665$)

Synthesis Example 4

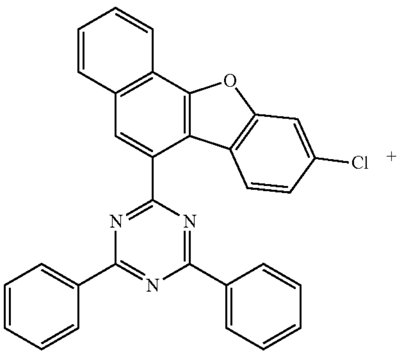

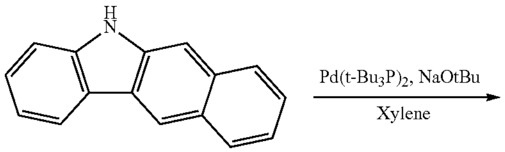

-continued

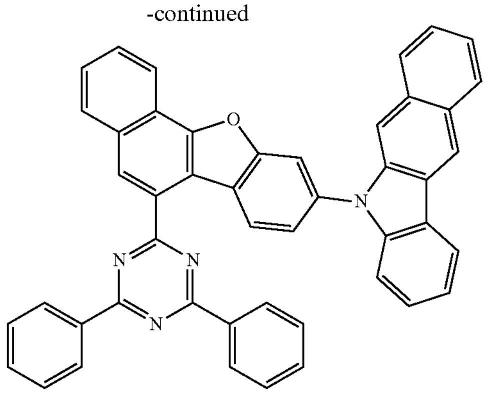

Intermediate 4 (20 g, 41.4 mmol), Chemical Formula a (9 g, 41.4 mmol) and sodium tert-butoxide (8 g, 82.8 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 4 (16.2 g). (Yield 59%, MS: $[M+H]^+$=665)

Synthesis Example 5

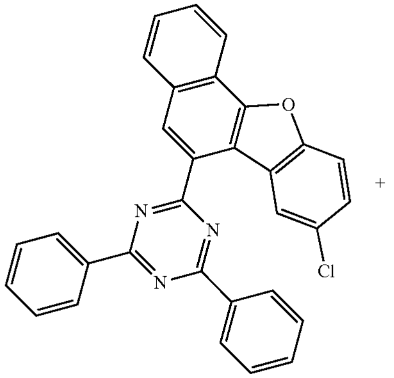

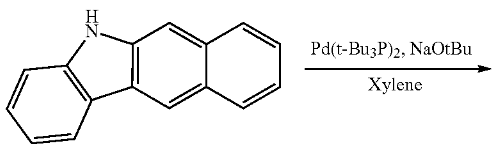

-continued

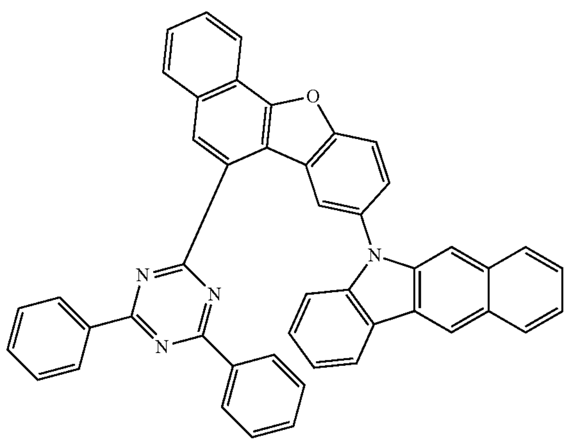

Intermediate 5 (20 g, 41.4 mmol), Chemical Formula a (9 g, 41.4 mmol) and sodium tert-butoxide (8 g, 82.8 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 5 (13.7 g). (Yield 50%, MS: $[M+H]^+$=665)

Synthesis Example 6

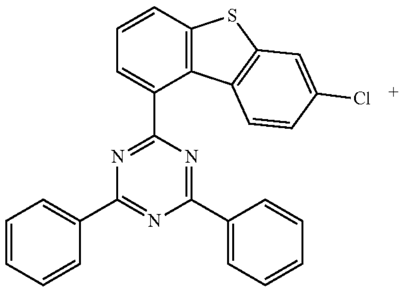

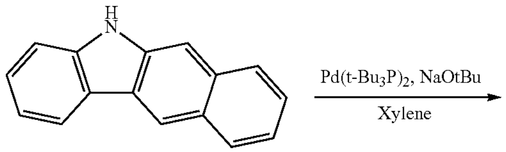

-continued

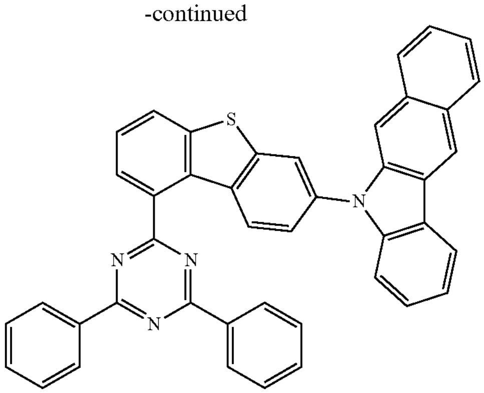

Intermediate 6 (20 g, 44.5 mmol), Chemical Formula a (9.7 g, 44.5 mmol) and sodium tert-butoxide (8.6 g, 89.1 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 6 (14.9 g). (Yield 53%, MS: $[M+H]^+=631$)

Synthesis Example 7

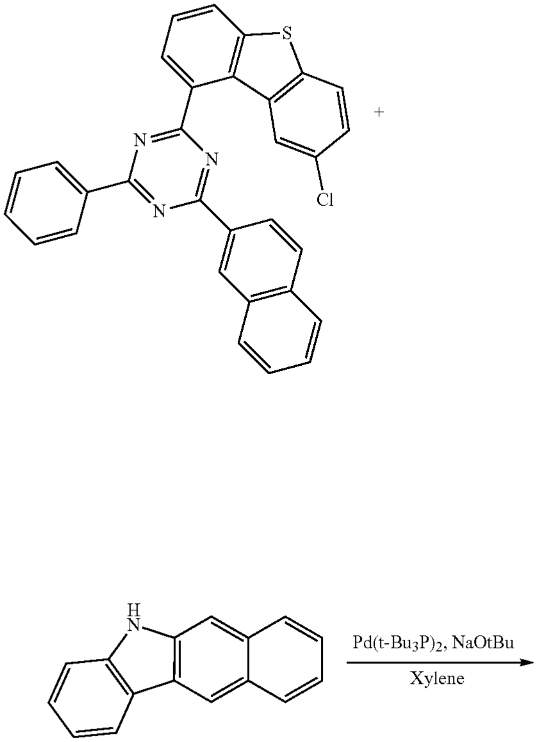

-continued

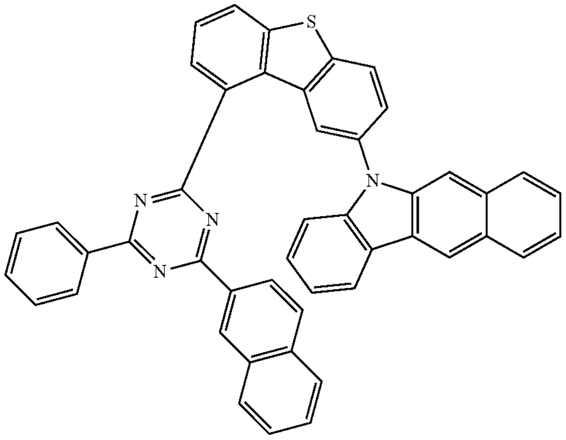

Intermediate 7 (20 g, 40.1 mmol), Chemical Formula a (8.7 g, 40.1 mmol) and sodium tert-butoxide (7.7 g, 80.1 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 7 (14.2 g). (Yield 52%, MS: $[M+H]^+=681$)

Synthesis Example 8

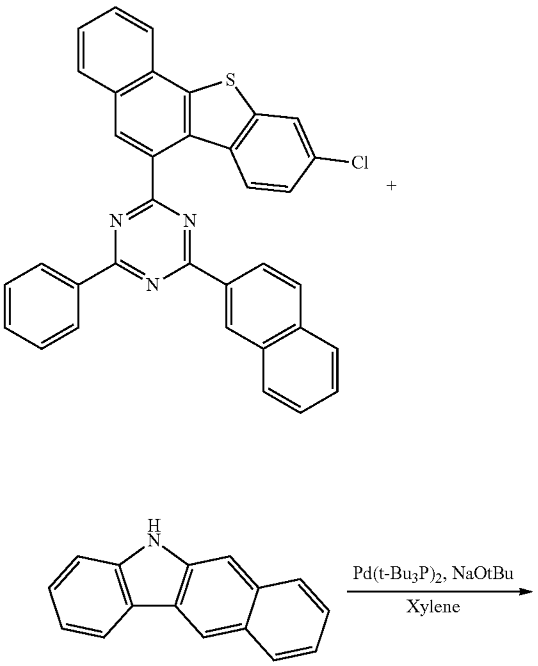

-continued

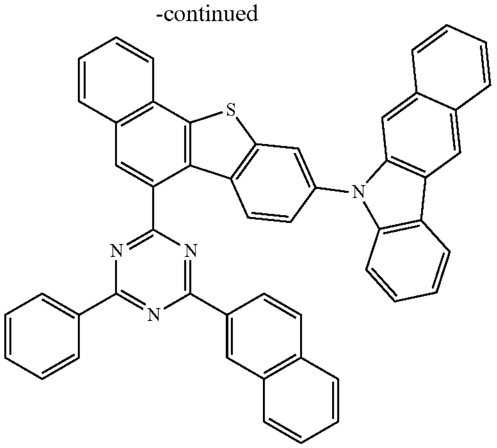

Intermediate 8 (20 g, 36.4 mmol), Chemical Formula a (7.9 g, 36.4 mmol) and sodium tert-butoxide (7 g, 72.8 mmol) were introduced to xylene (400 ml) under the nitrogen atmosphere, and the result was stirred and refluxed. After that, bis(tri-tert-butylphosphine)palladium(0) (0.4 g, 0.7 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 8 (13.3 g). (Yield 50%, MS: $[M+H]^+=731$)

Synthesis Example 9

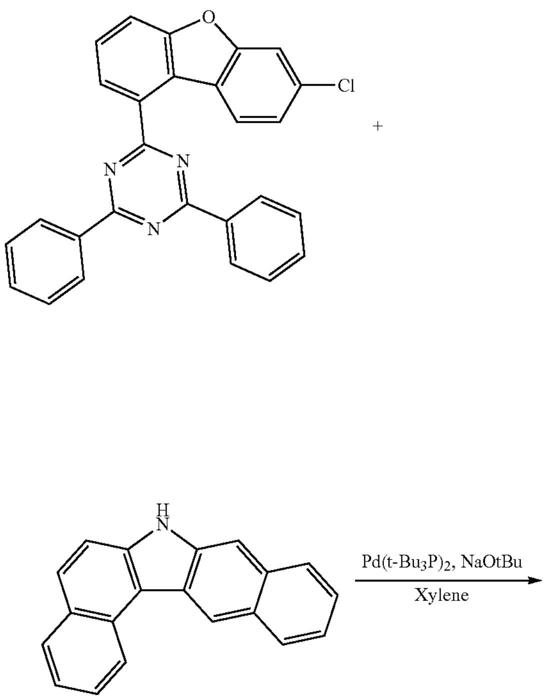

-continued

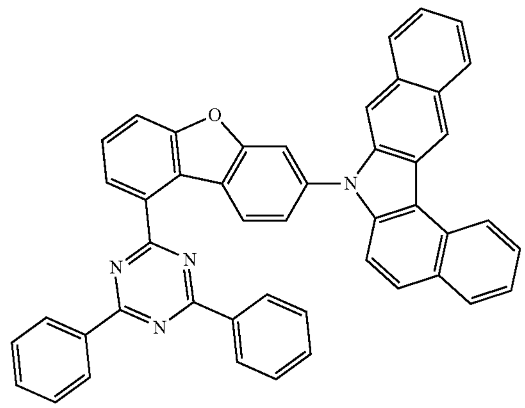

Intermediate 1 (20 g, 36.4 mmol), Chemical Formula b (9.7 g, 36.4 mmol) and sodium tert-butoxide (7 g, 72.8 mmol) were introduced to xylene (400 ml) under the nitrogen atmosphere, and the result was stirred and refluxed. After that, bis(tri-tert-butylphosphine)palladium(0) (0.4 g, 0.7 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 9 (14.8 g). (Yield 61%, MS: $[M+H]^+=665$)

Synthesis Example 10

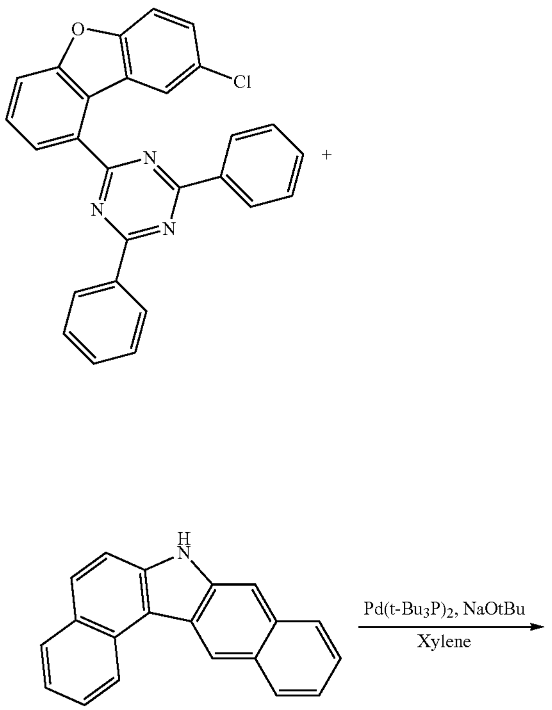

-continued

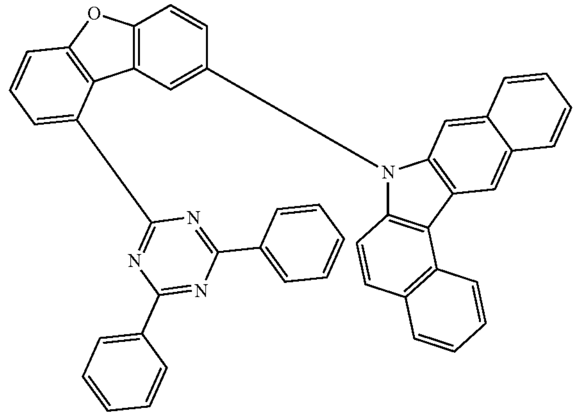

Intermediate 2 (20 g, 46.2 mmol), Chemical Formula b (12.3 g, 46.2 mmol) and sodium tert-butoxide (8.9 g, 92.4 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 10 (18.4 g). (Yield 60%, MS: $[M+H]^+=665$)

Synthesis Example 11

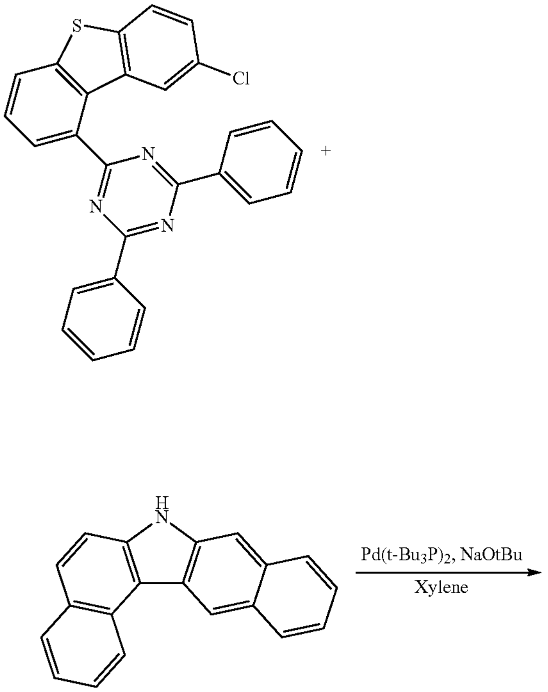

-continued

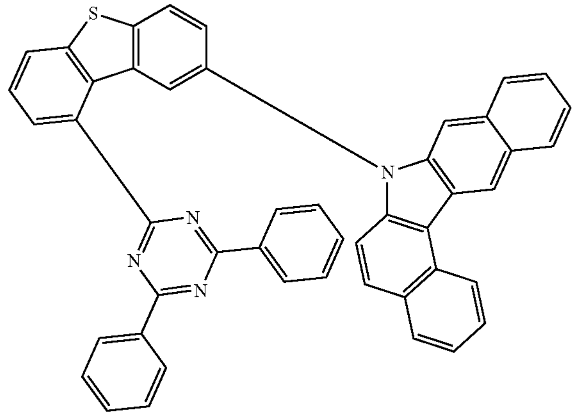

Intermediate 11 (20 g, 44.5 mmol), Chemical Formula b (11.9 g, 44.5 mmol) and sodium tert-butoxide (8.6 g, 89.1 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 11 (17.6 g). (Yield 58%, MS: $[M+H]^+=681$)

Synthesis Example 12

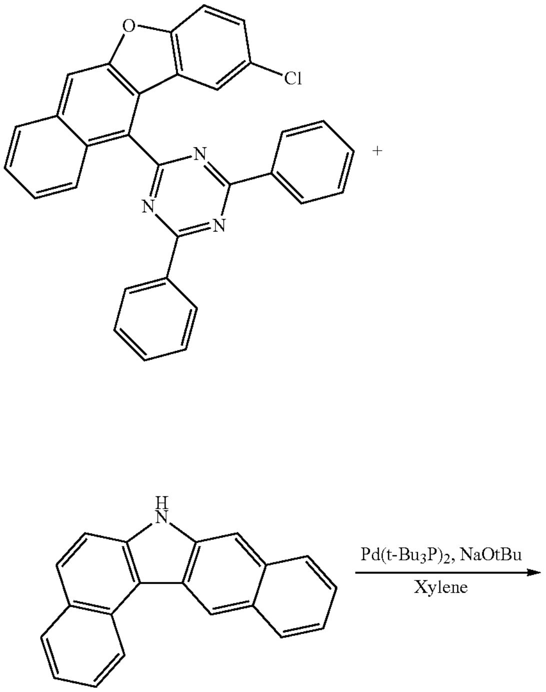

-continued

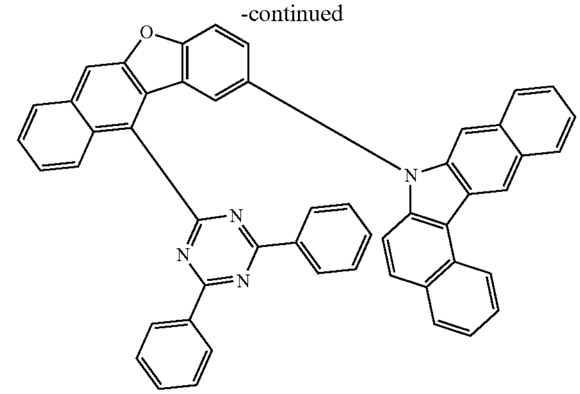

Intermediate 12 (20 g, 41.4 mmol), Chemical Formula b (11.1 g, 41.4 mmol) and sodium tert-butoxide (8 g, 82.8 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 12 (14.8 g). (Yield 50%, MS: $[M+H]^+=715$)

Synthesis Example 13

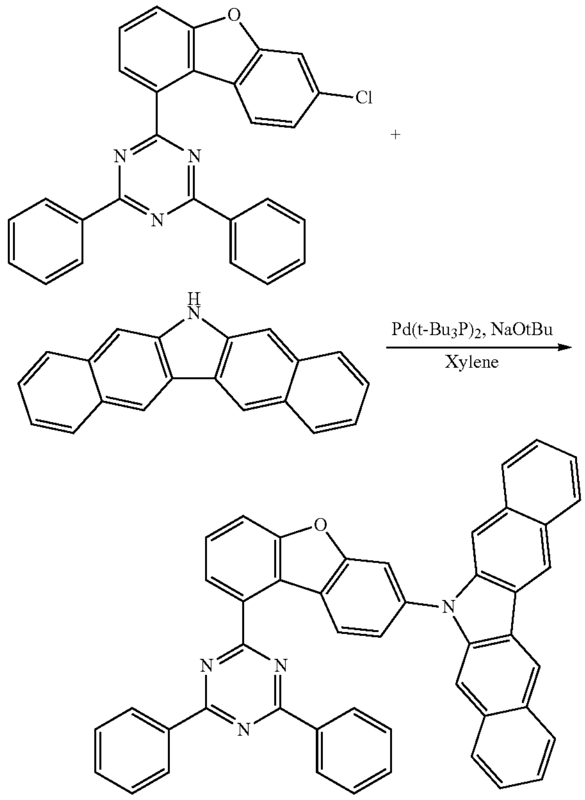

Intermediate 1 (20 g, 46.2 mmol), Chemical Formula c (12.3 g, 46.2 mmol) and sodium tert-butoxide (8.9 g, 92.4 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 13 (17.8 g). (Yield 58%, MS: $[M+H]^+=665$)

Synthesis Example 14

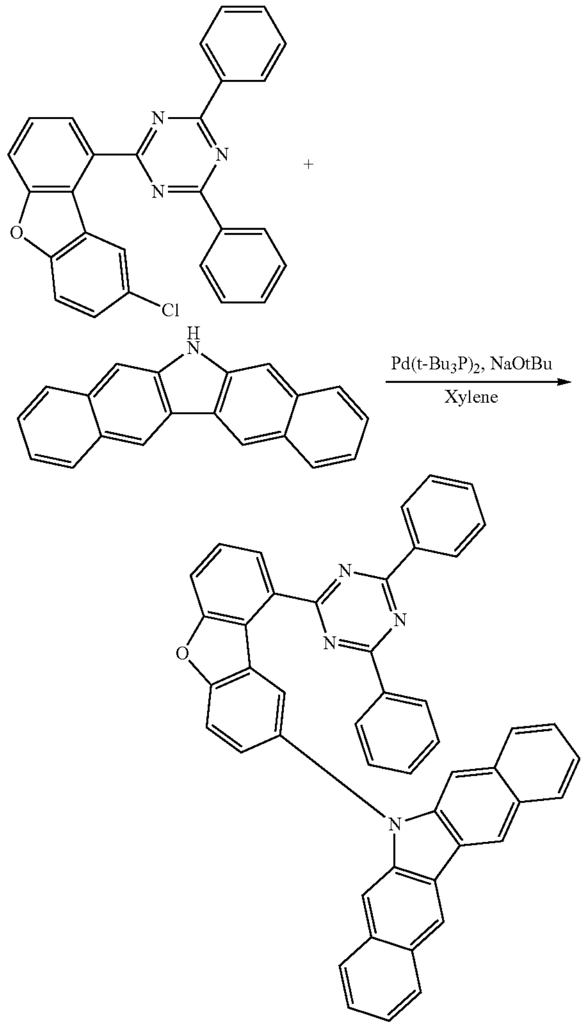

Intermediate 2 (20 g, 46.2 mmol), Chemical Formula c (12.3 g, 46.2 mmol) and sodium tert-butoxide (8.9 g, 92.4 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 14 (15.3 g). (Yield 50%, MS: [M+H]$^+$=665)

Synthesis Example 15

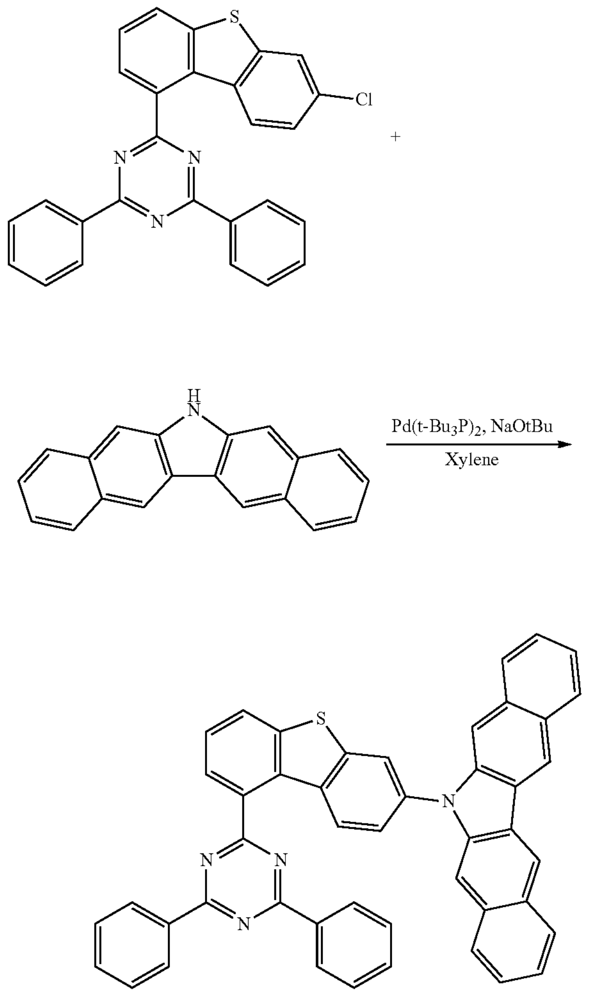

Intermediate 6 (20 g, 44.5 mmol), Chemical Formula c (11.9 g, 44.5 mmol) and sodium tert-butoxide (8.6 g, 89.1 mmol) were introduced to xylene (400 ml) under the nitrogen atmosphere, and the result was stirred and refluxed. After that, bis(tri-tert-butylphosphine)palladium(0) (0.5 g, 0.9 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 15 (15.4 g). (Yield 51%, MS: [M+H]$^+$=681)

Synthesis Example 16

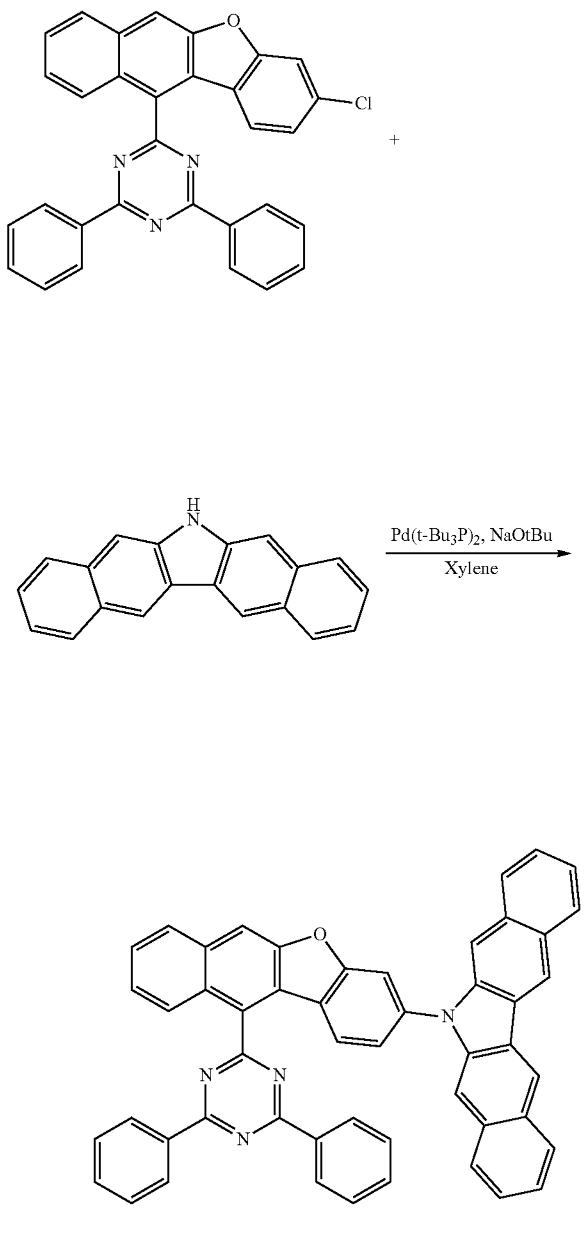

Intermediate 3 (20 g, 41.4 mmol), Chemical Formula c (11.1 g, 41.4 mmol) and sodium tert-butoxide (8 g, 82.8 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 16 (16.9 g). (Yield 57%, MS: [M+H]$^+$=715)

Synthesis Example 17

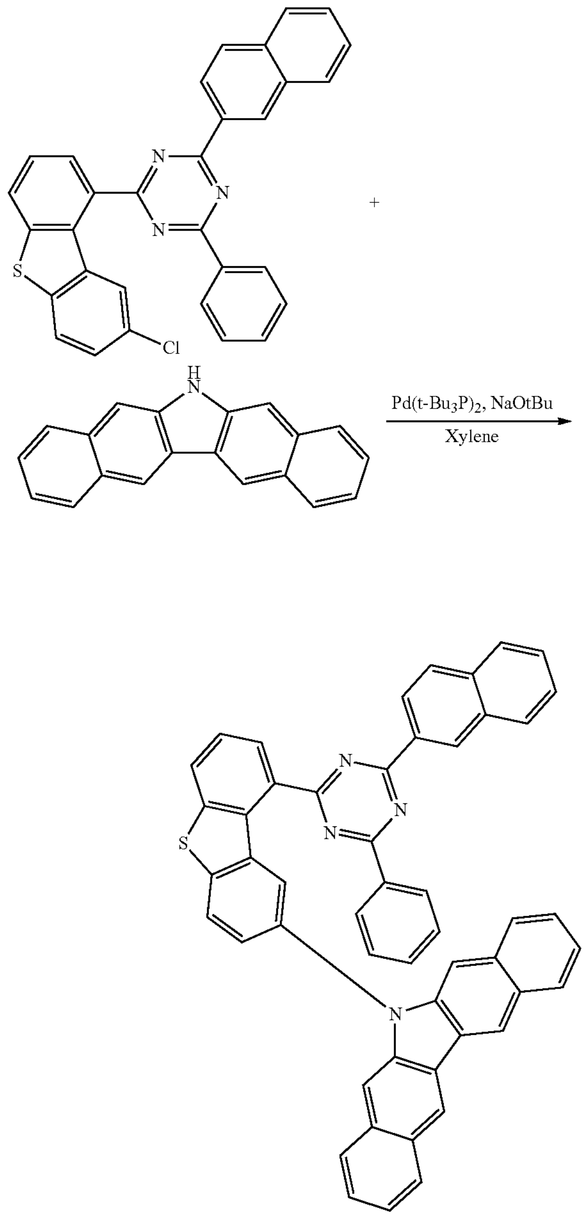

Intermediate 7 (20 g, 40.1 mmol), Chemical Formula c (10.7 g, 40.1 mmol) and sodium tert-butoxide (7.7 g, 80.1 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 17 (19.9 g). (Yield 68%, MS: $[M+H]^+$=731)

Synthesis Example 18

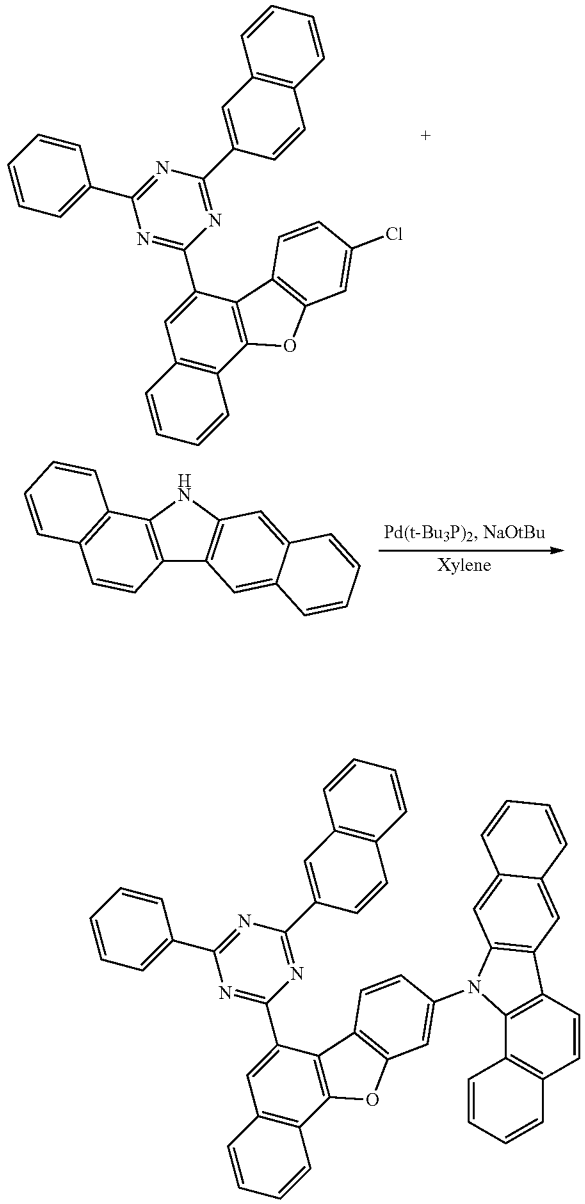

Intermediate 18 (20 g, 37.5 mmol), Chemical Formula d (10 g, 37.5 mmol) and sodium tert-butoxide (7.2 g, 75 mmol) were introduced to xylene (400 ml) under the nitrogen atmosphere, and the result was stirred and refluxed. After that, bis(tri-tert-butylphosphine)palladium(0) (0.4 g, 0.8 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 18 (15.2 g). (Yield 53%, MS: $[M+H]^+$=765)

Synthesis Example 19

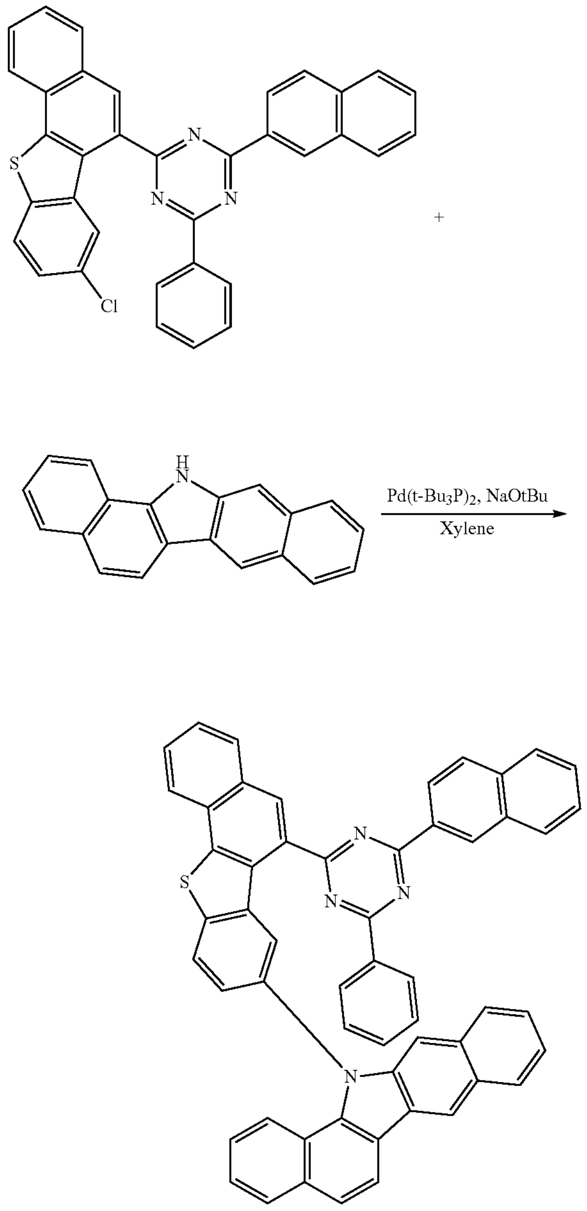

Intermediate 19 (20 g, 36.4 mmol), Chemical Formula d (9.7 g, 36.4 mmol) and sodium tert-butoxide (7 g, 72.8 mmol) were introduced to xylene (400 ml) under the nitrogen atmosphere, and the result was stirred and refluxed. After that, bis(tri-tert-butylphosphine)palladium(0) (0.4 g, 0.7 mmol) was introduced thereto. The reaction was terminated after 2 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 19 (14.2 g). (Yield 50%, MS: $[M+H]^+$=781)

Synthesis Example 20

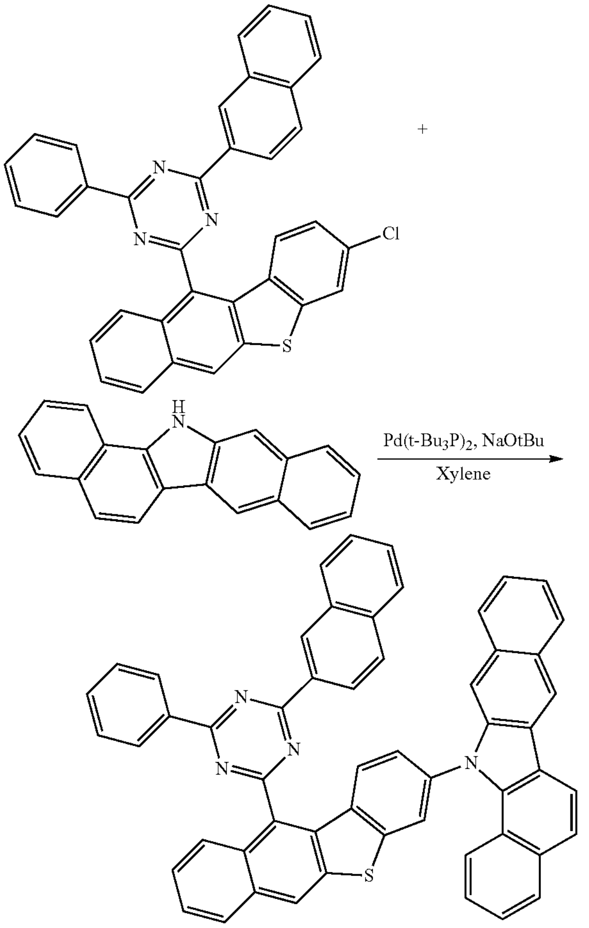

Intermediate 20 (20 g, 36.4 mmol), Chemical Formula d (9.7 g, 36.4 mmol) and sodium tert-butoxide (7 g, 72.8 mmol) were introduced to xylene (400 ml) under the nitrogen atmosphere, and the result was stirred and refluxed. After that, bis(tri-tert-butylphosphine)palladium(0) (0.4 g, 0.7 mmol) was introduced thereto. The reaction was terminated after 3 hours, and the result was cooled to room temperature and vacuumed to remove the solvent. After that, the compound was completely dissolved in chloroform again, and washed twice with water. Then, the organic layer was separated, treated with anhydrous magnesium sulfate, then filtered, and the filtrate was vacuum distilled. The concentrated compound was purified using silica gel column chromatography to obtain Compound 20 (19.3 g). (Yield 68%, MS: $[M+H]^+$=781)

EXAMPLES AND COMPARATIVE EXAMPLES

Comparative Example 1

A glass substrate on which indium tin oxide (ITO) coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 compound was formed to a thickness of 1150 Å as a hole injection layer while p-doping the following A-1 compound thereto in a concentration of 1.5%. On the hole injection layer, the following HT-1 compound was vacuum deposited to form a hole transfer layer having a film thickness of 800 Å. Subsequently, the following EB-1 compound was vacuum deposited on the hole transfer layer to a film thickness of 150 Å to form an electron blocking layer. Then, on the EB-1 deposited film, the following RH-1 compound and the following Dp-7 compound were vacuum deposited in a weight ratio of 98:2 to form a red light emitting layer having a thickness of 400 Å. On the light emitting layer, a hole blocking layer was formed by vacuum depositing the following HB-1 compound to a film thickness of 30 Å. Subsequently, an electron injection and transfer layer was formed on the hole blocking layer to a thickness of 300 Å by vacuum depositing the following ET-1 Compound and the following LiQ compound in a weight ratio of 2:1. On the electron injection and transfer layer, a cathode was formed by consecutively depositing lithium fluoride (LiF) and aluminum to a thickness of 12 Å and a thickness of 1,000 Å, respectively.

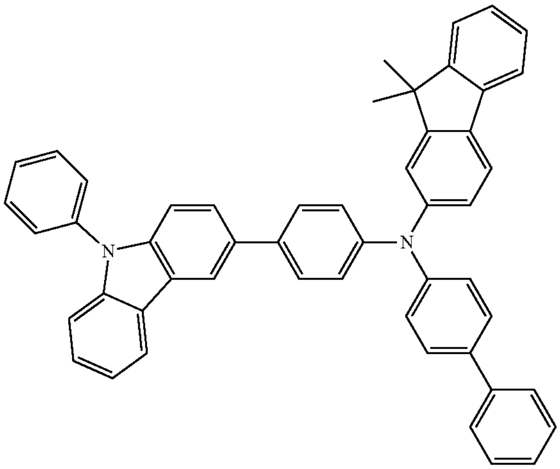

HI-1

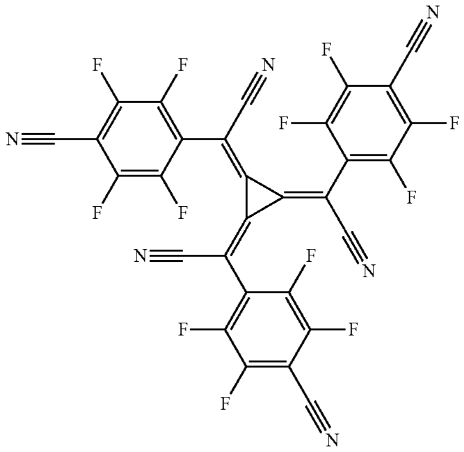

A-1

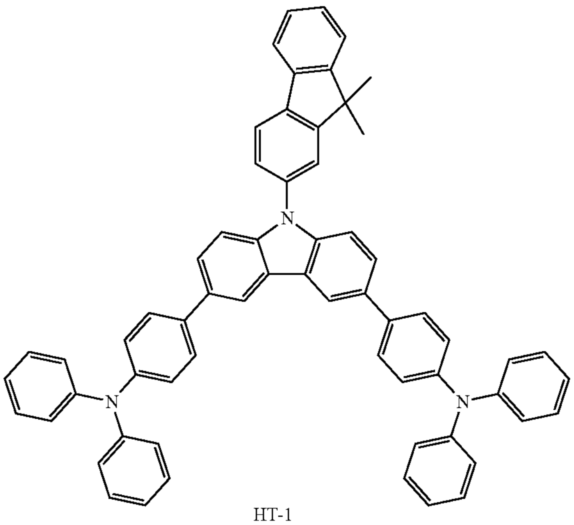

HT-1

-continued
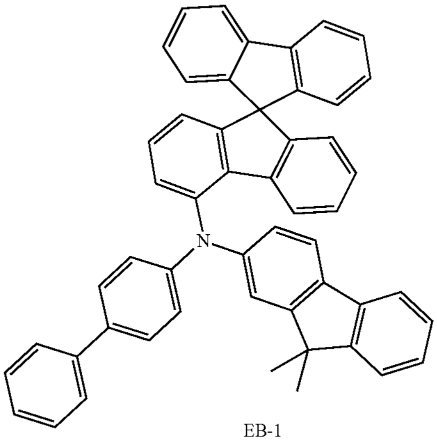
EB-1
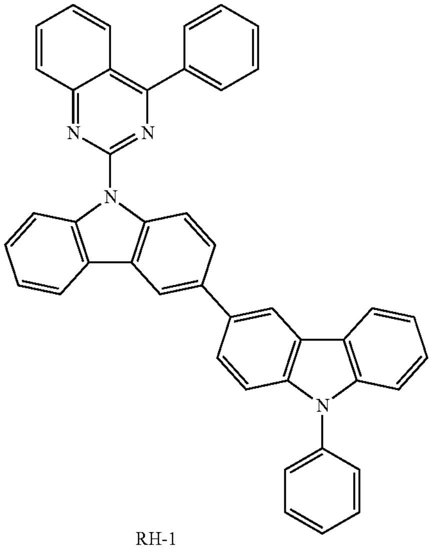
RH-1
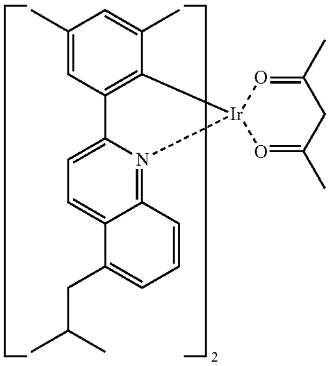
Dp-7
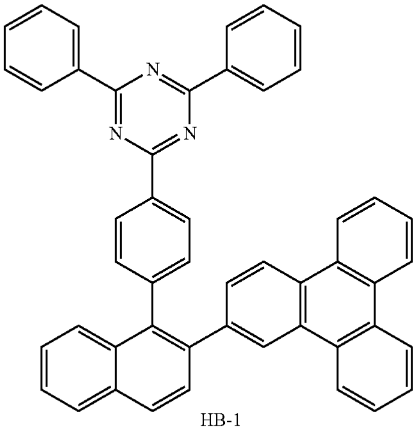
HB-1
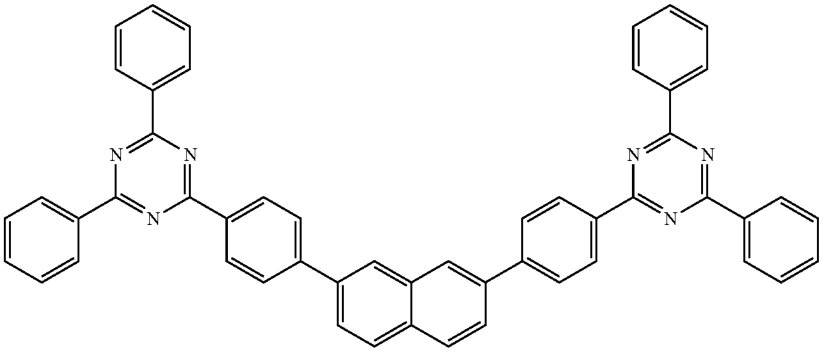
ET-1
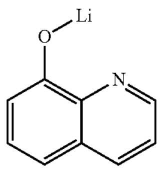
LiQ In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2\times10^{-7}$ torr to $5\times10^{-6}$ torr, and as a result, an organic light emitting device was manufactured.

Example 1 to Example 20

Organic light emitting devices were manufactured in the same manner as the organic light emitting device of Comparative Example 1 except that compounds described in the following Table 1 were used instead of RH-1.

Comparative Example 2 to Comparative Example 15

Organic light emitting devices were manufactured in the same manner as the organic light emitting device of Comparative Example 1 except that compounds described in the following Table 1 were used instead of RH-1.

Compounds C-1 to C-14 used in the comparative examples described in the following Table 1 are as follows.

C-1

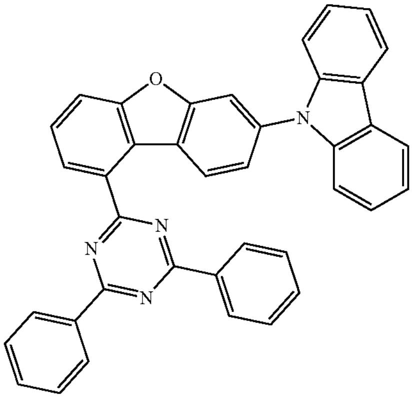

C-2

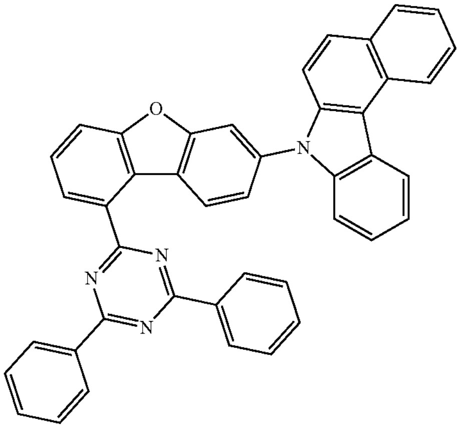

-continued

C-3

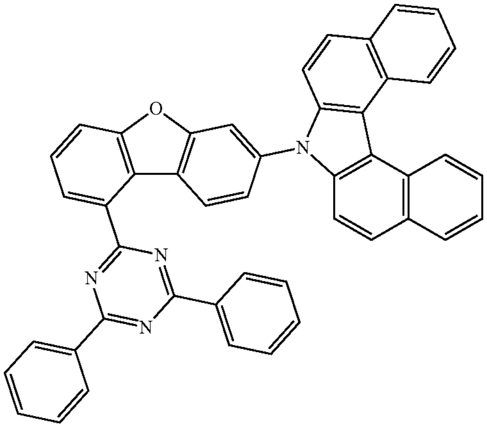

C-4

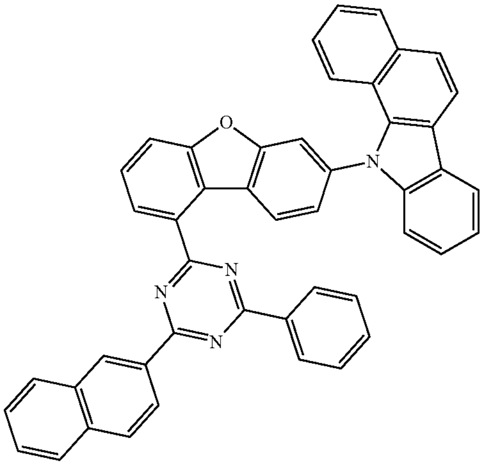

C-5

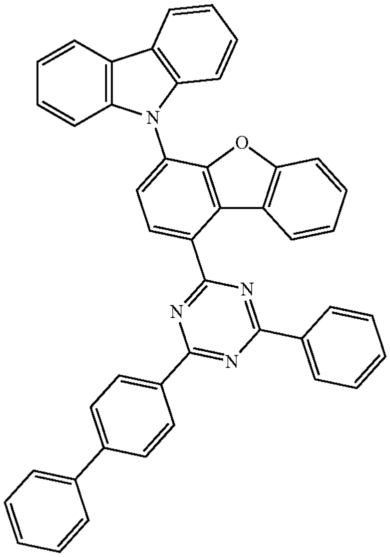

-continued
C-6
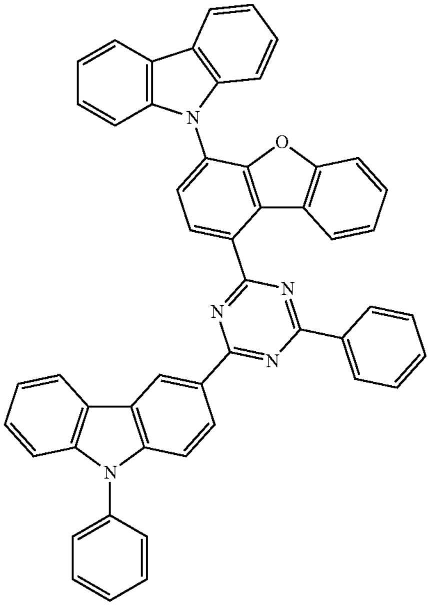
C-7
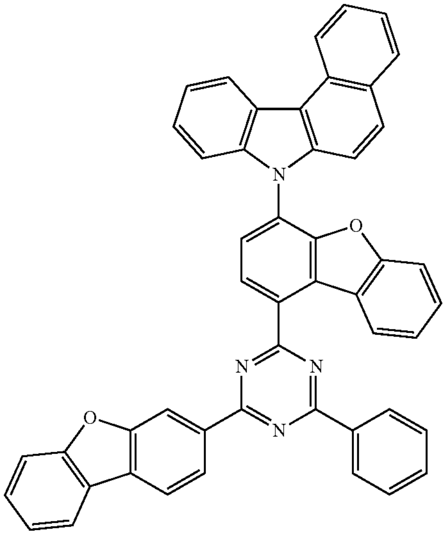
C-8
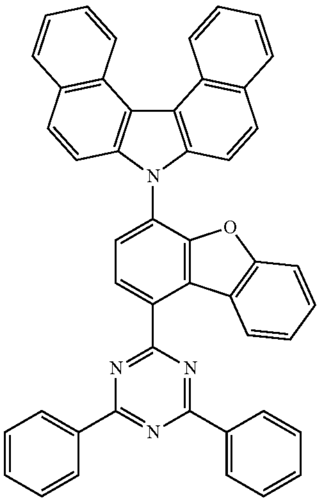
-continued
C-9
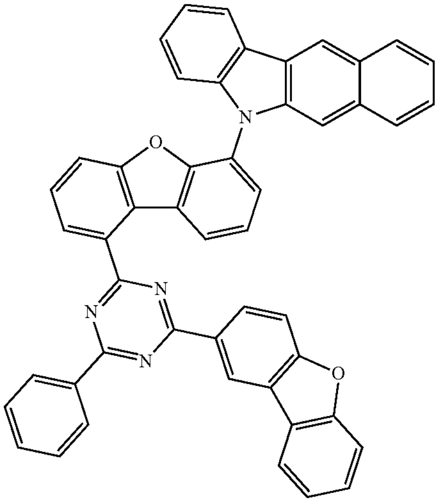
C-10
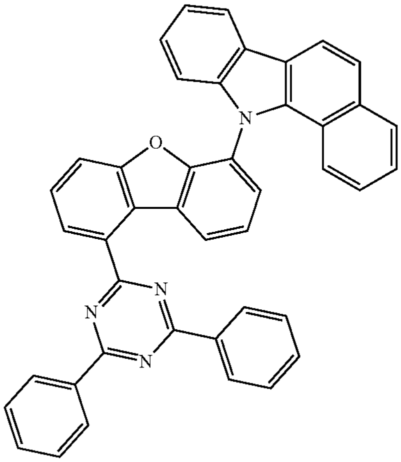
C-11
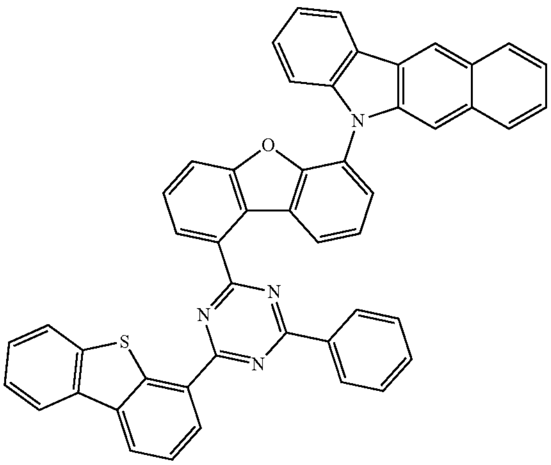

-continued

C-12

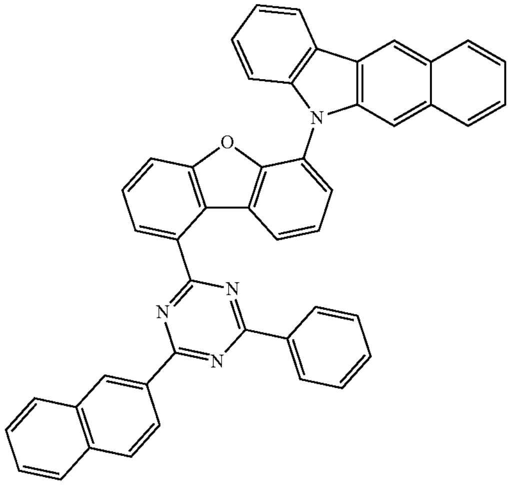

C-13

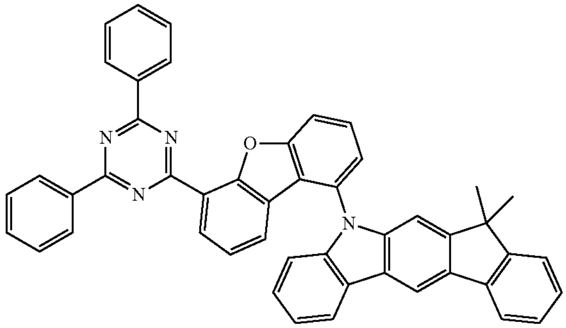

-continued

C-14

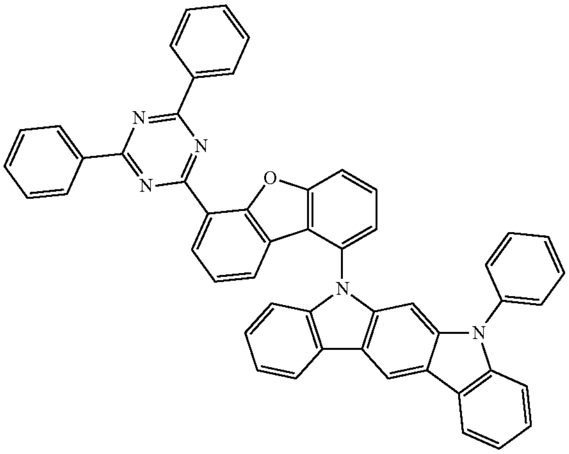

When a current was applied to each of the organic light emitting devices manufactured in Example 1 to Example 74 and Comparative Example 1 to Comparative Example 15, voltage, efficiency and lifetime were measured (based on 6000 nit), and the results are shown in the following Table 1 and Table 2. The lifetime T95 means time taken for luminance to decrease to 95% from initial luminance (6000 nit).

TABLE 1

| Category | Material | Driving Voltage (V) | Efficiency (cd/A) | Lifetime T95 (hr) | Light Emission Color |
|---|---|---|---|---|---|
| Comparative Example 1 | RH-1 | 4.34 | 38.3 | 193 | Red |
| Example 1 | Compound 1 | 3.63 | 44.3 | 301 | Red |
| Example 2 | Compound 2 | 3.61 | 43.7 | 278 | Red |
| Example 3 | Compound 3 | 3.67 | 45.8 | 323 | Red |
| Example 4 | Compound 4 | 3.62 | 45.1 | 315 | Red |
| Example 5 | Compound 5 | 3.60 | 44.5 | 287 | Red |
| Example 6 | Compound 6 | 3.71 | 46.3 | 274 | Red |
| Example 7 | Compound 7 | 3.72 | 45.9 | 253 | Red |
| Example 8 | Compound 8 | 3.74 | 46.5 | 281 | Red |
| Example 9 | Compound 9 | 3.51 | 47.8 | 319 | Red |
| Example 10 | Compound 10 | 3.53 | 47.2 | 313 | Red |
| Example 11 | Compound 11 | 3.63 | 48.4 | 291 | Red |
| Example 12 | Compound 12 | 3.50 | 47.3 | 302 | Red |
| Example 13 | Compound 13 | 3.54 | 48.9 | 351 | Red |
| Example 14 | Compound 14 | 3.47 | 47.1 | 324 | Red |
| Example 15 | Compound 15 | 3.50 | 49.0 | 305 | Red |
| Example 16 | Compound 16 | 3.53 | 48.2 | 337 | Red |
| Example 17 | Compound 17 | 3.51 | 47.6 | 292 | Red |
| Example 18 | Compound 18 | 3.40 | 43.9 | 253 | Red |
| Example 19 | Compound 19 | 3.42 | 45.1 | 242 | Red |
| Example 20 | Compound 20 | 3.37 | 44.5 | 231 | Red |
| Comparative Example 2 | C-1 | 4.13 | 37.2 | 131 | Red |
| Comparative Example 3 | C-2 | 4.81 | 34.1 | 140 | Red |
| Comparative Example 4 | C-3 | 4.30 | 35.1 | 167 | Red |
| Comparative Example 5 | C-4 | 4.68 | 33.0 | 79 | Red |

TABLE 1-continued

| Category | Material | Driving Voltage (V) | Efficiency (cd/A) | Lifetime T95 (hr) | Light Emission Color |
|---|---|---|---|---|---|
| Comparative Example 6 | C-5 | 4.41 | 32.4 | 97 | Red |
| Comparative Example 7 | C-6 | 4.77 | 29.7 | 61 | Red |
| Comparative Example 8 | C-7 | 4.21 | 34.0 | 103 | Red |
| Comparative Example 9 | C-8 | 4.19 | 35.7 | 114 | Red |
| Comparative Example 10 | C-9 | 4.21 | 37.3 | 178 | Red |
| Comparative Example 11 | C-10 | 4.59 | 35.7 | 142 | Red |
| Comparative Example 12 | C-11 | 4.71 | 31.3 | 73 | Red |
| Comparative Example 13 | C-12 | 4.60 | 32.3 | 121 | Red |
| Comparative Example 14 | C-13 | 4.61 | 34.3 | 73 | Red |
| Comparative Example 15 | C-14 | 4.49 | 36.7 | 133 | Red |

Example 21 to Example 74

Organic light emitting devices were manufactured in the same manner as in Comparative Example 1 except that a first host and a second host described in the following Table 2 were vacuum deposited in a ratio of 1:1 instead of RH-1.

Compounds used as the second host listed in the following Table 2 are as follows.

Z-1

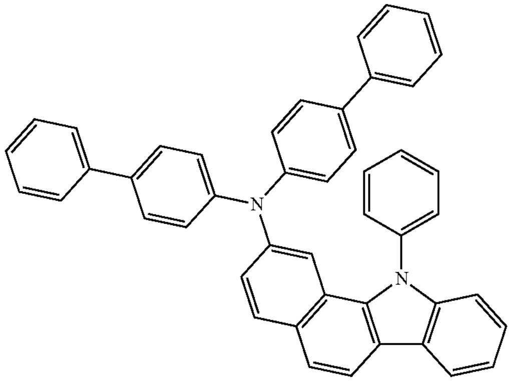

Z-2

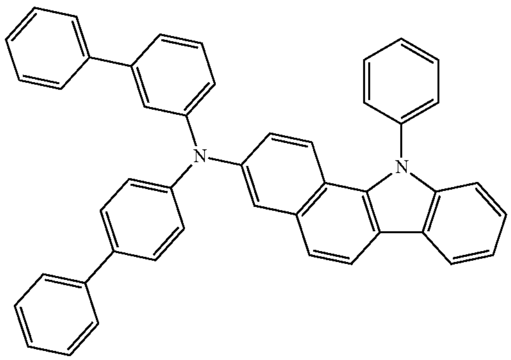

-continued

Z-3

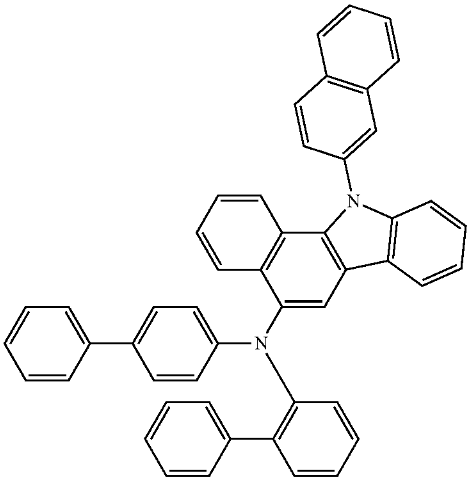

Z-4

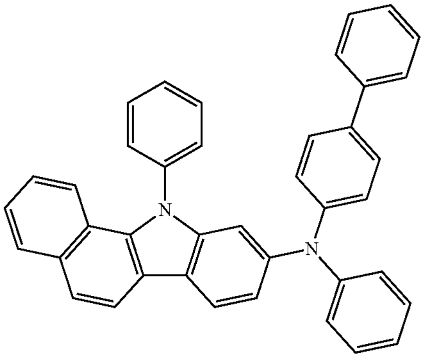

-continued
Z-5
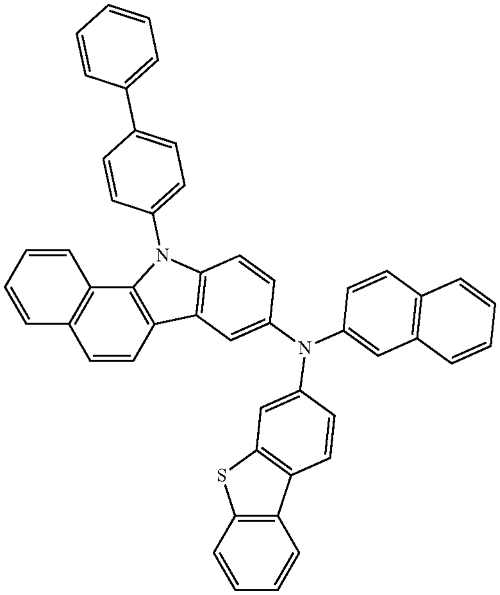
Z-6
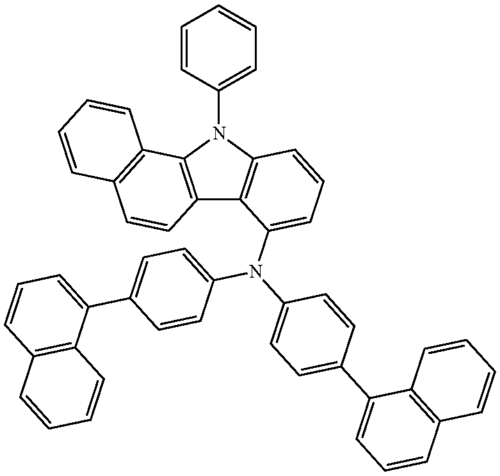
Z-7
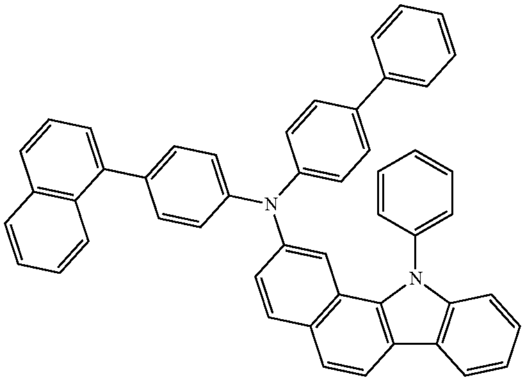
-continued
Z-8
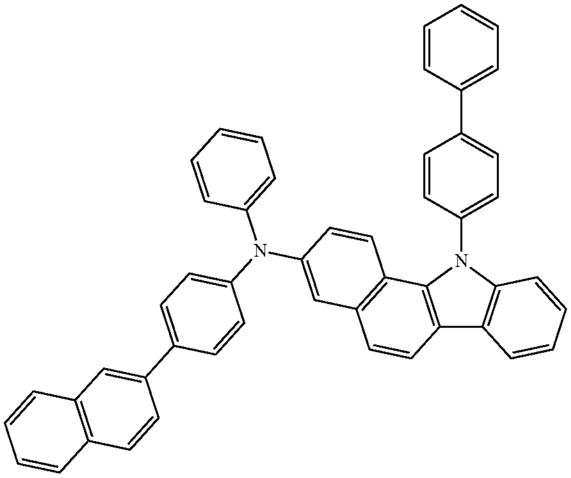
Z-9
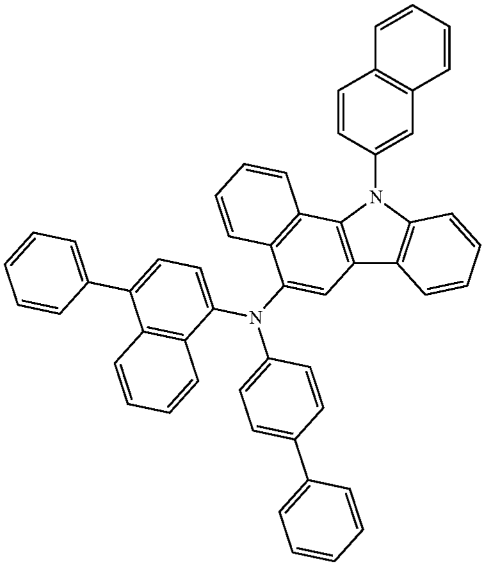
Z-10
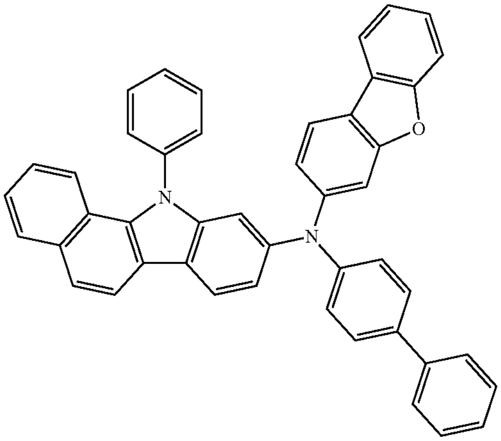

-continued
Z-11
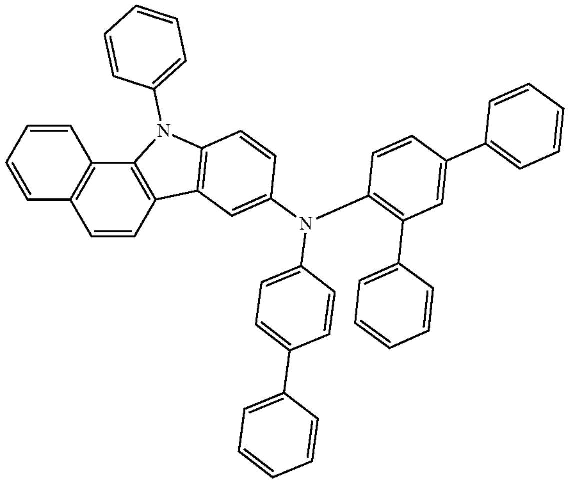
Z-12
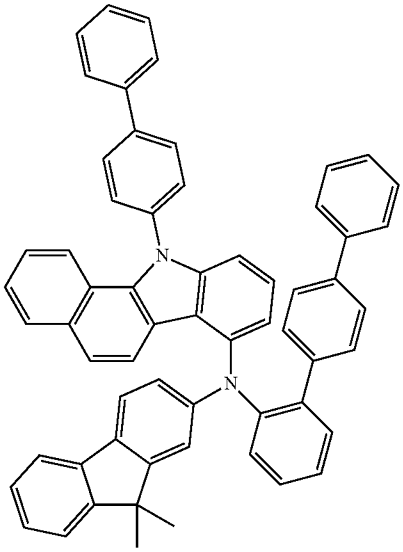
Z-13
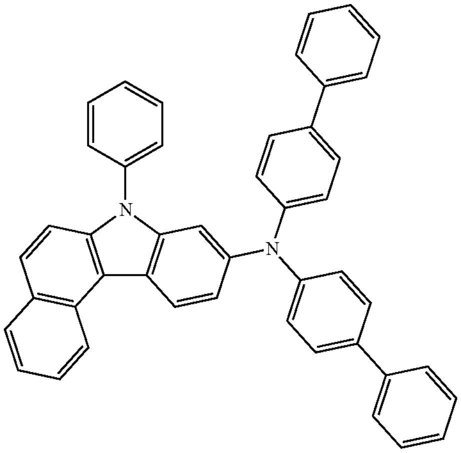
-continued
Z-14
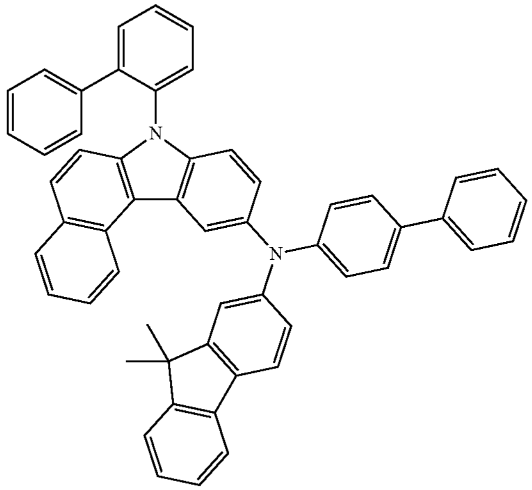
Z-15
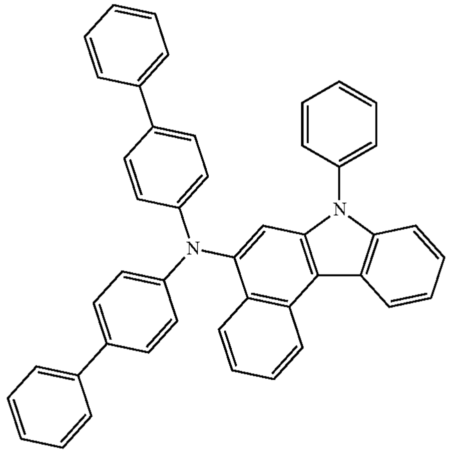
Z-16
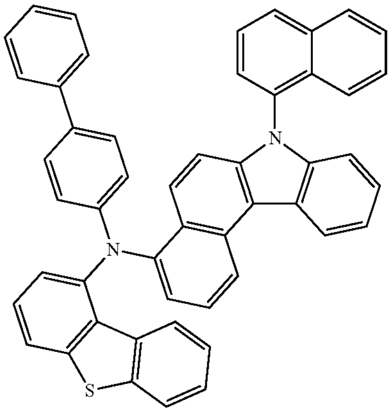

Z-17
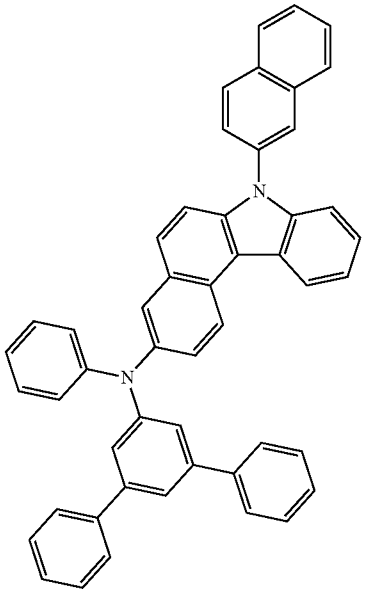
Z-18
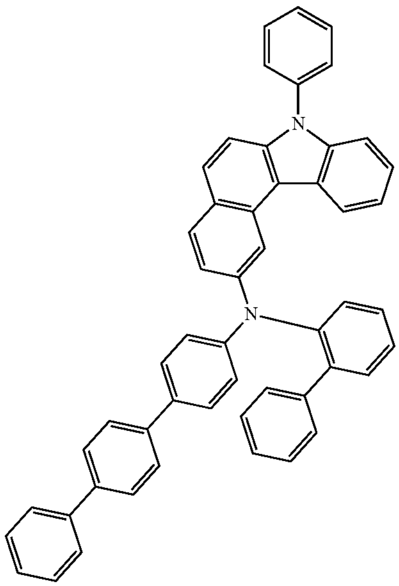
Z-19
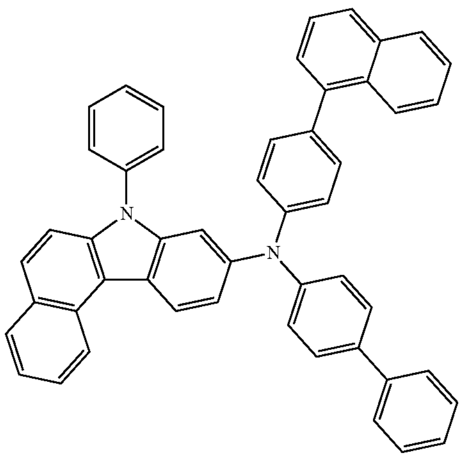
Z-20
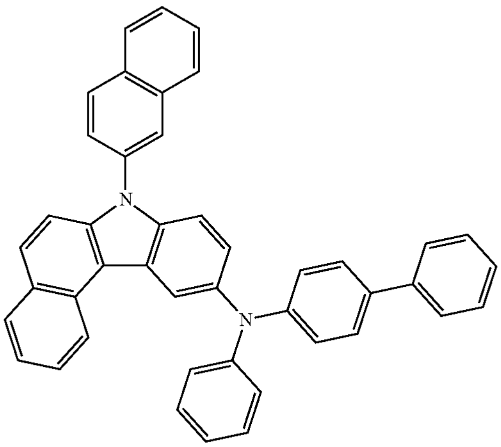
Z-21
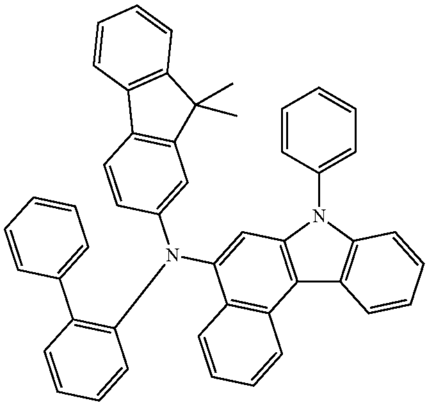
Z-22
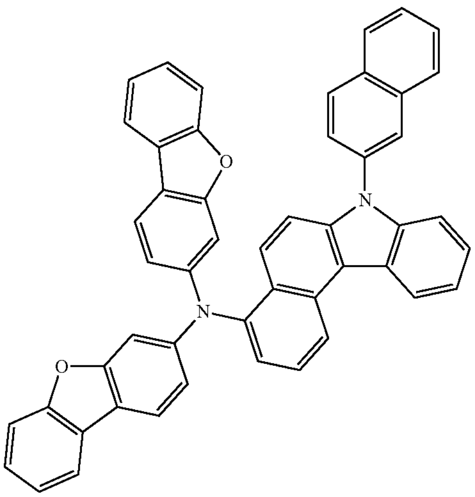

-continued
Z-23
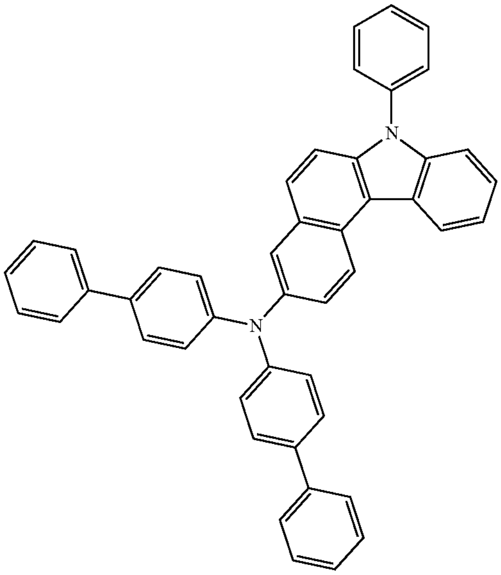
Z-24
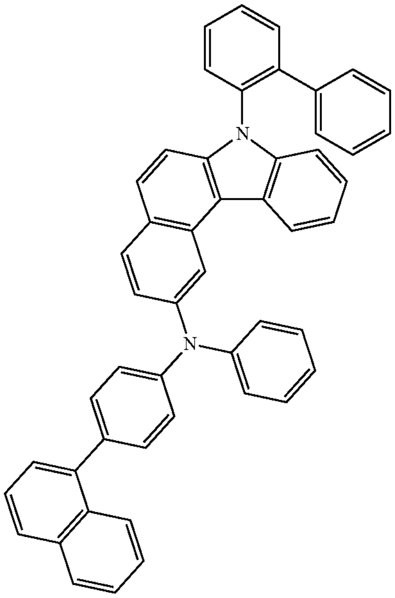
Z-25
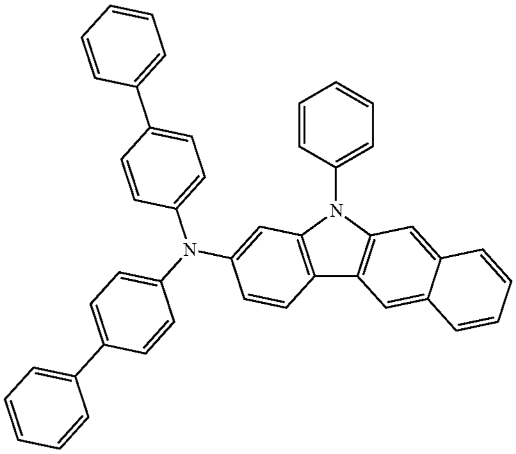
-continued
Z-26
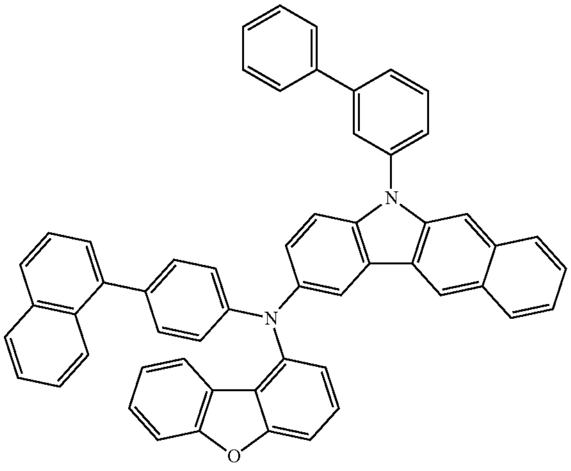
Z-27
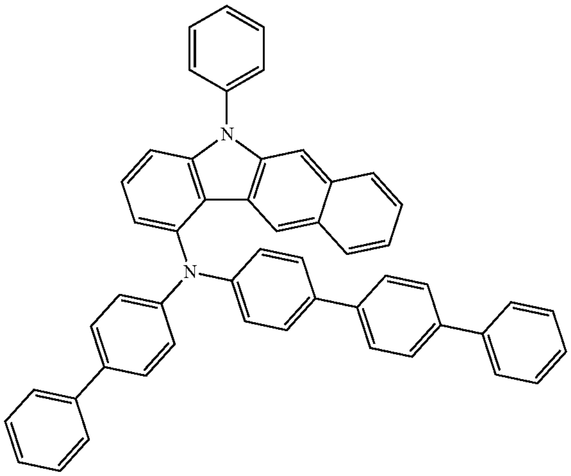
Z-28
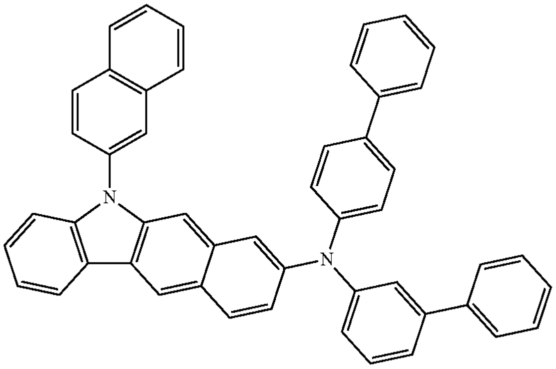

-continued
Z-29
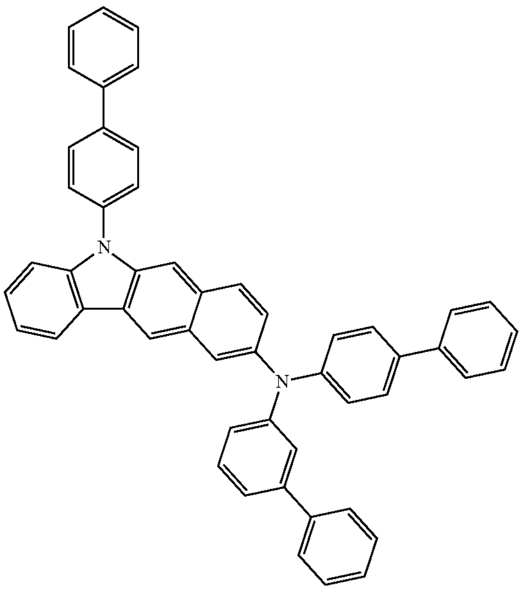
Z-30
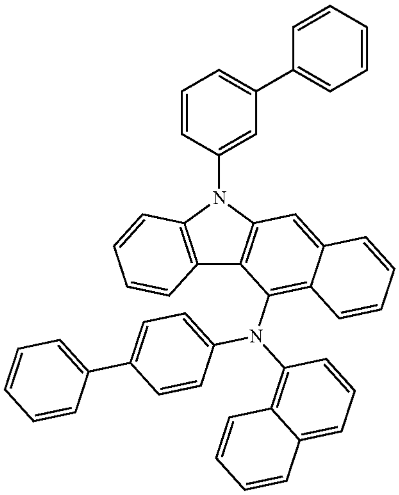
Z-31
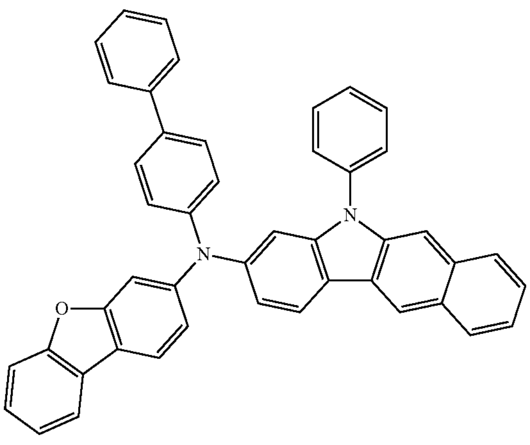
-continued
Z-32
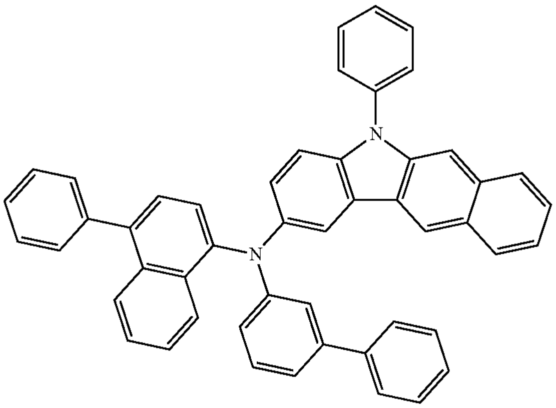
Z-33
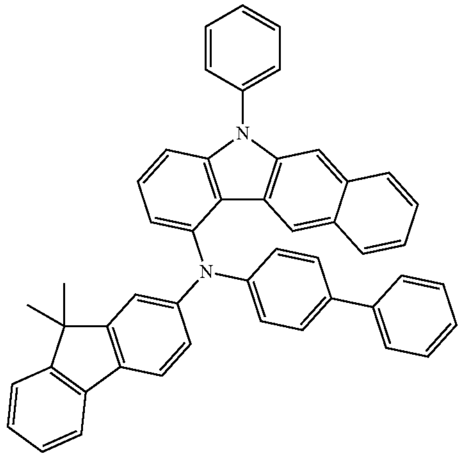
Z-34
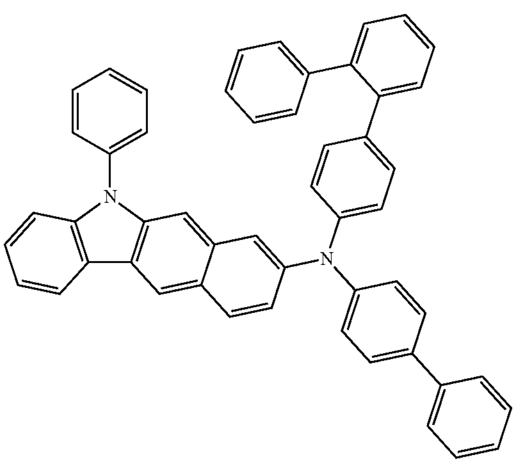

-continued

Z-35

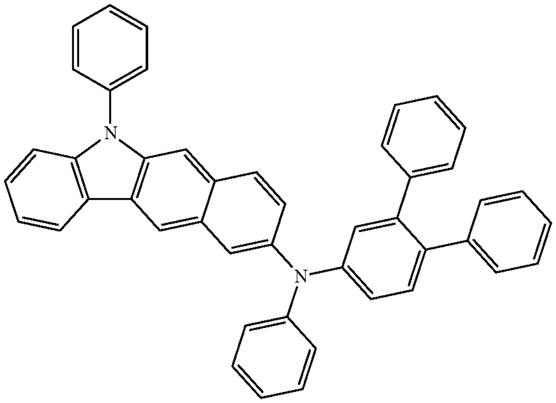

Z-36

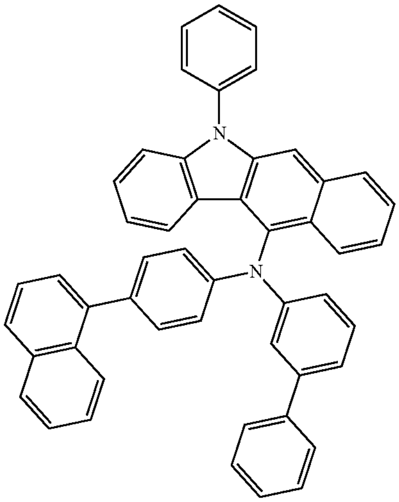

TABLE 2

| Category | First Host | Second Host | Driving Voltage (V) | Efficiency (cd/A) | Lifetime T95 (hr) | Light Emission Color |
|---|---|---|---|---|---|---|
| Example 21 | Compound | Z-1 | 3.65 | 46.2 | 402 | Red |
| Example 22 | 1 | Z-4 | 3.68 | 46.9 | 411 | Red |
| Example 23 | | Z-10 | 3.69 | 46.2 | 408 | Red |
| Example 24 | | Z-13 | 3.68 | 45.2 | 423 | Red |
| Example 25 | | Z-21 | 3.65 | 45.9 | 417 | Red |
| Example 26 | | Z-25 | 3.67 | 45.1 | 408 | Red |
| Example 27 | | Z-31 | 3.70 | 46.3 | 421 | Red |
| Example 28 | | Z-33 | 3.68 | 45.0 | 417 | Red |
| Example 29 | Compound | Z-1 | 3.69 | 44.5 | 465 | Red |
| Example 30 | 2 | Z-4 | 3.68 | 44.8 | 469 | Red |
| Example 31 | | Z-10 | 3.72 | 45.9 | 458 | Red |
| Example 32 | | Z-13 | 3.68 | 44.5 | 461 | Red |
| Example 33 | | Z-21 | 3.63 | 45.7 | 454 | Red |
| Example 34 | | Z-25 | 3.60 | 45.9 | 451 | Red |
| Example 35 | | Z-31 | 3.62 | 45.2 | 467 | Red |
| Example 36 | | Z-33 | 3.67 | 45.8 | 462 | Red |
| Example 37 | Compound | Z-1 | 3.78 | 46.6 | 453 | Red |
| Example 38 | 8 | Z-4 | 3.77 | 47.9 | 451 | Red |
| Example 39 | | Z-10 | 3.79 | 48.1 | 449 | Red |
| Example 40 | | Z-13 | 3.75 | 47.8 | 467 | Red |
| Example 41 | | Z-21 | 3.71 | 47.5 | 452 | Red |
| Example 42 | | Z-25 | 3.79 | 48.9 | 461 | Red |
| Example 43 | | Z-31 | 3.72 | 48.9 | 468 | Red |
| Example 44 | | Z-33 | 3.78 | 48.0 | 455 | Red |
| Example 45 | Compound | Z-2 | 3.60 | 49.2 | 427 | Red |
| Example 46 | 13 | Z-7 | 3.68 | 50.9 | 3.97 | Red |

TABLE 2-continued

| Category | First Host | Second Host | Driving Voltage (V) | Efficiency (cd/A) | Lifetime T95 (hr) | Light Emission Color |
|---|---|---|---|---|---|---|
| Example 47 | | Z-11 | 3.60 | 49.9 | 419 | Red |
| Example 48 | | Z-15 | 3.58 | 50.7 | 410 | Red |
| Example 49 | | Z-18 | 3.57 | 51.5 | 391 | Red |
| Example 50 | | Z-19 | 3.61 | 49.8 | 415 | Red |
| Example 51 | | Z-22 | 3.59 | 50.7 | 493 | Red |
| Example 52 | | Z-23 | 3.60 | 51.9 | 395 | Red |
| Example 53 | | Z-27 | 3.62 | 50.7 | 411 | Red |
| Example 54 | | Z-34 | 3.58 | 51.8 | 498 | Red |
| Example 55 | Compound | Z-2 | 3.59 | 50.9 | 461 | Red |
| Example 56 | 15 | Z-7 | 3.54 | 51.3 | 472 | Red |
| Example 57 | | Z-11 | 3.50 | 52.8 | 462 | Red |
| Example 58 | | Z-15 | 3.51 | 49.5 | 454 | Red |
| Example 59 | | Z-18 | 3.45 | 50.3 | 458 | Red |
| Example 60 | | Z-19 | 3.48 | 51.7 | 449 | Red |
| Example 61 | | Z-22 | 3.52 | 50.9 | 486 | Red |
| Example 62 | | Z-23 | 3.50 | 50.4 | 467 | Red |
| Example 63 | | Z-27 | 3.57 | 50.5 | 466 | Red |
| Example 64 | | Z-34 | 3.55 | 50.0 | 458 | Red |
| Example 65 | Compound | Z-2 | 3.50 | 49.7 | 462 | Red |
| Example 66 | 16 | Z-7 | 3.57 | 49.3 | 481 | Red |
| Example 67 | | Z-11 | 3.52 | 49.4 | 473 | Red |
| Example 68 | | Z-15 | 3.59 | 49.9 | 462 | Red |
| Example 69 | | Z-18 | 3.55 | 50.5 | 468 | Red |
| Example 70 | | Z-19 | 3.54 | 49.7 | 477 | Red |
| Example 71 | | Z-22 | 3.51 | 49.5 | 486 | Red |
| Example 72 | | Z-23 | 3.58 | 50.3 | 471 | Red |
| Example 73 | | Z-27 | 3.53 | 49.7 | 469 | Red |
| Example 74 | | Z-34 | 3.55 | 50.5 | 473 | Red |

The results of Table 1 were obtained by applying a current to each of the organic light emitting devices manufactured in Examples 1 to 20 and Comparative Examples 1 to 15. In the red organic light emitting device of the comparative example, materials widely used in the art were used, and Compound [EB-1] was used as the electron blocking layer, and RH-1/Dp-7 was used as the red light emitting layer. In Comparative Examples 2 to 15, organic light emitting devices were manufactured using C-1 to C-14 instead of RH-1. From the results of Table 1, it was seen that, when using the compound of the present disclosure as a host of a red light emitting layer, energy was favorably transferred from the host to the red dopant based on the fact that, compared to the materials of the comparative examples, the driving voltage decreased by almost up to 30% and efficiency increased by 25% or greater. In addition, it was seen that the lifetime properties were significantly improved by two times or greater while maintaining high efficiency. This is considered to be due to the fact that the compound of the present disclosure has higher stability for electrons and holes compared to the compounds of the comparative examples. The results of Table 2 showed results of co-depositing two types of hosts, and, when using the first host and the second host in a ratio of 1:1, superior results were obtained compared when using only the first host. It was identified that holes and electrons maintained a more stable balance in the red light emitting layer as the amount of the holes increased by using the second host, which resulted in a significant increase in the efficiency and the lifetime. In conclusion, it may be identified that, when using the compound of the present disclosure as a host of a red light emitting layer, driving voltage, light emission efficiency and lifetime properties of an organic light emitting device may be improved.

DESCRIPTION OF REFERENCE NUMERAL

1: Substrate
2: First Electrode
3: Hole Injection Layer
4: Hole Transfer Layer
5: Light Emitting Layer
6: Second Electrode

The invention claimed is:

1. An organic light emitting device comprising:

a first electrode, a second electrode provided to face the first electrode, and one or more organic material layers provided between the first electrode and the second electrode, wherein the one or more organic material layers include a light emitting layer, the light emitting layer includes:

a host material, the host material includes a compound of any one of Chemical Formulae 1-1-2, 1-1-3, 1-2-2, or 1-2-3 as a first host, and the compound of Chemical Formulae 1-1-2, 1-1-3, 1-2-2, or 1-2-3 is a red light emitting compound, and further includes a compound selected from among the following Z-4 to Z-6, Z-8 to Z-12, Z-26, Z-30 to Z-32, and Z-35 as a second host:

-continued

[Chemical Formula 1-1-2]

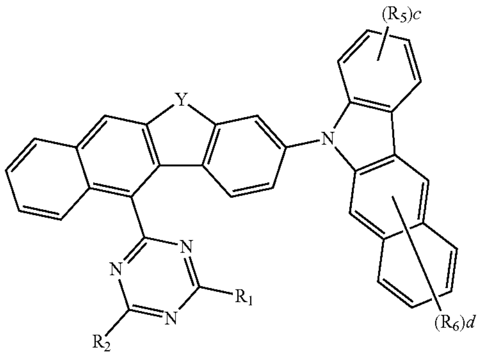

[Chemical Formula 1-1-3]

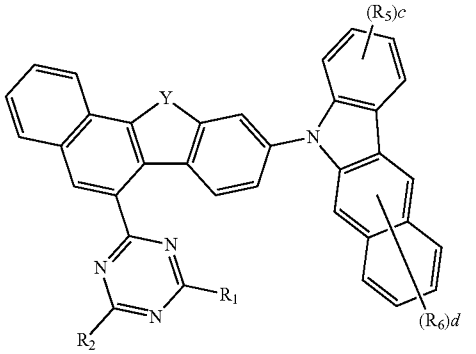

[Chemical Formula 1-2-2]

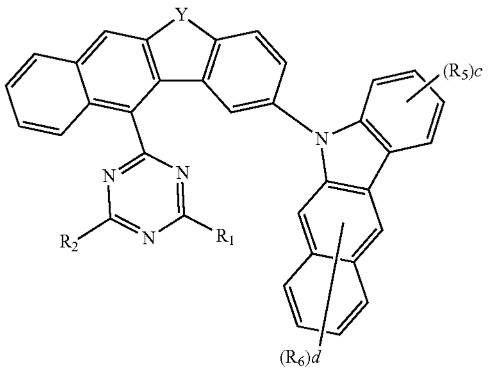

[Chemical Formula 1-2-3]

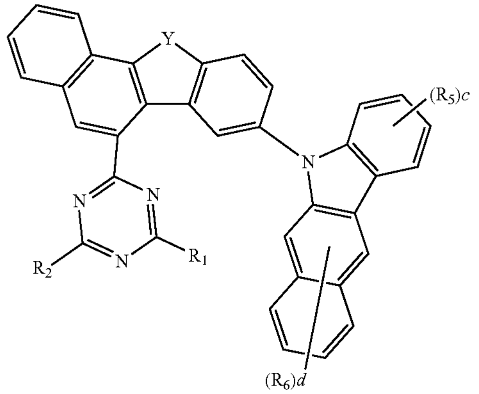

wherein, in Chemical Formulae 1-1-2, 1-1-3, 1-2-2, and 1-2-3:

Y is O or S;

$R_1$ and $R_2$ are the same as or different from each other, and are each independently a substituted or unsubstituted aryl group;

$R_5$ and $R_6$ are the same as or different from each other, and are each independently hydrogen or deuterium, or adjacent groups bond to each other to form a ring;

c is an integer of 1 to 4;

d is an integer of 1 to 6; and substituents in the parentheses are the same as or different from each other provided that c and d are 2 or greater,

Z-4

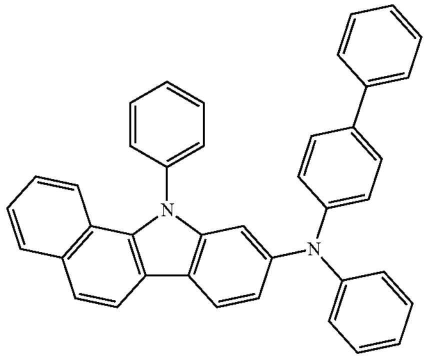

-continued
Z-5
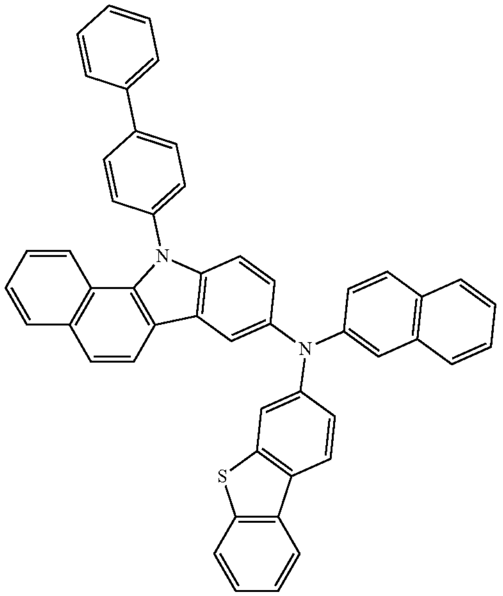
Z-6
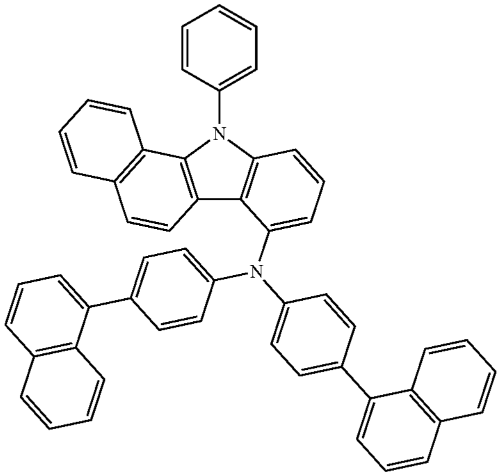
Z-8
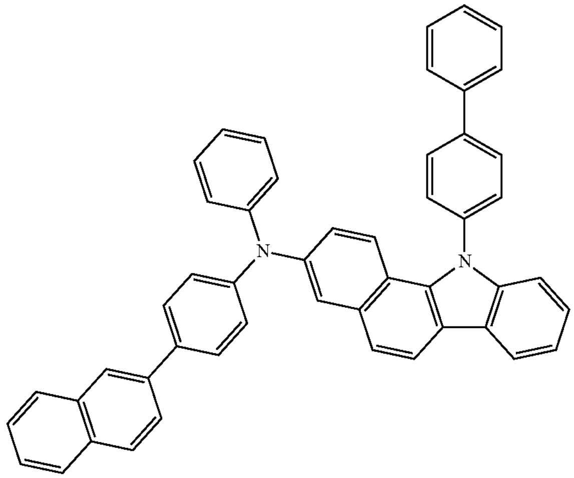
-continued
Z-9
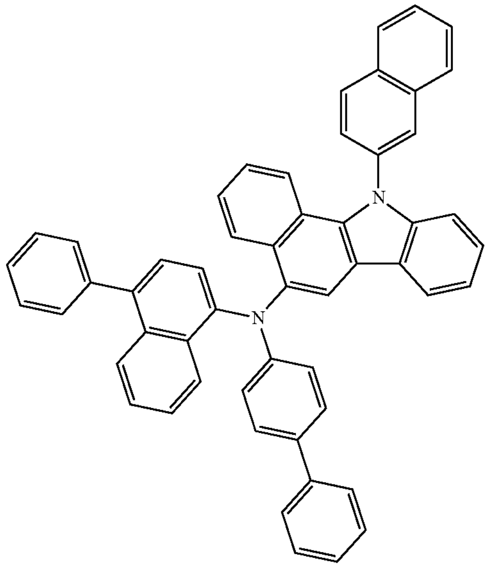
Z-10
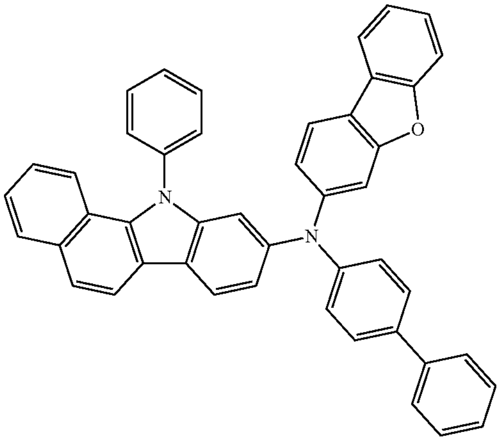
Z-11
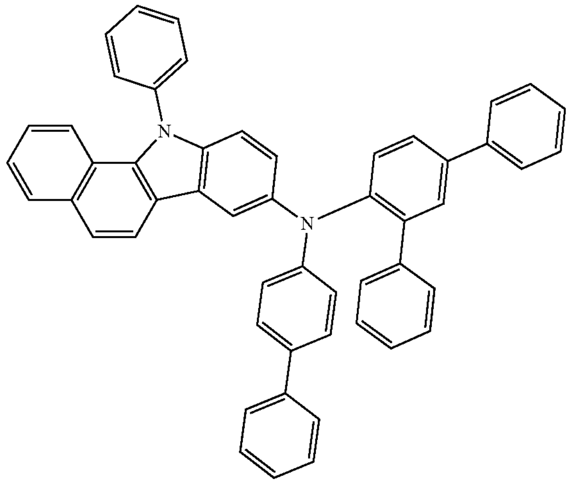

-continued
Z-12
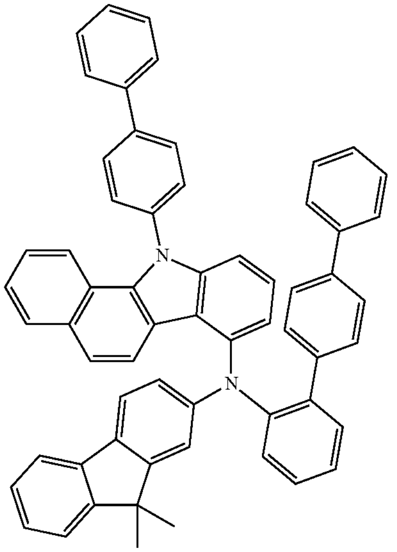
Z-26
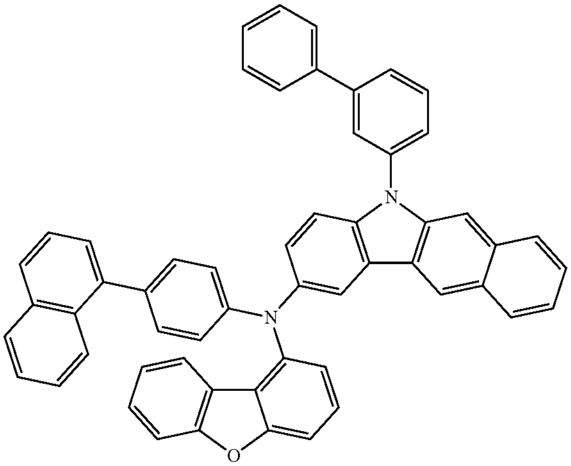
Z-30
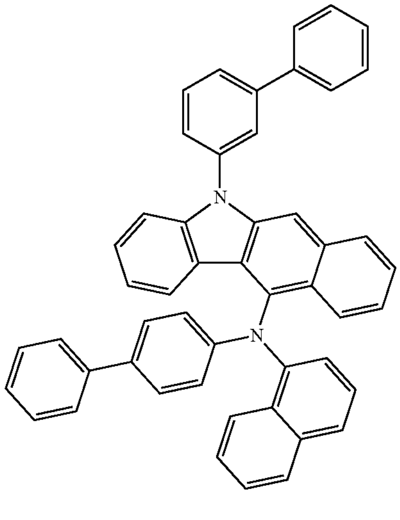
-continued
Z-31
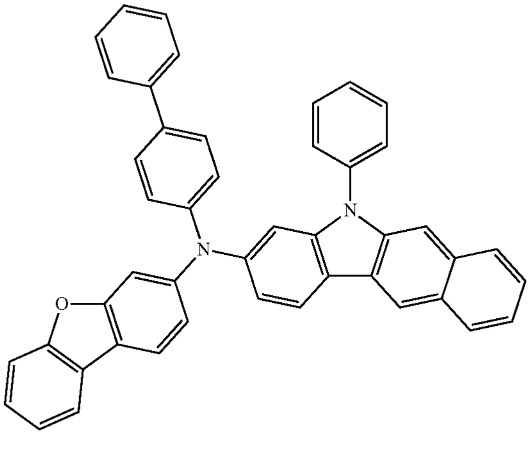
Z-32
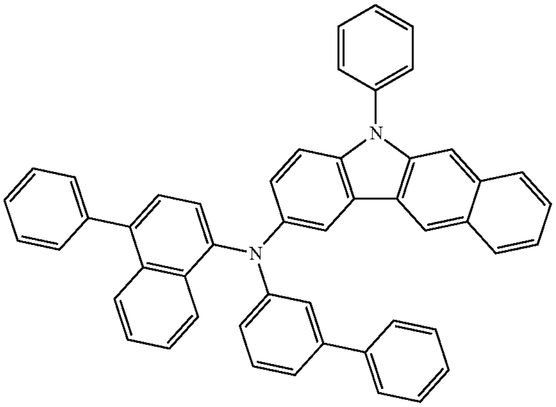
Z-35
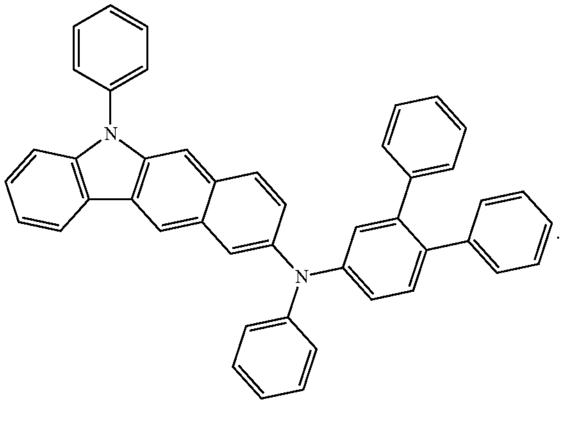
2. The organic light emitting device of claim 1, wherein the compound of Chemical Formulae 1-1-2, 1-1-3, 1-2-2, or 1-2-3 is any one compound selected from the following compounds:

-continued
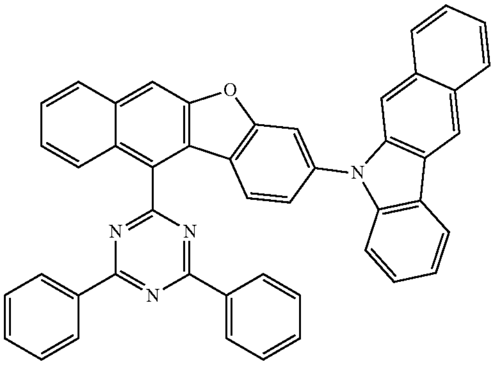
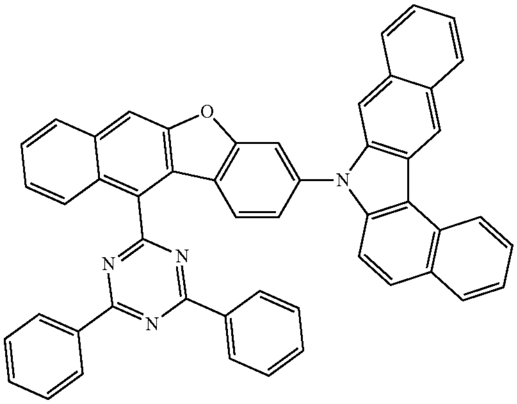
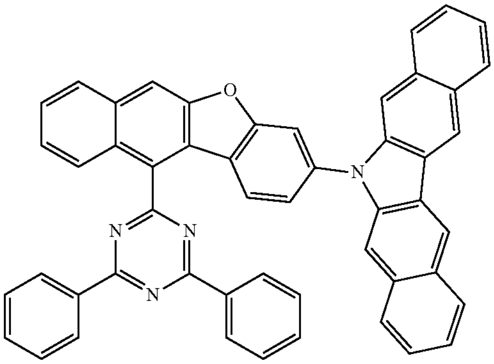
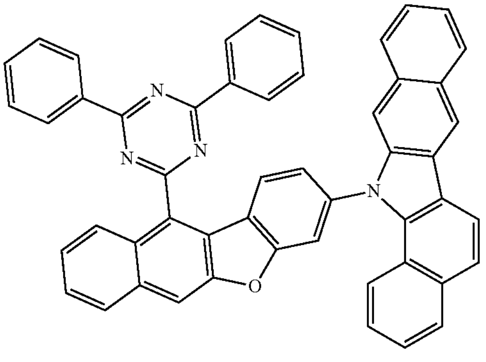
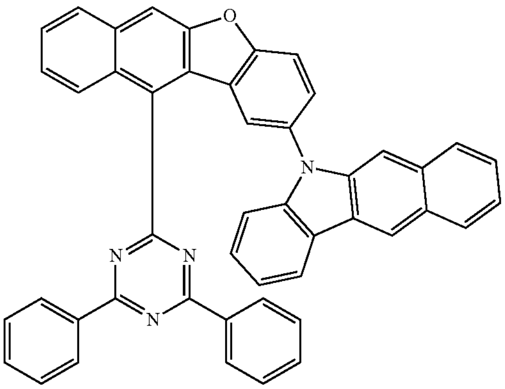
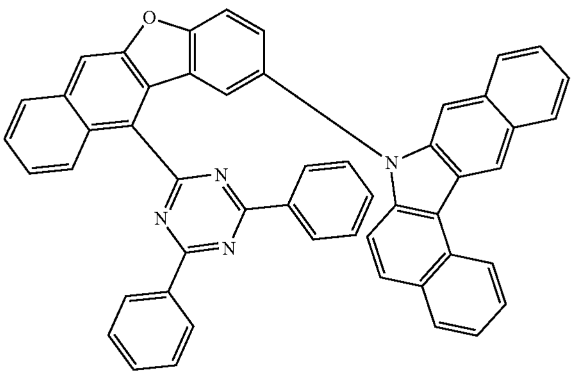
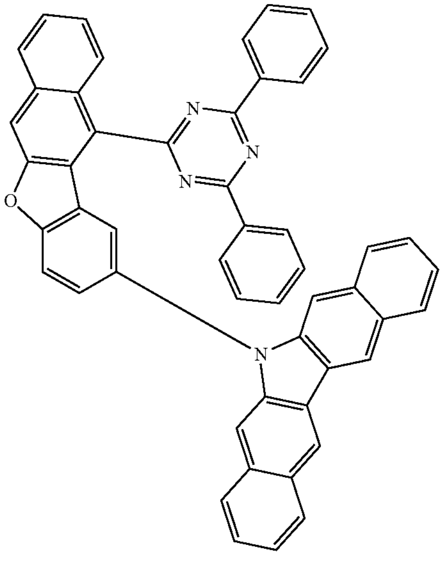

-continued
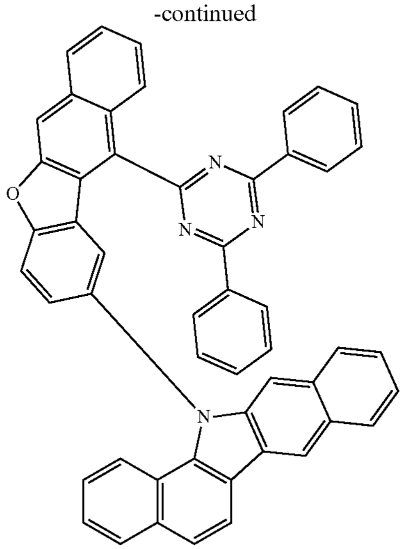
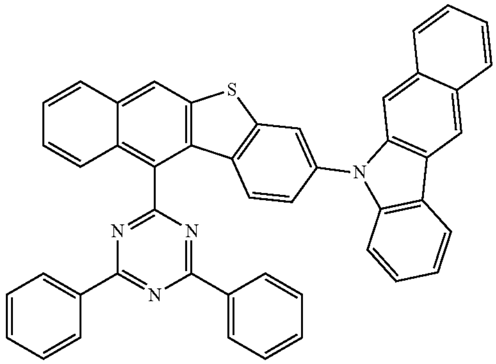
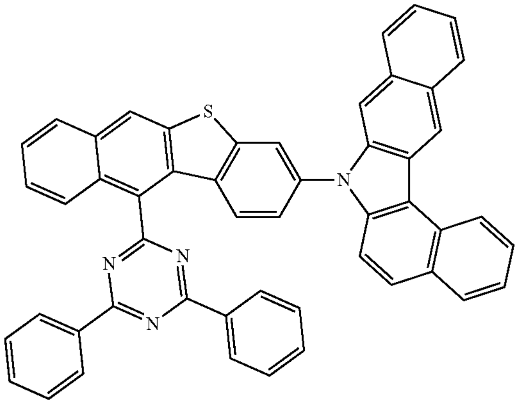
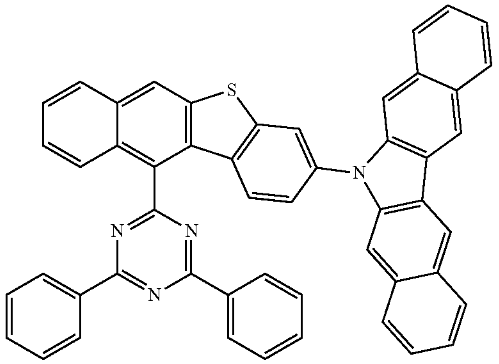
-continued
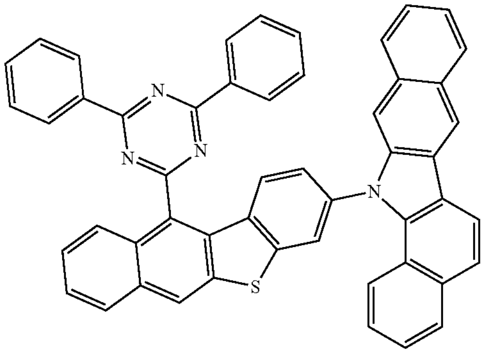
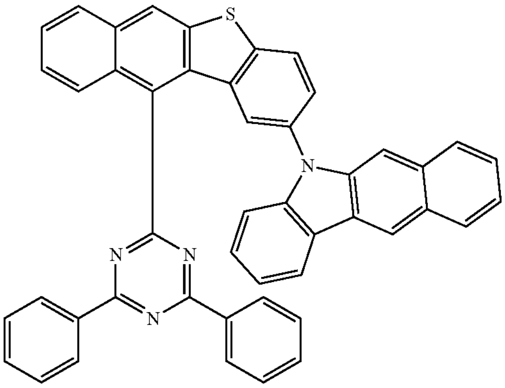
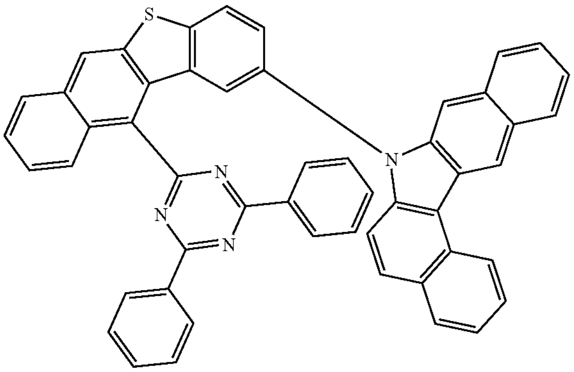
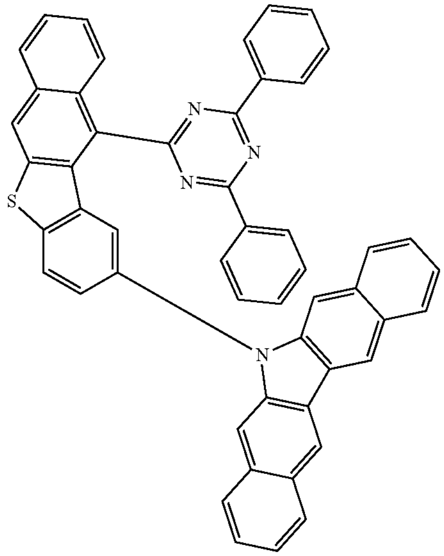

-continued
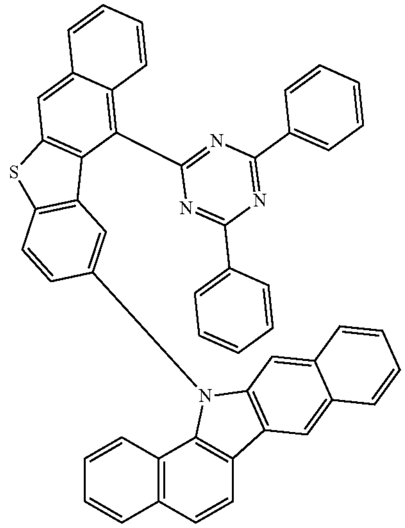
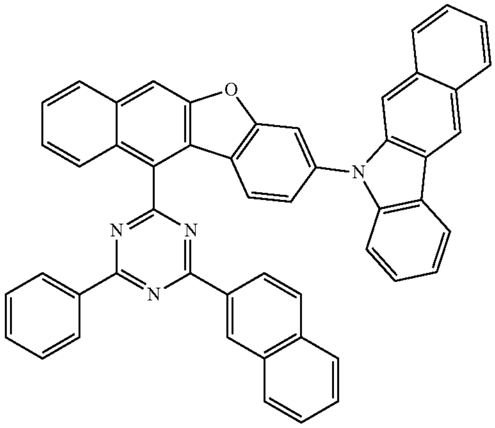
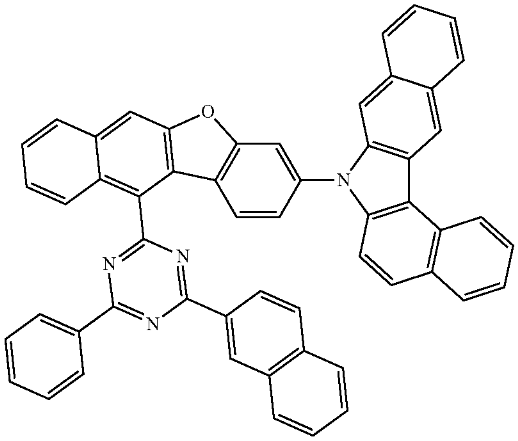
-continued
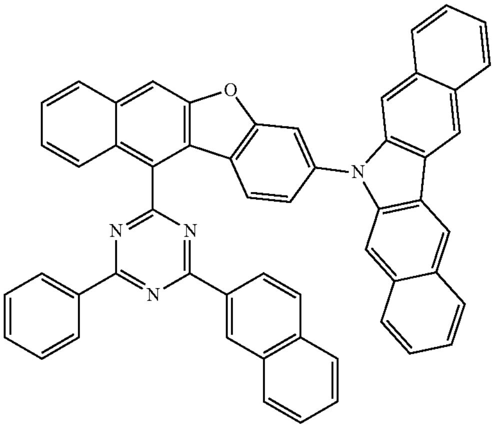
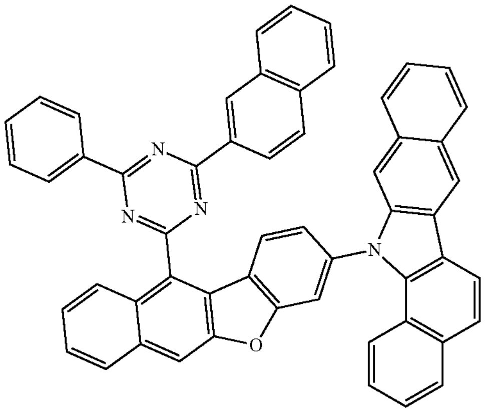
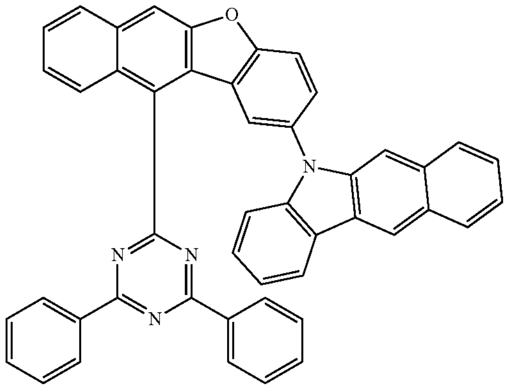
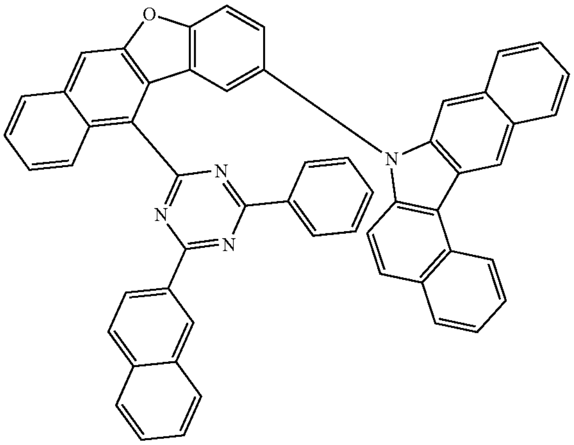

-continued
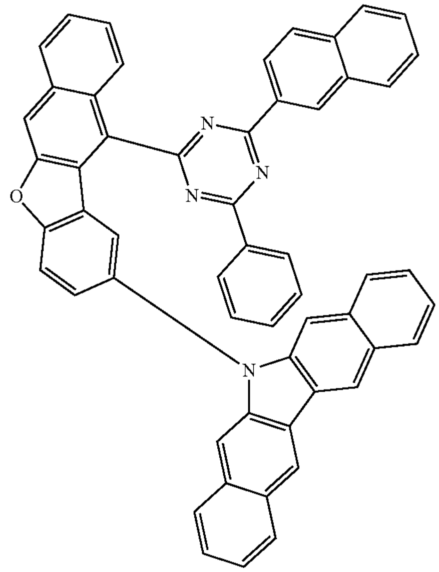
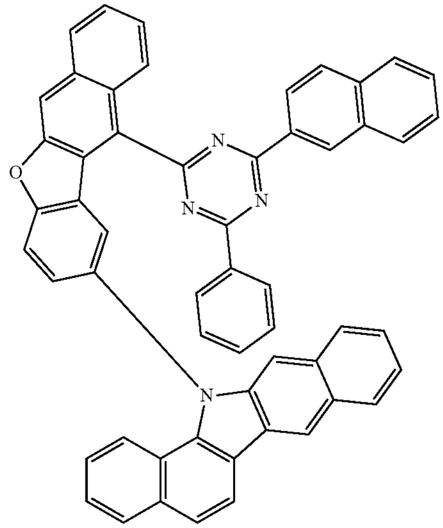
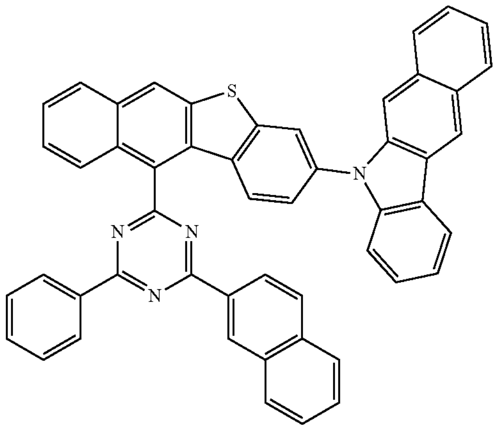
-continued
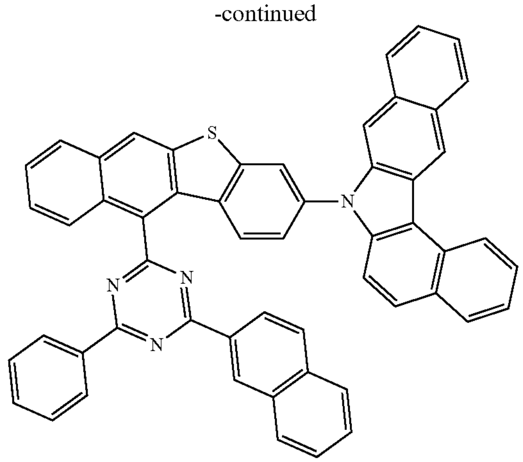
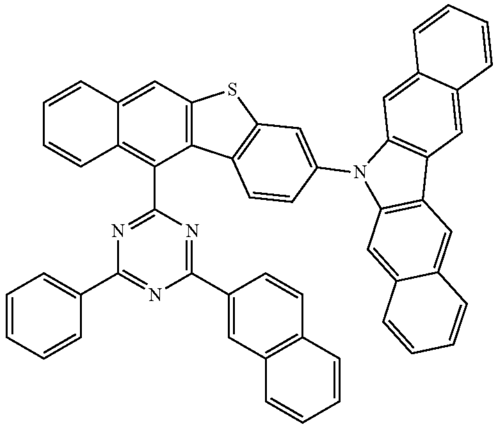
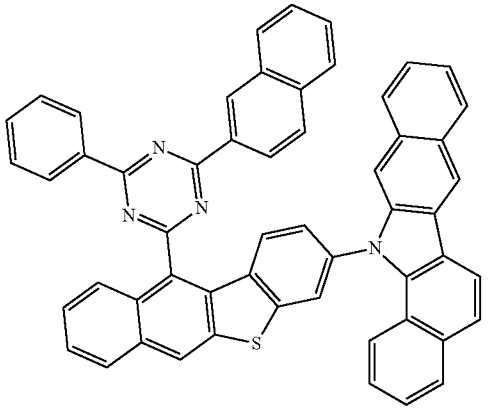
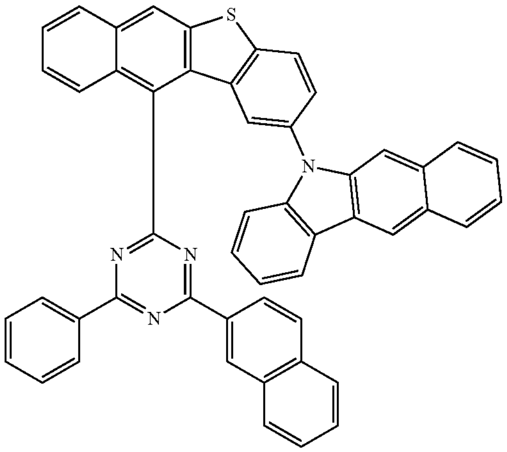

-continued
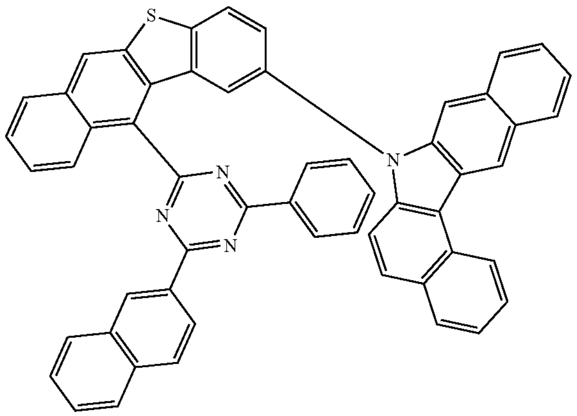
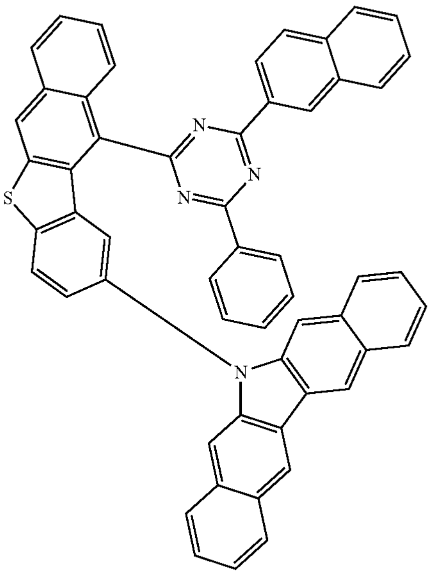
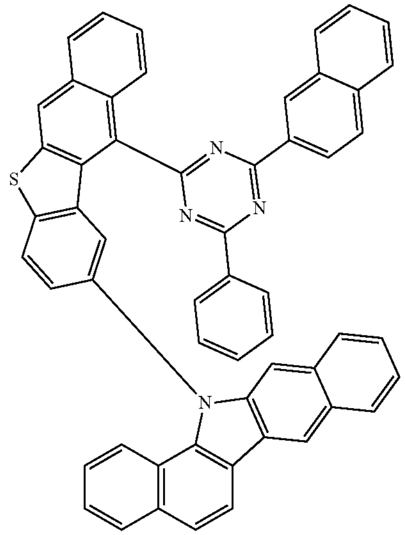 [SMILES: c1ccc(-c2nc(-c3ccc4ccccc4c3)nc(-c3c4ccccc4cc4sc5ccc(-n6c7cc8ccccc8cc7c7ccc8ccccc8c76)cc5c34)n2)cc1]
-continued
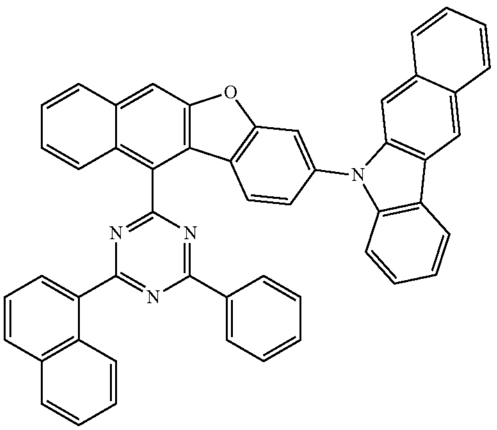
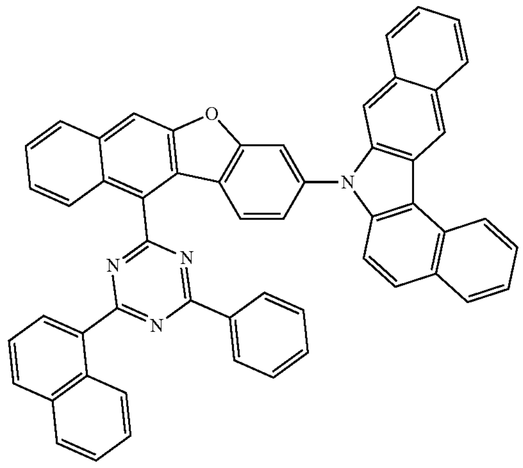
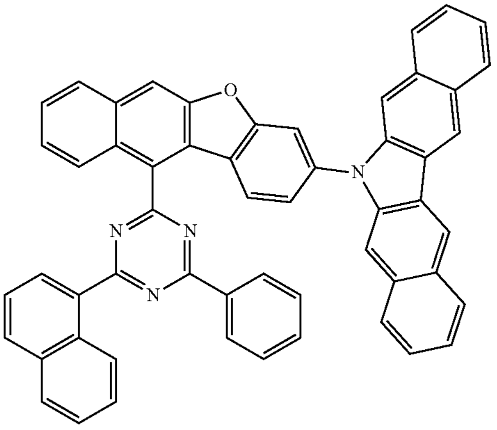
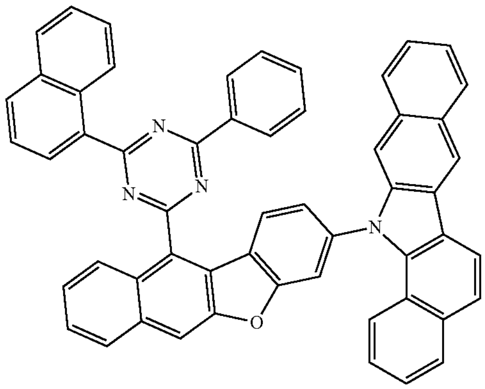

-continued
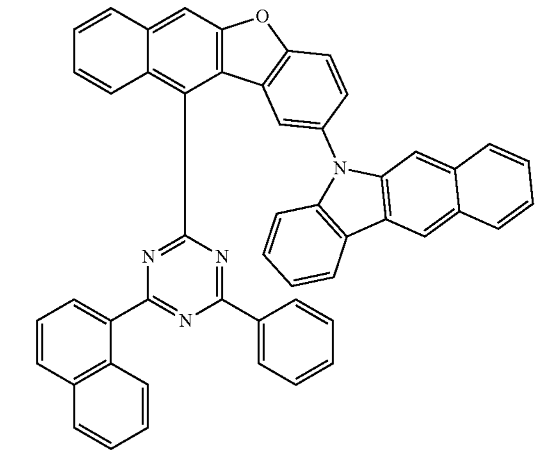
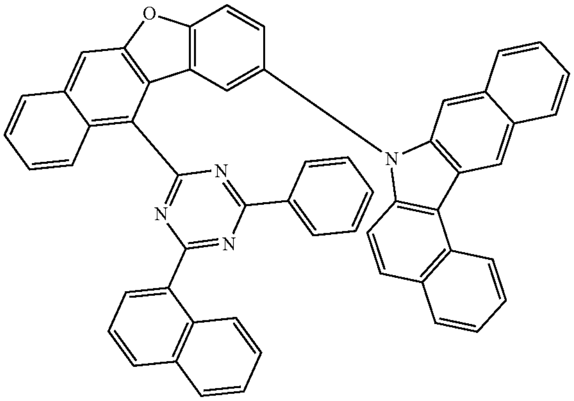
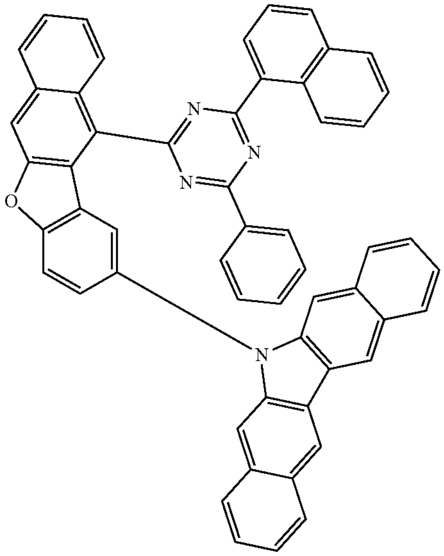
-continued
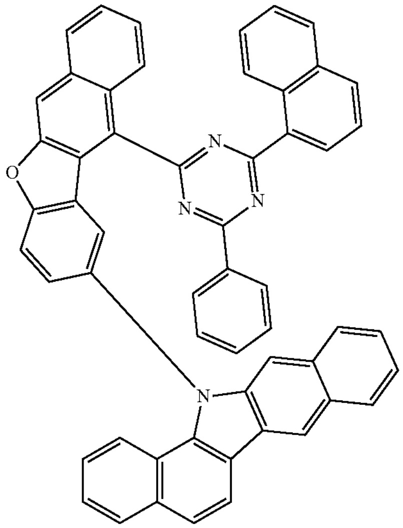
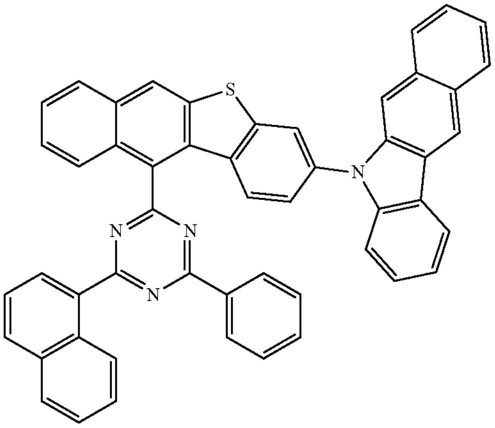
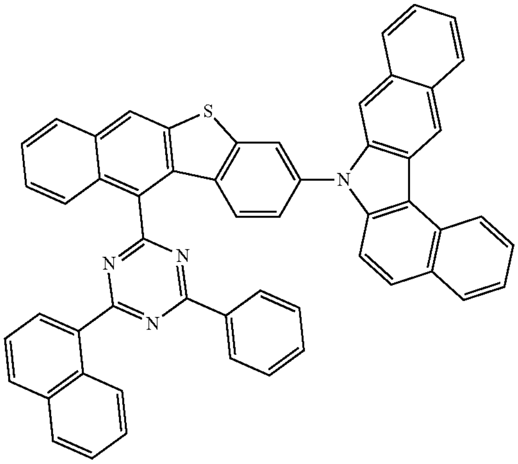

-continued
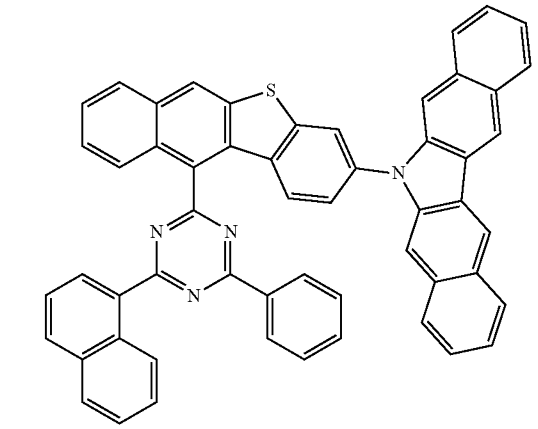
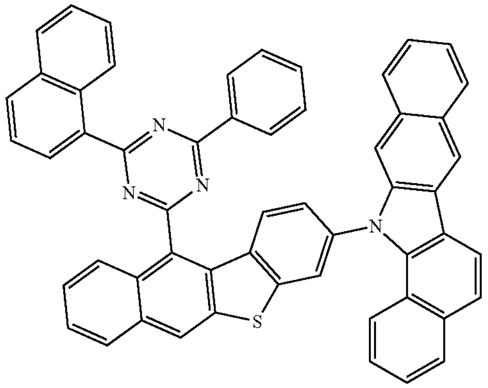
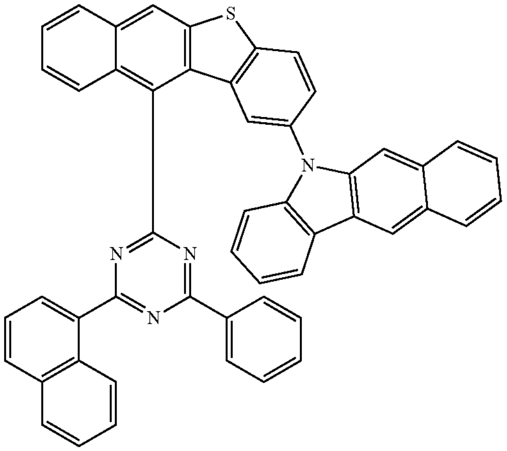
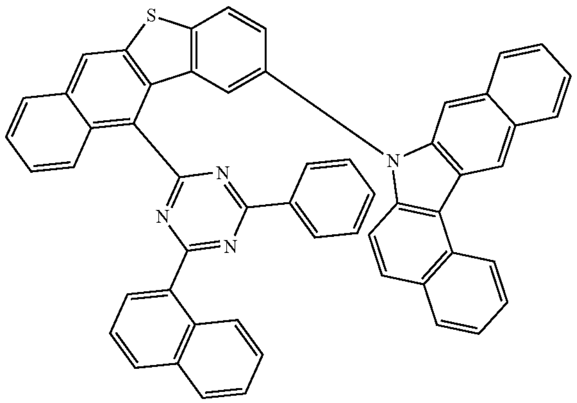
-continued
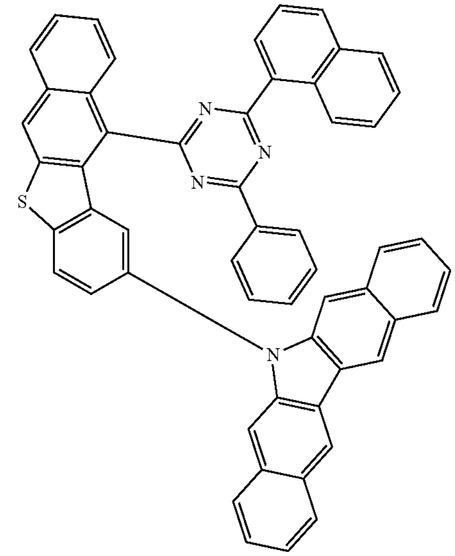
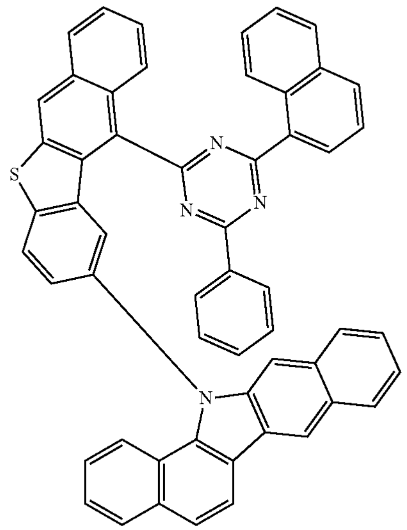
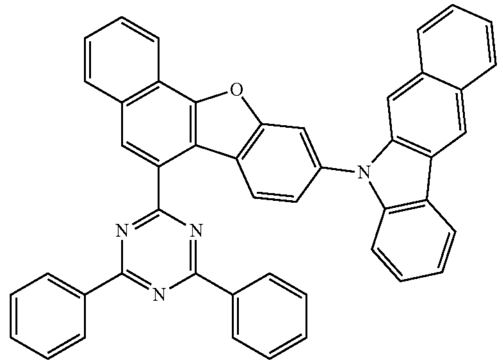

-continued
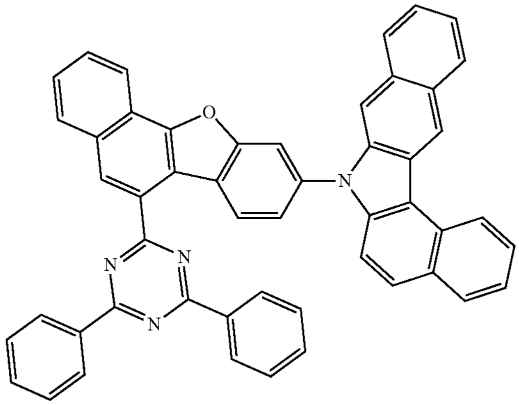
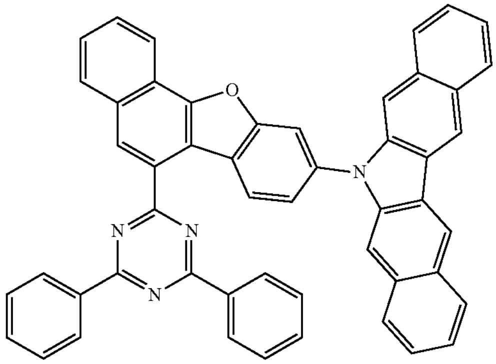
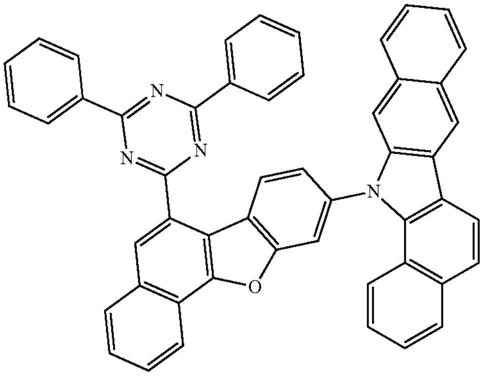
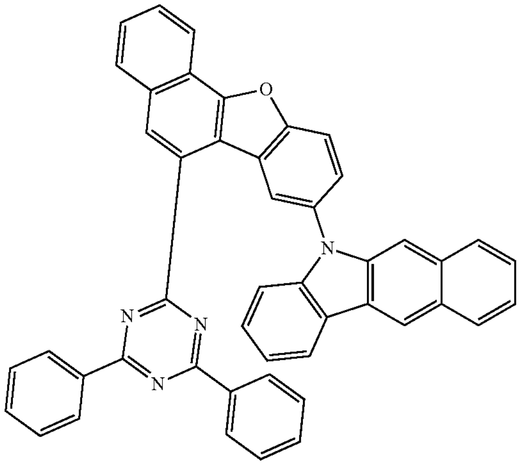
-continued
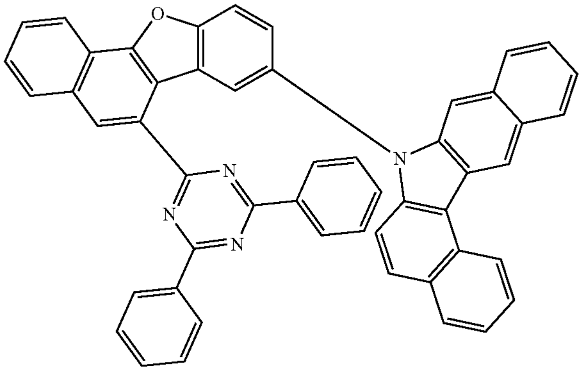
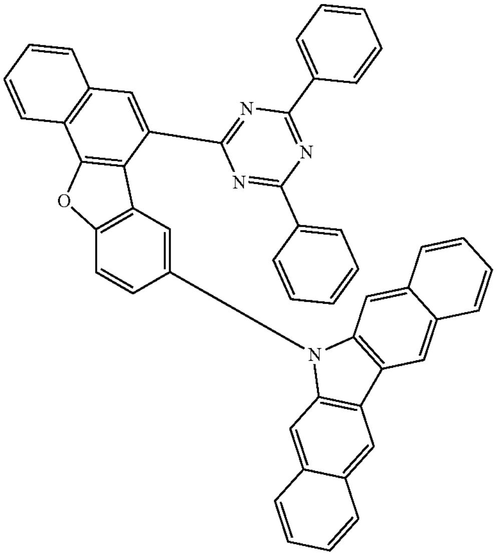
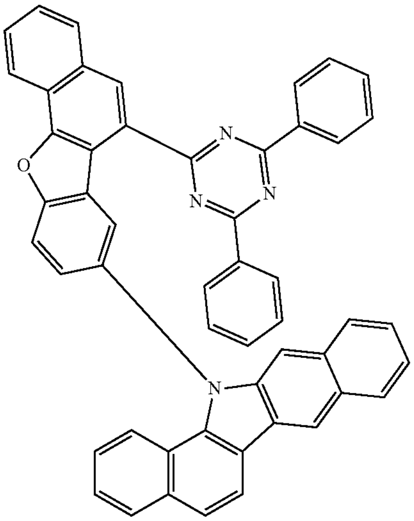

-continued
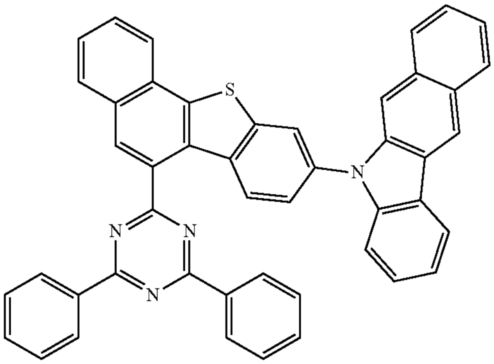
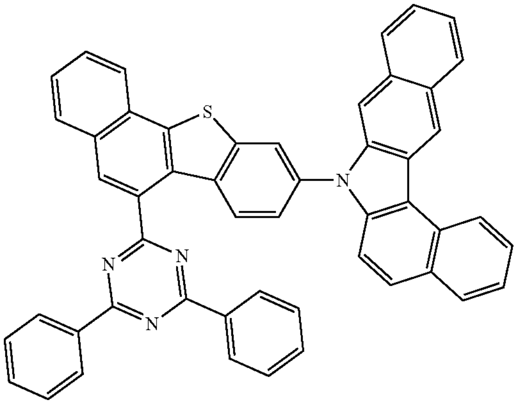
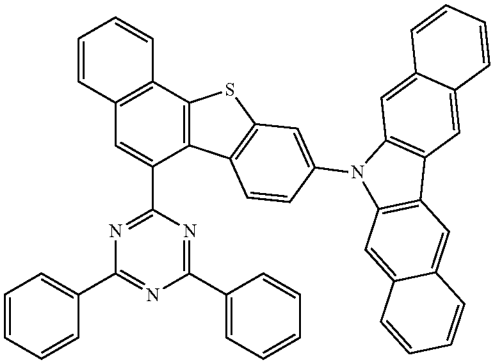
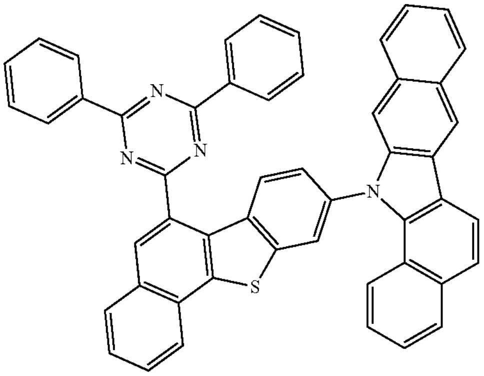
-continued
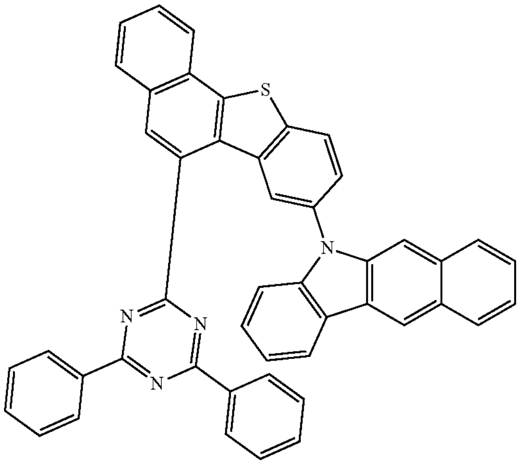
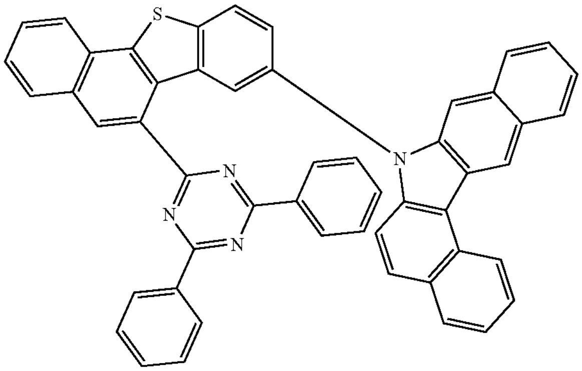
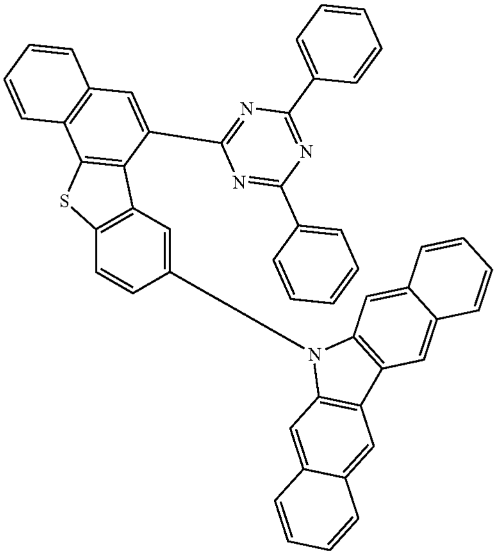

-continued
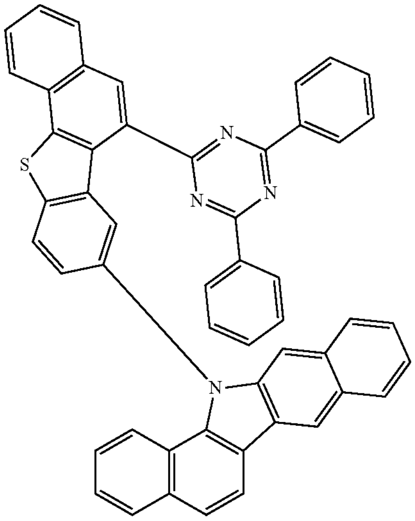
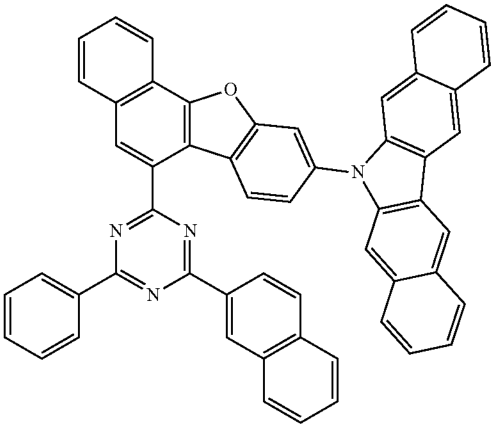
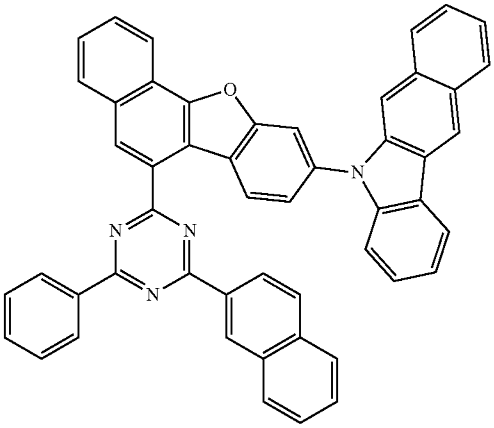
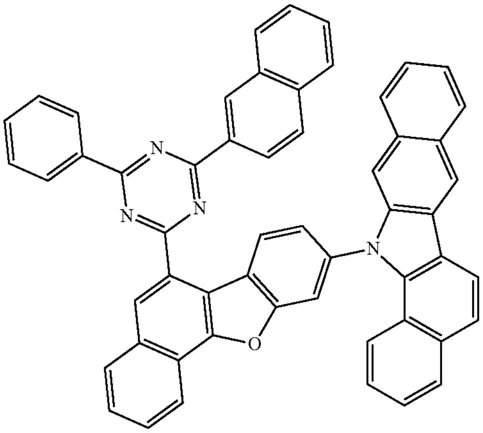
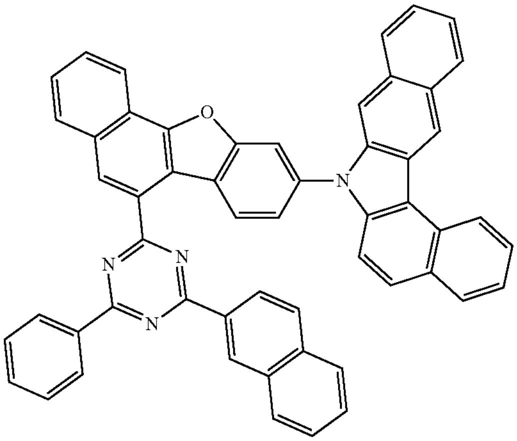
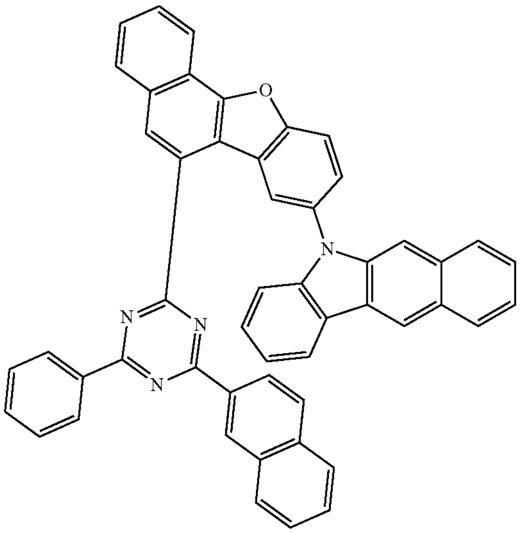
-continued -continued
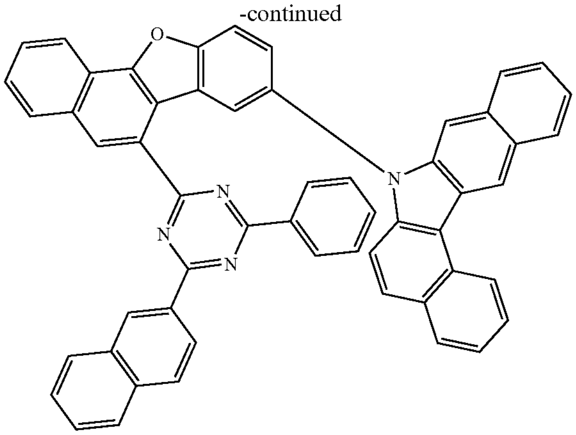
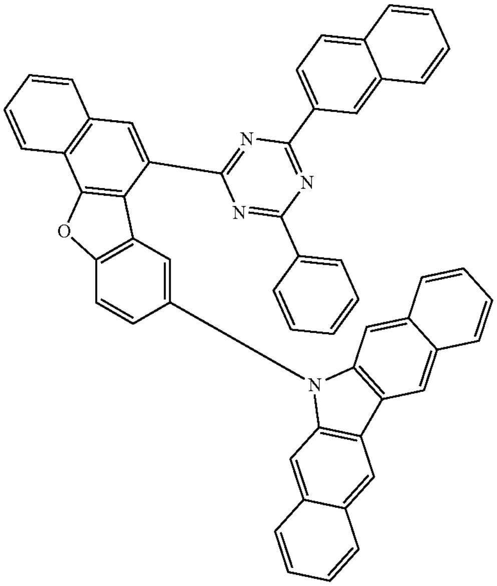
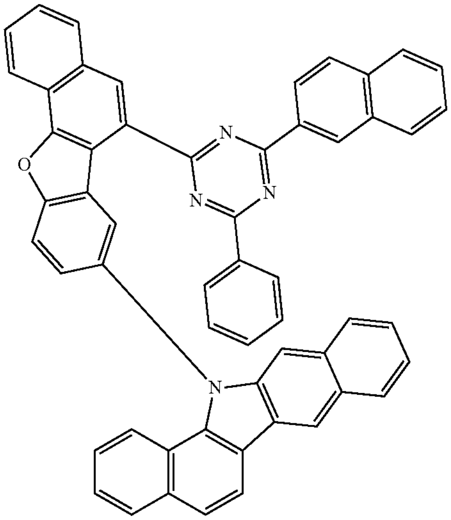 [SMILES: c1ccc(-c2nc(-c3ccc4ccccc4c3)nc(-c3cc4ccccc4c4oc5ccc(-n6c7cc8ccccc8cc7c7ccc8ccccc8c76)cc5c34)n2)cc1]
-continued
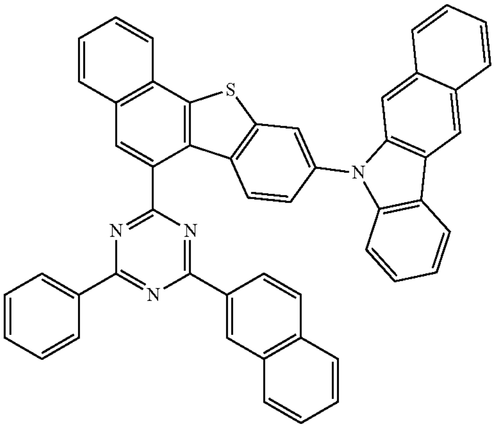
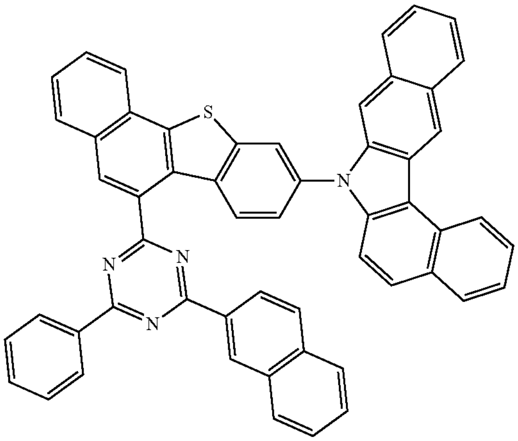
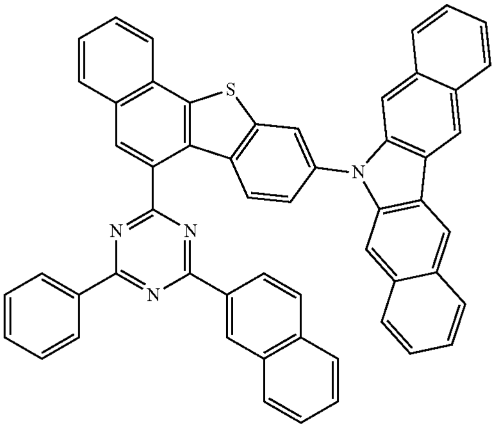
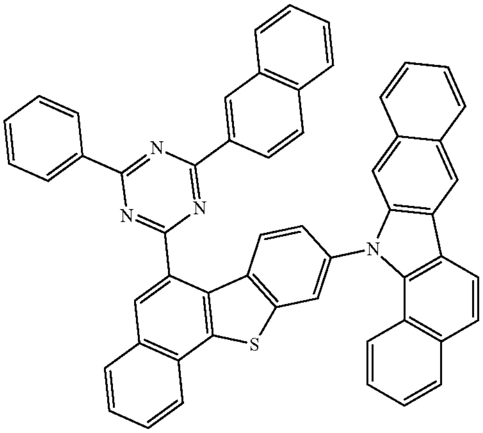

-continued
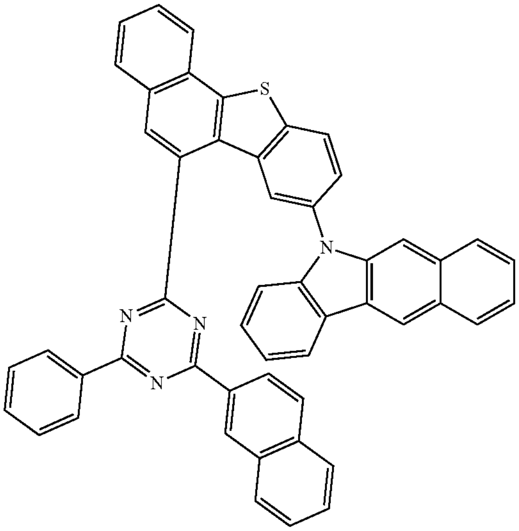
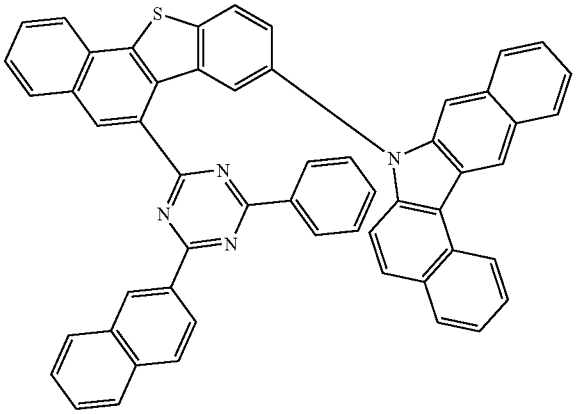
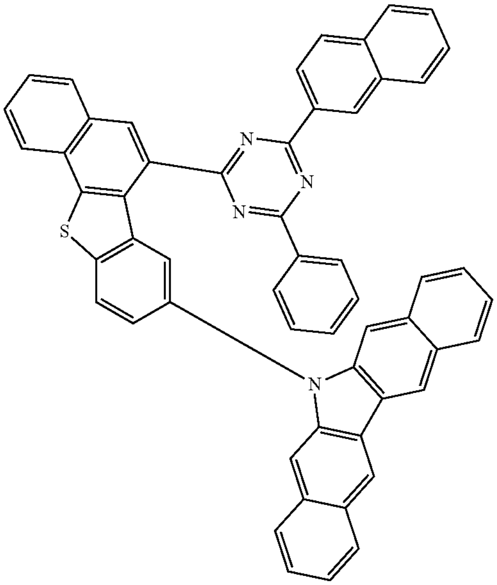
-continued
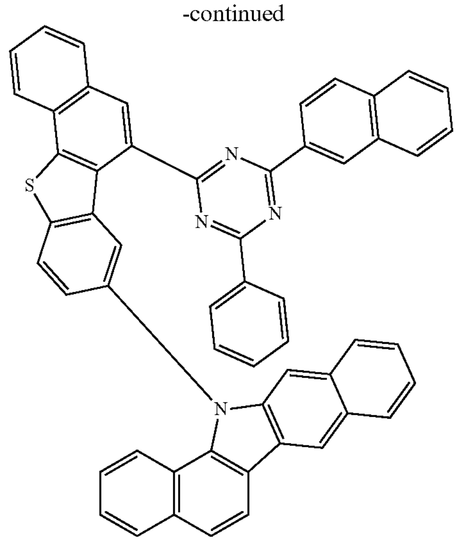
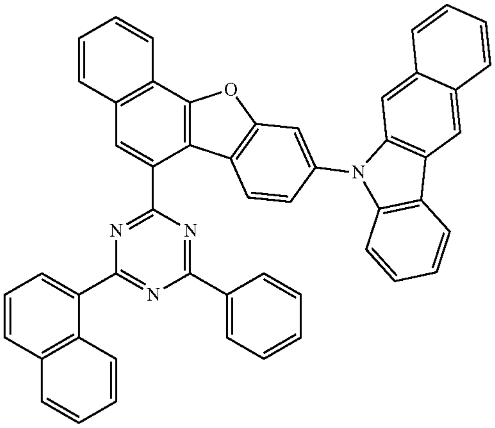
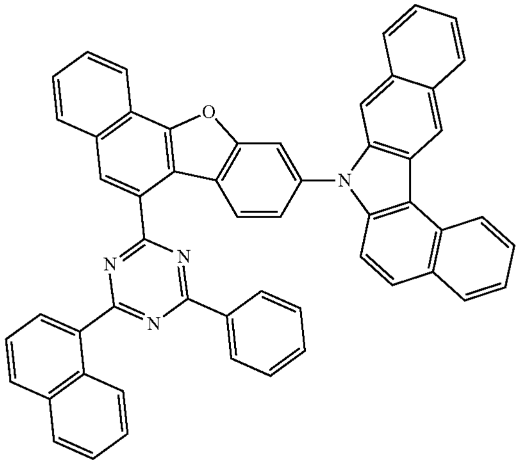

-continued
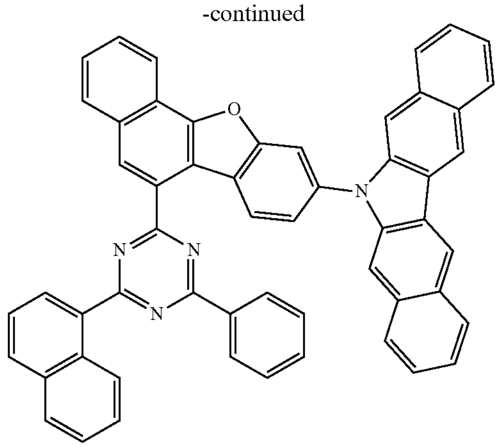
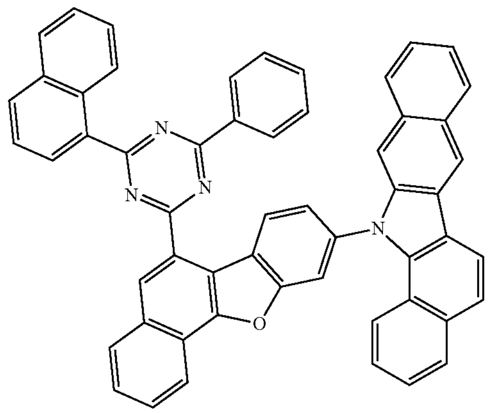
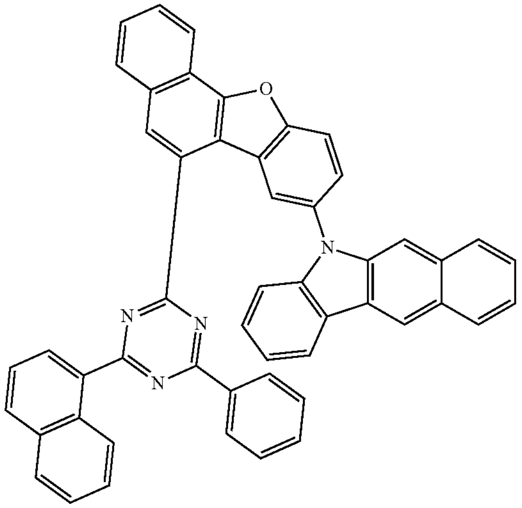
-continued
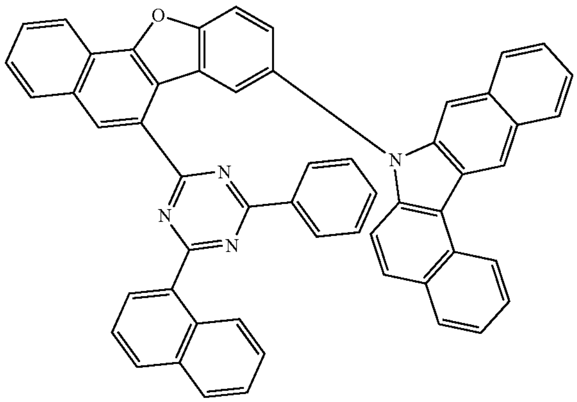
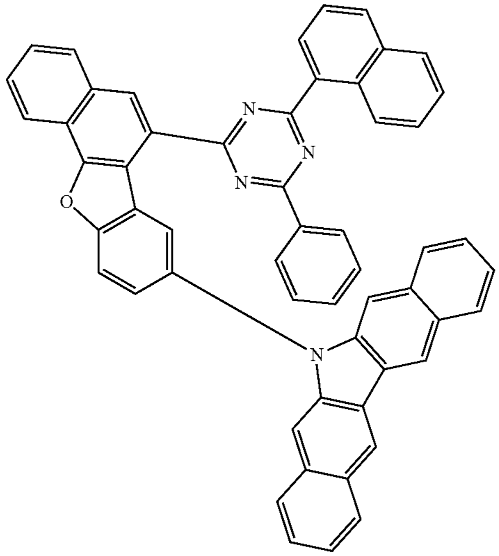
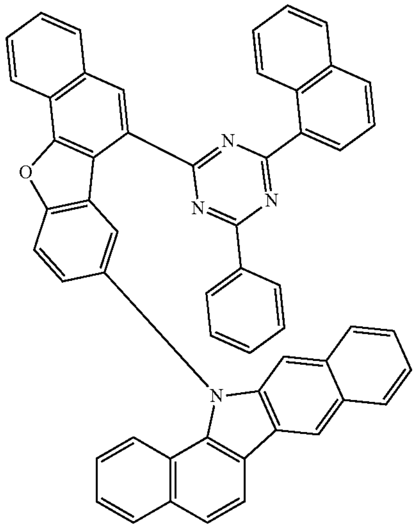 [SMILES: c1ccc(-c2nc(-c3cccc4ccccc34)nc(-c3cc4ccccc4c4oc5ccc(-n6c7cc8ccccc8cc7c7ccc8ccccc8c76)cc5c34)n2)cc1]

-continued
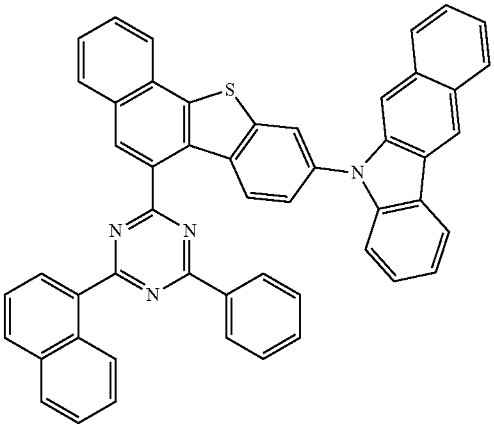
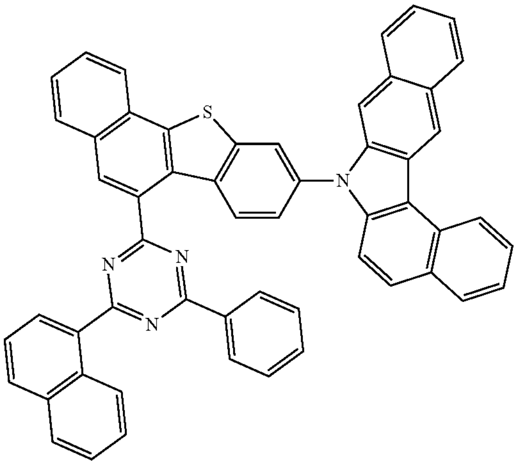
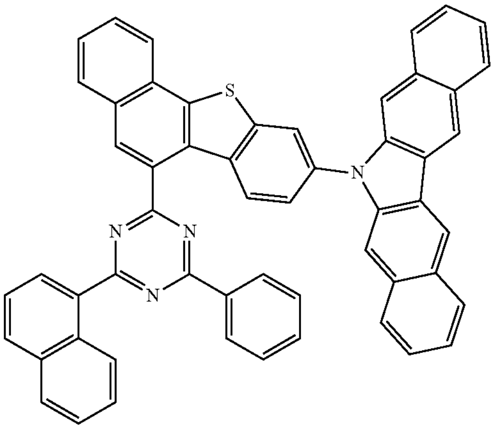
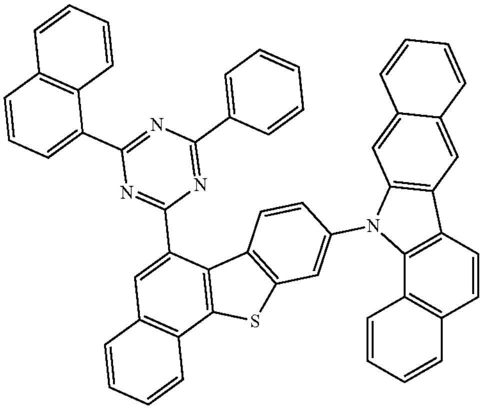
-continued
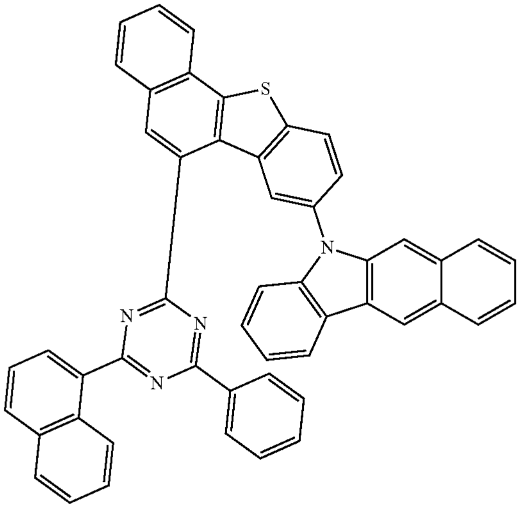
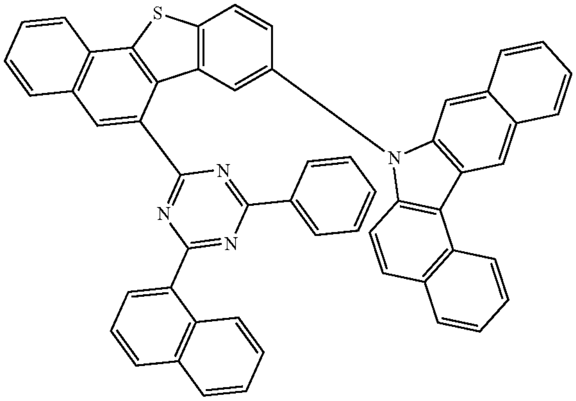
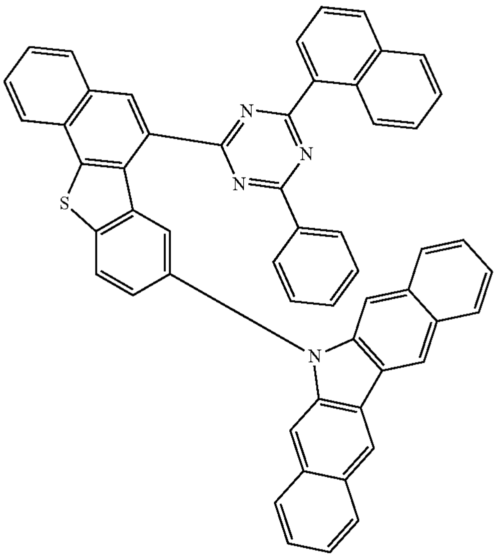

-continued

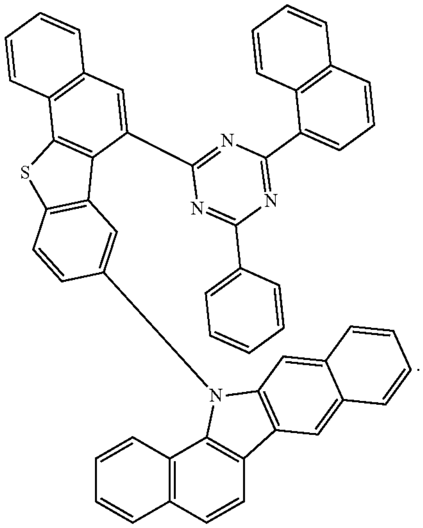 [SMILES: c1ccc(-c2nc(-c3cccc4ccccc34)nc(-c3cc4ccccc4c4sc5ccc(-n6c7cc8ccccc8cc7c7ccc8ccccc8c76)cc5c34)n2)cc1]

3. The organic light emitting device of claim 1, wherein the one or more organic material layers further include one, two or more layers selected from the group consisting of a second light emitting layer, a hole injection layer, a hole transfer layer, an electron injection layer, an electron transfer layer, an electron blocking layer and a hole blocking layer.

4. The organic light emitting device of claim 1, wherein the light emitting layer further includes a dopant, and the dopant is one selected from among the following compounds of Dp-1 to Dp5 and Dp-7 to Dp-38:

Dp-1

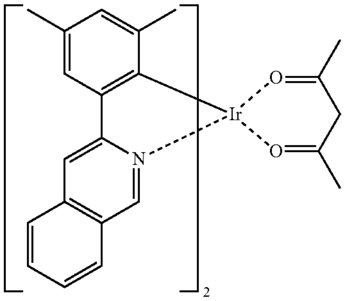

Dp-2

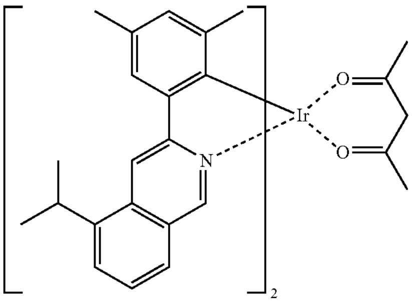

-continued

Dp-3

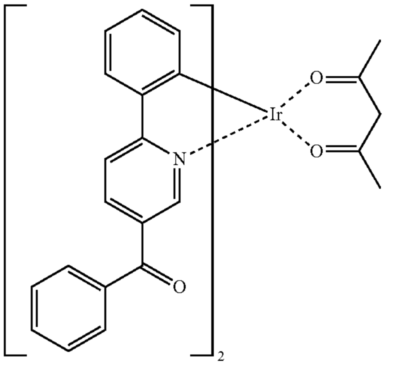

Dp-4

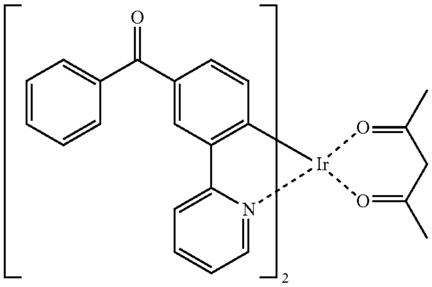

Dp-5

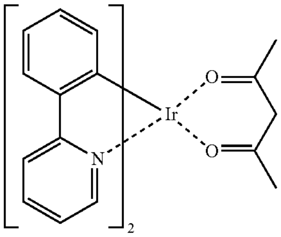

Dp-7

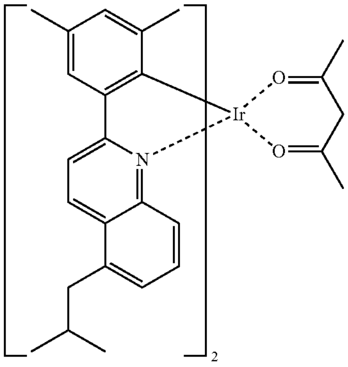

Dp-8

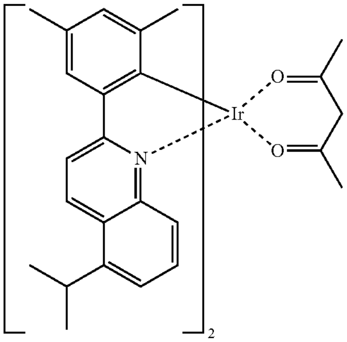

-continued
Dp-9
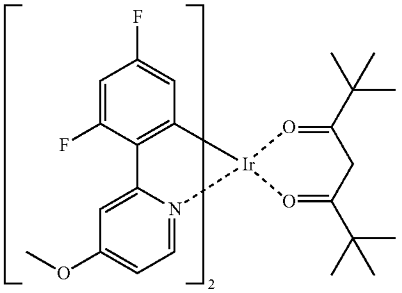
Dp-10
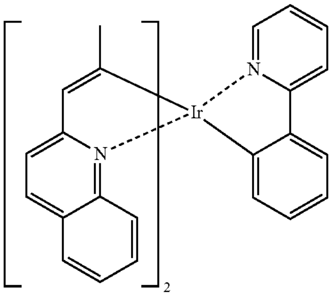
Dp-11
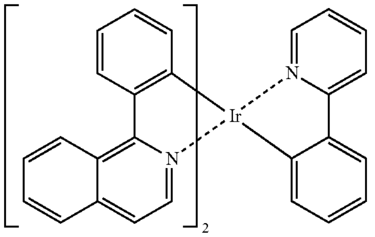
Dp-12
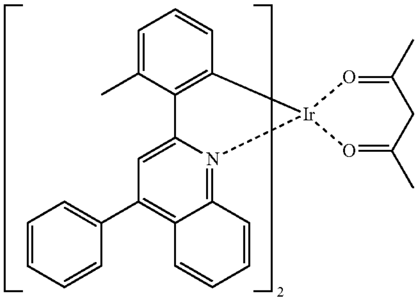
DP-13
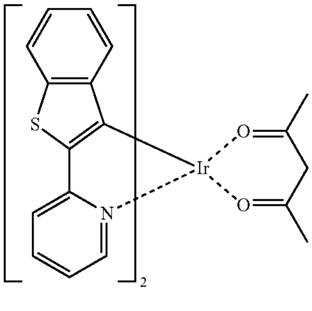
-continued
Dp-14
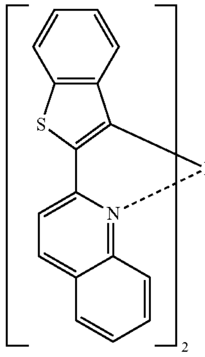
Dp-15
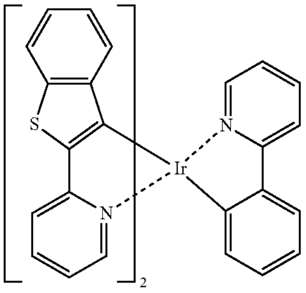
DP-16
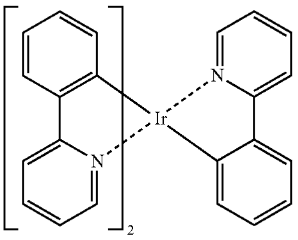
Dp-17
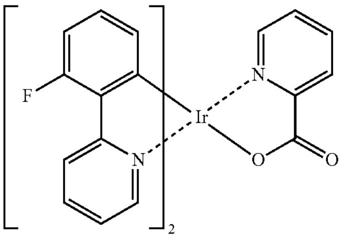
Dp-18
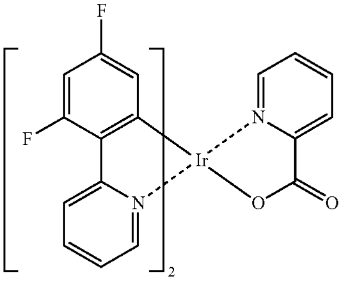

-continued
Dp-19
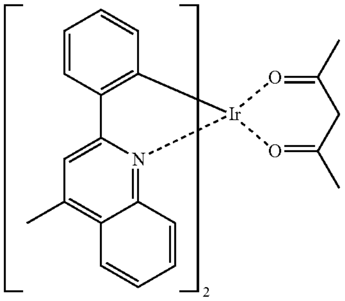
Dp-20
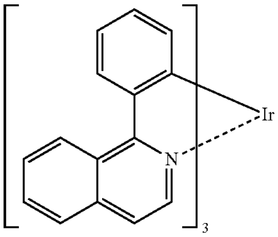
Dp-21
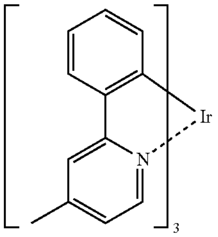
Dp-22
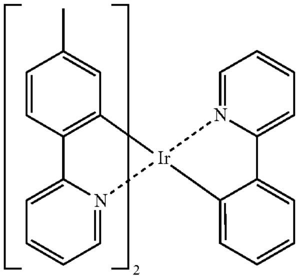
Dp-23
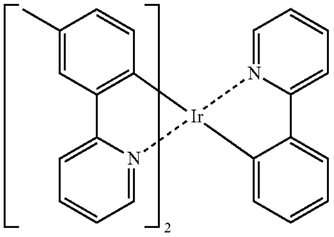
-continued
Dp-24
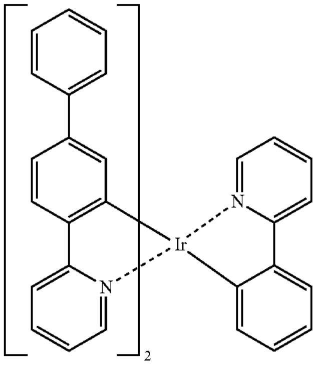
Dp-25
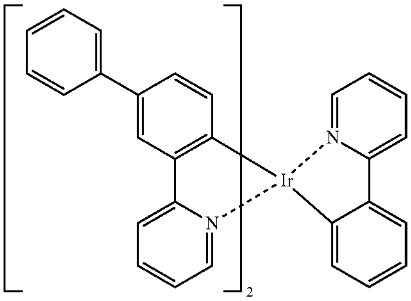
Dp-26
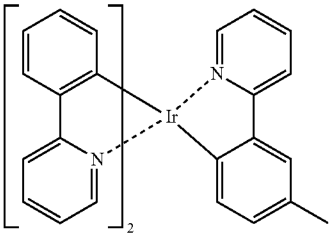
Dp-27
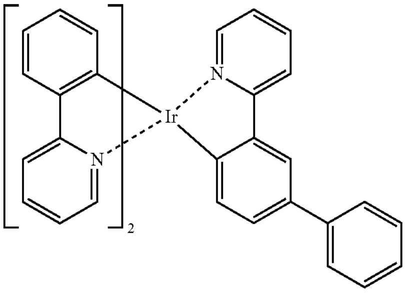
Dp-28
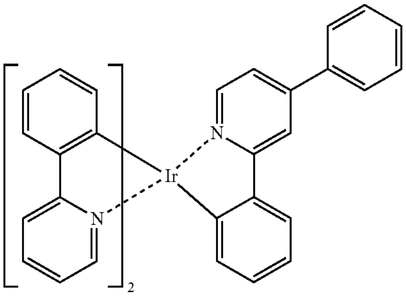

-continued
Dp-29
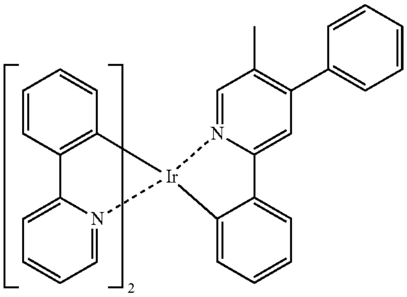
Dp-30
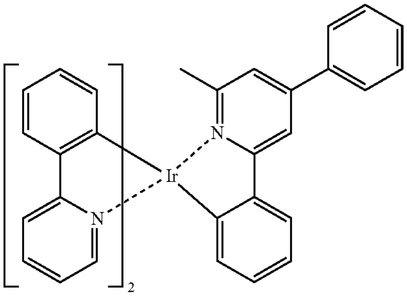
Dp-31
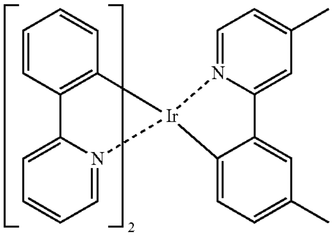
Dp-32
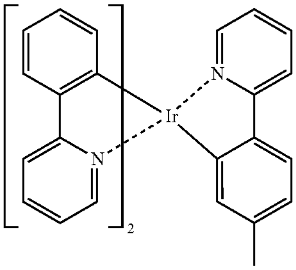
Dp-33
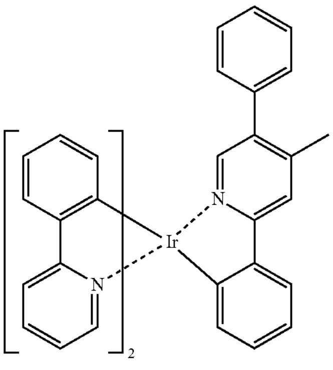
-continued
Dp-34
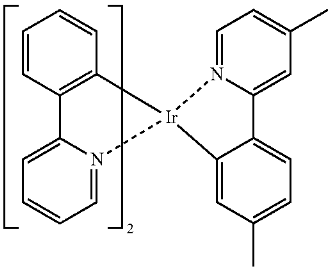
Dp-35
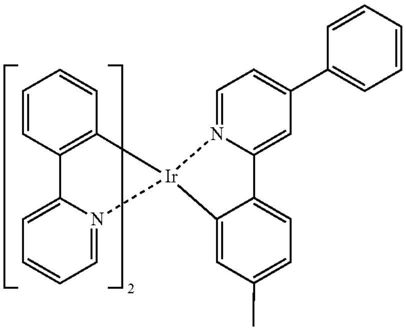
Dp-36
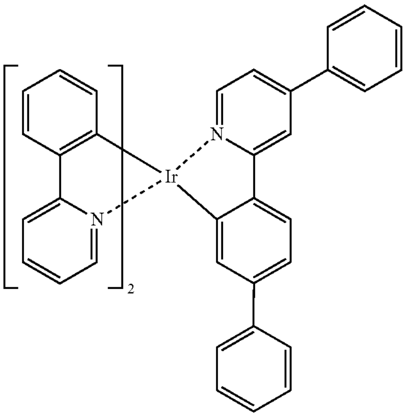
Dp-37
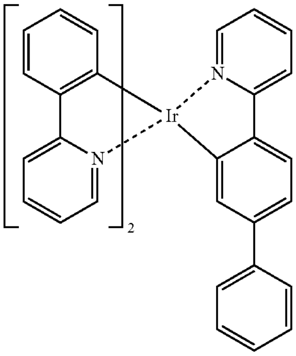

-continued

Dp-38

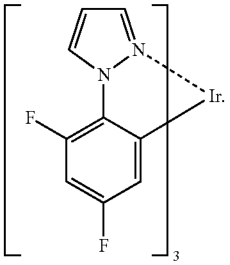

5. The organic light emitting device of claim 1, wherein $R_1$ and $R_2$ are the same as or different from each other, and are each independently a substituted or unsubstituted aryl group having 6 to 30 of carbon atoms.

6. The organic light emitting device of claim 1, wherein $R_1$ and $R_2$ are the same as or different from each other, and are each independently a substituted or unsubstituted phenyl group, or a substituted or unsubstituted naphthyl group.

7. An organic light emitting device comprising:

a first electrode, a second electrode provided to face the first electrode, and one or more organic material layers provided between the first electrode and the second electrode, wherein the one or more organic material layers include a light emitting layer, and the light emitting layer includes a host material comprising a first host and a second host, wherein:

the first host is a compound selected from among the following compounds:

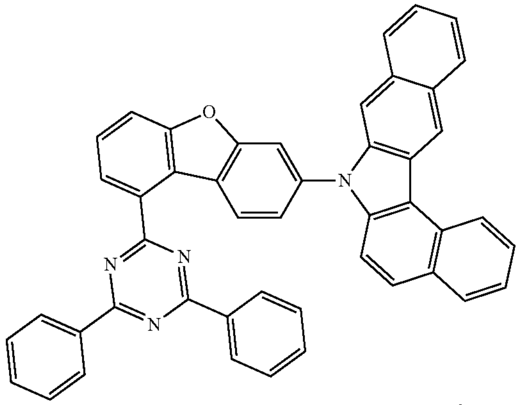

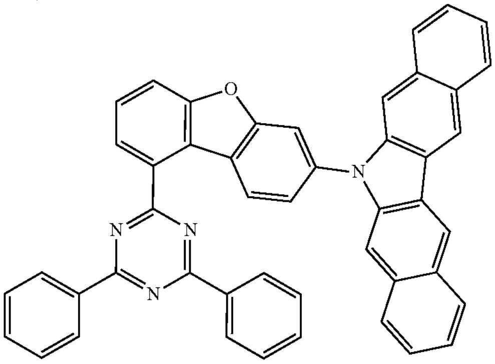

-continued

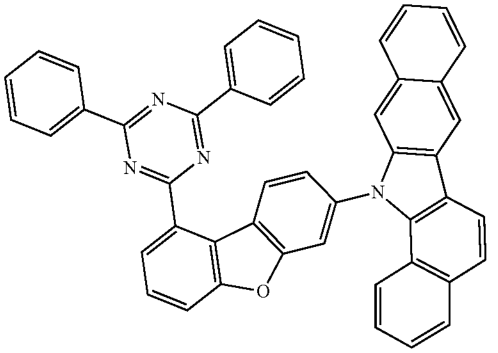

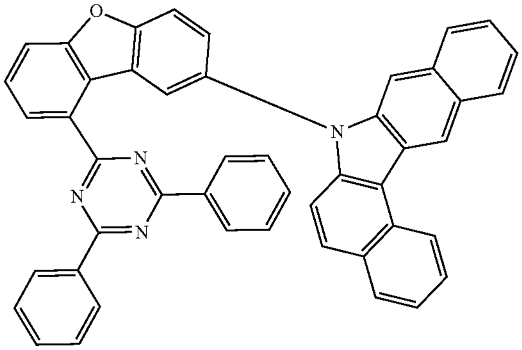

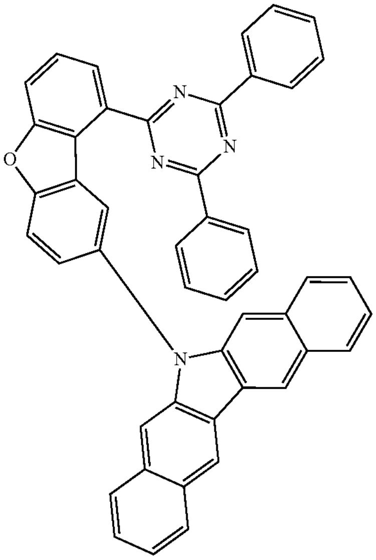

-continued
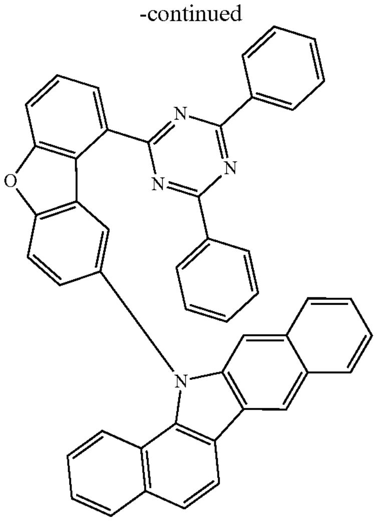
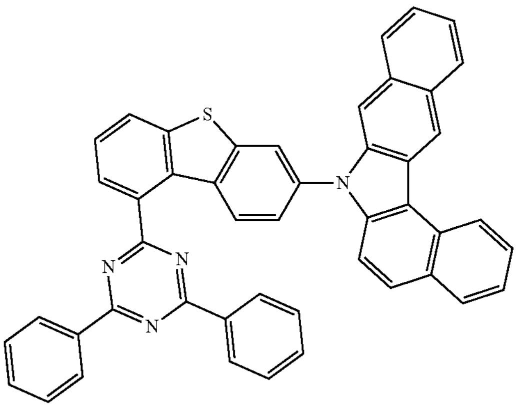
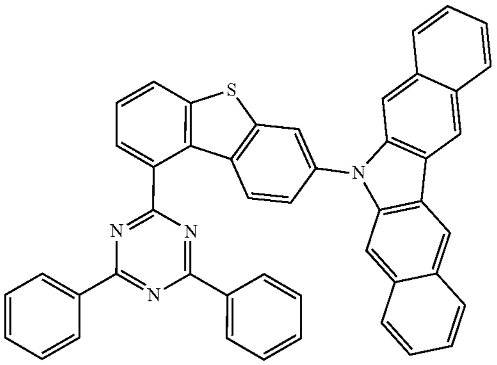
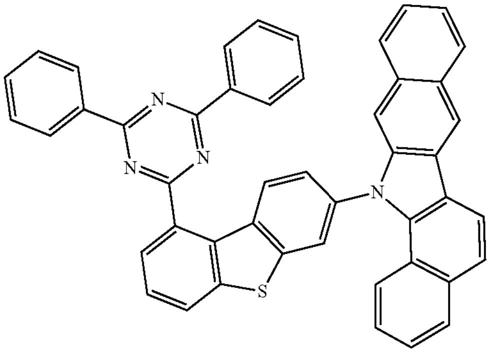
-continued
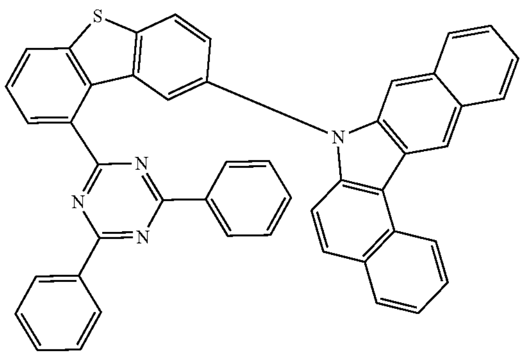
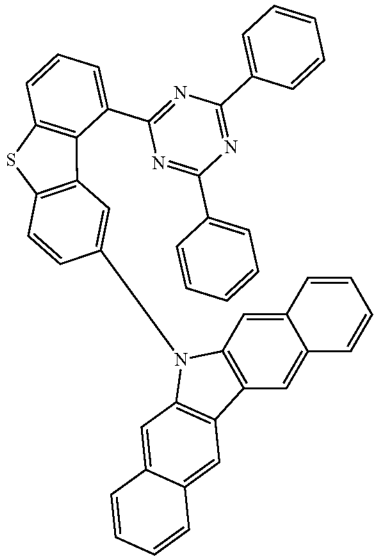
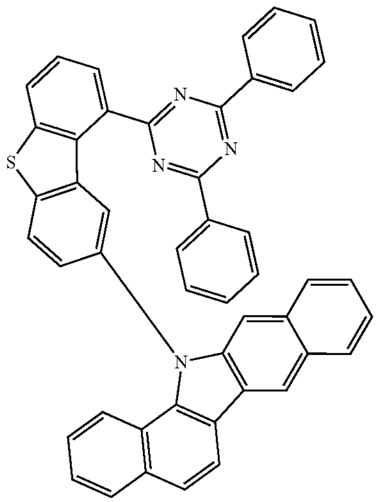

-continued
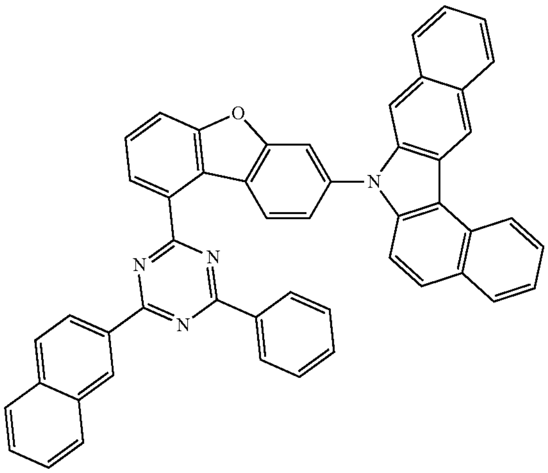
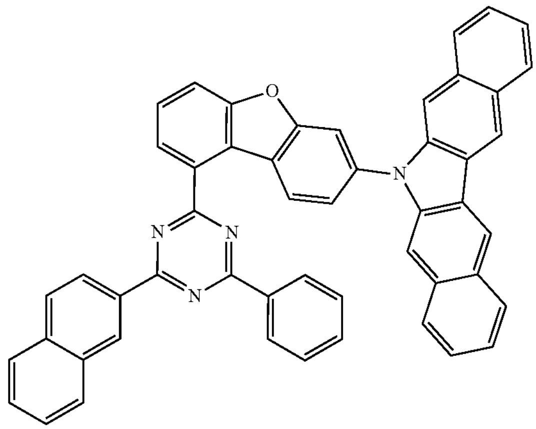
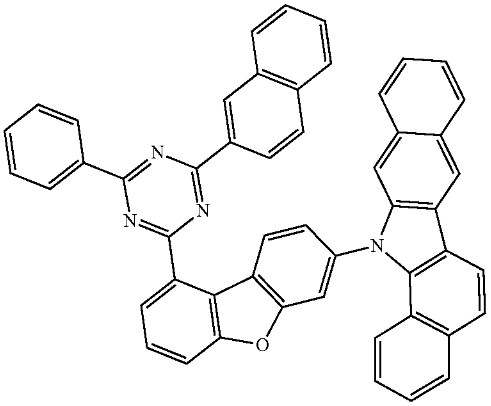
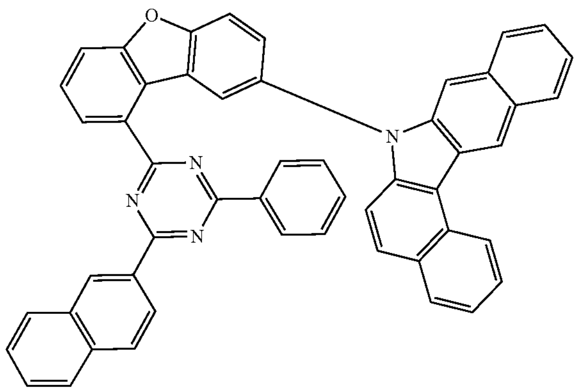
-continued
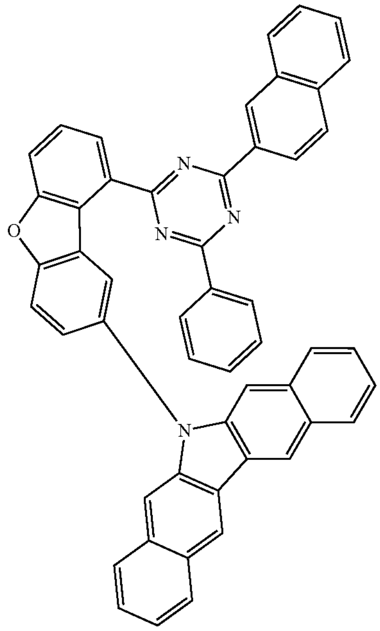
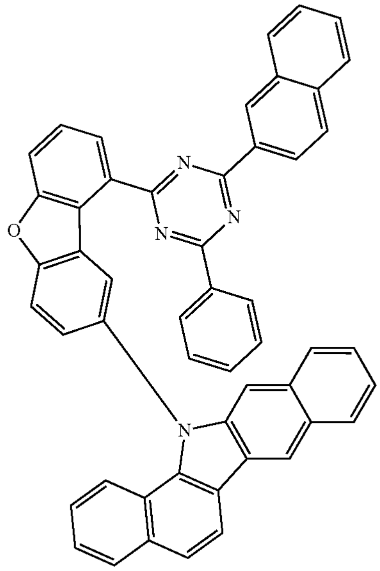
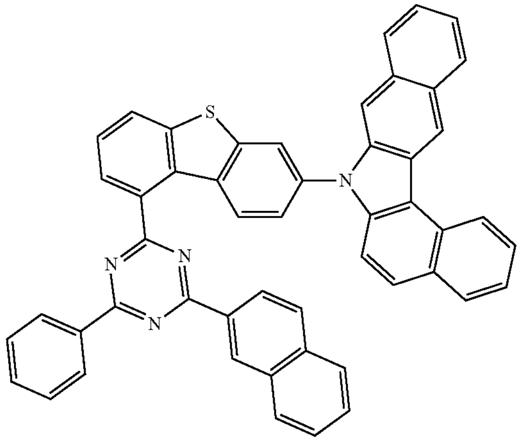

-continued
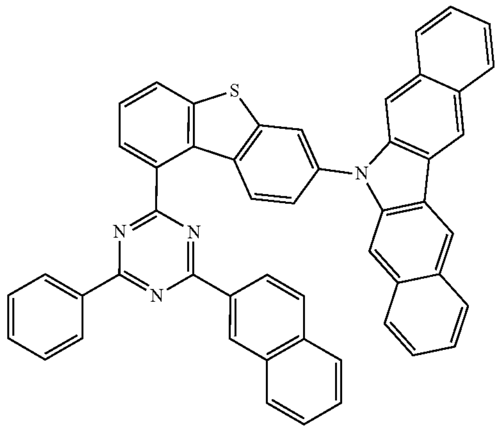
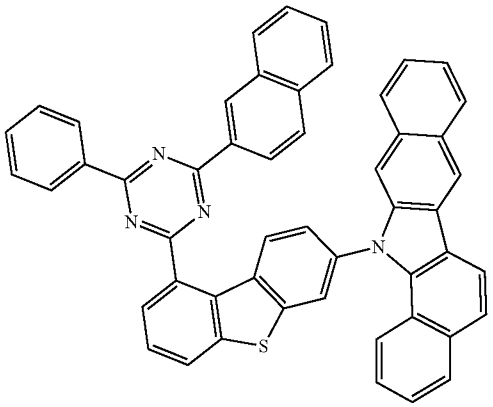
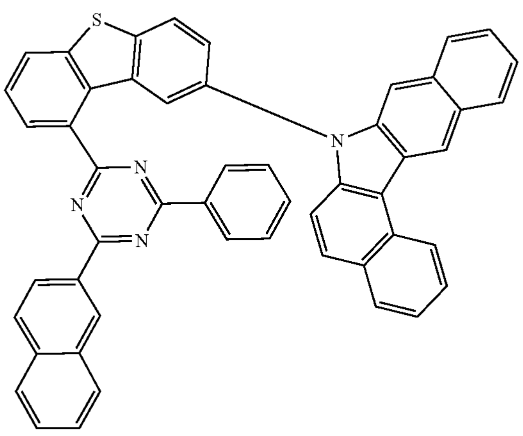
-continued
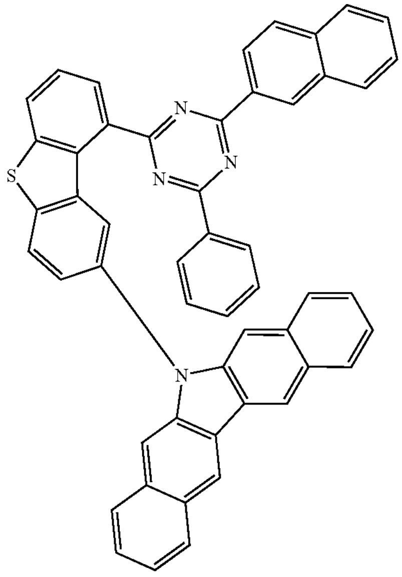
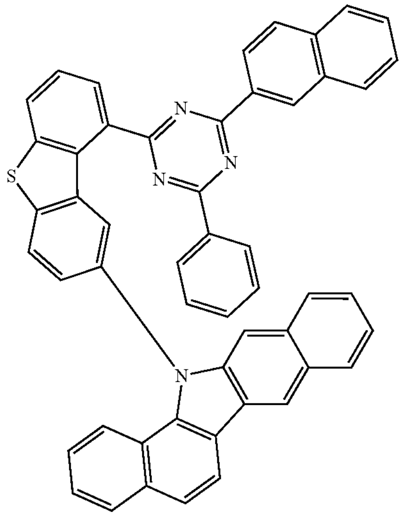
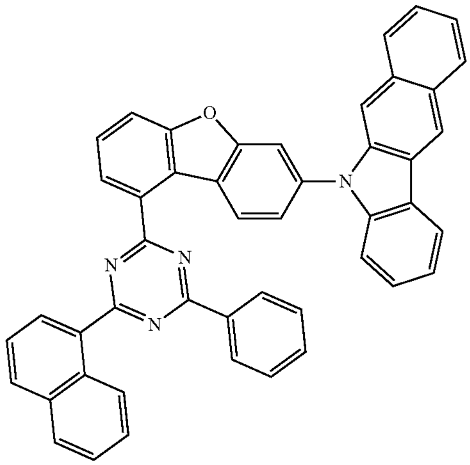

-continued
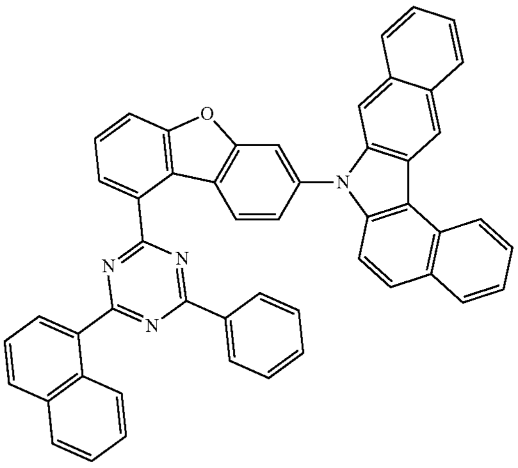
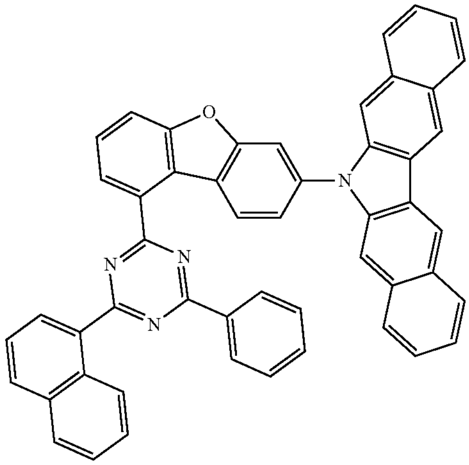
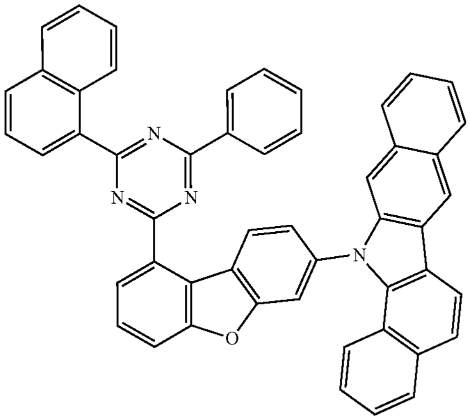
-continued
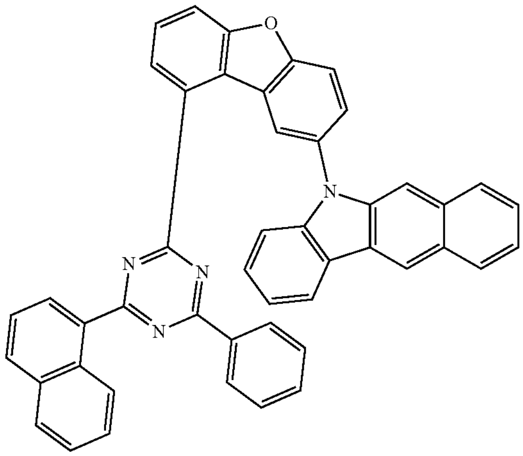
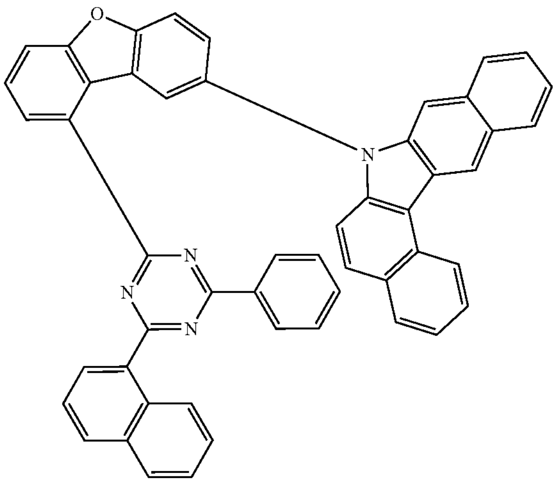
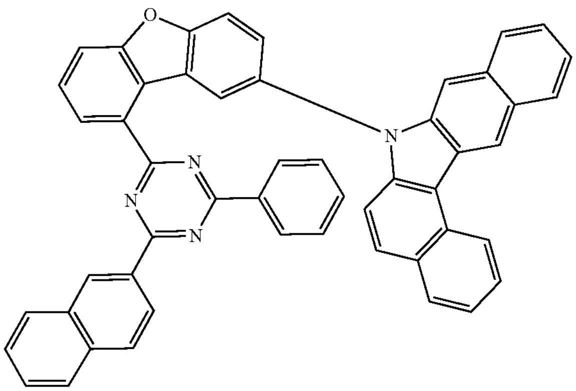

-continued
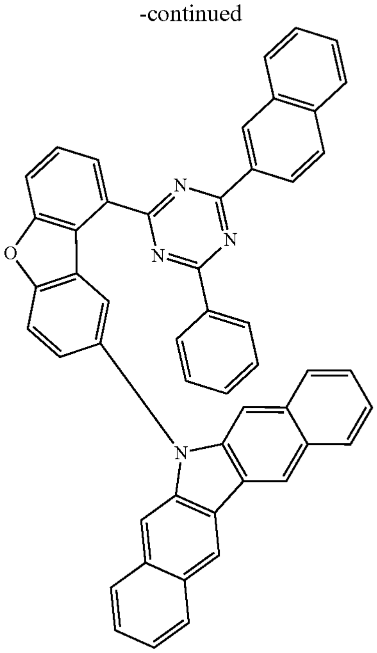
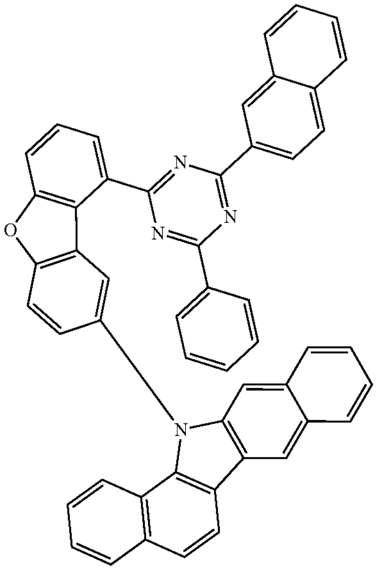
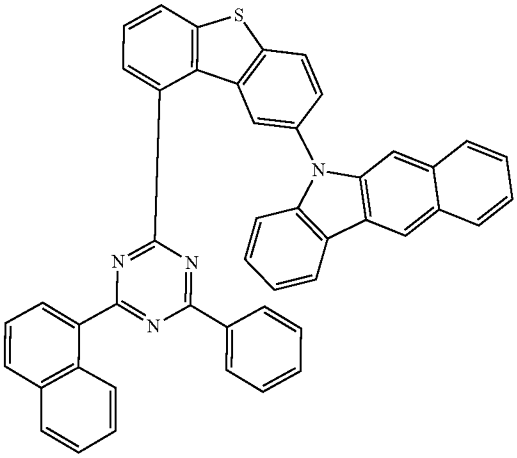
-continued
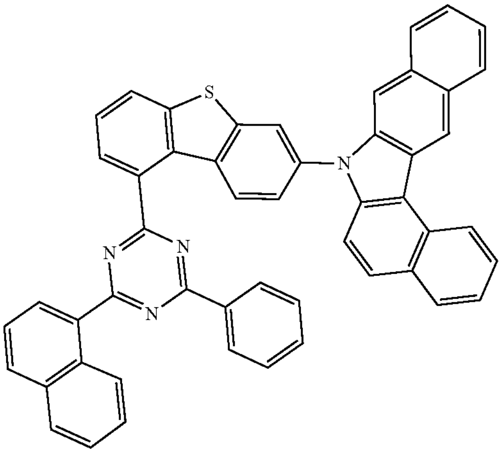
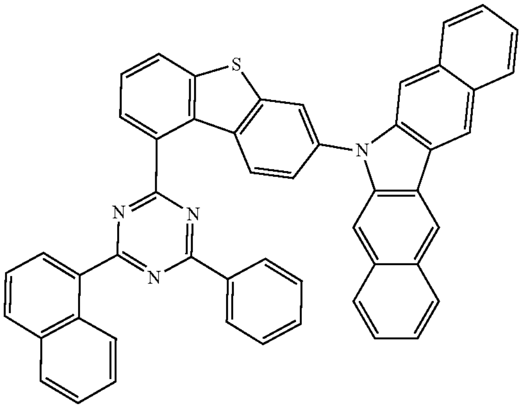
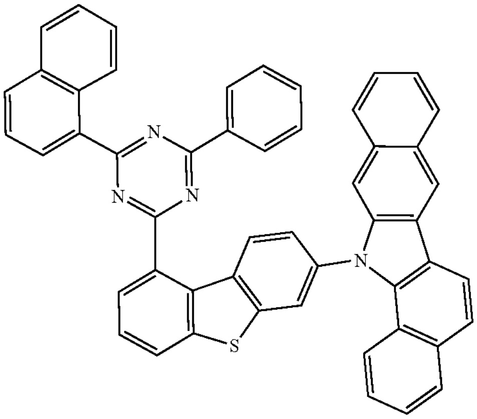

-continued
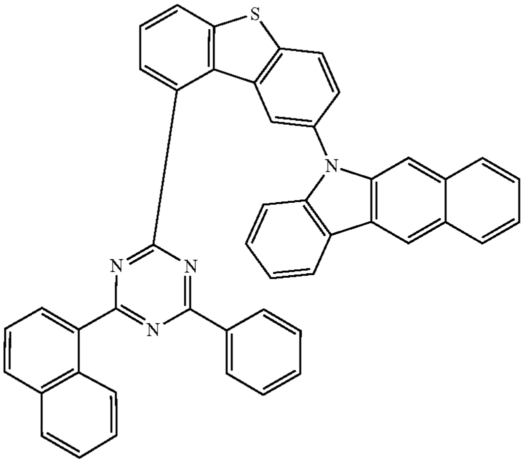
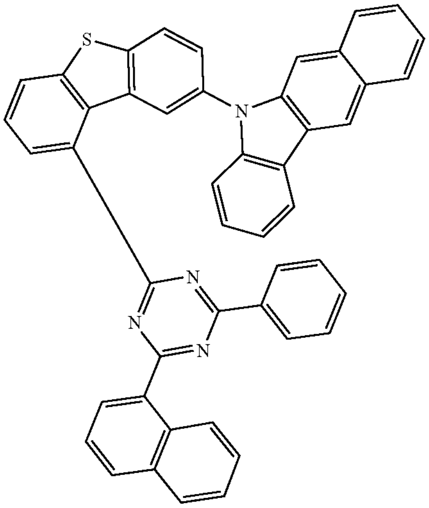
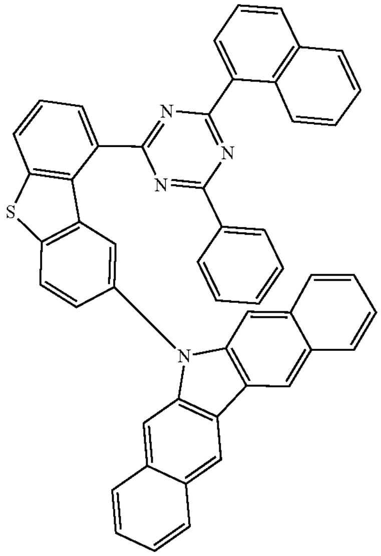
-continued
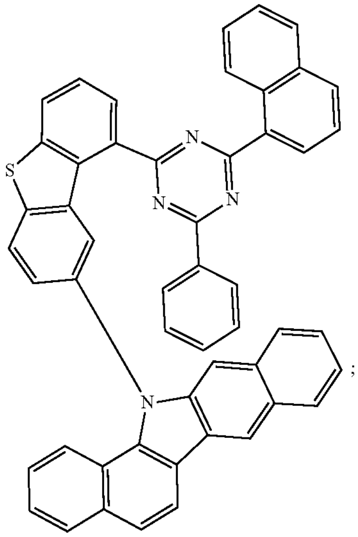
;
and
the second host is a compound selected from among the following compounds:
Z-5
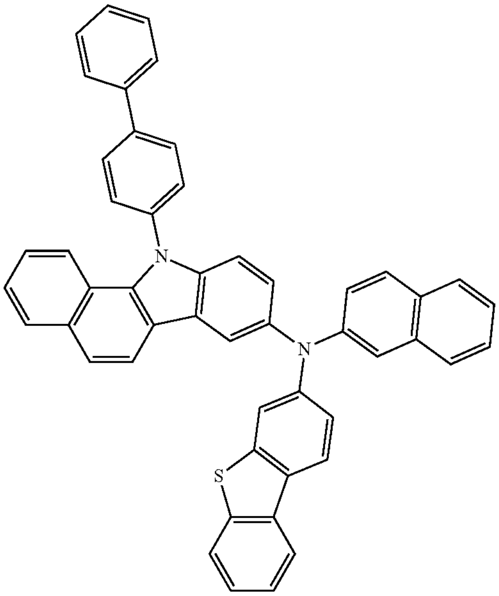

-continued
Z-6
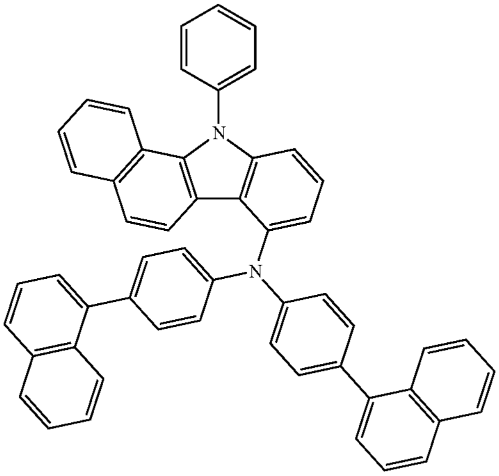
Z-8
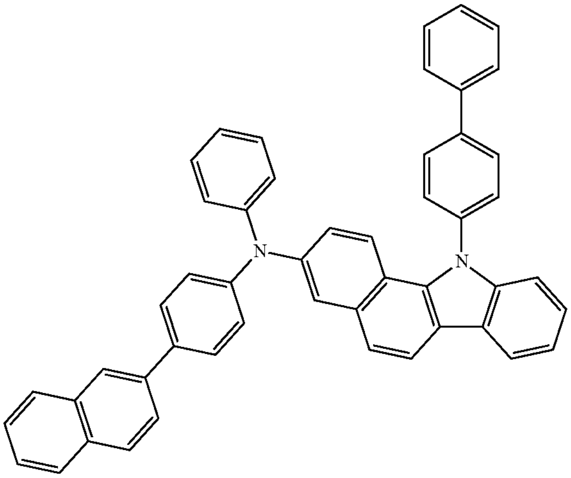
Z-9
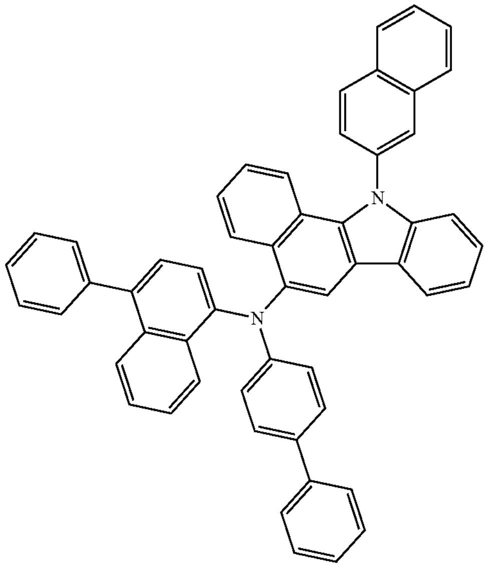
-continued
Z-10
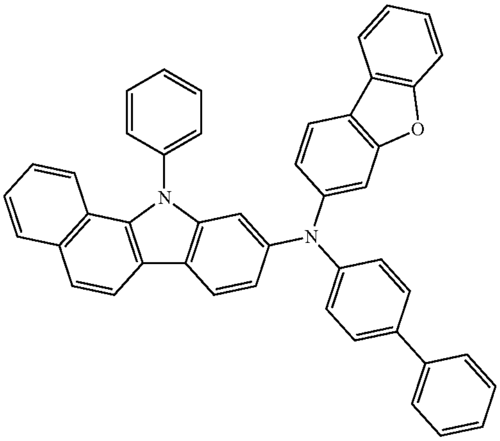
Z-11
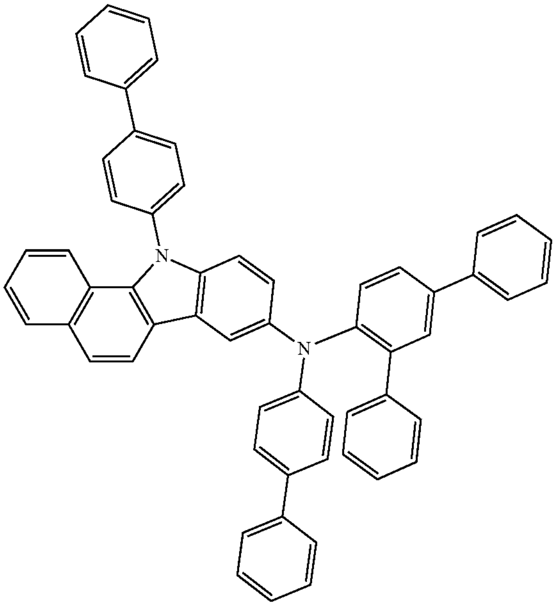
Z-12
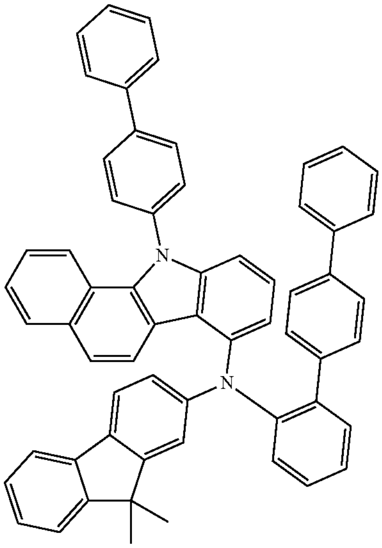

-continued

Z-26

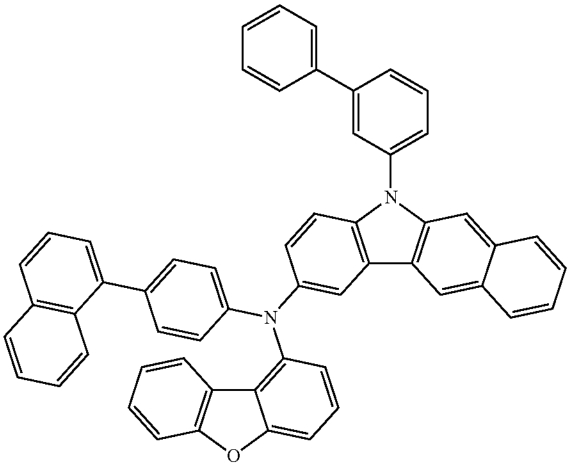

Z-30

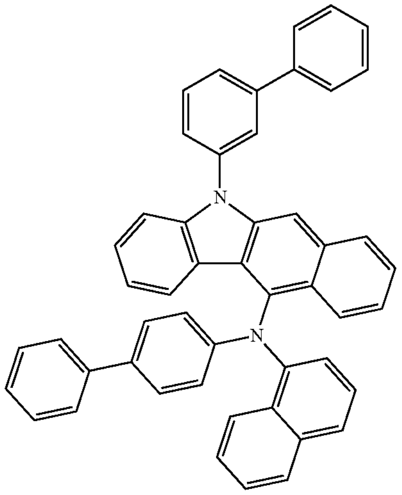

Z-31

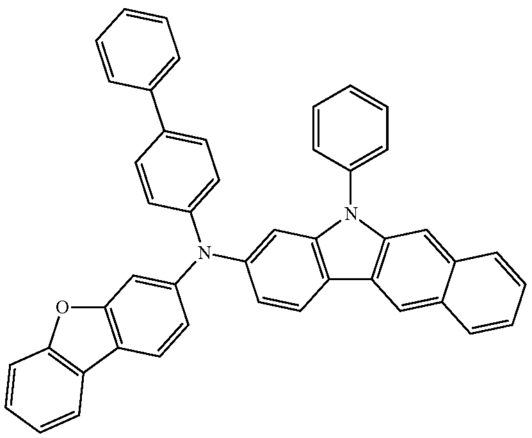

-continued

Z-32

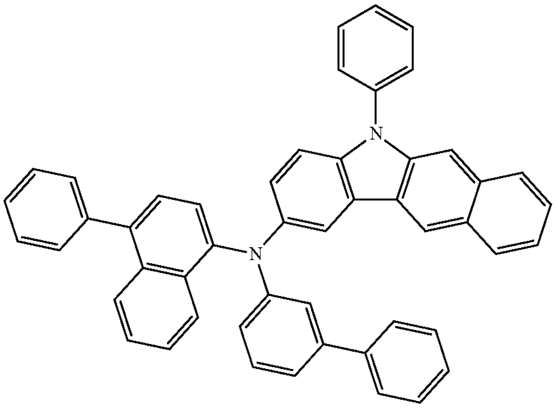

Z-35

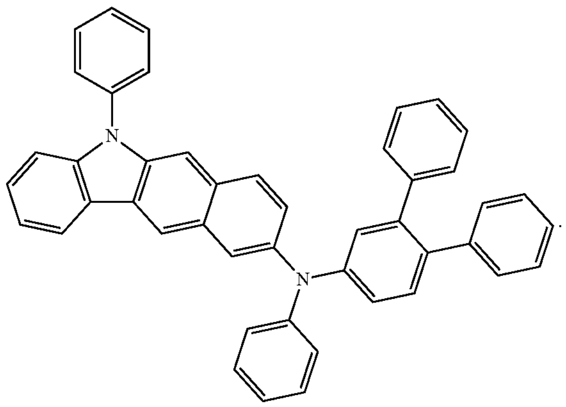

8. The organic light emitting device of claim 7, wherein the one or more organic material layers further include one, two or more layers selected from the group consisting of a second light emitting layer, a hole injection layer, a hole transfer layer, an electron injection layer, an electron transfer layer, an electron blocking layer and a hole blocking layer.

9. The organic light emitting device of claim 7, wherein the light emitting layer further includes a dopant, and the dopant is one selected from among the following compounds of Dp-1 to Dp5 and Dp-7 to Dp-38:

Dp-1

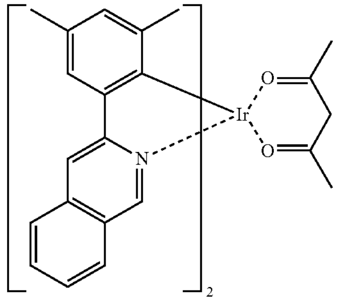

-continued
Dp-2
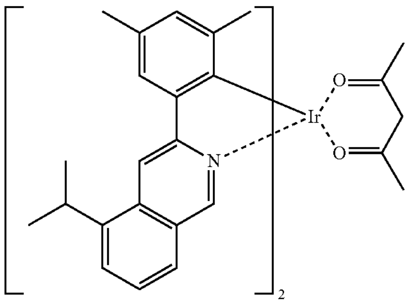
Dp-3
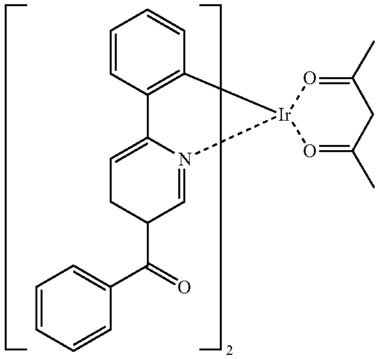
Dp-4
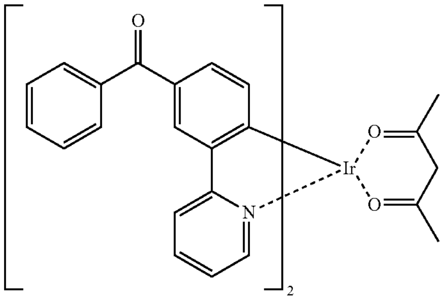
Dp-5
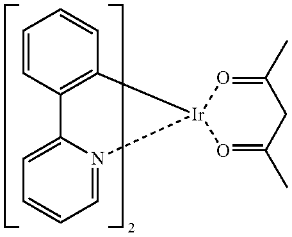
Dp-7
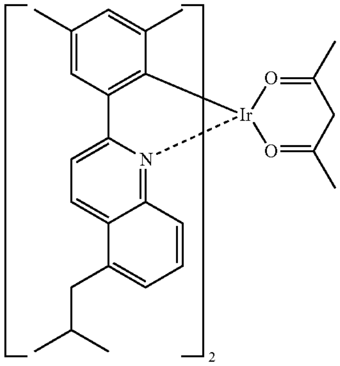
-continued
Dp-8
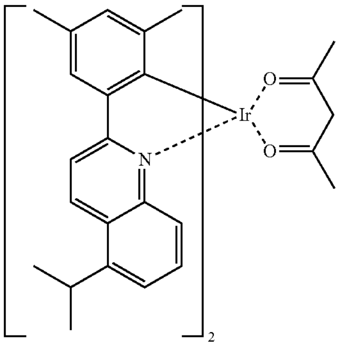
Dp-9
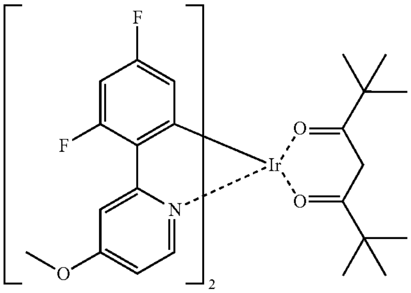
Dp-10
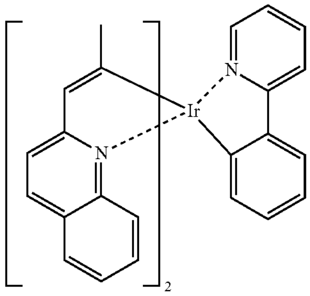
Dp-11
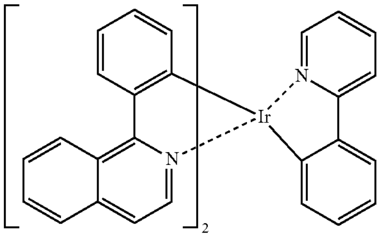
Dp-12
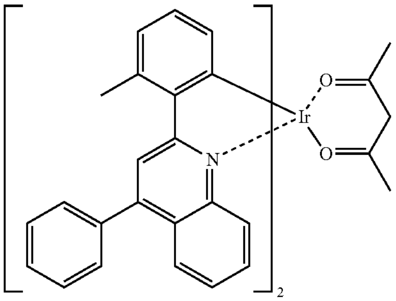

-continued
DP-13
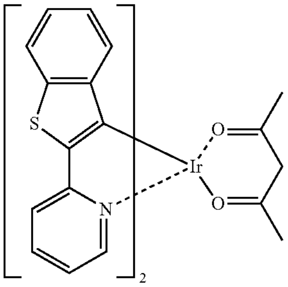
Dp-14
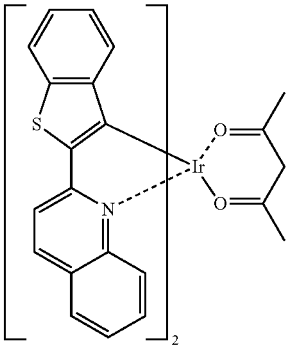
Dp-15
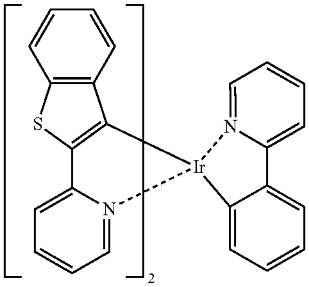
DP-16
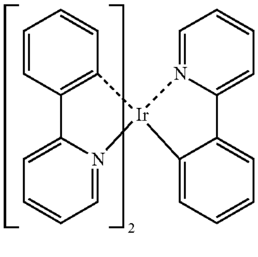
Dp-17
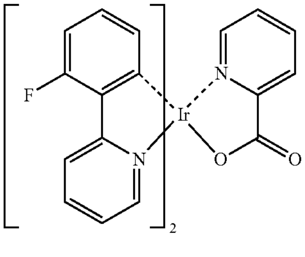
-continued
Dp-18
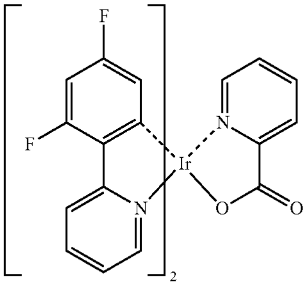
Dp-19
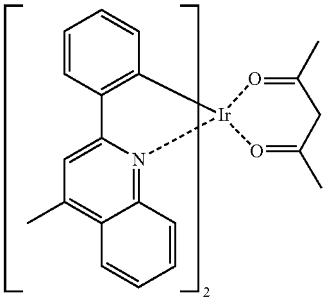
Dp-20
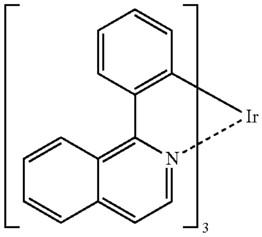
Dp-21
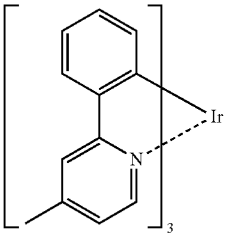
Dp-22
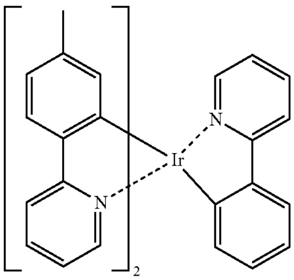
Dp-23
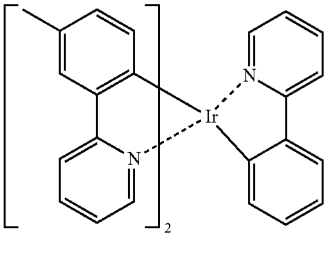

Dp-24
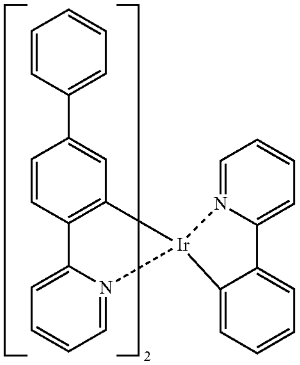
Dp-25
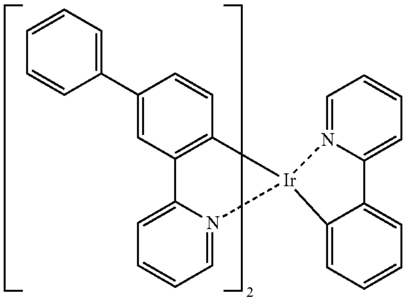
Dp-26
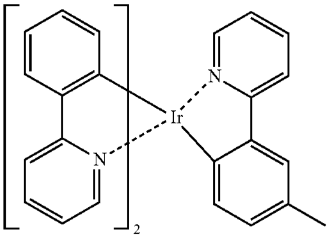
Dp-27
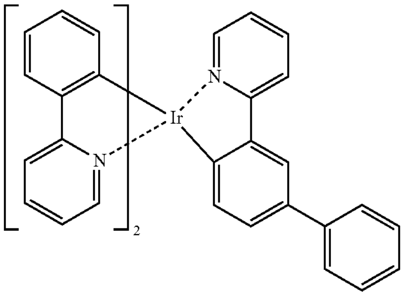
Dp-28
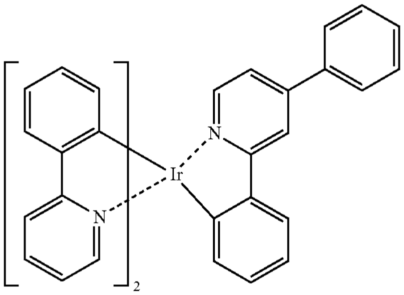
Dp=29
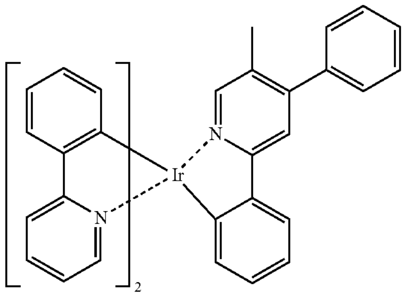
Dp-30
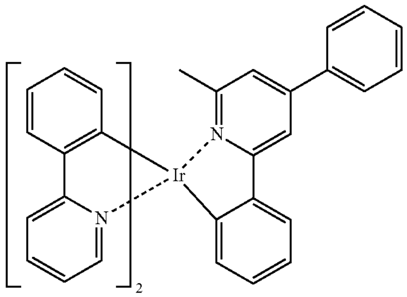
Dp-31
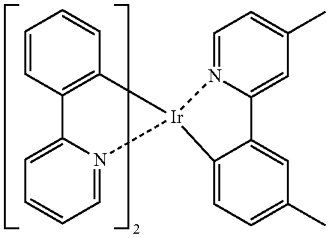
Dp-32
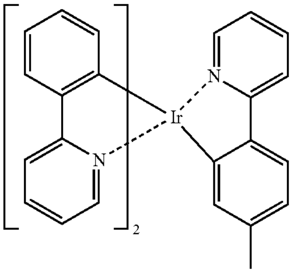

-continued
Dp-33
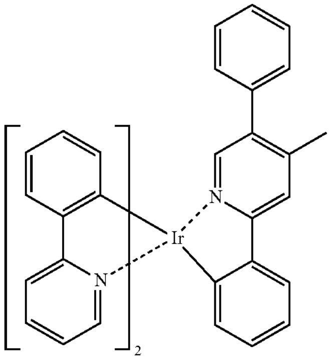
Dp-34
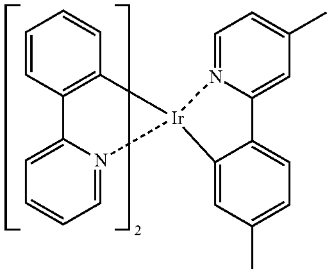
Dp-35
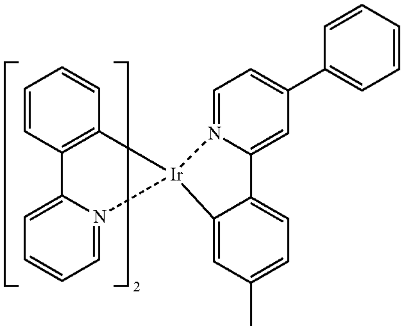
-continued
Dp-36
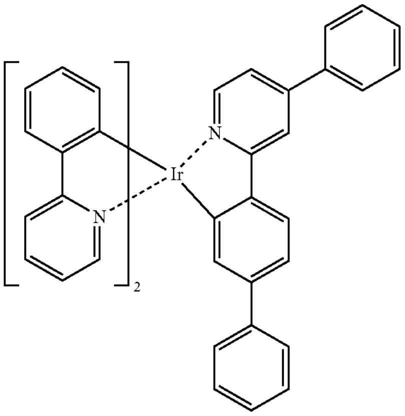
Dp-37
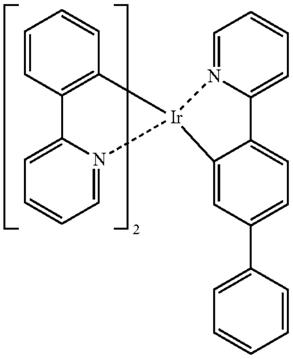
Dp-38
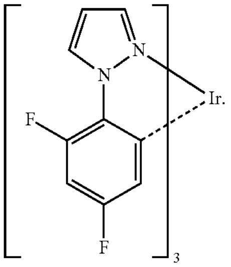
* * * * *